United States Patent
Benatuil et al.

(10) Patent No.: US 9,915,665 B2
(45) Date of Patent: Mar. 13, 2018

(54) HIGH-THROUGHPUT SYSTEM AND METHOD FOR IDENTIFYING ANTIBODIES HAVING SPECIFIC ANTIGEN BINDING ACTIVITIES

(71) Applicant: AbbVie, Inc., Worcester, MA (US)

(72) Inventors: Lorenzo Benatuil, Northborough, MA (US); Jennifer Perez, Worcester, MA (US); Chung-Ming Hsieh, Newton, MA (US)

(73) Assignee: ABBVIE INC., North Chicago, IL (US)

( * ) Notice: Subject to any disclaimer, the term of this patent is extended or adjusted under 35 U.S.C. 154(b) by 509 days.

(21) Appl. No.: 14/141,498

(22) Filed: Dec. 27, 2013

(65) Prior Publication Data

US 2014/0243228 A1    Aug. 28, 2014

Related U.S. Application Data

(60) Provisional application No. 61/786,829, filed on Mar. 15, 2013, provisional application No. 61/755,288, (Continued)

(51) Int. Cl.
  *G01N 33/68*    (2006.01)
  *C40B 20/04*    (2006.01)
  (Continued)

(52) U.S. Cl.
  CPC ....... *G01N 33/6854* (2013.01); *C07K 16/005* (2013.01); *C07K 16/18* (2013.01); (Continued)

(58) Field of Classification Search
  None
  See application file for complete search history.

(56) References Cited

U.S. PATENT DOCUMENTS

| 5,624,821 A | 4/1997 | Winter et al. |
| 5,641,870 A | 6/1997 | Rinderknecht et al. |

(Continued)

FOREIGN PATENT DOCUMENTS

| EP | 1 176 195 B1 | 5/2013 |
| EP | 2 647 704 A1 | 10/2013 |

(Continued)

OTHER PUBLICATIONS

Cao et al., "Construction and characterization of an enhanced GFP-tagged anti-BAFF scFv antibody," Appl. Microbiol. Biotechnol. 2008, 79:423-431.*

(Continued)

*Primary Examiner* — Kaijiang Zhang
(74) *Attorney, Agent, or Firm* — Lathrop Gage LLP; James H. Velema, Esq.

(57) ABSTRACT

System and methods are disclosed for identifying and isolating antibodies with specific affinity with an antigen of interest. Multiple DNA libraries encoding antibodies or their fragments are designed such that the encoded antibodies from different libraries are tagged differently. These libraries may be transformed into yeast cells. The variants of the antibodies are displayed on the surface of the yeast cells and flow cytometry may be used to sort the cells based on antigen affinity and the different tags on the antibodies. By allowing multiple libraries to be screened simultaneously, the disclosed methods help improve the efficiency of affinity.

44 Claims, 36 Drawing Sheets

Related U.S. Application Data filed on Jan. 22, 2013, provisional application No. 61/746,663, filed on Dec. 28, 2012, provisional application No. 61/746,659, filed on Dec. 28, 2012, provisional application No. 61/746,629, filed on Dec. 28, 2012, provisional application No. 61/746,619, filed on Dec. 28, 2012, provisional application No. 61/746,617, filed on Dec. 28, 2012, provisional application No. 61/746,615, filed on Dec. 28, 2012.

(51) Int. Cl.
| | |
|---|---|
| C40B 30/04 | (2006.01) |
| C07K 16/46 | (2006.01) |
| C12N 15/10 | (2006.01) |
| C07K 16/00 | (2006.01) |
| C07K 16/18 | (2006.01) |
| C07K 16/22 | (2006.01) |
| C07K 16/24 | (2006.01) |

(52) U.S. Cl.
CPC ............ *C07K 16/22* (2013.01); *C07K 16/244* (2013.01); *C07K 16/245* (2013.01); *C07K 16/468* (2013.01); *C12N 15/1037* (2013.01); *C07K 2317/64* (2013.01); *C07K 2317/92* (2013.01); *C40B 20/04* (2013.01); *C40B 30/04* (2013.01)

(56) References Cited

U.S. PATENT DOCUMENTS

| | | | |
|---|---|---|---|
| 5,648,260 | A | 7/1997 | Winter et al. |
| 5,714,350 | A | 2/1998 | Co et al. |
| 6,350,861 | B1 | 2/2002 | Co et al. |
| 6,699,658 | B1 | 3/2004 | Wittrup et al. |
| 8,258,268 | B2 | 9/2012 | Wu et al. |
| 2002/0137134 | A1 | 9/2002 | Gemgross |
| 2004/0018590 | A1 | 1/2004 | Gemgross et al. |
| 2007/0071675 | A1 | 3/2007 | Wu et al. |
| 2009/0291081 | A1* | 11/2009 | Hsieh et al. ......... C07K 16/245 424/136.1 |
| 2011/0076752 | A1 | 3/2011 | Wu et al. |
| 2012/0237442 | A1 | 9/2012 | Rossi et al. |

FOREIGN PATENT DOCUMENTS

| | | |
|---|---|---|
| WO | 1990/005144 A1 | 5/1990 |
| WO | 1999/054342 A1 | 10/1999 |
| WO | 2001/077342 A1 | 10/2001 |
| WO | 2002/000729 A2 | 1/2002 |
| WO | 2003/016466 A2 | 2/2003 |
| WO | 2003/035835 A2 | 5/2003 |
| WO | 2005/100584 A2 | 10/2005 |
| WO | 2007/048037 A2 | 4/2007 |
| WO | 2012/074029 A1 | 6/2012 |
| WO | 2012088302 A2 | 6/2012 |
| WO | 2012135345 A1 | 10/2012 |
| WO | 2013063114 A1 | 5/2013 |

OTHER PUBLICATIONS

Rajpal et al. 'A general method for greatly improving the affinity of antibodies by using combinatorial libraries'. Proceedings of the National Academy of Sciences of the United States of America. 2005, vol. 102, No. 24, pp. 8466-8471.
Larman et al. 'Construction of a rationally designed antibody platform for sequencing-assisted selection'. Proceedings of the National Academy of Sciences. 2012, vol. 109, No. 45, pp. 18523-18528.
Hoogenboom et al. 'Selecting and screening recombinant antibody libraries'. Nature Biotechnology. 2005, vol. 23, No. 9, pp. 1105-1116.
International Search Report and Written Opinion for International Applicaton No. PCT/US2013/077912, dated Jul. 16, 2014. 24 pages.
Benatuil et al. (2010) "An improved yeast transformation method for the generation of very large human antibody libraries," Protein Engineering Design and Selection. 23(4):155-159.
Benhar (2007) "Design of synthetic antibody libraries," Expert Opinion on Biological Therapy. 7(5):763-779.
Biewanga et al. (1983) "IgA1 Half Molecules in Human Multiple Myeloma and the in vitro Production of Similar Fragments from Intact IgA1 Molecules," Clinical and Experimental Immunology. 51:395-400.
Bird et al. (1988) "Single-Chain Antigen-Binding Proteins," Science. 242:423-426.
Caravella et al. (2010) "Design of next-generation protein therapeutics," Curr. Opin. Chem. Biol. 14(4):520-528.
Chothia et al. (1987) "Canonical Structures for the Hypervariable Regions of Immunoglobulins," Journal of Molecular Biology. 196:901-917.
Dall'Acqua et al. (1998) "Contribution of Domain Interface Residues to the Stability of Antibody CH3 Domain Homodimers," Biochemistry. 37:9266-9273.
Gunasekaran et al. (2010) "Enhancing Antibody Fc Heterodimer Formation through Electrostatic Steering Effects," J. Biol. Chem. 285(25):19637-19646.
Holliger et al. (1993) "Diabodies': Small Bivalent and Bispecific Antibody Fragments," Proc. Natl. Acad. Sci. USA. 90:6444-6448.
Holliger et al. (2005) "Engineered antibody fragments and the rise of single domains," Nat. Biotechnol. 23(9):1126-1136.
Hornig et al. (Jan. 1, 2012) "Production of Bispecific Antibodies: Diabodies and Tandem scFv," Ch. 40 In; Antibody Engineering:Methods and Protocols. 2nd Ed. pp. 713-727.
Huber et al. (1976) "Cystallographic Structure Studies of an IgG Molecule and an Fc Fragment," Nature. 264:415-420.
Hudson et al. (2003) "Engineered antibodies," Nat. Med. 9(1):129-134.
Huston et al. (1988) "Protein Engineering of Antibody Binding Sites: Recovery of Specific Activity in an Anti-digoxin Single-chain Fv Analogue Produced in *Escherichia coil*," Proc. Natl. Acad. Sci. USA. 85:5879-5883.
Kabat et al. (1977) "Unusual Distributions of Amino Acids in Complementarity-determining (Hypervariable) Segments of Heavy and Light Chains of Immunoglobulins and Their Possible Roles in Specificity of Antibody-combining Sites," The Journal of Biological Chemistry. 252:6609-6616.
Kaufman et al. (1982) "Amplification and Expression of Sequences Cotransfected with a Modular Dihydrofolate Reductase Complementary DNA Gene," Journal of Molecular Biology. 159:601-621.
Kim et al. (1994) "Identifying Amino Acid Residues that Influence Plasma Clearance of Murine IgG1 Fragments by Site-directed Mutagenesis," European Journal of Immunology. 24:542-548.
Klein et al. (Nov. 1, 2012) "Progress in overcoming the chain association issue in bispecific heterodimeric IgG antibodies," mAbs. 4:653-663.
Kontermann (Mar. 1, 2012) "Dual targeting strategies with bispecific antibodies," mAbs. 4(2):182-197.
Kriangkum et al. (2001) "Bispecific and Bifunctional Single Chain Recombinant Antibodies," Biomolecular Engineering. 18(2):31-40.
Leong et al. (2008) "Preparing recombinant single chain antibodies," Chemical Engineering Science. 63(6):1401-1414.
Lu et al. (2004) "Simultaneous Blockade of Both the Epidermal Growth Factor Receptor and the Insulin-like Growth Factor Receptor Signaling Pathways in Cancer Cells with a Fully Human Recombinant Bispecific Antibody," The Journal of Biological Chemistry. 279(4):2856-2865.
Lu et al. (Dec. 26, 2012) "Frontier of therapeutic antibody discovery: the challenges and how to face them," World Journal of Biological Chemistry. 3(12):187.
MacCallum et al. (1996) "Antibody-antigen Interactions: Contact Analysis and Binding site Topography," Journal of Molecular Biology. 262:732-745.

(56) References Cited

OTHER PUBLICATIONS

Mack et al. (1995) "A small bispecific antibody construct expressed as a functional single-chain molecule with high tumor cell cytotoxicity," Proc. Natl. Acad. Sci. USA. 92(15):7021-7025.

Miller et al. (2003) "Design, Construction, and In Vitro Analyses of Multivalent Antibodies," The Journal of Immunology. 170(9):4854-4861.

Nagorsen et al. (Dec. 1, 2012) "Blinatumomab: a historical perspective," Pharmacology & Therapeutics. 136(3):334-342.

Poljak et al. (1994) "Production and Structure of Diabodies," Structure. 2:1121-1123.

Presta et al. (2008) "Molecular engineering and design of therapeutic antibodies," Current Opinion in Immunology. 20(4):460-470.

Schafer et al. (Jul. 5, 2011) "Immunoglobulin domain crossover as a generic approach for the production of bispecific IgG antibodies," Proc. Natl. Acad. Sci. USA. 108(27):11187-11192.

Seligmann et al. (1978) "Immunochemical Study of a Human Myeloma IgG1 Half Molecule," Ann. Immunol. 129:855-870.

Shields et al. (2002) "Lack of Fucose on Human IgG1 N-Linked Oligosaccharide Improves Binding to Human FcγRIII and Antibody-dependent Cellular Toxicity," Journal of Biological Chemistry. 277:26733-26740.

Sidhu et al. (2004) "Phage-displayed Antibody Libraries of Synthetic Heavy Chain Complementarity Determining Regions," J. Mol. Biol. 338(2):299-310.

Thiery et al. (Aug. 7, 2012) "Targeted multiplex imaging mass spectrometry with single chain fragment variable (SCFV) recombinant antibodies," Journal of the American Society for Mass Spectrometry. 23(10):1689-1696.

Thies et al. (1999) "Folding and Association of the Antibody Domain CH3: Prolyl Isomerization Preceeds Dimerization," Journal of Molecular Biology. 293:67-79.

Umana et al. (1999) "Engineered glycoforms of an antineuroblastoma IgG1 with optimized antibody dependent cellular cytotoxic activity," Nature Biotechnology. 17:176-180.

Urlaub et al. (1980) "Isolation of Chinese Hamster Cell Mutants Deficient in Dihydrofolate Reductase Activity," Proc. Natl. Acad. Sci. USA. 77(7):4216-4220.

Walker et al. (2009) "Efficient recovery of high-affinity antibodies from a single-chain Fab yeast display library," J. Mol. Biol. 389(2):365-375.

Ward et al. (1989) "Binding Activities of a Repertoire of Single Immunoglobulin Variable Domains Seceted from *Escherichia coil*," Letters to Nature. 341:544-546.

Weaver-Feldhaus et al. (2004) "Yeast mating for combinatorial Fab library generation and surface display," FEBS Letters. 564(1):24-34.

West et al. (2000) "Crystal Structure and Immunoglobulin G Binding Properties of the Human Major Histocompatibility Complex-Related Fc Receptor," Biochemistry. 39:9698-9708.

Wolf et al. (2005) "BiTEs: bispecific antibody constructs with unique anti-tumor activity," Drug Discovery Today. 10(18):1237-1244.

Zapata et al. (1995) "Engineering Linear F(ab')2 Fragments for Efficient Production in *Escherichia coli* and Enhanced Antiproliferative Activity," Protein Engineering. 8(10):1057-1062.

International Search Report with Written Opinion corresponding to International Patent Application No. PCT/US2013/077933, dated Jan. 8, 2014.

* cited by examiner

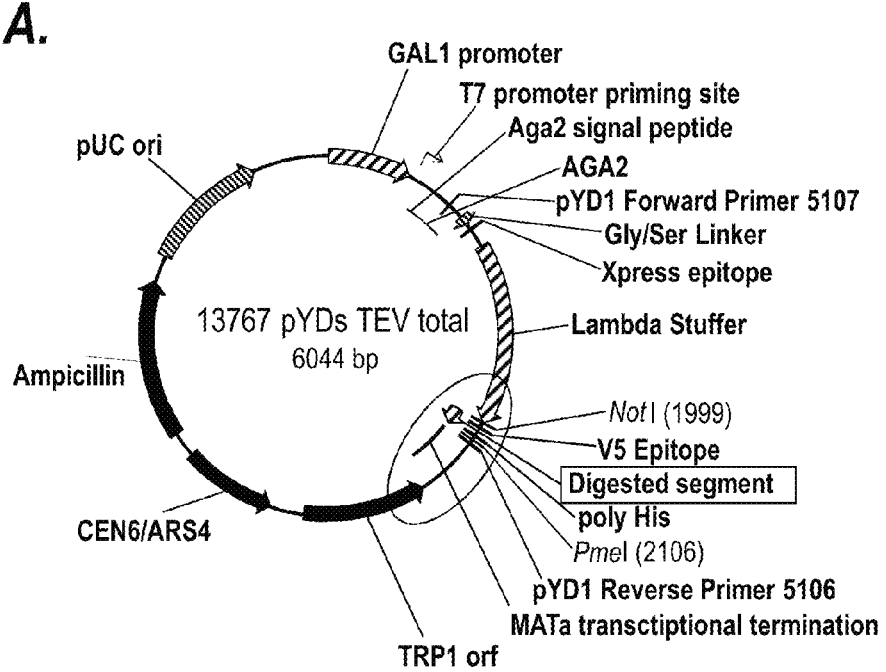
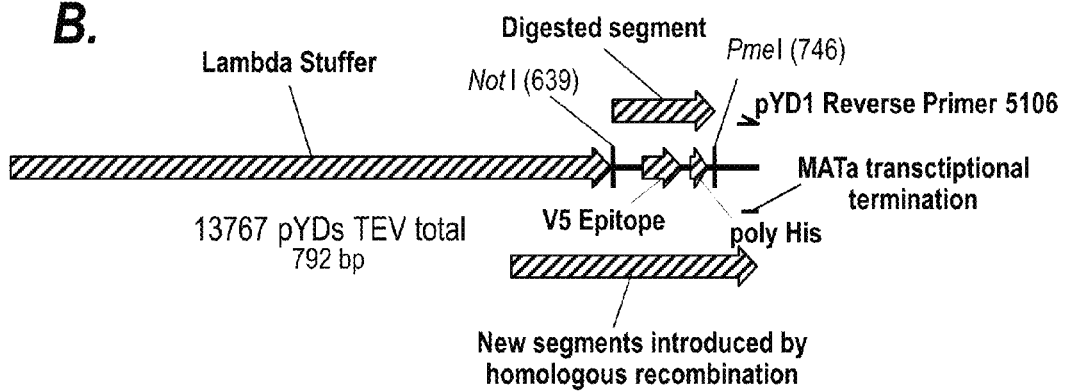
Fig. 3

CDRs are underline

| Linker | Initial Library (%) | R2 (%) | Enrichment Folds Pos | Enrichment Folds neg |
|---|---|---|---|---|
| SL11 | 0.0 | 1.4 | - | - |
| SL9 | 5.3 | 7.1 | 1.4 | 1.1 |
| SL7 | 9.2 | 8.6 | | 5.1 |
| SL5 | 14.5 | 2.9 | | |
| GS11 | 2.6 | 2.9 | 1.1 | 8.3 |
| GS9 | 11.8 | 1.4 | | 4.6 |
| GS7 | 13.2 | 2.9 | | 6.4 |
| GS5 | 9.2 | 1.4 | | |
| RL11 | 3.9 | 25.7 | 6.5 | |
| RL9 | 5.3 | 17.1 | 3.3 | |
| RL7 | 10.5 | 18.6 | 1.8 | |
| RL5 | 11.8 | 7.1 | | 1.7 |

| Type of Linker | Initial Library (%) | R2 (%) | Enrichment Folds Pos | Enrichment Folds neg |
|---|---|---|---|---|
| SL | 28.9 | 20.0 | - | 1.4 |
| GS | 36.8 | 8.6 | | 4.6 |
| RL | 31.6 | 68.6 | 2.2 | |

Fig. 21B

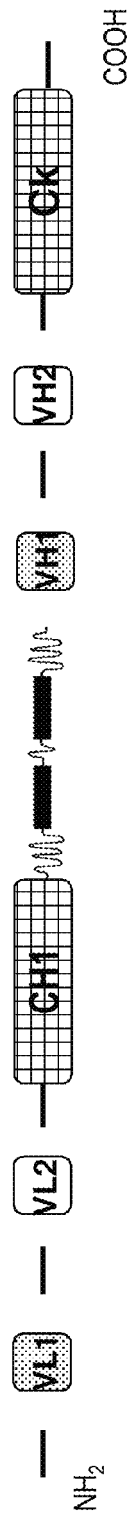
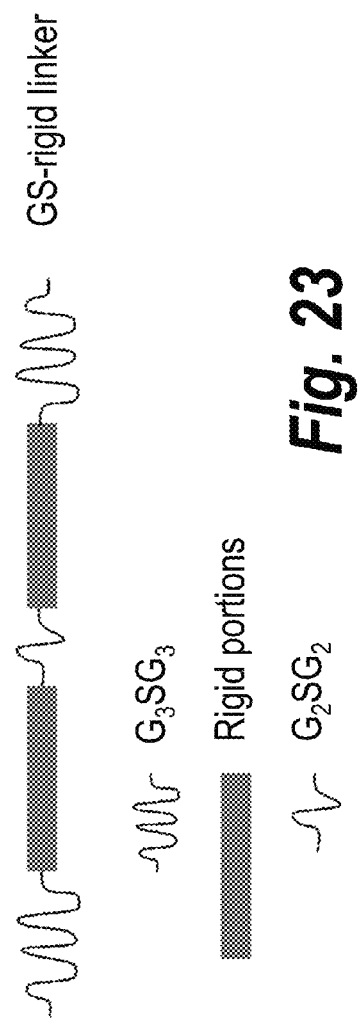

A. Linear sequence cartoon of a scDVDFab

B. GS-rigid linker sequences

41 GS-rigid linker: GGGSGGGGGGTPLPAPLPAPLPAPTGGSGGGTPAPLPAPLPTGGGSGGG
49 GS-rigid linker: GGGSGGGGGGTPLPAPLPAPLPAPTGGSGGGTPAPLPAPLPTGGGSGGG
57 GS-rigid linker: GGGSGGGGGGTPLPAPLPAPLPTPLPAPLPAPTGGSGGGTPAPTPAPLPAPLPTGGGSGGG
65 GS-rigid linker:
GGGSGGGGGGTPLPAPLPAPLPTPLPAPLPAPTGGSGGGTPAPTPAPTPAPLPAPLPTGGGSGGG

C. Linear sequence cartoon of a GS-rigid linker

∿ $G_3SG_3$
▬ Rigid portions
∿ $G_2SG_2$

Fig. 23

SEQUENCE LISTING

<160> NUMBER OF SEQ ID NOS: 252

<210> SEQ ID NO 1
<211> LENGTH: 50
<212> TYPE: PRT
<213> ORGANISM: Artificial Sequence -continued

```
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(50)
<223> OTHER INFORMATION: This sequence may encompass 1-10 "Gly Gly Gly
      Gly Ser" repeating units

<400> SEQUENCE: 1

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
catcatcacc atcaccat                                                  18

<210> SEQ ID NO 3
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ggtaagccta tccctaaccc tctcctcggt ctcgattcta cg                        42

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gaacaaaaac ttatttctga agaagatctg                                     30

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tacccatacg atgttccgga ttacgct                                        27

<210> SEQ ID NO 6
<211> LENGTH: 36
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 6
agccagccag aactcgctcc tgaagaccca gaggac                              36

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gactacaagg acgacgacga caag                                           24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tggagccatc cgcagtttga gaag                                           24

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tccagcacct cgagtgattt tcgagatcgc                                     30

<210> SEQ ID NO 10
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
aaggaaaccg cggctgccaa gtttgaacgc cagcatatgg atagc                    45

<210> SEQ ID NO 11
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ggagcgcctg taccatatcc ggatccgctg gaaccgcgc                           39

<210> SEQ ID NO 12
<211> LENGTH: 27
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 12
agctggaagg atgcgagcgg ctggagc                                          27

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
atggcgagca tgaccggcgg ccagcagatg ggc                                   33

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
aagcctccaa ctccacctcc ggaaccggaa acc                                   33

<210> SEQ ID NO 15
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
cataaccatc gccacaaaca tggtggaggc tgc                                   33

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
aactcccagc ctgccaatcc aggtacgact gcaact                                36

<210> SEQ ID NO 17
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gattattctt cggagacttc cgaggatgac gatagtttga ag                         42

<210> SEQ ID NO 18
<211> LENGTH: 36
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 18
aaattgaatt ccatcaagga cgttgaacag aagaaa                                36

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gaagaagaat atatgccaat ggag                                            24

<210> SEQ ID NO 20
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gatacttaca gatacatcga cacttatcgc tacatt                               36

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

His His His His His His
1               5

<210> SEQ ID NO 22
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Lys Pro Ile Pro Asn Pro Leu Leu Gly Leu Asp Ser Thr
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Glu Gln Lys Leu Ile Ser Glu Glu Asp Leu
1               5                   10

<210> SEQ ID NO 24
<211> LENGTH: 9
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 24

Tyr Pro Tyr Asp Val Pro Asp Tyr Ala
1               5

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ser Gln Pro Glu Leu Ala Pro Glu Asp Pro Glu Asp
1               5                   10

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Asp Tyr Lys Asp Asp Asp Asp Lys
1               5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Trp Ser His Pro Gln Phe Glu Lys
1               5

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ser Ser Thr Ser Ser Asp Phe Arg Asp Arg
1               5                   10

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Lys Glu Thr Ala Ala Ala Lys Phe Glu Arg Gln His Met Asp Ser
1               5                   10                  15
```

<210> SEQ ID NO 30
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Ala Pro Val Pro Tyr Pro Asp Pro Leu Glu Pro Arg
1               5                   10

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ser Trp Lys Asp Ala Ser Gly Trp Ser
1               5

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Met Ala Ser Met Thr Gly Gly Gln Gln Met Gly
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Lys Pro Pro Thr Pro Pro Pro Glu Pro Glu Thr
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

His Asn His Arg His Lys His Gly Gly Gly Cys
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 35

Asn Ser Gln Pro Ala Asn Pro Gly Thr Thr Ala Thr
1               5                   10

<210> SEQ ID NO 36
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Asp Tyr Ser Ser Glu Thr Ser Glu Asp Asp Ser Leu Lys
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Lys Leu Asn Ser Ile Lys Asp Val Glu Gln Lys Lys
1               5                   10

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Glu Glu Glu Tyr Met Pro Met Glu
1               5

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Asp Thr Tyr Arg Tyr Ile Asp Thr Tyr Arg Tyr Ile
1               5                   10

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Gly Gly Gly Ser
1               5

<210> SEQ ID NO 41
<211> LENGTH: 14
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ala Ser Thr Lys Gly Pro Ser Val Phe Pro Leu Ala Pro Ser
1               5                   10

<210> SEQ ID NO 42
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Arg Thr Val Ala Ala Pro Ser Val Phe Ile Phe Pro Pro Ser
1               5                   10

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Gly Gly Ser Gly Gly Gly
1               5

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Gly Ser Gly Gly
1               5

<210> SEQ ID NO 45
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Thr Pro Ala Pro Leu Pro Ala Pro Leu Pro Thr
1               5                   10

<210> SEQ ID NO 46
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Thr Pro Ala Pro Thr Pro Ala Pro Leu Pro Ala Pro Leu Pro Thr
```

```
<210> SEQ ID NO 47
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Thr Pro Ala Pro Leu Pro Ala Pro Thr Pro Ala Pro Leu Pro Ala Pro
1               5                   10                  15

Leu Pro Thr

<210> SEQ ID NO 48
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Thr Pro Ala Pro Leu Pro Ala Pro Leu Pro Ala Pro Thr Pro Ala Pro
1               5                   10                  15

Leu Pro Ala Pro Leu Pro Thr
            20

<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Thr Pro Leu Pro Ala Pro Leu Pro Ala Pro Thr
1               5                   10

<210> SEQ ID NO 50
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Thr Pro Leu Pro Thr Pro Leu Pro Ala Pro Leu Pro Ala Pro Thr
1               5                   10                  15

<210> SEQ ID NO 51
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Thr Pro Leu Pro Ala Pro Leu Pro Thr Pro Leu Pro Ala Pro Leu Pro
1               5                   10                  15

Ala Pro Thr
```

```
<210> SEQ ID NO 52
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Thr Pro Leu Pro Ala Pro Leu Pro Ala Pro Leu Pro Thr Pro Leu Pro
1               5                   10                  15

Ala Pro Leu Pro Ala Pro Thr
            20

<210> SEQ ID NO 53
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gly Gly Gly Ser Gly Gly Gly Thr Pro Leu Pro Ala Pro Leu Pro Ala
1               5                   10                  15

Pro Thr Gly Gly Ser Gly Gly Thr Pro Ala Pro Leu Pro Ala Pro Leu
            20                  25                  30

Pro Thr Gly Gly Gly Ser Gly Gly Gly
        35                  40

<210> SEQ ID NO 54
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gly Gly Gly Ser Gly Gly Gly Thr Pro Leu Pro Thr Pro Leu Pro Ala
1               5                   10                  15

Pro Leu Pro Ala Pro Thr Gly Gly Ser Gly Gly Thr Pro Ala Pro Thr
            20                  25                  30

Pro Ala Pro Leu Pro Ala Pro Leu Pro Thr Gly Gly Ser Gly Gly
        35                  40                  45

Gly

<210> SEQ ID NO 55
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gly Gly Gly Ser Gly Gly Gly Thr Pro Leu Pro Ala Pro Leu Pro Thr
1               5                   10                  15

Pro Leu Pro Ala Pro Leu Pro Ala Pro Thr Gly Gly Ser Gly Gly Thr
            20                  25                  30

Pro Ala Pro Thr Pro Ala Pro Thr Pro Ala Pro Leu Pro Ala Pro Leu
        35                  40                  45
```

```
Pro Thr Gly Gly Gly Ser Gly Gly Gly
    50              55
```

<210> SEQ ID NO 56
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

```
Gly Gly Gly Ser Gly Gly Gly Thr Pro Leu Pro Ala Pro Leu Pro Ala
1               5                   10                  15

Pro Leu Pro Thr Pro Leu Pro Ala Pro Leu Pro Ala Pro Thr Gly Gly
            20                  25                  30

Ser Gly Gly Thr Pro Ala Pro Thr Pro Ala Pro Thr Pro Ala Pro Thr
            35                  40                  45

Pro Ala Pro Leu Pro Ala Pro Leu Pro Thr Gly Gly Gly Ser Gly Gly
    50                  55                  60

Gly
65
```

<210> SEQ ID NO 57
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

```
Ala Ser Thr Lys Gly Pro
1               5
```

<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

```
Thr Val Ala Ala Pro
1               5
```

<210> SEQ ID NO 59
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (30)..(30)
<223> OTHER INFORMATION: Ser, Arg, Asn, Lys, Ile, Gly, Thr, Pro, Met,
      Leu, His, Phe, Asp, Cys or Ala
<220> FEATURE:
<221> NAME/KEY: MOD_RES
<222> LOCATION: (31)..(31)
<223> OTHER INFORMATION: Asn, Lys, Ile, Thr, Tyr, Ser, Arg, Pro, His,
      Glu, Asp or Cys
<220> FEATURE:
<221> NAME/KEY: MOD_RES
<222> LOCATION: (32)..(32)
<223> OTHER INFORMATION: Phe, Leu, Tyr, Val, Ile, Arg, Pro, Cys, Ser,

```
        Asn, His or Asp
<220> FEATURE:
<221> NAME/KEY: MOD_RES
<222> LOCATION: (35)..(35)
<223> OTHER INFORMATION: Ala, Thr, Pro, Lys, Gly, Asp, Val, Ser, Glu,
      Gln, Asn, Met, Leu or Phe
<220> FEATURE:
<221> NAME/KEY: MOD_RES
<222> LOCATION: (50)..(50)
<223> OTHER INFORMATION: Thr, Ser, Lys, Ile, Pro, Ala, Asn, Glu, Arg or
      Cys
<220> FEATURE:
<221> NAME/KEY: MOD_RES
<222> LOCATION: (52)..(52)
<223> OTHER INFORMATION: Ser, Arg, Asn, Ile, Thr, Cys, Phe, Trp, Gly,
      Asp or Ala
<220> FEATURE:
<221> NAME/KEY: MOD_RES
<222> LOCATION: (53)..(53)
<223> OTHER INFORMATION: Ser, Trp, Leu, Tyr, Arg, Phe, Val, Thr, Lys or
      Gly
<220> FEATURE:
<221> NAME/KEY: MOD_RES
<222> LOCATION: (56)..(56)
<223> OTHER INFORMATION: Gly, Ala, Val, Arg, Asp, Trp, Ser, Cys, Tyr,
      Gln, Met or Leu
<220> FEATURE:
<221> NAME/KEY: MOD_RES
<222> LOCATION: (57)..(57)
<223> OTHER INFORMATION: Thr, Asn, Arg, Met, Lys, Ile, Ala, Tyr, Ser,
      Phe, Val, Pro Leu or Gly
<220> FEATURE:
<221> NAME/KEY: MOD_RES
<222> LOCATION: (58)..(58)
<223> OTHER INFORMATION: Thr, Ser, Ile, Pro, Asn, Met, Ala, Lys, Arg or
      Cys
<220> FEATURE:
<221> NAME/KEY: MOD_RES
<222> LOCATION: (59)..(59)
<223> OTHER INFORMATION: Tyr, Phe, Cys, Ser, Asn, Leu, Arg, Gln, Pro,
      Ile or His
<220> FEATURE:
<221> NAME/KEY: MOD_RES
<222> LOCATION: (77)..(77)
<223> OTHER INFORMATION: Asn or Ser
<220> FEATURE:
<223> OTHER INFORMATION: See specification as filed for detailed
      description of substitutions and preferred embodiments

<400> SEQUENCE: 59

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Xaa Xaa Xaa
            20                  25                  30

Pro Met Xaa Trp Val Arg Gln Ala Pro Gly Lys Gly Leu Glu Trp Val
        35                  40                  45

Ala Xaa Ile Xaa Xaa Ser Asp Xaa Xaa Xaa Xaa Tyr Arg Asp Ser Val
    50                  55                  60

Lys Gly Arg Phe Thr Ile Ser Arg Asp Asn Ala Lys Xaa Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Tyr Asn Ser Pro Phe Ala Tyr Trp Gly Gln Gly Thr
            100                 105                 110

Leu Val Thr Val Ser Ser
            115

<210> SEQ ID NO 60
<211> LENGTH: 118
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 60

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser His Phe
            20                  25                  30

Pro Met Ala Trp Val Arg Gln Ala Pro Gly Lys Gly Leu Glu Trp Val
        35                  40                  45

Ala Ser Ile Ser Ser Ser Asp Ser Thr Thr Asn Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Tyr Asn Ser Pro Phe Ala Tyr Trp Gly Gln Gly Thr
            100                 105                 110

Leu Val Thr Val Ser Ser
        115

<210> SEQ ID NO 61
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ser His Phe Pro Met Ala
1               5

<210> SEQ ID NO 62
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ser Ile Ser Ser Ser Asp Ser Thr Thr Asn Tyr Arg Asp Ser Val Lys
1               5                   10                  15

Gly

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gly Tyr Tyr Asn Ser Pro Phe Ala Tyr
1               5

<210> SEQ ID NO 64
<211> LENGTH: 118
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 64

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Lys Asn Phe
            20                  25                  30

Pro Met Ala Trp Val Arg Gln Ala Pro Gly Lys Gly Leu Glu Trp Val
        35                  40                  45

Ala Thr Ile Ser Ser Ser Asp Leu Ser Thr Asn Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Tyr Asn Ser Pro Phe Ala Tyr Trp Gly Gln Gly Thr
            100                 105                 110

Leu Val Thr Val Ser Ser
        115

<210> SEQ ID NO 65
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Lys Asn Phe Pro Met Ala
1               5

<210> SEQ ID NO 66
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Thr Ile Ser Ser Ser Asp Leu Ser Thr Asn Tyr Arg Asp Ser Val Lys
1               5                   10                  15

Gly

<210> SEQ ID NO 67
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Asn Phe
            20                  25                  30

Pro Met Ala Trp Val Arg Gln Ala Pro Gly Lys Gly Leu Glu Trp Val
```

```
              35                  40                  45
Ala Ser Ile Ser Ser Asp Gly Thr Thr Asn Tyr Arg Asp Ser Val
    50                  55                  60
Lys Gly Arg Phe Thr Ile Ser Arg Asp Asn Ala Lys Ser Ser Leu Tyr
65                  70                  75                  80
Leu Gln Met Asn Ser Leu Arg Ala Glu Asp Thr Ala Val Tyr Tyr Cys
                85                  90                  95
Ala Arg Gly Tyr Tyr Asn Ser Pro Phe Ala Tyr Trp Gly Gln Gly Thr
            100                 105                 110
Leu Val Thr Val Ser Ser
        115

<210> SEQ ID NO 68
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Arg Asn Phe Pro Met Ala
1               5

<210> SEQ ID NO 69
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ser Ile Ser Ser Ser Asp Gly Thr Thr Asn Tyr Arg Asp Ser Val Lys
1               5                   10                  15
Gly

<210> SEQ ID NO 70
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Arg His Phe
            20                  25                  30
Pro Met Thr Trp Val Arg Gln Ala Pro Gly Lys Gly Leu Glu Trp Val
        35                  40                  45
Ala Ser Ile Ser Ser Asp Gly Thr Ile Asn Tyr Arg Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Gly Tyr Tyr Asn Ser Pro Phe Ala Tyr Trp Gly Gln Gly Thr
            100                 105                 110
```

Leu Val Thr Val Ser Ser
            115

<210> SEQ ID NO 71
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Arg His Phe Pro Met Thr
1               5

<210> SEQ ID NO 72
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ser Ile Ser Ser Ser Asp Gly Thr Ile Asn Tyr Arg Asp Ser Val Lys
1               5                   10                  15

Gly

<210> SEQ ID NO 73
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Asn Phe
            20                  25                  30

Pro Met Ala Trp Val Arg Gln Ala Pro Gly Lys Gly Leu Glu Trp Val
        35                  40                  45

Ala Thr Ile Ser Ser Asp Gly Thr Pro Ala Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Tyr Asn Ser Pro Phe Ala Tyr Trp Gly Gln Gly Thr
            100                 105                 110

Leu Val Thr Val Ser Ser
            115

<210> SEQ ID NO 74
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Thr Ile Ser Ser Ser Asp Gly Thr Pro Ala Tyr Arg Asp Ser Val Lys
1               5                   10                  15

Gly

<210> SEQ ID NO 75
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Tyr Phe
            20                  25                  30

Pro Met Ala Trp Val Arg Gln Ala Pro Gly Lys Gly Leu Glu Trp Val
        35                  40                  45

Ala Ala Ile Ser Gly Ser Asp Gly Thr Ala Ser Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Tyr Asn Ser Pro Phe Ala Tyr Trp Gly Gln Gly Thr
            100                 105                 110

Leu Val Thr Val Ser Ser
        115

<210> SEQ ID NO 76
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Arg Tyr Phe Pro Met Ala
1               5

<210> SEQ ID NO 77
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ala Ile Ser Gly Ser Asp Gly Thr Ala Ser Tyr Arg Asp Ser Val Lys
1               5                   10                  15

Gly

<210> SEQ ID NO 78
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 78

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn His Phe
            20                  25                  30

Pro Met Ala Trp Val Arg Gln Ala Pro Gly Lys Gly Leu Glu Trp Val
        35                  40                  45

Ala Thr Ile Ser Ser Ser Asp Trp Thr Pro Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Tyr Asn Ser Pro Phe Ala Tyr Trp Gly Gln Gly Thr
            100                 105                 110

Leu Val Thr Val Ser Ser
        115

<210> SEQ ID NO 79
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Asn His Phe Pro Met Ala
1               5

<210> SEQ ID NO 80
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Thr Ile Ser Ser Ser Asp Trp Thr Pro Tyr Tyr Arg Asp Ser Val Lys
1               5                   10                  15

Gly

<210> SEQ ID NO 81
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gln Lys Tyr
            20                  25                  30

Pro Met Ala Trp Val Arg Gln Ala Pro Gly Lys Gly Leu Glu Trp Val
        35                  40                  45

Ala Thr Ile Ser Cys Ser Asp Gly Ile Thr His Tyr Arg Asp Ser Val
    50                  55                  60
```

-continued

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Tyr Asn Ser Pro Phe Ala Tyr Trp Gly Gln Gly Thr
            100                 105                 110

Leu Val Thr Val Ser Ser
        115

<210> SEQ ID NO 82
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gln Lys Tyr Pro Met Ala
1               5

<210> SEQ ID NO 83
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Thr Ile Ser Cys Ser Asp Gly Ile Thr His Tyr Arg Asp Ser Val Lys
1               5                   10                  15

Gly

<210> SEQ ID NO 84
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg His Phe
                20                  25                  30

Pro Met Ala Trp Val Arg Gln Ala Pro Gly Lys Gly Leu Glu Trp Val
            35                  40                  45

Ala Thr Ile Ser Ser Ser Asp Gly Ala Thr Tyr Tyr Arg Asp Ser Val
        50                  55                  60

Lys Gly Arg Phe Thr Ile Ser Arg Asp Asn Ala Lys Ser Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Tyr Asn Ser Pro Phe Ala Tyr Trp Gly Gln Gly Thr
            100                 105                 110

Leu Val Thr Val Ser Ser
        115

<210> SEQ ID NO 85

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Arg His Phe Pro Met Ala
1               5

<210> SEQ ID NO 86
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Thr Ile Ser Ser Ser Asp Gly Ala Thr Tyr Tyr Arg Asp Ser Val Lys
1               5                   10                  15

Gly

<210> SEQ ID NO 87
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg His Phe
            20                  25                  30

Pro Met Ala Trp Val Arg Gln Ala Pro Gly Lys Gly Leu Glu Trp Val
        35                  40                  45

Ala Ser Ile Ser Ser Ser Asp Gly Thr Ser Asn Tyr Arg Asp Ser Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Tyr Asn Ser Pro Phe Ala Tyr Trp Gly Gln Gly Thr
            100                 105                 110

Leu Val Thr Val Ser Ser
        115

<210> SEQ ID NO 88
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ser Ile Ser Ser Ser Asp Gly Thr Ser Asn Tyr Arg Asp Ser Val Lys
1               5                   10                  15

Gly
```

<210> SEQ ID NO 89
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly His Phe
            20                  25                  30

Pro Met Ala Trp Val Arg Gln Ala Pro Gly Lys Gly Leu Glu Trp Val
        35                  40                  45

Ala Thr Ile Ser Ser Asp Gly Ala Thr Asn Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Tyr Asn Ser Pro Phe Ala Tyr Trp Gly Gln Gly Thr
            100                 105                 110

Leu Val Thr Val Ser Ser
        115

<210> SEQ ID NO 90
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gly His Phe Pro Met Ala
1               5

<210> SEQ ID NO 91
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Thr Ile Ser Ser Ser Asp Gly Ala Thr Asn Tyr Arg Asp Ser Val Lys
1               5                   10                  15

Gly

<210> SEQ ID NO 92
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Ala Ser Thr Lys Gly Pro Ser Val Phe Pro Leu Ala Pro
1               5                   10

<210> SEQ ID NO 93
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Thr Val Ala Ala Pro Ser Val Phe Ile Phe Pro Pro
1               5                   10

<210> SEQ ID NO 94
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ala Ser Thr Lys Gly Pro Ser Val Phe Pro Leu Ala
1               5                   10

<210> SEQ ID NO 95
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Thr Val Ala Ala Pro Ser Val Phe Ile Phe Pro
1               5                   10

<210> SEQ ID NO 96
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ala Ser Thr Lys Gly Pro Ser Val Phe Pro Leu
1               5                   10

<210> SEQ ID NO 97
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Thr Val Ala Ala Pro Ser Val Phe Ile Phe
1               5                   10

<210> SEQ ID NO 98
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 98

Ala Ser Thr Lys Gly Pro Ser Val Phe Pro
1               5                   10

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Thr Val Ala Ala Pro Ser Val Phe Ile
1               5

<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ala Ser Thr Lys Gly Pro Ser Val Phe
1               5

<210> SEQ ID NO 101
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Thr Val Ala Ala Pro Ser Val Phe
1               5

<210> SEQ ID NO 102
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Ala Ser Thr Lys Gly Pro Ser Val
1               5

<210> SEQ ID NO 103
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Thr Val Ala Ala Pro Ser Val
1               5

<210> SEQ ID NO 104
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 104

Ala Ser Thr Lys Gly Pro Ser
1               5

<210> SEQ ID NO 105
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Thr Val Ala Ala Pro Ser
1               5

<210> SEQ ID NO 106
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Ala Ser Thr Lys Gly Pro
1               5

<210> SEQ ID NO 107
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Thr Val Ala Ala Pro
1               5

<210> SEQ ID NO 108
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Gly Gly Gly Gly Ser Gly Gly Gly Gly Ser Gly Gly Gly Gly
1               5                   10

<210> SEQ ID NO 109
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Gly Gly Ser Gly Gly Gly Gly Ser Gly Gly Gly Gly Ser
1               5                   10
```

<210> SEQ ID NO 110
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gly Gly Gly Gly Ser Gly Gly Gly Gly Ser Gly Gly Gly
1               5                   10

<210> SEQ ID NO 111
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gly Gly Ser Gly Gly Gly Gly Ser Gly Gly Gly Gly
1               5                   10

<210> SEQ ID NO 112
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gly Gly Gly Gly Ser Gly Gly Gly Gly Ser Gly Gly
1               5                   10

<210> SEQ ID NO 113
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Gly Gly Ser Gly Gly Gly Gly Ser Gly Gly Gly
1               5                   10

<210> SEQ ID NO 114
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Gly Gly Gly Gly Ser Gly Gly Gly Gly Ser Gly
1               5                   10

<210> SEQ ID NO 115
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 115

Gly Gly Ser Gly Gly Gly Gly Ser Gly Gly
1               5                   10

<210> SEQ ID NO 116
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Gly Gly Gly Gly Ser Gly Gly Gly Gly Ser
1               5                   10

<210> SEQ ID NO 117
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Gly Gly Ser Gly Gly Gly Gly Ser Gly
1               5

<210> SEQ ID NO 118
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Gly Gly Gly Gly Ser Gly Gly Gly Gly
1               5

<210> SEQ ID NO 119
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Gly Gly Ser Gly Gly Gly Gly Ser
1               5

<210> SEQ ID NO 120
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Gly Gly Gly Gly Ser Gly Gly Gly
1               5

<210> SEQ ID NO 121
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Gly Gly Ser Gly Gly Gly Gly
1               5

<210> SEQ ID NO 122
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Gly Gly Gly Gly Ser Gly Gly
1               5

<210> SEQ ID NO 123
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Gly Gly Ser Gly Gly Gly
1               5

<210> SEQ ID NO 124
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Gly Gly Gly Gly Ser Gly
1               5

<210> SEQ ID NO 125
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Gly Gly Ser Gly Gly
1               5

<210> SEQ ID NO 126
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Thr Pro Ala Pro Leu Pro Ala Pro Leu Pro Ala Pro Thr Thr
```

<210> SEQ ID NO 127
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Thr Pro Ala Pro Leu Pro Ala Pro Leu Pro Ala Pro Thr
1               5                   10

<210> SEQ ID NO 128
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Thr Pro Ala Pro Leu Pro Ala Pro Ala Pro Thr Thr
1               5                   10

<210> SEQ ID NO 129
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Thr Pro Ala Pro Leu Pro Ala Pro Ala Pro Thr
1               5                   10

<210> SEQ ID NO 130
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Thr Pro Ala Pro Leu Pro Ala Pro Thr Thr
1               5                   10

<210> SEQ ID NO 131
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Thr Pro Ala Pro Leu Pro Ala Pro Thr
1               5

<210> SEQ ID NO 132
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 132

Thr Pro Ala Pro Leu Pro Thr Thr
1               5

<210> SEQ ID NO 133
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Thr Pro Ala Pro Leu Pro Thr
1               5

<210> SEQ ID NO 134
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Thr Pro Ala Pro Thr Thr
1               5

<210> SEQ ID NO 135
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Thr Pro Ala Pro Thr
1               5

<210> SEQ ID NO 136
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Ile
        35                  40                  45

Gly Leu Ile Trp Gly Ser Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Thr Asn Ile Trp Ala Tyr Asp Leu Tyr Ser Met Asp Tyr Trp

```
                  100                 105                 110

Gly Gln Gly Thr Leu Val Thr Val Ser Ser
            115                 120

<210> SEQ ID NO 137
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Glu Phe
            20                  25                  30

Gly Val Ser Trp Ile Arg Gln Pro Pro Gly Lys Gly Leu Glu Trp Ile
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Asn Leu Trp Ala Tyr Asp Leu Tyr Gly Met Asp Tyr Trp
            100                 105                 110

Gly Gln Gly Thr Leu Val Thr Val Ser Ser
            115                 120

<210> SEQ ID NO 138
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Ile
        35                  40                  45

Gly Leu Ile Trp Gly Ser Gly Asp Thr Tyr Tyr Asn Ser Pro Leu Lys
    50                  55                  60

Ser Arg Leu Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Thr Asn Leu Trp Ala Tyr Asp Leu Tyr Ser Met Asp Tyr Trp
            100                 105                 110

Gly Gln Gly Thr Leu Val Thr Val Ser Ser
            115                 120

<210> SEQ ID NO 139
<211> LENGTH: 122
<212> TYPE: PRT
```

<213> ORGANISM: Artificial Sequence
<220> FEATURE:
<223> OTHER INFORMATION: Description of Artificial Sequence: Synthetic
     polypeptide

<400> SEQUENCE: 139

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Arg Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Ser Gly Asp Thr Tyr Tyr Asn Ser Pro Leu Lys
    50                  55                  60

Ser Arg Leu Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Thr Asn Ile Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 140
<211> LENGTH: 122
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 140

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Ile
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Arg Gln Thr Asn Leu Trp Ala Tyr Asp Leu Tyr Ser Met Asp Tyr Trp
            100                 105                 110

Gly Gln Gly Thr Leu Val Thr Val Ser Ser
        115                 120

<210> SEQ ID NO 141
<211> LENGTH: 119
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 141

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Ile Phe Ser Arg Tyr
            20                  25                  30

Asp Met Ser Trp Val Arg Gln Ala Pro Gly Lys Gly Leu Glu Trp Val
        35                  40                  45

Ala Tyr Ile Ser His Gly Gly Ala Gly Thr Tyr Tyr Pro Asp Ser Val
    50                  55                  60

Lys Gly Arg Phe Thr Ile Ser Arg Asp Asn Ser Lys Asn Thr Leu Phe
65                  70                  75                  80

Leu Gln Met Asp Ser Leu Arg Pro Glu Asp Thr Val Tyr Phe Cys
                85                  90                  95

Ala Arg Gly Gly Val Thr Lys Gly Tyr Phe Asp Val Trp Gly Gln Gly
            100                 105                 110

Thr Pro Val Thr Val Ser Ser
            115

<210> SEQ ID NO 142
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Ile Phe Ser Arg Tyr
            20                  25                  30

Asp Met Ser Trp Val Arg Gln Ala Pro Gly Lys Gly Leu Glu Trp Val
        35                  40                  45

Ala Tyr Ile Ser His Gly Gly Ala Gly Thr Tyr Tyr Pro Asp Ser Val
    50                  55                  60

Lys Gly Arg Phe Thr Ile Ser Arg Asp Asn Ser Lys Asn Thr Leu Phe
65                  70                  75                  80

Leu Gln Met Asp Ser Leu Arg Ala Glu Asp Thr Ala Val Tyr Tyr Cys
                85                  90                  95

Ala Arg Gly Gly Val Tyr Lys Gly Tyr Phe Asp Val Trp Gly Gln Gly
            100                 105                 110

Thr Pro Val Thr Val Ser Ser
            115

<210> SEQ ID NO 143
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Glu Ile His Trp Val Arg Gln Ala Pro Gly Gln Gly Leu Glu Trp Met
        35                  40                  45

Gly Val Asn Asp Pro Glu Ser Gly Gly Thr Phe Tyr Asn Gln Lys Phe
    50                  55                  60

```
Asp Gly Arg Val Thr Leu Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Tyr Ser Lys Trp Asp Ser Phe Asp Gly Met Asp Tyr Trp Gly
            100                 105                 110

Gln Gly Thr Thr Val Thr Val Ser Ser
        115                 120

<210> SEQ ID NO 144
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Glu Val Gln Leu Val Gln Ser Gly Ala Glu Val Lys Lys Pro Gly Ser
1               5                   10                  15

Ser Val Lys Val Ser Cys Lys Ala Ser Gly Gly Ser Phe Gly Gly Tyr
            20                  25                  30

Gly Ile Gly Trp Val Arg Gln Ala Pro Gly Gln Gly Leu Glu Trp Met
        35                  40                  45

Gly Gly Ile Thr Pro Phe Phe Gly Phe Ala Asp Tyr Ala Gln Lys Phe
    50                  55                  60

Gln Gly Arg Val Thr Ile Thr Ala Asp Glu Ser Thr Thr Thr Ala Tyr
65                  70                  75                  80

Met Glu Leu Ser Gly Leu Thr Ser Asp Asp Thr Ala Val Tyr Tyr Cys
                85                  90                  95

Ala Arg Asp Pro Asn Glu Phe Trp Gly Gly Tyr Tyr Ser Thr His Asp
            100                 105                 110

Phe Asp Ser Trp Gly Gln Gly Thr Thr Val Thr Val Ser Ser
            115                 120                 125

<210> SEQ ID NO 145
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Glu Val Gln Leu Val Gln Ser Gly Ala Glu Val Lys Lys Pro Gly Glu
1               5                   10                  15

Ser Val Lys Ile Ser Cys Lys Ala Ser Gly Gly Ser Phe Arg Ser Tyr
            20                  25                  30

Gly Ile Ser Trp Val Arg Gln Ala Pro Gly Gln Gly Leu Glu Trp Met
        35                  40                  45

Gly Gly Ile Thr His Phe Phe Gly Ile Thr Asp Tyr Ala Gln Lys Phe
    50                  55                  60

Gln Gly Arg Val Thr Ile Thr Ala Asp Glu Ser Thr Thr Thr Ala Tyr
65                  70                  75                  80

Met Glu Leu Ser Gly Leu Thr Ser Asp Asp Thr Ala Val Tyr Tyr Cys
                85                  90                  95

Ala Arg Glu Pro Asn Asp Phe Trp Gly Gly Tyr Tyr Asp Thr His Asp
            100                 105                 110
```

Phe Asp Ser Trp Gly Gln Gly Thr Thr Val Thr Val Ser Ser
            115                 120                 125

<210> SEQ ID NO 146
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Asp Ile Gln Met Thr Gln Ser Pro Ser Ser Leu Ser Ala Ser Val Gly
1               5                   10                  15

Asp Arg Val Thr Ile Thr Cys Gln Thr Ser Thr Asp Ile Asp Asp Asp
            20                  25                  30

Leu Asn Trp Tyr Gln Gln Lys Pro Gly Lys Ala Pro Lys Leu Leu Ile
        35                  40                  45

Ser Leu Ala Ser Thr Leu Arg Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Arg Leu Pro Leu
                85                  90                  95

Thr Phe Gly Gln Gly Thr Lys Leu Glu Ile Lys Arg
            100                 105

<210> SEQ ID NO 147
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Asp Ile Gln Met Thr Gln Ser Pro Ser Ser Leu Ser Ala Ser Val Gly
1               5                   10                  15

Asp Arg Val Thr Ile Thr Cys Gln Thr Ser Gln Asp Ile Asp Met Asp
            20                  25                  30

Leu Asn Trp Tyr Gln Gln Lys Pro Gly Lys Ala Pro Lys Leu Leu Ile
        35                  40                  45

Ser Gln Gly Ser Thr Leu Trp Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Thr Asp Ser Phe Pro Leu
                85                  90                  95

Thr Phe Gly Gln Gly Thr Lys Leu Glu Ile Lys Arg
            100                 105

<210> SEQ ID NO 148
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Asp Asp
            20                  25                  30

Leu Asn Trp Tyr Gln Gln Lys Pro Gly Lys Ala Pro Lys Leu Leu Ile
        35                  40                  45

Ser Leu Ala Ser Ile Leu Arg Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Ser Phe Pro Leu
                85                  90                  95

Thr Phe Gly Gln Gly Thr Lys Leu Glu Ile Lys Arg
            100                 105
```

<210> SEQ ID NO 149
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Met Asp
            20                  25                  30

Leu Asn Trp Tyr Gln Gln Lys Pro Gly Lys Ala Pro Lys Leu Leu Ile
        35                  40                  45

Ser Gln Ala Asn Thr Leu Pro Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Trp Leu Pro Leu
                85                  90                  95

Thr Phe Gly Gln Gly Thr Lys Leu Glu Ile Lys Arg
            100                 105
```

<210> SEQ ID NO 150
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Thr Asp Ile Asp Asp Asp
            20                  25                  30

Leu Asn Trp Tyr Gln Gln Lys Pro Gly Lys Ala Pro Lys Leu Leu Ile
        35                  40                  45

Ser Leu Gly Ser Thr Leu Arg Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80
```

Glu Asp Phe Ala Thr Tyr Tyr Cys Leu Gln Ser Asp Arg Leu Pro Leu
                85                  90                  95

Thr Phe Gly Gln Gly Thr Lys Leu Glu Ile Lys Arg
            100                 105

<210> SEQ ID NO 151
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Asn Tyr
            20                  25                  30

Leu Thr Trp Tyr Gln Gln Thr Pro Gly Lys Ala Pro Lys Leu Leu Ile
        35                  40                  45

Tyr Asn Ala Lys Thr Leu Ala Asp Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln His Phe Trp Ser Ile Pro Tyr
                85                  90                  95

Thr Phe Gly Gln Gly Thr Lys Leu Glu Ile Lys Arg
            100                 105

<210> SEQ ID NO 152
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Gly Ile Ile Ser Tyr
            20                  25                  30

Ile Asp Trp Phe Gln Gln Lys Pro Gly Lys Ala Pro Lys Arg Leu Ile
        35                  40                  45

Tyr Ala Thr Phe Asp Leu Ala Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Arg Gln Val Gly Ser Tyr Pro Glu
                85                  90                  95

Thr Phe Gly Gln Gly Thr Lys Leu Glu Ile Lys Arg
            100                 105

<210> SEQ ID NO 153
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 153

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Asp Ile Gly Ser Glu
            20                  25                  30

Leu His Trp Tyr Gln Gln Lys Pro Asp Gln Pro Pro Lys Leu Leu Ile
        35                  40                  45

Lys Tyr Ala Ser His Ser Thr Ser Gly Val Pro Ser Arg Phe Ser Gly
    50                  55                  60

Ser Gly Ser Gly Thr Asp Phe Thr Leu Thr Ile Asn Gly Leu Glu Ala
65                  70                  75                  80

Glu Asp Ala Gly Thr Tyr Tyr Cys His Gln Thr Asp Ser Leu Pro Tyr
                85                  90                  95

Thr Phe Gly Pro Gly Thr Lys Val Asp Ile Lys Arg
            100                 105

<210> SEQ ID NO 154
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Asn Ile Gly Ser Glu
            20                  25                  30

Leu His Trp Tyr Gln Gln Lys Pro Asp Gln Ser Pro Lys Leu Leu Ile
        35                  40                  45

Lys Tyr Ala Ser His Ser Ile Ser Gly Val Pro Ser Arg Phe Ser Gly
    50                  55                  60

Ser Gly Ser Gly Thr Asp Phe Thr Leu Thr Ile Asn Gly Leu Glu Ala
65                  70                  75                  80

Glu Asp Ala Ala Thr Tyr Tyr Cys His Gln Ser Asp Thr Leu Pro His
                85                  90                  95

Thr Phe Gly Gln Gly Thr Lys Val Asp Ile Lys Arg
            100                 105

<210> SEQ ID NO 155
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Ile Phe Ser Arg Tyr
            20                  25                  30

Asp Met Ser Trp Val Arg Gln Ala Pro Gly Lys Gly Leu Glu Trp Val
        35                  40                  45

Ala Tyr Ile Ser His Gly Gly Ala Gly Thr Tyr Tyr Pro Asp Ser Val
    50                  55                  60

Lys Gly Arg Phe Thr Ile Ser Arg Asp Asn Ser Lys Asn Thr Leu Phe

```
65                  70                  75                  80
Leu Gln Met Asp Ser Leu Arg Ala Glu Asp Thr Ala Val Tyr Tyr Cys
                85                  90                  95

Ala Arg Gly Gly Val Tyr Lys Gly Tyr Phe Asp Val Trp Gly Gln Gly
            100                 105                 110

Thr Pro Val Thr Val Ser Ser Ala Ser Thr Lys Gly Pro Ser Val Phe
            115                 120                 125

Pro Glu Val Gln Leu Val Gln Ser Gly Ala Glu Val Lys Lys Pro Gly
130                 135                 140

Ser Ser Val Lys Val Ser Cys Lys Ala Ser Gly Tyr Thr Phe Thr Asp
145                 150                 155                 160

Tyr Glu Ile His Trp Val Arg Gln Ala Pro Gly Gln Gly Leu Glu Trp
            165                 170                 175

Met Gly Val Asn Asp Pro Glu Ser Gly Gly Thr Phe Tyr Asn Gln Lys
            180                 185                 190

Phe Asp Gly Arg Val Thr Leu Thr Ala Asp Glu Ser Thr Ser Thr Ala
            195                 200                 205

Tyr Met Glu Leu Ser Ser Leu Arg Ser Glu Asp Thr Ala Val Tyr Tyr
210                 215                 220

Cys Thr Arg Tyr Ser Lys Trp Asp Ser Phe Asp Gly Met Asp Tyr Trp
225                 230                 235                 240

Gly Gln Gly Thr Thr Val Thr Val Ser Ser
            245                 250

<210> SEQ ID NO 156
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Ile Phe Ser Arg Tyr
            20                  25                  30

Asp Met Ser Trp Val Arg Gln Ala Pro Gly Lys Gly Leu Glu Trp Val
        35                  40                  45

Ala Tyr Ile Ser His Gly Gly Ala Gly Thr Tyr Tyr Pro Asp Ser Val
    50                  55                  60

Lys Gly Arg Phe Thr Ile Ser Arg Asp Asn Ser Lys Asn Thr Leu Phe
65                  70                  75                  80

Leu Gln Met Asp Ser Leu Arg Ala Glu Asp Thr Ala Val Tyr Tyr Cys
                85                  90                  95

Ala Arg Gly Gly Val Tyr Lys Gly Tyr Phe Asp Val Trp Gly Gln Gly
            100                 105                 110

Thr Pro Val Thr Val Ser Ser Ala Ser Thr Lys Gly Pro Ser Val Phe
            115                 120                 125

Pro Leu Ala Pro Glu Val Gln Leu Val Gln Ser Gly Ala Glu Val Lys
130                 135                 140

Lys Pro Gly Ser Ser Val Lys Val Ser Cys Lys Ala Ser Gly Tyr Thr
145                 150                 155                 160

Phe Thr Asp Tyr Glu Ile His Trp Val Arg Gln Ala Pro Gly Gln Gly
            165                 170                 175
```

```
Leu Glu Trp Met Gly Val Asn Asp Pro Glu Ser Gly Gly Thr Phe Tyr
            180                 185                 190

Asn Gln Lys Phe Asp Gly Arg Val Thr Leu Thr Ala Asp Glu Ser Thr
        195                 200                 205

Ser Thr Ala Tyr Met Glu Leu Ser Ser Leu Arg Ser Glu Asp Thr Ala
    210                 215                 220

Val Tyr Tyr Cys Thr Arg Tyr Ser Lys Trp Asp Ser Phe Asp Gly Met
225                 230                 235                 240

Asp Tyr Trp Gly Gln Gly Thr Thr Val Thr Val Ser Ser
                245                 250
```

<210> SEQ ID NO 157
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

```
Glu Val Gln Leu Val Glu Ser Gly Gly Val Val Gln Pro Gly Arg
1               5                   10                  15

Ser Leu Arg Leu Ser Cys Ser Ala Ser Gly Phe Ile Phe Ser Arg Tyr
            20                  25                  30

Asp Met Ser Trp Val Arg Gln Ala Pro Gly Lys Gly Leu Glu Trp Val
        35                  40                  45

Ala Tyr Ile Ser His Gly Gly Ala Gly Thr Tyr Tyr Pro Asp Ser Val
    50                  55                  60

Lys Gly Arg Phe Thr Ile Ser Arg Asp Asn Ser Lys Asn Thr Leu Phe
65                  70                  75                  80

Leu Gln Met Asp Ser Leu Arg Ala Glu Asp Thr Ala Val Tyr Tyr Cys
                85                  90                  95

Ala Arg Gly Gly Val Tyr Lys Gly Tyr Phe Asp Val Trp Gly Gln Gly
            100                 105                 110

Thr Pro Val Thr Val Ser Ser Ala Ser Thr Lys Gly Pro Ser Val Phe
        115                 120                 125

Pro Leu Ala Glu Val Gln Leu Val Gln Ser Gly Ala Glu Val Lys Lys
    130                 135                 140

Pro Gly Ser Ser Val Lys Val Ser Cys Lys Ala Ser Gly Tyr Thr Phe
145                 150                 155                 160

Thr Asp Tyr Glu Ile His Trp Val Arg Gln Ala Pro Gly Gln Gly Leu
                165                 170                 175

Glu Trp Met Gly Val Asn Asp Pro Glu Ser Gly Gly Thr Phe Tyr Asn
            180                 185                 190

Gln Lys Phe Asp Gly Arg Val Thr Leu Thr Ala Asp Glu Ser Thr Ser
        195                 200                 205

Thr Ala Tyr Met Glu Leu Ser Ser Leu Arg Ser Glu Asp Thr Ala Val
    210                 215                 220

Tyr Tyr Cys Thr Arg Tyr Ser Lys Trp Asp Ser Phe Asp Gly Met Asp
225                 230                 235                 240

Tyr Trp Gly Gln Gly Thr Thr Val Thr Val Ser Ser
                245                 250
```

<210> SEQ ID NO 158
<211> LENGTH: 246
<212> TYPE: PRT
<213> ORGANISM: Artificial Sequence -continued

```
<220> FEATURE:
<223> OTHER INFORMATION: Description of Artificial Sequence: Synthetic
      polypeptide

<400> SEQUENCE: 158

Glu Val Gln Leu Val Glu Ser Gly Gly Val Val Gln Pro Gly Arg
1               5                   10                  15

Ser Leu Arg Leu Ser Cys Ser Ala Ser Gly Phe Ile Phe Ser Arg Tyr
            20                  25                  30

Asp Met Ser Trp Val Arg Gln Ala Pro Gly Lys Gly Leu Glu Trp Val
        35                  40                  45

Ala Tyr Ile Ser His Gly Gly Ala Gly Thr Tyr Tyr Pro Asp Ser Val
    50                  55                  60

Lys Gly Arg Phe Thr Ile Ser Arg Asp Asn Ser Lys Asn Thr Leu Phe
65                  70                  75                  80

Leu Gln Met Asp Ser Leu Arg Ala Glu Asp Thr Ala Val Tyr Tyr Cys
                85                  90                  95

Ala Arg Gly Gly Val Tyr Lys Gly Tyr Phe Asp Val Trp Gly Gln Gly
            100                 105                 110

Thr Pro Val Thr Val Ser Ser Ala Ser Thr Lys Gly Pro Glu Val Gln
        115                 120                 125

Leu Val Gln Ser Gly Ala Glu Val Lys Lys Pro Gly Ser Ser Val Lys
    130                 135                 140

Val Ser Cys Lys Ala Ser Gly Tyr Thr Phe Thr Asp Tyr Glu Ile His
145                 150                 155                 160

Trp Val Arg Gln Ala Pro Gly Gln Gly Leu Glu Trp Met Gly Val Asn
                165                 170                 175

Asp Pro Glu Ser Gly Gly Thr Phe Tyr Asn Gln Lys Phe Asp Gly Arg
            180                 185                 190

Val Thr Leu Thr Ala Asp Glu Ser Thr Ser Thr Ala Tyr Met Glu Leu
        195                 200                 205

Ser Ser Leu Arg Ser Glu Asp Thr Ala Val Tyr Tyr Cys Thr Arg Tyr
    210                 215                 220

Ser Lys Trp Asp Ser Phe Asp Gly Met Asp Tyr Trp Gly Gln Gly Thr
225                 230                 235                 240

Thr Val Thr Val Ser Ser
                245

<210> SEQ ID NO 159
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Glu Val Gln Leu Val Glu Ser Gly Gly Val Val Gln Pro Gly Arg
1               5                   10                  15

Ser Leu Arg Leu Ser Cys Ser Ala Ser Gly Phe Ile Phe Ser Arg Tyr
            20                  25                  30

Asp Met Ser Trp Val Arg Gln Ala Pro Gly Lys Gly Leu Glu Trp Val
        35                  40                  45

Ala Tyr Ile Ser His Gly Gly Ala Gly Thr Tyr Tyr Pro Asp Ser Val
    50                  55                  60

Lys Gly Arg Phe Thr Ile Ser Arg Asp Asn Ser Lys Asn Thr Leu Phe
65                  70                  75                  80
```

-continued

```
Leu Gln Met Asp Ser Leu Arg Ala Glu Asp Thr Ala Val Tyr Tyr Cys
                 85                  90                  95

Ala Arg Gly Gly Val Tyr Lys Gly Tyr Phe Asp Val Trp Gly Gln Gly
            100                 105                 110

Thr Pro Val Thr Val Ser Ser Ala Ser Thr Lys Gly Pro Ser Glu Val
        115                 120                 125

Gln Leu Val Gln Ser Gly Ala Glu Val Lys Lys Pro Gly Ser Ser Val
    130                 135                 140

Lys Val Ser Cys Lys Ala Ser Gly Tyr Thr Phe Thr Asp Tyr Glu Ile
145                 150                 155                 160

His Trp Val Arg Gln Ala Pro Gly Gln Gly Leu Glu Trp Met Gly Val
                165                 170                 175

Asn Asp Pro Glu Ser Gly Gly Thr Phe Tyr Asn Gln Lys Phe Asp Gly
            180                 185                 190

Arg Val Thr Leu Thr Ala Asp Glu Ser Thr Ser Thr Ala Tyr Met Glu
        195                 200                 205

Leu Ser Ser Leu Arg Ser Glu Asp Thr Ala Val Tyr Tyr Cys Thr Arg
    210                 215                 220

Tyr Ser Lys Trp Asp Ser Phe Asp Gly Met Asp Tyr Trp Gly Gln Gly
225                 230                 235                 240

Thr Thr Val Thr Val Ser Ser
                245
```

<210> SEQ ID NO 160
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

```
Glu Val Gln Leu Val Glu Ser Gly Gly Gly Val Val Gln Pro Gly Arg
1               5                   10                  15

Ser Leu Arg Leu Ser Cys Ser Ala Ser Gly Phe Ile Phe Ser Arg Tyr
            20                  25                  30

Asp Met Ser Trp Val Arg Gln Ala Pro Gly Lys Gly Leu Glu Trp Val
        35                  40                  45

Ala Tyr Ile Ser His Gly Gly Ala Gly Thr Tyr Tyr Pro Asp Ser Val
    50                  55                  60

Lys Gly Arg Phe Thr Ile Ser Arg Asp Asn Ser Lys Asn Thr Leu Phe
65                  70                  75                  80

Leu Gln Met Asp Ser Leu Arg Ala Glu Asp Thr Ala Val Tyr Tyr Cys
                85                  90                  95

Ala Arg Gly Gly Val Tyr Lys Gly Tyr Phe Asp Val Trp Gly Gln Gly
            100                 105                 110

Thr Pro Val Thr Val Ser Ser Ala Ser Thr Lys Gly Pro Ser Val Glu
        115                 120                 125

Val Gln Leu Val Gln Ser Gly Ala Glu Val Lys Lys Pro Gly Ser Ser
    130                 135                 140

Val Lys Val Ser Cys Lys Ala Ser Gly Tyr Thr Phe Thr Asp Tyr Glu
145                 150                 155                 160

Ile His Trp Val Arg Gln Ala Pro Gly Gln Gly Leu Glu Trp Met Gly
                165                 170                 175

Val Asn Asp Pro Glu Ser Gly Gly Thr Phe Tyr Asn Gln Lys Phe Asp
```

```
                    180                 185                 190
Gly Arg Val Thr Leu Thr Ala Asp Glu Ser Thr Ser Thr Ala Tyr Met
                195                 200                 205

Glu Leu Ser Ser Leu Arg Ser Glu Asp Thr Ala Val Tyr Tyr Cys Thr
    210                 215                 220

Arg Tyr Ser Lys Trp Asp Ser Phe Asp Gly Met Asp Tyr Trp Gly Gln
225                 230                 235                 240

Gly Thr Thr Val Thr Val Ser Ser
                245

<210> SEQ ID NO 161
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Ile Phe Ser Arg Tyr
            20                  25                  30

Asp Met Ser Trp Val Arg Gln Ala Pro Gly Lys Gly Leu Glu Trp Val
        35                  40                  45

Ala Tyr Ile Ser His Gly Gly Ala Gly Thr Tyr Tyr Pro Asp Ser Val
    50                  55                  60

Lys Gly Arg Phe Thr Ile Ser Arg Asp Asn Ser Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg Gly Gly Val Thr Lys Gly Tyr Phe Asp Val Trp Gly Gln Gly
            100                 105                 110

Thr Pro Val Thr Val Ser Ser Ala Ser Thr Lys Gly Pro Ser Val Phe
        115                 120                 125

Pro Glu Val Gln Leu Val Gln Ser Gly Ala Glu Val Lys Lys Pro Gly
    130                 135                 140

Ser Ser Val Lys Val Ser Cys Lys Ala Ser Gly Tyr Thr Phe Thr Asp
145                 150                 155                 160

Tyr Glu Ile His Trp Val Arg Gln Ala Pro Gly Gln Gly Leu Glu Trp
                165                 170                 175

Met Gly Val Asn Asp Pro Glu Ser Gly Gly Thr Phe Tyr Asn Gln Lys
            180                 185                 190

Phe Asp Gly Arg Val Thr Leu Thr Ala Asp Glu Ser Thr Ser Thr Ala
        195                 200                 205

Tyr Met Glu Leu Ser Ser Leu Arg Ser Glu Asp Thr Ala Val Tyr Tyr
    210                 215                 220

Cys Thr Arg Tyr Ser Lys Trp Asp Ser Phe Asp Gly Met Asp Tyr Trp
225                 230                 235                 240

Gly Gln Gly Thr Thr Val Thr Val Ser Ser
                245                 250

<210> SEQ ID NO 162
<211> LENGTH: 250
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 162

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Ile Phe Ser Arg Tyr
            20                  25                  30

Asp Met Ser Trp Val Arg Gln Ala Pro Gly Lys Gly Leu Glu Trp Val
        35                  40                  45

Ala Tyr Ile Ser His Gly Gly Ala Gly Thr Tyr Tyr Pro Asp Ser Val
    50                  55                  60

Lys Gly Arg Phe Thr Ile Ser Arg Asp Asn Ser Lys Asn Thr Leu Phe
65                  70                  75                  80

Leu Gln Met Asp Ser Leu Arg Ala Glu Asp Thr Ala Val Tyr Tyr Cys
                85                  90                  95

Ala Arg Gly Gly Val Tyr Lys Gly Tyr Phe Asp Val Trp Gly Gln Gly
            100                 105                 110

Thr Pro Val Thr Val Ser Ser Gly Gly Gly Ser Gly Gly Gly Gly
        115                 120                 125

Ser Glu Val Gln Leu Val Gln Ser Gly Ala Glu Val Lys Lys Pro Gly
    130                 135                 140

Ser Ser Val Lys Val Ser Cys Lys Ala Ser Gly Tyr Thr Phe Thr Asp
145                 150                 155                 160

Tyr Glu Ile His Trp Val Arg Gln Ala Pro Gly Gln Gly Leu Glu Trp
                165                 170                 175

Met Gly Val Asn Asp Pro Glu Ser Gly Gly Thr Phe Tyr Asn Gln Lys
            180                 185                 190

Phe Asp Gly Arg Val Thr Leu Thr Ala Asp Glu Ser Thr Ser Thr Ala
        195                 200                 205

Tyr Met Glu Leu Ser Ser Leu Arg Ser Glu Asp Thr Ala Val Tyr Tyr
    210                 215                 220

Cys Thr Arg Tyr Ser Lys Trp Asp Ser Phe Gly Met Asp Tyr Trp
225                 230                 235                 240

Gly Gln Gly Thr Thr Val Thr Val Ser Ser
                245                 250

<210> SEQ ID NO 163
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Ile Phe Ser Arg Tyr
            20                  25                  30

Asp Met Ser Trp Val Arg Gln Ala Pro Gly Lys Gly Leu Glu Trp Val
        35                  40                  45

Ala Tyr Ile Ser His Gly Gly Ala Gly Thr Tyr Tyr Pro Asp Ser Val
    50                  55                  60

Lys Gly Arg Phe Thr Ile Ser Arg Asp Asn Ser Lys Asn Thr Leu Phe
65                  70                  75                  80

```
Leu Gln Met Asp Ser Leu Arg Pro Glu Asp Thr Gly Val Tyr Phe Cys
                85                  90                  95

Ala Arg Gly Gly Val Thr Lys Gly Tyr Phe Asp Val Trp Gly Gln Gly
            100                 105                 110

Thr Pro Val Thr Val Ser Ser Ala Ser Thr Lys Gly Pro Ser Val Phe
            115                 120                 125

Pro Leu Ala Pro Glu Val Gln Leu Val Gln Ser Gly Ala Glu Val Lys
130                 135                 140

Lys Pro Gly Ser Ser Val Lys Val Ser Cys Lys Ala Ser Gly Tyr Thr
145                 150                 155                 160

Phe Thr Asp Tyr Glu Ile His Trp Val Arg Gln Ala Pro Gly Gln Gly
                165                 170                 175

Leu Glu Trp Met Gly Val Asn Asp Pro Glu Ser Gly Gly Thr Phe Tyr
            180                 185                 190

Asn Gln Lys Phe Asp Gly Arg Val Thr Leu Thr Ala Asp Glu Ser Thr
            195                 200                 205

Ser Thr Ala Tyr Met Glu Leu Ser Ser Leu Arg Ser Glu Asp Thr Ala
        210                 215                 220

Val Tyr Tyr Cys Thr Arg Tyr Ser Lys Trp Asp Ser Phe Asp Gly Met
225                 230                 235                 240

Asp Tyr Trp Gly Gln Gly Thr Thr Val Thr Val Ser Ser
                245                 250

<210> SEQ ID NO 164
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Ile Phe Ser Arg Tyr
            20                  25                  30

Asp Met Ser Trp Val Arg Gln Ala Pro Gly Lys Gly Leu Glu Trp Val
        35                  40                  45

Ala Tyr Ile Ser His Gly Gly Ala Gly Thr Tyr Tyr Pro Asp Ser Val
    50                  55                  60

Lys Gly Arg Phe Thr Ile Ser Arg Asp Asn Ser Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg Gly Gly Val Thr Lys Gly Tyr Phe Asp Val Trp Gly Gln Gly
            100                 105                 110

Thr Pro Val Thr Val Ser Ser Ala Ser Thr Lys Gly Pro Glu Val Gln
        115                 120                 125

Leu Val Gln Ser Gly Ala Glu Val Lys Lys Pro Gly Ser Ser Val Lys
    130                 135                 140

Val Ser Cys Lys Ala Ser Gly Tyr Thr Phe Thr Asp Tyr Glu Ile His
145                 150                 155                 160

Trp Val Arg Gln Ala Pro Gly Gln Gly Leu Glu Trp Met Gly Val Asn
                165                 170                 175

Asp Pro Glu Ser Gly Gly Thr Phe Tyr Asn Gln Lys Phe Asp Gly Arg
            180                 185                 190
```

```
Val Thr Leu Thr Ala Asp Glu Ser Thr Ser Thr Ala Tyr Met Glu Leu
        195                 200                 205

Ser Ser Leu Arg Ser Glu Asp Thr Ala Val Tyr Tyr Cys Thr Arg Tyr
    210                 215                 220

Ser Lys Trp Asp Ser Phe Asp Gly Met Asp Tyr Trp Gly Gln Gly Thr
225                 230                 235                 240

Thr Val Thr Val Ser Ser
                245

<210> SEQ ID NO 165
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Ile Phe Ser Arg Tyr
            20                  25                  30

Asp Met Ser Trp Val Arg Gln Ala Pro Gly Lys Gly Leu Glu Trp Val
        35                  40                  45

Ala Tyr Ile Ser His Gly Gly Ala Gly Thr Tyr Tyr Pro Asp Ser Val
    50                  55                  60

Lys Gly Arg Phe Thr Ile Ser Arg Asp Asn Ser Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg Gly Gly Val Thr Lys Gly Tyr Phe Asp Val Trp Gly Gln Gly
            100                 105                 110

Thr Pro Val Thr Val Ser Ser Ala Ser Thr Lys Gly Pro Ser Val Glu
        115                 120                 125

Val Gln Leu Val Gln Ser Gly Ala Glu Val Lys Lys Pro Gly Ser Ser
    130                 135                 140

Val Lys Val Ser Cys Lys Ala Ser Gly Tyr Thr Phe Thr Asp Tyr Glu
145                 150                 155                 160

Ile His Trp Val Arg Gln Ala Pro Gly Gln Gly Leu Glu Trp Met Gly
                165                 170                 175

Val Asn Asp Pro Glu Ser Gly Gly Thr Phe Tyr Asn Gln Lys Phe Asp
            180                 185                 190

Gly Arg Val Thr Leu Thr Ala Asp Glu Ser Thr Ser Thr Ala Tyr Met
        195                 200                 205

Glu Leu Ser Ser Leu Arg Ser Glu Asp Thr Ala Val Tyr Tyr Cys Thr
    210                 215                 220

Arg Tyr Ser Lys Trp Asp Ser Phe Asp Gly Met Asp Tyr Trp Gly Gln
225                 230                 235                 240

Gly Thr Thr Val Thr Val Ser Ser
                245

<210> SEQ ID NO 166
<211> LENGTH: 251
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 166

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Ile Phe Ser Arg Tyr
            20                  25                  30

Asp Met Ser Trp Val Arg Gln Ala Pro Gly Lys Gly Leu Glu Trp Val
        35                  40                  45

Ala Tyr Ile Ser His Gly Gly Ala Gly Thr Tyr Tyr Pro Asp Ser Val
    50                  55                  60

Lys Gly Arg Phe Thr Ile Ser Arg Asp Asn Ser Lys Asn Thr Leu Phe
65                  70                  75                  80

Leu Gln Met Asp Ser Leu Arg Ala Glu Asp Thr Ala Val Tyr Tyr Cys
                85                  90                  95

Ala Arg Gly Gly Val Tyr Lys Gly Tyr Phe Asp Val Trp Gly Gln Gly
            100                 105                 110

Thr Pro Val Thr Val Ser Ser Ala Ser Thr Lys Gly Pro Ser Val Phe
        115                 120                 125

Pro Leu Glu Val Gln Leu Val Gln Ser Gly Ala Glu Val Lys Lys Pro
    130                 135                 140

Gly Ser Ser Val Lys Val Ser Cys Lys Ala Ser Gly Tyr Thr Phe Thr
145                 150                 155                 160

Asp Tyr Glu Ile His Trp Val Arg Gln Ala Pro Gly Gln Gly Leu Glu
                165                 170                 175

Trp Met Gly Val Asn Asp Pro Glu Ser Gly Gly Thr Phe Tyr Asn Gln
            180                 185                 190

Lys Phe Asp Gly Arg Val Thr Leu Thr Ala Asp Glu Ser Thr Ser Thr
        195                 200                 205

Ala Tyr Met Glu Leu Ser Ser Leu Arg Ser Glu Asp Thr Ala Val Tyr
    210                 215                 220

Tyr Cys Thr Arg Tyr Ser Lys Trp Asp Ser Phe Asp Gly Met Asp Tyr
225                 230                 235                 240

Trp Gly Gln Gly Thr Thr Val Thr Val Ser Ser
                245                 250

<210> SEQ ID NO 167
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Ile Phe Ser Arg Tyr
            20                  25                  30

Asp Met Ser Trp Val Arg Gln Ala Pro Gly Lys Gly Leu Glu Trp Val
        35                  40                  45

Ala Tyr Ile Ser His Gly Gly Ala Gly Thr Tyr Tyr Pro Asp Ser Val
    50                  55                  60

Lys Gly Arg Phe Thr Ile Ser Arg Asp Asn Ser Lys Asn Thr Leu Phe
65                  70                  75                  80

Leu Gln Met Asp Ser Leu Arg Ala Glu Asp Thr Ala Val Tyr Tyr Cys

```
                    85                  90                  95
Ala Arg Gly Gly Val Tyr Lys Gly Tyr Phe Asp Val Trp Gly Gln Gly
                100                 105                 110

Thr Pro Val Thr Val Ser Ser Ala Ser Thr Lys Gly Pro Ser Val Phe
            115                 120                 125

Glu Val Gln Leu Val Gln Ser Gly Ala Glu Val Lys Lys Pro Gly Ser
        130                 135                 140

Ser Val Lys Val Ser Cys Lys Ala Ser Gly Tyr Thr Phe Thr Asp Tyr
145                 150                 155                 160

Glu Ile His Trp Val Arg Gln Ala Pro Gly Gln Gly Leu Glu Trp Met
                165                 170                 175

Gly Val Asn Asp Pro Glu Ser Gly Gly Thr Phe Tyr Asn Gln Lys Phe
                180                 185                 190

Asp Gly Arg Val Thr Leu Thr Ala Asp Glu Ser Thr Ser Thr Ala Tyr
            195                 200                 205

Met Glu Leu Ser Ser Leu Arg Ser Glu Asp Thr Ala Val Tyr Tyr Cys
        210                 215                 220

Thr Arg Tyr Ser Lys Trp Asp Ser Phe Asp Gly Met Asp Tyr Trp Gly
225                 230                 235                 240

Gln Gly Thr Thr Val Thr Val Ser Ser
                245

<210> SEQ ID NO 168
<211> LENGTH: 256
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Ser Gly Asp Thr Tyr Tyr Asn Ser Pro Leu Lys
    50                  55                  60

Ser Arg Leu Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Thr Asn Ile Trp Gly Tyr Asp Leu Tyr Gly Met Asp Tyr Trp
                100                 105                 110

Gly Gln Gly Thr Leu Val Thr Val Ser Ser Ala Ser Thr Lys Gly Pro
            115                 120                 125

Ser Val Phe Pro Leu Ala Pro Glu Val Gln Leu Val Gln Ser Gly Ala
        130                 135                 140

Glu Val Lys Lys Pro Gly Ser Ser Val Lys Val Ser Cys Lys Ala Ser
145                 150                 155                 160

Gly Tyr Thr Phe Thr Asp Tyr Glu Ile His Trp Val Arg Gln Ala Pro
                165                 170                 175

Gly Gln Gly Leu Glu Trp Met Gly Val Asn Asp Pro Glu Ser Gly Gly
                180                 185                 190
```

```
Thr Phe Tyr Asn Gln Lys Phe Asp Gly Arg Val Thr Leu Thr Ala Asp
            195                 200                 205

Glu Ser Thr Ser Thr Ala Tyr Met Glu Leu Ser Ser Leu Arg Ser Glu
    210                 215                 220

Asp Thr Ala Val Tyr Tyr Cys Thr Arg Tyr Ser Lys Trp Asp Ser Phe
225                 230                 235                 240

Asp Gly Met Asp Tyr Trp Gly Gln Gly Thr Thr Val Thr Val Ser Ser
                245                 250                 255

<210> SEQ ID NO 169
<211> LENGTH: 256
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Ser Gly Asp Thr Tyr Tyr Asn Ser Pro Leu Lys
    50                  55                  60

Ser Arg Leu Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Thr Asn Ile Trp Gly Tyr Asp Leu Tyr Gly Met Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Glu Val Gln Leu Val Gln Ser Gly Ala
    130                 135                 140

Glu Val Lys Lys Pro Gly Ser Ser Val Lys Val Ser Cys Lys Ala Ser
145                 150                 155                 160

Gly Tyr Thr Phe Thr Asp Tyr Glu Ile His Trp Val Arg Gln Ala Pro
                165                 170                 175

Gly Gln Gly Leu Glu Trp Met Gly Val Asn Asp Pro Glu Ser Gly Gly
            180                 185                 190

Thr Phe Tyr Asn Gln Lys Phe Asp Gly Arg Val Thr Leu Thr Ala Asp
        195                 200                 205

Glu Ser Thr Ser Thr Ala Tyr Met Glu Leu Ser Ser Leu Arg Ser Glu
    210                 215                 220

Asp Thr Ala Val Tyr Tyr Cys Thr Arg Tyr Ser Lys Trp Asp Ser Phe
225                 230                 235                 240

Asp Gly Met Asp Tyr Trp Gly Gln Gly Thr Thr Val Thr Val Ser Ser
                245                 250                 255

<210> SEQ ID NO 170
<211> LENGTH: 255
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 170

```
Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Arg Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Ser Gly Asp Thr Tyr Tyr Asn Ser Pro Leu Lys
    50                  55                  60

Ser Arg Leu Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Thr Asn Ile Trp Gly Tyr Asp Leu Tyr Gly Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Glu Val Gln Leu Val Gln Ser Gly Ala Glu
    130                 135                 140

Val Lys Lys Pro Gly Ser Ser Val Lys Val Ser Cys Lys Ala Ser Gly
145                 150                 155                 160

Tyr Thr Phe Thr Asp Tyr Glu Ile His Trp Val Arg Gln Ala Pro Gly
                165                 170                 175

Gln Gly Leu Glu Trp Met Gly Val Asn Asp Pro Glu Ser Gly Gly Thr
            180                 185                 190

Phe Tyr Asn Gln Lys Phe Asp Gly Arg Val Thr Leu Thr Ala Asp Glu
        195                 200                 205

Ser Thr Ser Thr Ala Tyr Met Glu Leu Ser Ser Leu Arg Ser Glu Asp
    210                 215                 220

Thr Ala Val Tyr Tyr Cys Thr Arg Tyr Ser Lys Trp Asp Ser Phe Asp
225                 230                 235                 240

Gly Met Asp Tyr Trp Gly Gln Gly Thr Thr Val Thr Val Ser Ser
                245                 250                 255
```

<210> SEQ ID NO 171
<211> LENGTH: 256
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

```
Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Arg Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Ser Gly Asp Thr Tyr Tyr Asn Ser Pro Leu Lys
    50                  55                  60

Ser Arg Leu Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95
```

-continued

Lys Gln Thr Asn Ile Trp Gly Tyr Asp Leu Tyr Gly Met Asp Tyr Trp
                100                 105                 110

Gly Gln Gly Thr Leu Val Thr Val Ser Ser Ala Ser Thr Lys Gly Pro
            115                 120                 125

Ser Val Phe Pro Leu Ala Pro Glu Val Gln Leu Val Gln Ser Gly Ala
        130                 135                 140

Glu Val Lys Lys Pro Gly Ser Ser Val Lys Val Ser Cys Lys Ala Ser
145                 150                 155                 160

Gly Tyr Thr Phe Thr Asp Tyr Glu Ile His Trp Val Arg Gln Ala Pro
                165                 170                 175

Gly Gln Gly Leu Glu Trp Met Gly Val Asn Asp Pro Glu Ser Gly Gly
            180                 185                 190

Thr Phe Tyr Asn Gln Lys Phe Asp Gly Arg Val Thr Leu Thr Ala Asp
        195                 200                 205

Glu Ser Thr Ser Thr Ala Tyr Met Glu Leu Ser Ser Leu Arg Ser Glu
    210                 215                 220

Asp Thr Ala Val Tyr Tyr Cys Thr Arg Tyr Ser Lys Trp Asp Ser Phe
225                 230                 235                 240

Asp Gly Met Asp Tyr Trp Gly Gln Gly Thr Thr Val Thr Val Ser Ser
                245                 250                 255

<210> SEQ ID NO 172
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Ile Phe Ser Arg Tyr
            20                  25                  30

Asp Met Ser Trp Val Arg Gln Ala Pro Gly Lys Gly Leu Glu Trp Val
        35                  40                  45

Ala Tyr Ile Ser His Gly Gly Ala Gly Thr Tyr Tyr Pro Asp Ser Val
    50                  55                  60

Lys Gly Arg Phe Thr Ile Ser Arg Asp Asn Ser Lys Asn Thr Leu Phe
65                  70                  75                  80

Leu Gln Met Asp Ser Leu Arg Ala Glu Asp Thr Ala Val Tyr Tyr Cys
                85                  90                  95

Ala Arg Gly Gly Val Tyr Lys Gly Tyr Phe Asp Val Trp Gly Gln Gly
            100                 105                 110

Thr Pro Val Thr Val Ser Ser Gly Gly Gly Ser Gly Gly Gly Gly
        115                 120                 125

Ser Gly Glu Val Gln Leu Val Gln Ser Gly Ala Glu Val Lys Lys Pro
    130                 135                 140

Gly Ser Ser Val Lys Val Ser Cys Lys Ala Ser Gly Tyr Thr Phe Thr
145                 150                 155                 160

Asp Tyr Glu Ile His Trp Val Arg Gln Ala Pro Gly Gln Gly Leu Glu
                165                 170                 175

Trp Met Gly Val Asn Asp Pro Glu Ser Gly Gly Thr Phe Tyr Asn Gln
            180                 185                 190

Lys Phe Asp Gly Arg Val Thr Leu Thr Ala Asp Glu Ser Thr Ser Thr

```
                195                 200                 205
Ala Tyr Met Glu Leu Ser Ser Leu Arg Ser Glu Asp Thr Ala Val Tyr
            210                 215                 220
Tyr Cys Thr Arg Tyr Ser Lys Trp Asp Ser Phe Asp Gly Met Asp Tyr
225                 230                 235                 240
Trp Gly Gln Gly Thr Thr Val Thr Val Ser Ser
                245                 250
```

<210> SEQ ID NO 173
<211> LENGTH: 254
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 173

```
Glu Val Gln Leu Val Glu Ser Gly Gly Gly Val Val Gln Pro Gly Arg
1               5                   10                  15
Ser Leu Arg Leu Ser Cys Ser Ala Ser Gly Phe Ile Phe Ser Arg Tyr
            20                  25                  30
Asp Met Ser Trp Val Arg Gln Ala Pro Gly Lys Gly Leu Glu Trp Val
        35                  40                  45
Ala Tyr Ile Ser His Gly Gly Ala Gly Thr Tyr Tyr Pro Asp Ser Val
    50                  55                  60
Lys Gly Arg Phe Thr Ile Ser Arg Asp Asn Ser Lys Asn Thr Leu Phe
65                  70                  75                  80
Leu Gln Met Asp Ser Leu Arg Ala Glu Asp Thr Ala Val Tyr Tyr Cys
                85                  90                  95
Ala Arg Gly Gly Val Tyr Lys Gly Tyr Phe Asp Val Trp Gly Gln Gly
            100                 105                 110
Thr Pro Val Thr Val Ser Ser Gly Gly Gly Ser Gly Gly Gly Gly
        115                 120                 125
Ser Gly Gly Gly Gly Glu Val Gln Leu Val Gln Ser Gly Ala Glu Val
    130                 135                 140
Lys Lys Pro Gly Ser Ser Val Lys Val Ser Cys Lys Ala Ser Gly Tyr
145                 150                 155                 160
Thr Phe Thr Asp Tyr Glu Ile His Trp Val Arg Gln Ala Pro Gly Gln
                165                 170                 175
Gly Leu Glu Trp Met Gly Val Asn Asp Pro Glu Ser Gly Gly Thr Phe
            180                 185                 190
Tyr Asn Gln Lys Phe Asp Gly Arg Val Thr Leu Thr Ala Asp Glu Ser
        195                 200                 205
Thr Ser Thr Ala Tyr Met Glu Leu Ser Ser Leu Arg Ser Glu Asp Thr
    210                 215                 220
Ala Val Tyr Tyr Cys Thr Arg Tyr Ser Lys Trp Asp Ser Phe Asp Gly
225                 230                 235                 240
Met Asp Tyr Trp Gly Gln Gly Thr Thr Val Thr Val Ser Ser
                245                 250
```

<210> SEQ ID NO 174
<211> LENGTH: 247
<212> TYPE: PRT
<213> ORGANISM: Artificial Sequence
<220> FEATURE:
<223> OTHER INFORMATION: Description of Artificial Sequence: Synthetic
    polypeptide -continued

<400> SEQUENCE: 174

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Ile Phe Ser Arg Tyr
            20                  25                  30

Asp Met Ser Trp Val Arg Gln Ala Pro Gly Lys Gly Leu Glu Trp Val
        35                  40                  45

Ala Tyr Ile Ser His Gly Gly Ala Gly Thr Tyr Tyr Pro Asp Ser Val
    50                  55                  60

Lys Gly Arg Phe Thr Ile Ser Arg Asp Asn Ser Lys Asn Thr Leu Phe
65                  70                  75                  80

Leu Gln Met Asp Ser Leu Arg Ala Glu Asp Thr Ala Val Tyr Tyr Cys
                85                  90                  95

Ala Arg Gly Gly Val Tyr Lys Gly Tyr Phe Asp Val Trp Gly Gln Gly
            100                 105                 110

Thr Pro Val Thr Val Ser Ser Gly Gly Gly Ser Gly Gly Glu Val
        115                 120                 125

Gln Leu Val Gln Ser Gly Ala Glu Val Lys Lys Pro Gly Ser Ser Val
130                 135                 140

Lys Val Ser Cys Lys Ala Ser Gly Tyr Thr Phe Thr Asp Tyr Glu Ile
145                 150                 155                 160

His Trp Val Arg Gln Ala Pro Gly Gln Gly Leu Glu Trp Met Gly Val
                165                 170                 175

Asn Asp Pro Glu Ser Gly Gly Thr Phe Tyr Asn Gln Lys Phe Asp Gly
            180                 185                 190

Arg Val Thr Leu Thr Ala Asp Glu Ser Thr Ser Thr Ala Tyr Met Glu
        195                 200                 205

Leu Ser Ser Leu Arg Ser Glu Asp Thr Ala Val Tyr Tyr Cys Thr Arg
    210                 215                 220

Tyr Ser Lys Trp Asp Ser Phe Asp Gly Met Asp Tyr Trp Gly Gln Gly
225                 230                 235                 240

Thr Thr Val Thr Val Ser Ser
                245

<210> SEQ ID NO 175
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Ile Phe Ser Arg Tyr
            20                  25                  30

Asp Met Ser Trp Val Arg Gln Ala Pro Gly Lys Gly Leu Glu Trp Val
        35                  40                  45

Ala Tyr Ile Ser His Gly Gly Ala Gly Thr Tyr Tyr Pro Asp Ser Val
    50                  55                  60

Lys Gly Arg Phe Thr Ile Ser Arg Asp Asn Ser Lys Asn Thr Leu Phe
65                  70                  75                  80

Leu Gln Met Asp Ser Leu Arg Ala Glu Asp Thr Ala Val Tyr Tyr Cys
                85                  90                  95

Ala Arg Gly Gly Val Tyr Lys Gly Tyr Phe Asp Val Trp Gly Gln Gly
            100                 105                 110

Thr Pro Val Thr Val Ser Ser Gly Gly Gly Ser Gly Gly Gly Glu
            115                 120                 125

Val Gln Leu Val Gln Ser Gly Ala Glu Val Lys Lys Pro Gly Ser Ser
130                 135                 140

Val Lys Val Ser Cys Lys Ala Ser Gly Tyr Thr Phe Thr Asp Tyr Glu
145                 150                 155                 160

Ile His Trp Val Arg Gln Ala Pro Gly Gln Gly Leu Glu Trp Met Gly
                165                 170                 175

Val Asn Asp Pro Glu Ser Gly Gly Thr Phe Tyr Asn Gln Lys Phe Asp
            180                 185                 190

Gly Arg Val Thr Leu Thr Ala Asp Glu Ser Thr Ser Thr Ala Tyr Met
            195                 200                 205

Glu Leu Ser Ser Leu Arg Ser Glu Asp Thr Ala Val Tyr Tyr Cys Thr
            210                 215                 220

Arg Tyr Ser Lys Trp Asp Ser Phe Asp Gly Met Asp Tyr Trp Gly Gln
225                 230                 235                 240

Gly Thr Thr Val Thr Val Ser Ser
                245

<210> SEQ ID NO 176
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Ile Phe Ser Arg Tyr
            20                  25                  30

Asp Met Ser Trp Val Arg Gln Ala Pro Gly Lys Gly Leu Glu Trp Val
        35                  40                  45

Ala Tyr Ile Ser His Gly Gly Ala Gly Thr Tyr Tyr Pro Asp Ser Val
    50                  55                  60

Lys Gly Arg Phe Thr Ile Ser Arg Asp Asn Ser Lys Asn Thr Leu Phe
65                  70                  75                  80

Leu Gln Met Asp Ser Leu Arg Ala Glu Asp Thr Ala Val Tyr Tyr Cys
                85                  90                  95

Ala Arg Gly Gly Val Tyr Lys Gly Tyr Phe Asp Val Trp Gly Gln Gly
            100                 105                 110

Thr Pro Val Thr Val Ser Ser Gly Gly Gly Ser Gly Gly Gly Gly
            115                 120                 125

Glu Val Gln Leu Val Gln Ser Gly Ala Glu Val Lys Lys Pro Gly Ser
            130                 135                 140

Ser Val Lys Val Ser Cys Lys Ala Ser Gly Tyr Thr Phe Thr Asp Tyr
145                 150                 155                 160

Glu Ile His Trp Val Arg Gln Ala Pro Gly Gln Gly Leu Glu Trp Met
                165                 170                 175

Gly Val Asn Asp Pro Glu Ser Gly Gly Thr Phe Tyr Asn Gln Lys Phe
            180                 185                 190

Asp Gly Arg Val Thr Leu Thr Ala Asp Glu Ser Thr Ser Thr Ala Tyr
            195                 200                 205

```
Met Glu Leu Ser Ser Leu Arg Ser Glu Asp Thr Ala Val Tyr Tyr Cys
    210                 215                 220

Thr Arg Tyr Ser Lys Trp Asp Ser Phe Asp Gly Met Asp Tyr Trp Gly
225                 230                 235                 240

Gln Gly Thr Thr Val Thr Val Ser Ser
                245

<210> SEQ ID NO 177
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Asn Tyr
            20                  25                  30

Leu Thr Trp Tyr Gln Gln Thr Pro Gly Lys Ala Pro Lys Leu Leu Ile
        35                  40                  45

Tyr Asn Ala Lys Thr Leu Ala Asp Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln His Phe Trp Ser Ile Pro Tyr
                85                  90                  95

Thr Phe Gly Gln Gly Thr Lys Leu Glu Ile Lys Arg Gly Gly Ser Gly
            100                 105                 110

Gly Gly Gly Ser Gly Gly Gly Asp Ile Gln Met Thr Gln Ser Pro
        115                 120                 125

Ser Ser Leu Ser Ala Ser Val Gly Asp Arg Val Thr Ile Thr Cys Arg
    130                 135                 140

Ala Ser Gly Ile Ile Ser Tyr Ile Asp Trp Phe Gln Gln Lys Pro
145                 150                 155                 160

Gly Lys Ala Pro Lys Arg Leu Ile Tyr Ala Thr Phe Asp Leu Ala Ser
            165                 170                 175

Gly Val Pro Ser Arg Phe Ser Gly Ser Gly Ser Gly Thr Asp Tyr Thr
        180                 185                 190

Leu Thr Ile Ser Ser Leu Gln Pro Glu Asp Phe Ala Thr Tyr Tyr Cys
    195                 200                 205

Arg Gln Val Gly Ser Tyr Pro Glu Thr Phe Gly Gln Gly Thr Lys Leu
    210                 215                 220

Glu Ile Lys Arg
225

<210> SEQ ID NO 178
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Asp Ile Gln Met Thr Gln Ser Pro Ser Ser Leu Ser Ala Ser Val Gly
1               5                   10                  15
```

Asp Arg Val Thr Ile Thr Cys Arg Ala Ser Gly Asn Ile His Asn Tyr
            20                  25                  30

Leu Thr Trp Tyr Gln Gln Thr Pro Gly Lys Ala Pro Lys Leu Leu Ile
        35                  40                  45

Tyr Asn Ala Lys Thr Leu Ala Asp Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln His Phe Trp Ser Ile Pro Tyr
                85                  90                  95

Thr Phe Gly Gln Gly Thr Lys Leu Glu Ile Lys Arg Gly Gly Ser Gly
            100                 105                 110

Gly Gly Gly Ser Gly Gly Gly Ser Asp Ile Gln Met Thr Gln Ser
            115                 120                 125

Pro Ser Ser Leu Ser Ala Ser Val Gly Asp Arg Val Thr Ile Thr Cys
130                 135                 140

Arg Ala Ser Ser Gly Ile Ile Ser Tyr Ile Asp Trp Phe Gln Gln Lys
145                 150                 155                 160

Pro Gly Lys Ala Pro Lys Arg Leu Ile Tyr Ala Thr Phe Asp Leu Ala
                165                 170                 175

Ser Gly Val Pro Ser Arg Phe Ser Gly Ser Gly Ser Gly Thr Asp Tyr
            180                 185                 190

Thr Leu Thr Ile Ser Ser Leu Gln Pro Glu Asp Phe Ala Thr Tyr Tyr
        195                 200                 205

Cys Arg Gln Val Gly Ser Tyr Pro Glu Thr Phe Gly Gly Gly Thr Lys
    210                 215                 220

Leu Glu Ile Lys Arg
225

<210> SEQ ID NO 179
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Asn Tyr
            20                  25                  30

Leu Thr Trp Tyr Gln Gln Thr Pro Gly Lys Ala Pro Lys Leu Leu Ile
        35                  40                  45

Tyr Asn Ala Lys Thr Leu Ala Asp Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln His Phe Trp Ser Ile Pro Tyr
                85                  90                  95

Thr Phe Gly Gln Gly Thr Lys Leu Glu Ile Lys Arg Gly Gly Ser Gly
            100                 105                 110

Gly Gly Gly Ser Gly Asp Ile Gln Met Thr Gln Ser Pro Ser Ser Leu
            115                 120                 125

Ser Ala Ser Val Gly Asp Arg Val Thr Ile Thr Cys Arg Ala Ser Ser

```
Gly Ile Ile Ser Tyr Ile Asp Trp Phe Gln Gln Lys Pro Gly Lys Ala
145                 150                 155                 160

Pro Lys Arg Leu Ile Tyr Ala Thr Phe Asp Leu Ala Ser Gly Val Pro
                165                 170                 175

Ser Arg Phe Ser Gly Ser Gly Ser Gly Thr Asp Tyr Thr Leu Thr Ile
            180                 185                 190

Ser Ser Leu Gln Pro Glu Asp Phe Ala Thr Tyr Tyr Cys Arg Gln Val
        195                 200                 205

Gly Ser Tyr Pro Glu Thr Phe Gly Gln Gly Thr Lys Leu Glu Ile Lys
    210                 215                 220

Arg
225

<210> SEQ ID NO 180
<211> LENGTH: 226
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Asn Tyr
            20                  25                  30

Leu Thr Trp Tyr Gln Gln Thr Pro Gly Lys Ala Pro Lys Leu Leu Ile
        35                  40                  45

Tyr Asn Ala Lys Thr Leu Ala Asp Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln His Phe Trp Ser Ile Pro Tyr
                85                  90                  95

Thr Phe Gly Gln Gly Thr Lys Leu Glu Ile Lys Arg Gly Gly Ser Gly
            100                 105                 110

Gly Gly Gly Ser Gly Gly Asp Ile Gln Met Thr Gln Ser Pro Ser Ser
        115                 120                 125

Leu Ser Ala Ser Val Gly Asp Arg Val Thr Ile Thr Cys Arg Ala Ser
    130                 135                 140

Ser Gly Ile Ile Ser Tyr Ile Asp Trp Phe Gln Gln Lys Pro Gly Lys
145                 150                 155                 160

Ala Pro Lys Arg Leu Ile Tyr Ala Thr Phe Asp Leu Ala Ser Gly Val
                165                 170                 175

Pro Ser Arg Phe Ser Gly Ser Gly Ser Gly Thr Asp Tyr Thr Leu Thr
            180                 185                 190

Ile Ser Ser Leu Gln Pro Glu Asp Phe Ala Thr Tyr Tyr Cys Arg Gln
        195                 200                 205

Val Gly Ser Tyr Pro Glu Thr Phe Gly Gln Gly Thr Lys Leu Glu Ile
    210                 215                 220

Lys Arg
225

<210> SEQ ID NO 181
<211> LENGTH: 227
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Asn Tyr
            20                  25                  30

Leu Thr Trp Tyr Gln Gln Thr Pro Gly Lys Ala Pro Lys Leu Leu Ile
        35                  40                  45

Tyr Asn Ala Lys Thr Leu Ala Asp Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln His Phe Trp Ser Ile Pro Tyr
                85                  90                  95

Thr Phe Gly Gln Gly Thr Lys Leu Glu Ile Lys Arg Gly Gly Ser Gly
            100                 105                 110

Gly Gly Gly Ser Gly Gly Asp Ile Gln Met Thr Gln Ser Pro Ser
        115                 120                 125

Ser Leu Ser Ala Ser Val Gly Asp Arg Val Thr Ile Thr Cys Arg Ala
130                 135                 140

Ser Ser Gly Ile Ile Ser Tyr Ile Asp Trp Phe Gln Gln Lys Pro Gly
145                 150                 155                 160

Lys Ala Pro Lys Arg Leu Ile Tyr Ala Thr Phe Asp Leu Ala Ser Gly
                165                 170                 175

Val Pro Ser Arg Phe Ser Gly Ser Gly Ser Gly Thr Asp Tyr Thr Leu
            180                 185                 190

Thr Ile Ser Ser Leu Gln Pro Glu Asp Phe Ala Thr Tyr Tyr Cys Arg
        195                 200                 205

Gln Val Gly Ser Tyr Pro Glu Thr Phe Gly Gln Gly Thr Lys Leu Glu
    210                 215                 220

Ile Lys Arg
225

<210> SEQ ID NO 182
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Asn Tyr
            20                  25                  30

Leu Thr Trp Tyr Gln Gln Thr Pro Gly Lys Ala Pro Lys Leu Leu Ile
        35                  40                  45

Tyr Asn Ala Lys Thr Leu Ala Asp Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80
```

Glu Asp Ile Ala Thr Tyr Tyr Cys Gln His Phe Trp Ser Ile Pro Tyr
                85                  90                  95

Thr Phe Gly Gln Gly Thr Lys Leu Glu Ile Lys Arg Thr Val Ala Ala
            100                 105                 110

Pro Ser Val Asp Ile Gln Met Thr Gln Ser Pro Ser Ser Leu Ser Ala
            115                 120                 125

Ser Val Gly Asp Arg Val Thr Ile Thr Cys Arg Ala Ser Ser Gly Ile
130                 135                 140

Ile Ser Tyr Ile Asp Trp Phe Gln Gln Lys Pro Gly Lys Ala Pro Lys
145                 150                 155                 160

Arg Leu Ile Tyr Ala Thr Phe Asp Leu Ala Ser Gly Val Pro Ser Arg
                165                 170                 175

Phe Ser Gly Ser Gly Ser Gly Thr Asp Tyr Thr Leu Thr Ile Ser Ser
            180                 185                 190

Leu Gln Pro Glu Asp Phe Ala Thr Tyr Tyr Cys Arg Gln Val Gly Ser
            195                 200                 205

Tyr Pro Glu Thr Phe Gly Gln Gly Thr Lys Leu Glu Ile Lys Arg
210                 215                 220

<210> SEQ ID NO 183
<211> LENGTH: 224
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Asn Tyr
            20                  25                  30

Leu Thr Trp Tyr Gln Gln Thr Pro Gly Lys Ala Pro Lys Leu Leu Ile
        35                  40                  45

Tyr Asn Ala Lys Thr Leu Ala Asp Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln His Phe Trp Ser Ile Pro Tyr
                85                  90                  95

Thr Phe Gly Gln Gly Thr Lys Leu Glu Ile Lys Arg Gly Gly Ser Gly
            100                 105                 110

Gly Gly Gly Ser Asp Ile Gln Met Thr Gln Ser Pro Ser Ser Leu Ser
            115                 120                 125

Ala Ser Val Gly Asp Arg Val Thr Ile Thr Cys Arg Ala Ser Ser Gly
130                 135                 140

Ile Ile Ser Tyr Ile Asp Trp Phe Gln Gln Lys Pro Gly Lys Ala Pro
145                 150                 155                 160

Lys Arg Leu Ile Tyr Ala Thr Phe Asp Leu Ala Ser Gly Val Pro Ser
                165                 170                 175

Arg Phe Ser Gly Ser Gly Ser Gly Thr Asp Tyr Thr Leu Thr Ile Ser
            180                 185                 190

Ser Leu Gln Pro Glu Asp Phe Ala Thr Tyr Tyr Cys Arg Gln Val Gly
        195                 200                 205

Ser Tyr Pro Glu Thr Phe Gly Gln Gly Thr Lys Leu Glu Ile Lys Arg
    210                 215                 220

<210> SEQ ID NO 184
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Asn Tyr
            20                  25                  30

Leu Thr Trp Tyr Gln Gln Thr Pro Gly Lys Ala Pro Lys Leu Leu Ile
        35                  40                  45

Tyr Asn Ala Lys Thr Leu Ala Asp Gly Val Pro Ser Arg Phe Ser Gly
50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln His Phe Trp Ser Ile Pro Tyr
                85                  90                  95

Thr Phe Gly Gln Gly Thr Lys Leu Glu Ile Lys Arg Gly Gly Ser Gly
            100                 105                 110

Gly Gly Asp Ile Gln Met Thr Gln Ser Pro Ser Ser Leu Ser Ala Ser
        115                 120                 125

Val Gly Asp Arg Val Thr Ile Thr Cys Arg Ala Ser Ser Gly Ile Ile
130                 135                 140

Ser Tyr Ile Asp Trp Phe Gln Gln Lys Pro Gly Lys Ala Pro Lys Arg
145                 150                 155                 160

Leu Ile Tyr Ala Thr Phe Asp Leu Ala Ser Gly Val Pro Ser Arg Phe
                165                 170                 175

Ser Gly Ser Gly Ser Gly Thr Asp Tyr Thr Leu Thr Ile Ser Ser Leu
            180                 185                 190

Gln Pro Glu Asp Phe Ala Thr Tyr Tyr Cys Arg Gln Val Gly Ser Tyr
        195                 200                 205

Pro Glu Thr Phe Gly Gln Gly Thr Lys Leu Glu Ile Lys Arg
    210                 215                 220
```

<210> SEQ ID NO 185
<211> LENGTH: 224
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Met Asp
            20                  25                  30

Leu Asn Trp Tyr Gln Gln Lys Pro Gly Lys Ala Pro Lys Leu Leu Ile
        35                  40                  45

Ser Gln Ala Asn Thr Leu Pro Pro Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80
```

```
Glu Asp Phe Ala Thr Tyr Tyr Cys Leu Gln Ser Asp Trp Leu Pro Leu
                85                  90                  95

Thr Phe Gly Gln Gly Thr Lys Leu Glu Ile Lys Arg Thr Val Ala Ala
            100                 105                 110

Pro Ser Val Phe Asp Ile Gln Met Thr Gln Ser Pro Ser Ser Leu Ser
            115                 120                 125

Ala Ser Val Gly Asp Arg Val Thr Ile Thr Cys Arg Ala Ser Ser Gly
    130                 135                 140

Ile Ile Ser Tyr Ile Asp Trp Phe Gln Gln Lys Pro Gly Lys Ala Pro
145                 150                 155                 160

Lys Arg Leu Ile Tyr Ala Thr Phe Asp Leu Ala Ser Gly Val Pro Ser
                165                 170                 175

Arg Phe Ser Gly Ser Gly Ser Gly Thr Asp Tyr Thr Leu Thr Ile Ser
            180                 185                 190

Ser Leu Gln Pro Glu Asp Phe Ala Thr Tyr Tyr Cys Arg Gln Val Gly
            195                 200                 205

Ser Tyr Pro Glu Thr Phe Gly Gln Gly Thr Lys Leu Glu Ile Lys Arg
    210                 215                 220

<210> SEQ ID NO 186
<211> LENGTH: 221
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Asn Tyr
            20                  25                  30

Leu Thr Trp Tyr Gln Gln Thr Pro Gly Lys Ala Pro Lys Leu Leu Ile
        35                  40                  45

Tyr Asn Ala Lys Thr Leu Ala Asp Gly Val Pro Ser Arg Phe Ser Gly
50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln His Phe Trp Ser Ile Pro Tyr
                85                  90                  95

Thr Phe Gly Gln Gly Thr Lys Leu Glu Ile Lys Arg Gly Gly Ser Gly
            100                 105                 110

Gly Asp Ile Gln Met Thr Gln Ser Pro Ser Ser Leu Ser Ala Ser Val
            115                 120                 125

Gly Asp Arg Val Thr Ile Thr Cys Arg Ala Ser Ser Gly Ile Ile Ser
    130                 135                 140

Tyr Ile Asp Trp Phe Gln Gln Lys Pro Gly Lys Ala Pro Lys Arg Leu
145                 150                 155                 160

Ile Tyr Ala Thr Phe Asp Leu Ala Ser Gly Val Pro Ser Arg Phe Ser
                165                 170                 175

Gly Ser Gly Ser Gly Thr Asp Tyr Thr Leu Thr Ile Ser Ser Leu Gln
            180                 185                 190

Pro Glu Asp Phe Ala Thr Tyr Tyr Cys Arg Gln Val Gly Ser Tyr Pro
            195                 200                 205

Glu Thr Phe Gly Gln Gly Thr Lys Leu Glu Ile Lys Arg
```

<210> SEQ ID NO 187
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Met Asp
            20                  25                  30

Leu Asn Trp Tyr Gln Gln Lys Pro Gly Lys Ala Pro Lys Leu Leu Ile
        35                  40                  45

Ser Gln Ala Asn Thr Leu Pro Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Trp Leu Pro Leu
                85                  90                  95

Thr Phe Gly Gln Gly Thr Lys Leu Glu Ile Lys Arg Gly Gly Ser Gly
            100                 105                 110

Gly Gly Gly Asp Ile Gln Met Thr Gln Ser Pro Ser Ser Leu Ser Ala
        115                 120                 125

Ser Val Gly Asp Arg Val Thr Ile Thr Cys Arg Ala Ser Ser Gly Ile
    130                 135                 140

Ile Ser Tyr Ile Asp Trp Phe Gln Gln Lys Pro Gly Lys Ala Pro Lys
145                 150                 155                 160

Arg Leu Ile Tyr Ala Thr Phe Asp Leu Ala Ser Gly Val Pro Ser Arg
                165                 170                 175

Phe Ser Gly Ser Gly Ser Gly Thr Asp Tyr Thr Leu Thr Ile Ser Ser
            180                 185                 190

Leu Gln Pro Glu Asp Phe Ala Thr Tyr Tyr Cys Arg Gln Val Gly Ser
        195                 200                 205

Tyr Pro Glu Thr Phe Gly Gln Gly Thr Lys Leu Glu Ile Lys Arg
    210                 215                 220

<210> SEQ ID NO 188
<211> LENGTH: 226
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Met Asp
            20                  25                  30

Met Asn Trp Tyr Gln Gln Lys Pro Gly Lys Ala Pro Lys Leu Leu Ile
        35                  40                  45

Ser Gln Ala Asn Thr Leu Pro Pro Gly Val His Ser Arg Phe Ser Gly
    50                  55                  60

Ser Gly Ser Gly Thr Asp Phe Thr Phe Thr Ile Ser Ser Leu Gln Pro

```
                65                  70                  75                  80
        Glu Asp Phe Ala Thr Tyr Tyr Cys Leu Gln Ser Asp Trp Leu Pro Leu
                            85                  90                  95

Thr Phe Gly Gln Gly Thr Lys Leu Glu Ile Lys Arg Gly Gly Ser Gly
                        100                 105                 110

Gly Gly Gly Ser Gly Gly Asp Ile Gln Met Thr Gln Ser Pro Ser Ser
                    115                 120                 125

Leu Ser Ala Ser Val Gly Asp Arg Val Thr Ile Thr Cys Arg Ala Ser
                130                 135                 140

Ser Gly Ile Ile Ser Tyr Ile Asp Trp Phe Gln Gln Lys Pro Gly Lys
        145                 150                 155                 160

Ala Pro Lys Arg Leu Ile Tyr Ala Thr Phe Asp Leu Ala Ser Gly Val
                        165                 170                 175

Pro Ser Arg Phe Ser Gly Ser Gly Ser Gly Thr Asp Tyr Thr Leu Thr
                    180                 185                 190

Ile Ser Ser Leu Gln Pro Glu Asp Phe Ala Thr Tyr Tyr Cys Arg Gln
                195                 200                 205

Val Gly Ser Tyr Pro Glu Thr Phe Gly Gln Gly Thr Lys Leu Glu Ile
            210                 215                 220

Lys Arg
        225

<210> SEQ ID NO 189
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Asp Ile Gln Met Thr Gln Ser Pro Ser Ser Leu Ser Ala Ser Val Gly
        1               5                   10                  15

Asp Arg Val Thr Ile Thr Cys Arg Ala Ser Gly Asn Ile His Asn Tyr
                    20                  25                  30

Leu Thr Trp Tyr Gln Gln Thr Pro Gly Lys Ala Pro Lys Leu Leu Ile
                35                  40                  45

Tyr Asn Ala Lys Thr Leu Ala Asp Gly Val Pro Ser Arg Phe Ser Gly
            50                  55                  60

Ser Gly Ser Gly Thr Asp Tyr Thr Phe Thr Ile Ser Ser Leu Gln Pro
        65                  70                  75                  80

Glu Asp Ile Ala Thr Tyr Tyr Cys Gln His Phe Trp Ser Ile Pro Tyr
                        85                  90                  95

Thr Phe Gly Gln Gly Thr Lys Leu Glu Ile Lys Arg Thr Val Ala Ala
                    100                 105                 110

Pro Ser Val Phe Ile Phe Pro Pro Asp Ile Gln Met Thr Gln Ser Pro
                115                 120                 125

Ser Ser Leu Ser Ala Ser Val Gly Asp Arg Val Thr Ile Thr Cys Arg
            130                 135                 140

Ala Ser Gly Ile Ile Ser Tyr Ile Asp Trp Phe Gln Gln Lys Pro Gly
        145                 150                 155                 160

Lys Ala Pro Lys Arg Leu Ile Tyr Ala Thr Phe Asp Leu Ala Ser Gly
                        165                 170                 175

Val Pro Ser Arg Phe Ser Gly Ser Gly Ser Gly Thr Asp Tyr Thr
                    180                 185                 190
```

```
Leu Thr Ile Ser Ser Leu Gln Pro Glu Asp Phe Ala Thr Tyr Tyr Cys
            195                 200                 205

Arg Gln Val Gly Ser Tyr Pro Glu Thr Phe Gly Gln Gly Thr Lys Leu
        210                 215                 220

Glu Ile Lys Arg
225

<210> SEQ ID NO 190
<211> LENGTH: 221
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Asn Tyr
            20                  25                  30

Leu Thr Trp Tyr Gln Gln Thr Pro Gly Lys Ala Pro Lys Leu Leu Ile
        35                  40                  45

Tyr Asn Ala Lys Thr Leu Ala Asp Gly Val Pro Ser Arg Phe Ser Gly
50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln His Phe Trp Ser Ile Pro Tyr
                85                  90                  95

Thr Phe Gly Gln Gly Thr Lys Leu Glu Ile Lys Arg Thr Val Ala Ala
            100                 105                 110

Pro Asp Ile Gln Met Thr Gln Ser Pro Ser Ser Leu Ser Ala Ser Val
        115                 120                 125

Gly Asp Arg Val Thr Ile Thr Cys Arg Ala Ser Ser Gly Ile Ile Ser
    130                 135                 140

Tyr Ile Asp Trp Phe Gln Gln Lys Pro Gly Lys Ala Pro Lys Arg Leu
145                 150                 155                 160

Ile Tyr Ala Thr Phe Asp Leu Ala Ser Gly Val Pro Ser Arg Phe Ser
                165                 170                 175

Gly Ser Gly Ser Gly Thr Asp Tyr Thr Leu Thr Ile Ser Ser Leu Gln
            180                 185                 190

Pro Glu Asp Phe Ala Thr Tyr Tyr Cys Arg Gln Val Gly Ser Tyr Pro
        195                 200                 205

Glu Thr Phe Gly Gln Gly Thr Lys Leu Glu Ile Lys Arg
    210                 215                 220

<210> SEQ ID NO 191
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Asn Tyr
            20                  25                  30
```

Leu Thr Trp Tyr Gln Gln Pro Gly Lys Ala Pro Lys Leu Leu Ile
            35                  40                  45

Tyr Asn Ala Lys Thr Leu Ala Asp Gly Val Pro Ser Arg Phe Ser Gly
 50                  55                  60

Ser Gly Ser Gly Thr Asp Tyr Thr Phe Thr Ile Ser Ser Leu Gln Pro
 65                  70                  75                  80

Glu Asp Ile Ala Thr Tyr Tyr Cys Gln His Phe Trp Ser Ile Pro Tyr
                85                  90                  95

Thr Phe Gly Gln Gly Thr Lys Leu Glu Ile Lys Arg Thr Val Ala Ala
            100                 105                 110

Pro Ser Asp Ile Gln Met Thr Gln Ser Pro Ser Ser Leu Ser Ala Ser
            115                 120                 125

Val Gly Asp Arg Val Thr Ile Thr Cys Arg Ala Ser Ser Gly Ile Ile
130                 135                 140

Ser Tyr Ile Asp Trp Phe Gln Gln Lys Pro Gly Lys Ala Pro Lys Arg
145                 150                 155                 160

Leu Ile Tyr Ala Thr Phe Asp Leu Ala Ser Gly Val Pro Ser Arg Phe
                165                 170                 175

Ser Gly Ser Gly Ser Gly Thr Asp Tyr Thr Leu Thr Ile Ser Ser Leu
            180                 185                 190

Gln Pro Glu Asp Phe Ala Thr Tyr Tyr Cys Arg Gln Val Gly Ser Tyr
            195                 200                 205

Pro Glu Thr Phe Gly Gln Gly Thr Lys Leu Glu Ile Lys Arg
            210                 215                 220

<210> SEQ ID NO 192
<211> LENGTH: 508
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Asn Tyr
                20                  25                  30

Gly Ile Ile Trp Val Arg Gln Ala Pro Gly Gln Gly Leu Glu Trp Met
            35                  40                  45

Gly Trp Ile Asn Thr Tyr Thr Gly Lys Pro Thr Tyr Ala Gln Lys Phe
 50                  55                  60

Gln Gly Arg Val Thr Met Thr Thr Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Lys Leu Phe Thr Thr Met Asp Val Thr Asp Asn Ala Met Asp
            100                 105                 110

Tyr Trp Gly Gln Gly Thr Thr Val Thr Val Ser Ser Ala Ser Thr Lys
            115                 120                 125

Gly Pro Glu Val Gln Leu Val Glu Ser Gly Gly Gly Leu Val Gln Pro
130                 135                 140

Gly Arg Ser Leu Arg Leu Ser Cys Ala Ala Ser Gly Phe Thr Phe Asp
145                 150                 155                 160

Asp Tyr Ala Leu His Trp Val Arg Gln Ala Pro Gly Lys Gly Leu Glu
                165                 170                 175

```
Trp Val Ser Gly Ile Ser Trp His Gly Asp Phe Ile Asp Tyr Ala Asp
            180                 185                 190

Ser Val Lys Gly Arg Phe Thr Ile Ser Arg Asp Asn Ala Lys Asn Ser
        195                 200                 205

Leu Tyr Leu Gln Met Asn Ser Leu Arg Val Glu Asp Thr Ala Leu Tyr
    210                 215                 220

Tyr Cys Ala Gly Asn Asn Arg Gly Tyr Gly Gly Leu Asp Val Trp Gly
225                 230                 235                 240

Gln Gly Thr Thr Val Thr Val Ser Ser Gly Gly Gly Ser Gly Gly
                245                 250                 255

Gly Gly Ser Gly Gly Gly Gly Ser Gly Gly Gly Gly Ser Gly Gly Gly
            260                 265                 270

Gly Ser Gly Gly Gly Gly Ser Gly Gly Gly Gly Ser Asp Ile Gln Met
        275                 280                 285

Thr Gln Ser Pro Ser Ser Leu Ser Ala Ser Val Gly Asp Arg Val Thr
    290                 295                 300

Ile Thr Cys Arg Ala Ser Gln Asp Ile Ser Gln Tyr Leu Asn Trp Tyr
305                 310                 315                 320

Gln Gln Lys Pro Gly Lys Ala Pro Lys Leu Leu Ile Tyr Tyr Thr Ser
                325                 330                 335

Arg Leu Gln Ser Gly Val Pro Ser Arg Phe Ser Gly Ser Gly Ser Gly
            340                 345                 350

Thr Asp Phe Thr Leu Thr Ile Ser Ser Leu Gln Pro Glu Asp Phe Ala
        355                 360                 365

Thr Tyr Phe Cys Gln Gln Gly Asn Thr Trp Pro Thr Phe Gly Gln
    370                 375                 380

Gly Thr Lys Leu Glu Ile Lys Arg Thr Val Ala Ala Pro Gln Ser Val
385                 390                 395                 400

Leu Thr Gln Pro Pro Ser Ala Ser Gly Thr Pro Gly Gln Arg Val Thr
                405                 410                 415

Ile Ser Cys Ser Gly Ser Ser Asn Ile Gly Ser Asn Thr Val Asn
            420                 425                 430

Trp Tyr Gln Gln Leu Pro Gly Thr Ala Pro Lys Leu Leu Ile Tyr Ser
        435                 440                 445

Asn Asn Gln Arg Pro Ser Gly Val Pro Asp Arg Phe Ser Gly Ser Lys
    450                 455                 460

Ser Gly Thr Ser Ala Ser Leu Ala Ile Ser Gly Leu Gln Ser Glu Asp
465                 470                 475                 480

Glu Ala Asp Tyr Tyr Cys Ala Ala Trp Asp Asp Ser Leu Asn Gly Ser
                485                 490                 495

Tyr Val Phe Gly Gly Gly Thr Lys Leu Thr Val Leu
            500                 505

<210> SEQ ID NO 193
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
```

```
                    20                  25                  30
Ala Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Tyr Tyr Tyr Tyr Gly Met Asp Val Trp Gly Gln Gly
                    100                 105                 110

Thr Thr Val Thr Val Ser Ser
            115

<210> SEQ ID NO 194
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Thr Phe Asp Asp Tyr
            20                  25                  30

Ala Leu His Trp Val Arg Gln Ala Pro Gly Lys Gly Leu Glu Trp Val
        35                  40                  45

Ser Gly Ile Ser Trp His Gly Asp Phe Ile Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Gly Leu Arg Val Glu Asp Met Ala Ile Tyr Tyr Cys
                85                  90                  95

Ala Gly Asn Asn Arg Gly Tyr Gly Gly Leu Asp Val Trp Gly Gln Gly
                100                 105                 110

Thr Thr Val Thr Val Ser Ser
            115

<210> SEQ ID NO 195
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
```

```
                65                  70                  75                  80
Ser Glu Asp Glu Ala Asp Tyr Tyr Cys Ala Ala Trp Asp Asp Ser Leu
                    85                  90                  95

Asn Gly Pro Val Val Phe Gly Gly Gly Thr Lys Leu Thr Val Leu
                100                 105                 110
```

<210> SEQ ID NO 196
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

```
Gln Ser Gly Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                    85                  90                  95

Asn Gly Ser Tyr Val Phe Gly Gly Gly Thr Lys Leu Thr Val Leu
                100                 105                 110
```

<210> SEQ ID NO 197
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

```
Thr Leu Val Thr Val Ser Ser Gly Gly Gly Gly Ser Gly Gly Gly Gly
1               5                   10                  15

Ser Gly Gly Gly Gly Glu Val Gln Leu Val Glu Ser Gly
            20                  25
```

<210> SEQ ID NO 198
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

```
Thr Leu Val Thr Val Ser Ser Gly Gly Gly Gly Ser Gly Gly Gly Gly
1               5                   10                  15

Ser Gly Gly Gly Glu Val Gln Leu Val Glu Ser Gly
            20                  25
```

<210> SEQ ID NO 199
<211> LENGTH: 27
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 199

Thr Leu Val Thr Val Ser Ser Gly Gly Gly Gly Ser Gly Gly Gly Gly
1               5                   10                  15

Ser Gly Gly Glu Val Gln Leu Val Glu Ser Gly
            20                  25

<210> SEQ ID NO 200
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Thr Leu Val Thr Val Ser Ser Gly Gly Gly Gly Ser Gly Gly Gly Gly
1               5                   10                  15

Ser Gly Glu Val Gln Leu Val Glu Ser Gly
            20                  25

<210> SEQ ID NO 201
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Thr Leu Val Thr Val Ser Ser Gly Gly Gly Gly Ser Gly Gly Gly Gly
1               5                   10                  15

Ser Glu Val Gln Leu Val Glu Ser Gly
            20                  25

<210> SEQ ID NO 202
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Thr Leu Val Thr Val Ser Ser Gly Gly Gly Gly Ser Gly Gly Gly Gly
1               5                   10                  15

Glu Val Gln Leu Val Glu Ser Gly
            20

<210> SEQ ID NO 203
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Thr Leu Val Thr Val Ser Ser Gly Gly Gly Gly Ser Gly Gly Gly Glu
1               5                   10                  15

Val Gln Leu Val Glu Ser Gly
            20
```

<210> SEQ ID NO 204
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Thr Leu Val Thr Val Ser Ser Gly Gly Gly Gly Ser Gly Gly Glu Val
1               5                   10                  15

Gln Leu Val Glu Ser Gly
            20

<210> SEQ ID NO 205
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Thr Leu Val Thr Val Ser Ser Gly Gly Gly Gly Ser Gly Glu Val Gln
1               5                   10                  15

Leu Val Glu Ser Gly
            20

<210> SEQ ID NO 206
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Thr Leu Val Thr Val Ser Ser Ala Ser Thr Lys Gly Pro Ser Val Phe
1               5                   10                  15

Pro Leu Ala Pro Glu Val Gln Leu Val Glu Ser Gly
            20                  25

<210> SEQ ID NO 207
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Thr Leu Val Thr Val Ser Ser Ala Ser Thr Lys Gly Pro Ser Val Phe
1               5                   10                  15

Pro Leu Ala Glu Val Gln Leu Val Glu Ser Gly
            20                  25

<210> SEQ ID NO 208
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

```
Thr Leu Val Thr Val Ser Ser Ala Ser Thr Lys Gly Pro Ser Val Phe
1               5                   10                  15

Pro Leu Glu Val Gln Leu Val Glu Ser Gly
            20                  25

<210> SEQ ID NO 209
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Thr Leu Val Thr Val Ser Ser Ala Ser Thr Lys Gly Pro Ser Val Phe
1               5                   10                  15

Pro Glu Val Gln Leu Val Glu Ser Gly
            20                  25

<210> SEQ ID NO 210
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Thr Leu Val Thr Val Ser Ser Ala Ser Thr Lys Gly Pro Ser Val Phe
1               5                   10                  15

Glu Val Gln Leu Val Glu Ser Gly
            20

<210> SEQ ID NO 211
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Thr Leu Val Thr Val Ser Ser Ala Ser Thr Lys Gly Pro Ser Val Glu
1               5                   10                  15

Val Gln Leu Val Glu Ser Gly
            20

<210> SEQ ID NO 212
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Thr Leu Val Thr Val Ser Ser Ala Ser Thr Lys Gly Pro Ser Glu Val
1               5                   10                  15

Gln Leu Val Glu Ser Gly
            20

<210> SEQ ID NO 213
<211> LENGTH: 21
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 213

Thr Leu Val Thr Val Ser Ser Ala Ser Thr Lys Gly Pro Glu Val Gln
1               5                   10                  15

Leu Val Glu Ser Gly
            20

<210> SEQ ID NO 214
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Thr Leu Val Thr Val Ser Ser Thr Pro Ala Pro Leu Pro Ala Pro Leu
1               5                   10                  15

Pro Ala Pro Thr Thr Glu Val Gln Leu Val Glu Ser Gly
            20                  25

<210> SEQ ID NO 215
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Thr Leu Val Thr Val Ser Ser Thr Pro Ala Pro Leu Pro Ala Pro Ala
1               5                   10                  15

Pro Thr Thr Glu Val Gln Leu Val Glu Ser Gly
            20                  25

<210> SEQ ID NO 216
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Thr Leu Val Thr Val Ser Ser Thr Pro Ala Pro Leu Pro Ala Pro Thr
1               5                   10                  15

Thr Glu Val Gln Leu Val Glu Ser Gly
            20                  25

<210> SEQ ID NO 217
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Thr Leu Val Thr Val Ser Ser Thr Pro Ala Pro Leu Pro Thr Thr Glu
1               5                   10                  15

Val Gln Leu Val Glu Ser Gly
```

```
<210> SEQ ID NO 218
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Thr Leu Val Thr Val Ser Ser Thr Pro Ala Pro Thr Thr Glu Val Gln
1               5                   10                  15

Leu Val Glu Ser Gly
            20

<210> SEQ ID NO 219
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Gly Thr Lys Leu Glu Ile Lys Arg Gly Gly Ser Gly Gly Gly Gly Ser
1               5                   10                  15

Gly Gly Gly Gly Ser Asp Ile Gln Met Thr Gln Ser Pro
            20                  25

<210> SEQ ID NO 220
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Gly Thr Lys Leu Glu Ile Lys Arg Gly Gly Ser Gly Gly Gly Gly Ser
1               5                   10                  15

Gly Gly Gly Gly Asp Ile Gln Met Thr Gln Ser Pro
            20                  25

<210> SEQ ID NO 221
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Gly Thr Lys Leu Glu Ile Lys Arg Gly Gly Ser Gly Gly Gly Gly Ser
1               5                   10                  15

Gly Gly Gly Asp Ile Gln Met Thr Gln Ser Pro
            20                  25

<210> SEQ ID NO 222
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 222

Gly Thr Lys Leu Glu Ile Lys Arg Gly Gly Ser Gly Gly Gly Gly Ser
1               5                   10                  15

Gly Gly Asp Ile Gln Met Thr Gln Ser Pro
            20                  25

<210> SEQ ID NO 223
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Gly Thr Lys Leu Glu Ile Lys Arg Gly Gly Ser Gly Gly Gly Gly Ser
1               5                   10                  15

Gly Asp Ile Gln Met Thr Gln Ser Pro
            20                  25

<210> SEQ ID NO 224
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Gly Thr Lys Leu Glu Ile Lys Arg Gly Gly Ser Gly Gly Gly Gly Ser
1               5                   10                  15

Asp Ile Gln Met Thr Gln Ser Pro
            20

<210> SEQ ID NO 225
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Gly Thr Lys Leu Glu Ile Lys Arg Gly Gly Ser Gly Gly Gly Gly Asp
1               5                   10                  15

Ile Gln Met Thr Gln Ser Pro
            20

<210> SEQ ID NO 226
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Gly Thr Lys Leu Glu Ile Lys Arg Gly Gly Ser Gly Gly Gly Asp Ile
1               5                   10                  15

Gln Met Thr Gln Ser Pro
            20

<210> SEQ ID NO 227
<211> LENGTH: 21
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Gly Thr Lys Leu Glu Ile Lys Arg Gly Gly Ser Gly Gly Asp Ile Gln
1               5                   10                  15

Met Thr Gln Ser Pro
            20

<210> SEQ ID NO 228
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Gly Thr Lys Leu Glu Ile Lys Arg Thr Val Ala Ala Pro Ser Val Phe
1               5                   10                  15

Ile Phe Pro Pro Asp Ile Gln Met Thr Gln Ser Pro
            20                  25

<210> SEQ ID NO 229
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Gly Thr Lys Leu Glu Ile Lys Arg Thr Val Ala Ala Pro Ser Val Phe
1               5                   10                  15

Ile Phe Pro Asp Ile Gln Met Thr Gln Ser Pro
            20                  25

<210> SEQ ID NO 230
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Gly Thr Lys Leu Glu Ile Lys Arg Thr Val Ala Ala Pro Ser Val Phe
1               5                   10                  15

Ile Phe Asp Ile Gln Met Thr Gln Ser Pro
            20                  25

<210> SEQ ID NO 231
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Gly Thr Lys Leu Glu Ile Lys Arg Thr Val Ala Ala Pro Ser Val Phe
1               5                   10                  15
```

Ile Asp Ile Gln Met Thr Gln Ser Pro
            20                  25

<210> SEQ ID NO 232
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Gly Thr Lys Leu Glu Ile Lys Arg Thr Val Ala Ala Pro Ser Val Phe
1               5                   10                  15

Asp Ile Gln Met Thr Gln Ser Pro
            20

<210> SEQ ID NO 233
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Gly Thr Lys Leu Glu Ile Lys Arg Thr Val Ala Ala Pro Ser Val Asp
1               5                   10                  15

Ile Gln Met Thr Gln Ser Pro
            20

<210> SEQ ID NO 234
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Gly Thr Lys Leu Glu Ile Lys Arg Thr Val Ala Ala Pro Ser Asp Ile
1               5                   10                  15

Gln Met Thr Gln Ser Pro
            20

<210> SEQ ID NO 235
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Gly Thr Lys Leu Glu Ile Lys Arg Thr Val Ala Ala Pro Asp Ile Gln
1               5                   10                  15

Met Thr Gln Ser Pro
            20

<210> SEQ ID NO 236
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Gly Thr Lys Leu Glu Ile Lys Arg Thr Pro Ala Pro Leu Pro Ala Pro
1               5                   10                  15
Leu Pro Ala Pro Thr Asp Ile Gln Met Thr Gln Ser Pro
            20                  25

<210> SEQ ID NO 237
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Gly Thr Lys Leu Glu Ile Lys Arg Thr Pro Ala Pro Leu Pro Ala Pro
1               5                   10                  15
Ala Pro Thr Asp Ile Gln Met Thr Gln Ser Pro
            20                  25

<210> SEQ ID NO 238
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Gly Thr Lys Leu Glu Ile Lys Arg Thr Pro Ala Pro Leu Pro Ala Pro
1               5                   10                  15
Thr Asp Ile Gln Met Thr Gln Ser Pro
            20                  25

<210> SEQ ID NO 239
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Gly Thr Lys Leu Glu Ile Lys Arg Thr Pro Ala Pro Leu Pro Thr Asp
1               5                   10                  15
Ile Gln Met Thr Gln Ser Pro
            20

<210> SEQ ID NO 240
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Gly Thr Lys Leu Glu Ile Lys Arg Thr Pro Ala Pro Thr Asp Ile Gln
1               5                   10                  15
Met Thr Gln Ser Pro
            20

<210> SEQ ID NO 241

```
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Gln Gly Thr Lys Leu Glu Ile Lys Arg Thr Val Ala Ala Pro Ser Val
1               5                   10                  15

Phe Ile Phe Pro Gln Ser Val Leu Thr Gln Pro Pro
            20                  25

<210> SEQ ID NO 242
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Gln Gly Thr Lys Leu Glu Ile Lys Arg Thr Val Ala Ala Pro Ser Val
1               5                   10                  15

Phe Ile Gln Ser Val Leu Thr Gln Pro Pro
            20                  25

<210> SEQ ID NO 243
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Gln Gly Thr Lys Leu Glu Ile Lys Arg Thr Val Ala Ala Pro Ser Val
1               5                   10                  15

Gln Ser Val Leu Thr Gln Pro Pro
            20

<210> SEQ ID NO 244
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Gln Gly Thr Lys Leu Glu Ile Lys Arg Thr Val Ala Ala Pro Gln Ser
1               5                   10                  15

Val Leu Thr Gln Pro Pro
            20

<210> SEQ ID NO 245
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Gln Gly Thr Lys Leu Glu Ile Lys Arg Gly Gly Ser Gly Gly Gly Gly
1               5                   10                  15
```

Ser Gly Gly Gly Gln Ser Val Leu Thr Gln Pro Pro
            20                  25

<210> SEQ ID NO 246
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Gln Gly Thr Lys Leu Glu Ile Lys Arg Gly Gly Ser Gly Gly Gly Gly
1               5                   10                  15

Ser Gly Gln Ser Val Leu Thr Gln Pro Pro
            20                  25

<210> SEQ ID NO 247
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Gln Gly Thr Lys Leu Glu Ile Lys Arg Gly Gly Ser Gly Gly Gly Gly
1               5                   10                  15

Gln Ser Val Leu Thr Gln Pro Pro
            20

<210> SEQ ID NO 248
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Gln Gly Thr Lys Leu Glu Ile Lys Arg Gly Gly Ser Gly Gly Gln Ser
1               5                   10                  15

Val Leu Thr Gln Pro Pro
            20

<210> SEQ ID NO 249
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Gln Gly Thr Lys Leu Glu Ile Lys Arg Thr Pro Ala Pro Leu Pro Ala
1               5                   10                  15

Pro Ala Pro Thr Gln Ser Val Leu Thr Gln Pro Pro
            20                  25

<210> SEQ ID NO 250
<211> LENGTH: 26
<212> TYPE: PRT
<213> ORGANISM: Artificial Sequence
<220> FEATURE:
<223> OTHER INFORMATION: Description of Artificial Sequence: Synthetic

```
                        peptide

<400> SEQUENCE: 250

Gln Gly Thr Lys Leu Glu Ile Lys Arg Thr Pro Ala Pro Leu Pro Ala
1               5                   10                  15

Pro Thr Gln Ser Val Leu Thr Gln Pro Pro
            20                  25

<210> SEQ ID NO 251
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Gln Gly Thr Lys Leu Glu Ile Lys Arg Thr Pro Ala Pro Leu Pro Thr
1               5                   10                  15

Gln Ser Val Leu Thr Gln Pro Pro
            20

<210> SEQ ID NO 252
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Gln Gly Thr Lys Leu Glu Ile Lys Arg Thr Pro Ala Pro Thr Gln Ser
1               5                   10                  15

Val Leu Thr Gln Pro Pro
            20
```

HIGH-THROUGHPUT SYSTEM AND METHOD FOR IDENTIFYING ANTIBODIES HAVING SPECIFIC ANTIGEN BINDING ACTIVITIES

RELATED APPLICATIONS

This application claims priority from U.S. Provisional Application Nos. 61/746,629, 61/746,659, 61/746,663, 61/746,617, 61/746,615, and 61/746,619, filed on Dec. 28, 2012, U.S. provisional application 61/755,288, filed Jan. 22, 2013, and U.S. provisional application 61/786,829, filed Mar. 15, 2013. The contents of each of the foregoing applications are hereby incorporated by reference herein in their entireties.

SEQUENCE LISTING

The instant application contains a Sequence Listing which has been submitted electronically in ASCII format and is hereby incorporated by reference in its entirety. Said ASCII copy, created on Mar. 20, 2014, is named 553278BBI-328_SL.txt and is 179,855 bytes in size.

BACKGROUND

I. Field

The present disclosure pertains to high throughput screening of antibodies. More specifically, the disclosure relates to the use of multiple antibody libraries in simultaneous screening of antibodies using yeast display technology.

II. Description of Related Art

Traditionally, monoclonal antibodies are prepared using antibodies obtained from animal immunizations. However, developing therapeutic antibodies from animal immunizations requires humanizing the non-human antibodies or utilizing transgenic animals expressing human antibodies. Direct selection of fully human antibodies from pre-established antibody libraries or affinity maturation of humanized antibodies by in vitro display technologies offers a valuable alternative approach.

Among in vitro display technologies that have been developed, yeast surface display of antibody fragments has proven to be a robust technology for engineering therapeutic antibodies. Not only does yeast display provide exquisite selection power to enrich high affinity antigen binders, its capability to quantitatively select for antibodies of different binding kinetics by fluorescence activated sorting of the yeast cells is also more advantageous than other in vitro display technologies.

U.S. Patent Publication No. 2011/0076752 and U.S. Patent Publication No. 2011/0076752 describe methods for displaying recombinant whole immunoglobulins or immunoglobulin libraries on the surface of eukaryotic cells and methods for screening the libraries to identify immunoglobulins that are specific for an antigen of interest. Although significant progress has been made in enhancing the throughput of the yeast display technology, major obstacles remain because of the relatively low transformation efficiency in yeast and the potential loss of productivity due to library cross-contamination.

SUMMARY

This disclosure provides a population of cells, e.g., yeast cells. The population includes a first subpopulation of cells and a second subpopulation of cells. The first subpopulation of cells includes at least one cell comprising a first polynucleotide encoding a first antibody, binding protein or a fragment thereof and a first tag. The second subpopulation of cells comprises at least one cell comprising a second polynucleotide encoding a second antibody, binding protein or a fragment thereof and a second tag.

The first subpopulation of cells can include cells that have antibodies, binding proteins or fragments thereof with mutations in a first complementarity determining region (CDR) and the second subpopulation of cells can include cells that have antibodies, binding proteins or fragments thereof with mutations in a second CDR, said first CDR differing from or being the same as said second CDR. In one embodiment, when the first and second CDRs are different, the antibodies or fragments thereof in the first subpopulation of cells differ from each other only in mutations within said first CDR, and said antibodies or fragments thereof in the second subpopulation of cells differ from each other only in mutations within said second CDR.

The first tag and said second tag can each include His, HA, c-myc, Flag, HSV, S, AcV5, E2, E, and StrepII tags. The first tag and said second tag can also each include a fluorophore or fluorochrome. The population can be a population of cells selected from bacterial, yeast, or mammalian cells. In certain embodiments, the population of cells is a population of yeast cells.

The disclosure also provides a method of identifying an antibody having a desired binding characteristic with a ligand. The method includes contacting the population of cells described above with the ligand; sorting the population of cells based on interaction of the first or second antibodies or fragments thereof with the ligand; sorting the population of cells based on said first tag and said second tag; and identifying one or more antibodies or fragments thereof having the desired binding characteristic with said ligand.

The ligand can be a protein. The interaction of the first or second antibodies or fragments thereof with said ligand can be a specific binding interaction. The sorting can be performed by fluorescence-activated cell sorting (FACS).

In one embodiment, first antibodies or fragments thereof with a specific interaction with said ligand and comprising said first tag are sorted into a first selection output, first antibodies or fragments thereof without a specific interaction with said ligand and comprising said first tag are sorted into a second selection output, second antibodies or fragments thereof with a specific interaction with said ligand and comprising said second tag are sorted into a third selection output and second antibodies or fragments thereof without a specific interaction with said ligand and comprising said second tag are sorted into a fourth selection output.

The first antibody or fragment thereof and said second antibody or fragment thereof can both include a single chain variable fragment (ScFv). Also, the first antibody or fragment thereof can include a light chain variable fragment while the second antibody or fragment thereof includes a heavy chain variable fragment. In this case, the first antibody or fragment thereof includes mutations in a light chain CDR, and the second antibody or fragments thereof includes mutations in a heavy chain CDR.

The disclosure also provides a method of selecting binding proteins that specifically binds to a target comprising transfecting nucleic acids from a first nucleic acid library, a second nucleic acid library and a third nucleic acid library into host cells of an organism, wherein the nucleic acids encode binding proteins, wherein the nucleic acids in each nucleic acid library comprise a variable region in distinct regions of the nucleic acid molecules and wherein the nucleic acid molecules of each library encode a distinct tag; expressing the binding proteins encoded by the nucleic acid molecules on the surface of the host cells; exposing the host cells in each library to the target; and selecting host cells expressing binding proteins that specifically bind to the target.

In certain embodiments, the nucleic acid molecules in each library are 75, 80, 85, 90, 95, 96, 97, 98 or 99% homologous in the sequences outside of their respective variable regions. In other embodiments, the variable regions of the nucleic acids of the first library do not overlap with the corresponding nucleic acids of variable regions of the nucleic acids of the second or third library. In other embodiments, the variable regions of the nucleic acids of the second library do not overlap with the corresponding nucleic acids of variable regions of the nucleic acids of the first or third library. In other embodiments, the variable regions of the nucleic acids of the third library do not overlap with the corresponding nucleic acids of variable regions of the nucleic acids of the first or second library.

In certain embodiments, substantially all of the nucleic acids in the first library comprise substantially the same tag. In other embodiments, the tag of substantially all of the nucleic acids of the first library is distinct from a tag of the nucleic acids of the second or third libraries. In other embodiments, substantially all of the nucleic acids in the second library comprise substantially the same tag. In other embodiments, the tag of substantially all of the nucleic acids of the second library is distinct from a tag of the nucleic acids of the first or third libraries.

In certain embodiments, substantially all of the nucleic acids in the third library comprise substantially the same tag. In other embodiments, the tag of substantially all of the nucleic acids of the third library is distinct from a tag of the nucleic acids of the first or second libraries.

In certain embodiments, the methods described herein alo include the steps of amplifying the nucleic acid molecules that encode the selected binding proteins; and combining the amplified nucleic acid molecules, thereby forming a fourth library. In certain embodiments, the combination comprises recombining the amplified nucleic acids to form a fourth library comprising nucleic acid molecules comprising variable regions from two or more of nucleic acids expressing selected binding proteins from the first, second and/or third libraries.

In certain embodiments, the methods described herein alo include the steps of expressing the binding proteins encoded by the fourth library on the cell surface of a population of host cells from an organism; exposing the binding proteins on the surface of the host cells to the target; and selecting binding proteins that bind to the target.

In certain embodiments, the binding protein is anchored on the surface of host cell with an anchoring molecule. In other embodiments, the organism is selected from the group consisting of prokaryotic organisms or eukaryotic organisms. In other embodiments, the eukaryotic organism is selected from the group consisting of fungus, mammal, insect, fish, or bird. In other embodiments, the fungus is yeast. Specifically, the yeast can be selected from the group consisting of *Saccharomyces cerevisiae, Saccharomyces carlsbergensis, Candida albicans, Candida kefyr, Candida tropicalis, Cryptococcus laurentii, Cryptococcus neoformans, Hansenula anomala, Hansenula polymorpha, Kluyveromyces fragilis, Kluyveromyces lactis, Kluyveromyces marxianus, Pichia pastoris, Rhodotorula rubra, Schizosaccharomyces pombe* and *Yarrowia lipolytica*. In certain embodiments, the yeast is *Saccharomyces cerevisiae*. In certain embodiments, the mammal is selected from human, ape, monkey, rat, mouse, dog, cat, hamster, goat and sheep. In other embodiments, the prokaryotic organism is *E. coli*.

In certain embodiments, the selection is performed using fluorescence activated cell sorting (FACS). In other embodiments, the tag is selected from the group consisting of histidine (His), hemagglutinin (HA), c-myc, Flag, HSV, S, AcV5, E2, E, T7, KT3, MAT, AAV5, ABCA5, ABCE1, Glu-Glu, 2AU1 and StrepII tags. In other embodiments, the tag further comprises a fluorophore or fluorochrome.

In certain embodiments, the binding protein comprises an amino acid sequence that is 70, 75, 80, 85, 90, 95, 96, 97, 98, 99 or 100% homologous to a complementarity determining region (CDR) of a mammalian antibody. In other embodiments, the mammal is selected from the group consisting of from human, ape, monkey, rat, mouse, dog, cat, hamster, goat and sheep. In other embodiments, the binding protein further comprises a sequence 70, 75, 80, 85, 90, 95, 96, 97, 98, 99 or 100% homologous to the constant region of an antibody. In other embodiments, the antibody is selected from the group consisting of an IgG, IgA, IgD and IgM antibody. In other embodiments, the IgG antibody is selected from the group consisting of IgG1, IgG2, IgG3 and IgG4 antibodies. In other embodiments, the binding protein is a DVD-Ig. In other embodiments, the DVD-Ig is selected from the group consisting of an scDVD-Ig, an scDVDFab-Ig an fDVD-Ig, a pDVD-Ig, an mDVD-Ig and a coDVD-Ig or a half-DVD-Ig of any of these formats.

In certain embodiments expression of the binding proteins is under control of an inducible promoter. In other embodiments, the inducible promoter is induced by the presence of a chemical, a metabolic substrate or a temperature range. In other embodiments the binding proteins are 70, 75, 80, 85, 90, 95, 96, 97, 98, 99 or 100% homologous to the same antibody. In other embodiments the antibody specifically binds the target. In other embodiments, the variable region of the first library comprise a first CDR. In other embodiments, the variable region of the second library comprise a second CDR. In other embodiments, the variable region of the third library comprise a third CDR. In other embodiments, the first, second and third CDRs are 70, 75, 80, 85, 90, 95, 96, 97, 98, 99 or 100% homologous to the first, second and third CDRs of the same antibody.

In certain embodiments, the binding proteins are single chain variable fragments (ScFv). In other embodiments, the single chain variable fragment is a light chain variable fragment or a heavy chain variable fragment. In other embodiments, the variable region of the first library comprises a light chain variable fragment. In other embodiments, the variable region of the second library comprises a heavy chain variable fragment.

In certain embodiments, the selecting step comprises attaching the target to a substrate, a fixed surface or a detectable tag. In other embodiments, the methods described herein include the use of 1, 2, 3, 4, 5, 6, 7, 8, 9, 10, 11, 12, 13, 14, 15, 16 or 17 additional nucleic acid libraries wherein the nucleic acids encode binding proteins, wherein the nucleic acids in each nucleic acid library comprise a variable region in distinct regions of the nucleic acid molecules and wherein the nucleic acid molecules of each library encode a distinct tag.

In certain embodiments, the fluorochrome is selected from the group consisting of PerCP; R-PE; DyLight-488; Alexafluor 488; Alexafluor 633; APC; PE; DyLight-633; 1,5 IAEDANS; 1,8-ANS; 4-Methylumbelliferone; 5-carboxy-2, 7-dichlorofluorescein; 5-Carboxyfluorescein (5-FAM); 5-Carboxynapthofluorescein; 5-Carboxytetramethylrhodamine (5-TAMRA); 5-Hydroxy Tryptamine (5-HAT); 5-ROX (carboxy-X-rhodamine); 6-Carboxyrhodamine 6G; 6-CR 6G; 6-JOE; 7-Amino-4-methylcoumarin; 7-Aminoactinomycin D (7-AAD); 7-Hydroxy-4-I methylcoumarin; 9-Amino-6-chloro-2-methoxyacridine (ACMA); ABQ; Acid Fuchsin; Acridine Orange; Acridine Red; Acridine Yellow; Acriflavin; Acriflavin Feulgen SITSA; Aequorin (Photoprotein); Alizarin Complexon; Alizarin Red; Allophycocyanin (APC); AMC, AMCA-S; Aminomethylcoumarin (AMCA); AMCA-X; Aminoactinomycin D; Aminocoumarin; Anilin Blue; Anthrocyl stearate; APC-Cy7; APTRA-BTC; APTS; Astrazon Brilliant Red 4G; Astrazon Orange R; Astrazon Red 6B; Astrazon Yellow 7 GLL; Atabrine; Auramine; Aurophosphine G; Aurophosphine; BAO 9 (Bisaminophenyloxadiazole); BCECF (high pH); BCECF (low pH); Berberine Sulphate; Beta Lactamase; BFP blue shifted GFP (Y66H); Blue Fluorescent Protein; BFP/GFP FRET; Bimane; Bisbenzemide; Bisbenzimide (Hoechst); bis-BTC; Blancophor FFG; Blancophor SV; Bodipy 492/515; Bodipy 493/503; Bodipy 500/510; Bodipy; 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; Brilliant Sulphoflavin FF; BTC; BTC-5N; Calcein; Calcein Blue; Calcium Crimson; Calcium Green; Calcium Green-1$Ca^{2+}$ Dye; Calcium Green-2 $Ca^{2+}$; Calcium Green-5N $Ca^{2+}$; Calcium Green-C18 $Ca^{2+}$; Calcium Orange; Calcofluor White; Carboxy-X-rhodamine (5-ROX); Cascade Blue™; Cascade Yellow; Catecholamine; CCF2 (GeneBlazer); CFDA; CFP (Cyan Fluorescent Protein); CFP/YFP FRET; Chlorophyll; Chromomycin A; Chromomycin A; CL-NERF; CMFDA; Coelenterazine; Coelenterazine cp; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM I Methylcoumarin; CTC; CTC Formazan; Cy2®; Cy3.1 8®; Cy3.5®; Cy3®; Cy5.1 8®; Cy5.5®; Cy5®; Cy7®; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3'DCFDA; DCFH (Dichlorodihydrofluorescein Diacetate); DDAO; DHR (Dihydrorhodamine 123); Di-4-ANEPPS; Di-8-ANEPPS (non-ratio); DiA (4-Di 16-ASP); Dichlorodihydrofluorescein Diacetate (DCFH); DiD-Lipophilic Tracer; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (111) chloride; EYFP; Fast Blue; FDA; Feulgen (Pararosaniline); FIF (Formaldehyd Induced Fluorescence); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; Fluor X; Fura Red® (high pH); Fura Red®/Fluo-3; Fura-2; Fura-2/BCECF; Genacryl Brilliant Red B; Genacryl Brilliant Yellow 10GF; Genacryl Pink 3G; Genacryl Yellow SGF; GeneBlazer; (CCF2); GFP (S65T); GFP red shifted (rsGFP); GFP wild type' non-UV excitation (wtGFP); GFP wild type, UV excitation (wtGFP); GFPuv; Gloxalic Acid; Granular blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1, high calcium; Indo-1 low calcium; Indodicarbocyanine (DiD); Indotricarbocyanine (DiR); Intrawhite Cf; JC-1; JO JO-1; JO-PRO-1; LaserPro; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; I Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxedidole; Noradrenaline; Nuclear Fast Red; i Nuclear Yellow; Nylosan Brilliant lavin E8G; Oregon Green™; Oregon Green® 488; Oregon Green® 500; Oregon Green® 514; Pacific Blue; Pararosaniline (Feulgen); PBFI; PE-Cy5; PE-Cy7; PerCP; PerCP-Cy5.5; PE-TexasRed (Red 613); Phloxin B (Magdala Red); Phorwite AR; Phorwite BKL; Phorwite Rev; Phorwite RPA; Phosphine 3R; PhotoResist; Phycoerythrin B [PE]; Phycoerythrin R [PE]; PKH26 (Sigma); PKH67; PMIA; Pontochrome Blue Black; POPO-1; POPO-3; PO-PRO-1; PO-I PRO-3; Primuline; Procion Yellow; Propidium lodid (P1); PyMPO; Pyrene; Pyronine; Pyronine B; Pyrozal Brilliant Flavin 7GF; QSY 7; Quinacrine Mustard; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine: Phalloidine; Rhodamine Red; Rhodamine WT; Rose Bengal; R-phycocyanine; R-phycoerythrin (PE); rsGFP; S65A; S65C; S65L; S65T; Sapphire GFP; SBFI; Serotonin; Sevron Brilliant Red 2B; Sevron Brilliant Red 4G; Sevron I Brilliant Red B; Sevron Orange; Sevron Yellow L; sgBFP® (super glow BFP); sgGFP™ (super glow GFP); SITS (Primuline; Stilbene Isothiosulphonic Acid); SNAFL calcein; SNAFL-1; SNAFL-2; SNARF calcein; SNARFI; Sodium Green; SpectrumAqua; SpectrumGreen; SpectrumOrange; Spectrum Red; SPQ (6-methoxy-N-(3 sulfopropyl) quinolinium); Stilbene; Sulphorhodamine B and C; Sulphorhodamine Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Reds; Texas Red-X™ conjugate; Thiadicarbocyanine (DiSC3); Thiazine Red™; Thiazole Orange; Thioflavin 5; Thioflavin S; Thioflavin TON; Thiolyte; Thiozole Orange; Tinopol CBS (Calcofluor White); TIER; TO-PRO-1; TO-PRO-3; TO-PRO-5; TOTO-1; TOTO-3; TriColor (PE-Cy5); TRITC TetramethylRodaminelsoThioCyanate; True Blue; Tru Red; Ultralite; Uranine B; Uvitex SFC; wt GFP; WW 781; X-Rhodamine; XRITC; Xylene Orange; Y66F; Y66H; Y66W; Yellow GFP; YFP; YO-PRO-1; YO-PRO3; YOYO-1; YOYO-3; Sybr Green; Thiazole orange (interchelating dyes); semiconductor nanoparticles such as quantum dots; or caged fluorophores (which can be activated with light or other electromagnetic energy source), or a combination thereof.

In certain embodiments, in the methods described herein substantially all of the nucleic acids in the nucleic acid libraries comprise vectors. In other embodiments, the vector is a yeast vector. In other embodiments, the yeast vector is pYDsTEV. In other embodiments, the antibody is h1A11.

In another aspect, the disclosure provides a diverse library of binding proteins.

In certain embodiments, the diverse library of binding proteins comprises a polypeptide chain having the general formula VH1-(X1)n-VH2-X2-VL1-(X3)n-VL2, wherein VH1 is a first heavy chain variable domain, X1 is a linker with the proviso that it is not a constant domain, VH2 is a second heavy chain variable domain, X2 is a linker, VL1 is a first light chain variable domain, X3 is a linker with the proviso that it is not a constant domain, VL2 is a second light chain variable domain, and n is 0 or 1, wherein the VH1 and VL1, and the VH2 and VL2 respectively combine to form two functional antigen binding sites, and wherein the amino acid sequences of VH1, X1, VH2, X2, VL1, X3, and/or VL2 independently vary within the library.

In certain embodiments, the diverse library of binding proteins comprises a polypeptide chain having the general formula CH1-X0-VH1-(X1)n-VH2-X2-CL1-X4-VL1-(X3)n-VL2, wherein CH1 is a heavy chain constant domain, X0 is a linker with the proviso that it is not a constant domain, VH1 is a first antibody heavy chain variable domain, X1 is a linker with the proviso that it is not a constant domain, VH2 is a second antibody heavy chain variable domain, X2 is a linker, CL1 is a light chain constant domain, X4 is a linker with the proviso that it is not a constant domain, VL1 is a first antibody light chain variable domain, X3 is a linker with the proviso that it is not a constant domain, VL2 is a second antibody light chain variable domain, and n is 0 or 1, and wherein the VH1 and VL1, the VH2 and VL2 respectively combine to form two functional antigen binding sites, and wherein the amino acid sequences of VH1, X1, VH2, X2, VL1, X3, and/or VL2 independently vary within the library. Optionally, the CL1 domain can be a kappa (hcκor cκ) or a lambda (hcλor cλ) constant domain. In certain embodiments, CL1 is cκ.

In certain embodiments, X2 is a GS-rigid linker sequence. The GS rigid linker sequence can comprise an amino acid sequence selected from the sequences shown in FIG. 23B.

In certain embodiments, the diverse library of binding proteins comprises a polypeptide chain having the general formula (VL1-(X1)n-VL2-X2-VH1-(X3)n-VH2, wherein VL1 is a first antibody light chain variable domain, X1 is a linker with the proviso that it is not a constant domain, VL2 is a second antibody light chain variable domain, X2 is a linker, VH1 is a first antibody heavy chain variable domain, X3 is a linker with the proviso that it is not a constant domain, VH2 is a second antibody heavy chain variable domain, and n is 0 or 1, wherein the VH1 and VL1, and the VH2 and VL2 respectively combine to form two functional antigen binding sites, and wherein the amino acid sequences of VL1, X1, VL2, X2, VH1, X3, and/or VH2 independently vary within the library.

In certain embodiments, the diverse library of binding proteins comprises a polypeptide chain having the general formula CL1-X0-VL1-(X1)n-VL2-X2-CH1-X4-VH1-(X3)n-VH2, wherein CL1 is a light chain constant domain, X0 is a linker with the proviso that it is not a constant domain, VL1 is a first antibody light chain variable domain, X1 is a linker with the proviso that it is not a constant domain, VL2 is a second antibody light chain variable domain, X2 is a linker, CH1 is a heavy chain constant domain, X4 is a linker with the proviso that it is not a constant domain, VH1 is a first antibody heavy chain variable domain, X3 is a linker with the proviso that it is not a constant domain, VH2 is a second antibody heavy chain variable domain, and n is 0 or 1, and wherein the VH1 and VL1, the VH2 and VL2 respectively combine to form two functional antigen binding site, and wherein the amino acid sequences of VH1, X1, VH2, X2, VL1, X3, and/or VL2 independently vary within the library. In certain embodiments, the CL1 light chain. Optionally, the CL1 domain can be a kappa (hcκcor cκ) or a lambda (haλor cλ) constant domain. In certain embodiments, CL1 is cκ.

In certain embodiments, X2 is a GS-rigid linker sequence. The GS rigid linker sequence can comprise an amino acid sequence selected from the sequences shown in FIG. 23B.

In certain embodiments, each binding proteins further comprises a cell surface anchoring moiety linked to the N or C terminus. In certain embodiments, the anchoring moiety is a cell surface protein. In one embodiment, the anchoring moiety is Aga2p.

In certain embodiments, the polypeptide chain is a scDVD or scDVDFab.

In certain embodiments, the amino acid sequence of at least one CDR of VH1, VH2, VL1 or VL2 independently varies within the library. In one embodiment, the amino acid sequence of HCDR3 of VH1, VH2 independently vary within the library. In one embodiment, the amino acid sequence of HCDR1 and HCDR2 of VH1 or VH2 independently vary within the library. In one embodiment, the amino acid sequence of HCDR1, HCDR2 and HCDR3 of VH1 or VH2 independently vary within the library. In one embodiment, the amino acid sequence of HCDR3 of VL1 or VL2 independently vary within the library. In one embodiment, the amino acid sequence of HCDR1 and HCDR2 of VL1 or VL2 independently vary within the library. In one embodiment, the amino acid sequence of HCDR1, HCDR2 and HCDR3 of VL1 or VL2 independently vary within the library.

In certain embodiments, X1 independently varies within the library and wherein X1 is selected from the amino acid sequences set forth in FIG. 2. In certain embodiments, X2 independently varies within the library and wherein X2 is $(G_4S)n$, where n=1-10 (SEQ ID NO:1). In other embodiments, X2 is selected from the amino acid sequences set forth in FIG. 11B. In specific embodiments, X2 is selected from the amino acid sequences set forth in FIG. 11B when the polypeptide chain includes CH and CL domain. In certain embodiments, X3 independently varies within the library and X3 is selected from the amino acid sequences set forth in FIG. 2.

In certain embodiments, the library of binding proteins share at least 70, 75, 80, 85, 90, 95, 96, 97, 98, or 99 amino acid sequence identity with a reference binding protein. In certain embodiments, VH1 and VH2 of the reference binding protein specifically bind to different antigens.

In another aspect, the disclosure provides a diverse library of polynucleotides encoding a diverse library of binding proteins disclosed herein.

In another aspect, the disclosure provides a diverse library of expression vectors comprising a diverse library of polynucleotides disclosed herein.

In another aspect, the disclosure provides a library of transformed host cells, expressing the diverse library of binding proteins disclosed herein.

In certain embodiments, the binding proteins are anchored on the cell surface of a transformed host cell. In certain embodiments, the binding proteins are anchored on the cell surface through Aga1p.

In certain embodiments, the host cells are eukaryotic. In certain embodiments, the host cells are yeast, e.g., *Saccharomyces cerevisiae, Saccharomyces carlsbergensis, Can-* dida albicans, Candida kefyr, Candida tropicalis, Cryptococcus laurentii, Cryptococcus neoformans, Hansenula anomala, Hansenula polymorpha, Kluyveromyces fragilis, Kluyveromyces lactis, Kluyveromyces marxianus, Pichia pastoris, Rhodotorula rubra, Schizosaccharomyces pombe and Yarrowia lipolytica. In one embodiment, the yeast is Saccharomyces cerevisiae.

In another aspect, the disclosure provides a method of selecting a binding protein that specifically binds to a target antigen, the method comprising: providing a diverse library of transformed host cells expressing a diverse library of binding proteins disclosed herein; contacting the host cells with the target antigen; and selecting a host cell that bind to the target antigen, thereby identifying a binding protein that specifically binds to a target antigen.

In another aspect, the disclosure provides a method of selecting a binding protein that specifically binds to a first and a second target antigen simultaneously, the method comprising: providing a diverse library of transformed host cells expressing a diverse library of binding proteins disclosed herein; contacting the host cells with the first and second target antigen; and selecting a host cell that bind to the first and second target antigen, thereby identifying a binding protein that specifically binds to a first and a second target antigen simultaneously.

In certain embodiments of the methods disclosed herein, host cells that bind to the first and/or second antigen are selected by Magnetic Activated Cell Sorting using magnetically labeled antigen. In certain embodiments of the methods disclosed herein, host cells that bind to the first and/or second antigen are selected by Fluorescence Activated Cell Sorting using fluorescently labeled antigen.

In certain embodiments, the methods disclosed herein further comprise isolating the binding protein-encoding polynucleotide sequences from the selected host cells.

In another aspect, the disclosure provides a method of producing a binding protein comprising expressing in a host cell a binding protein that was selected using the methods disclosed herein.

In another aspect, the disclosure provides method of producing a diverse library of binding proteins that specifically binds to a target antigen, the method comprising: providing a first diverse library of scDVD or scDVDFab molecules, wherein the amino acid sequence of a first region of the scDVD or scDVDFab molecules is varied in the library, and wherein each member of the library binds to the target antigen; providing a second diverse library of scDVD or scDVDFab molecules, wherein the amino acid sequence of a second region of the scDVD or scDVDFab molecules is varied in the library, and wherein each member of the library binds to the target antigen; recombining the first and second libraries to produce a third diverse library of scDVD or scDVDFab molecules, wherein the third library comprises the first regions from the first library and the second region from the second library, thereby producing a diverse library of binding proteins that specifically binds to a target antigen.

In certain embodiments, the first and second libraries are recombined by yeast gap repair of polynucleotides encoding the libraries.

Accordingly, in one aspect the invention provides a diverse library of binding proteins comprising a first polypeptide chain having the general formula VH1-(X1)n-VH2-C-(X2)n, wherein VH1 is a first heavy chain variable domain, X1 is a linker with the proviso that it is not a constant domain, VH2 is a second heavy chain variable domain, C is a heavy chain constant domain, X2 is a cell surface protein, and n is 0 or 1, and wherein the amino acid sequences of VH1, VH2 and/or X1 independently vary within the library.

In certain embodiments, the binding proteins further comprise a second polypeptide chain having the general formula VL1-(Y1)n-VL2-C, wherein VL1 is a first light chain variable domain, Y1 is a linker with the proviso that it is not a constant domain, VL2 is a second light chain variable domain, C is a light chain constant domain, n is 0 or 1, wherein the VH1 and VH2 of the first polypeptide chain and VL1 and VL2 of second polypeptide chains of the binding protein combine form two functional antigen binding sites.

In certain embodiments, the first and second polypeptide chains combine to form a DVD-Fab or a full length DVD-Ig. In certain embodiments, the first and second polypeptide chains combine to form a full length DVD-Ig.

In certain embodiments, the amino acid sequences of VL1, VL2 and/or Y1 independently vary within the library.

In certain embodiments, the amino acid sequences of at least one CDR of VH1, VH2, VL1 or VL2 independently varies within the library. In one embodiment, the amino acid sequences of HCDR3 of VH1, VH2 independently vary within the library. In one embodiment, the amino acid sequences of HCDR1 and HCDR2 of VH1 or VH2 independently vary within the library. In one embodiment, the amino acid sequences of HCDR1, HCDR2 and HCDR3 of VH1 or VH2 independently vary within the library. In one embodiment, the amino acid sequences of HCDR3 of VL1 or VL2 independently vary within the library. In one embodiment, the amino acid sequences of HCDR1 and HCDR2 of VL1 or VL2 independently vary within the library. In one embodiment, the amino acid sequences of HCDR1, HCDR2 and HCDR3 of VL1 or VL2 independently vary within the library.

In certain embodiments, X1 independently varies within the library and wherein X1 is selected from the amino acid sequences set forth in Table 13 and/or 17. In certain embodiments, Y1 independently varies within the library and wherein Y1 is selected from the amino acid sequences set forth in Table 13 and/or 17. In certain embodiments, X2 comprises the Aga2p polypeptide.

In certain embodiments, the library of binding proteins share at least 70, 75, 80, 85, 90, 95, 96, 97, 98, or 99 amino acid sequence identity with a reference binding protein. In certain embodiments, VH1 and VH2 of the reference binding protein specifically bind to different antigens.

In another aspect, the invention provides a diverse library of polynucleotides encoding the first and/or second polypeptide chains of a diverse library of binding proteins disclosed herein.

In another aspect, the invention provides a diverse library of expression vectors comprising the diverse library of polynucleotides disclosed herein.

In another aspect, the invention provides a library of transformed host cells, expressing a diverse library of binding proteins disclosed herein.

In certain embodiments, the binding proteins are anchored on the cell surface of the host cells. In one embodiment, the binding proteins are anchored on the cell surface through Aga1p.

In certain embodiments, the host cells are eukaryotic. In one embodiment, the host cells are yeast, e.g., Saccharomyces cerevisiae, Saccharomyces carlsbergensis, Candida albicans, Candida kefyr, Candida tropicalis, Cryptococcus laurentii, Cryptococcus neoformans, Hansenula anomala, Hansenula polymorpha, Kluyveromyces fragilis, Kluyvero-

*myces lactis, Kluyveromyces marxianus, Pichia pastoris, Rhodotorula rubra, Schizosaccharomyces pombe* and *Yarrowia lipolytica*. In one embodiment, the host cells are *Saccharomyces cerevisiae*.

In another aspect, the invention provides a method of selecting a binding protein that specifically binds to a target antigen, the method comprising: providing a diverse library of transformed host cells expressing a diverse library of binding proteins disclosed herein; contacting the host cells with the target antigen; and selecting a host cell that bind to the target antigen, thereby identifying a binding protein that specifically binds to a target antigen.

In another aspect, the invention provides a method of selecting a binding protein that specifically binds to a first and a second target antigen simultaneously, the method comprising: providing a diverse library of transformed host cells expressing a diverse library of binding proteins disclosed herein; contacting the host cells with the first and second target antigen; and selecting a host cell that bind to the first and second target antigen, thereby identifying a binding protein that specifically binds to a first and a second target antigen simultaneously.

In certain embodiments of the methods of the invention, the host cells that bind to the first and/or second antigen are selected by Magnetic Activated Cell Sorting using magnetically labeled antigen. In certain embodiments of the methods of the invention, the host cells that bind to the first and/or second antigen are selected by Fluorescence Activated Cell Sorting using fluorescently labeled antigen.

In certain embodiments, the methods of the invention further comprise isolating the binding protein-encoding polynucleotide sequences from the selected host cells.

In another aspect, the invention provides a method of producing a binding protein comprising expressing in a host cell a binding protein that was selected using the methods disclosed herein.

BRIEF DESCRIPTION OF THE DRAWINGS

FIG. 1A depicts the steps involved in construction of a YD library. FIG. 1B depicts the steps involved in display of the YD library on the surface of yeast cells and the selection of desired antibodies using flow cytometry.

FIG. 2A depicts the steps involved in construction of three separate and differentially labeled YD scFv libraries comprising variability in different portions of the antibody sequence: Library 1 comprises variability in the CDRH1 and CDRH2 segments of the VH domain and is differentially labeled with Tag 1; Library 2 comprises variability in the CDRH3 segment of the VH domain and is differentially labeled with Tag 2; Library 3 comprises variability in the CDRL1, CDR L2 and CDR L3 segment of the VL domain and is differentially labeled with Tag 3. FIG. 2B depicts the screening of the individual scFv YD libraries (Libraries 1-3) using flow cytometry. FIG. 2C depicts the construction of a fourth "master library" comprising variability in all CDR portions of the antibody sequence using the antibody sequences isolated from the initial screens (FIG. 2B). The master library is labeled with any one of Tags 1-3, or a fourth, unrelated label (Tag 4) and screened using another round of cell sorting to identify an scFv clone with desired binding affinity (FIG. 2D).

FIG. 3 illustrates schematically the plasmid map of an exemplary yeast display (YD) vector: 13767_pYDs_TEV_total vector. FIG. 3A depicts the plasmid map. FIG. 3B depicts the polylinker region of the plasmid.

FIG. 13 is a pie chart showing the relative prevalence of libraries made up of various germlines.

FIG. 15A discloses "G$_4$S" as SEQ ID NO: 40.

FIG. 16 discloses "G$_4$S" as SEQ ID NO: 40.

FIG. 21 depicts (A) a schematic representation of an scDVD molecule and exemplary inter-VL domain linker amino acid sequences (SEQ ID NOS 241-252, respectively, in order of appearance), and (B) and results (as fold enrichment) of yeast display screens of SOST/TNFa-binding scDVD library comprising various inter-VL domain linker amino acid sequences.

FIG. 22C discloses "G₄S" as SEQ ID NO: 40.

FIG. 23 depicts (A) a schematic representation of an scDVDFab molecule, (B) GS-rigid linker amino acid sequences (SEQ ID NOS 53-56, respectively, in order of appearance) and (C) a schematic of a scDVDFab with a GS-rigid linker ("G₃SG₃" and "G₂SG₂" disclosed as SEQ ID NOS 43 and 44, respectively).

DETAILED DESCRIPTION

Figure 1A:
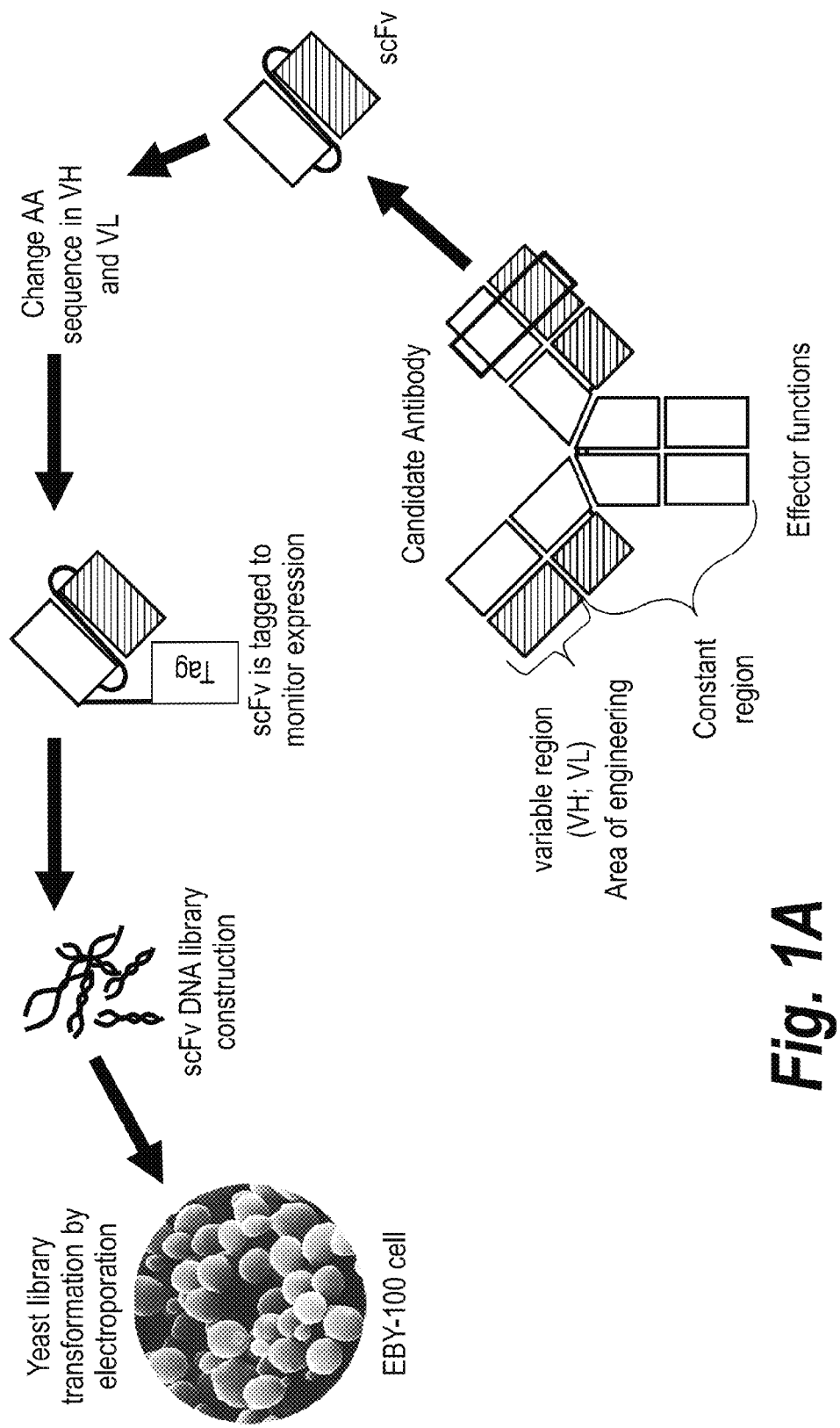
FIGS. 1A and 1B depict a general scheme for affinity maturation (AM) of a known antibody (Ab) sequence with binding affinity against a known target using Yeast Display (YD).
Figure 1B:
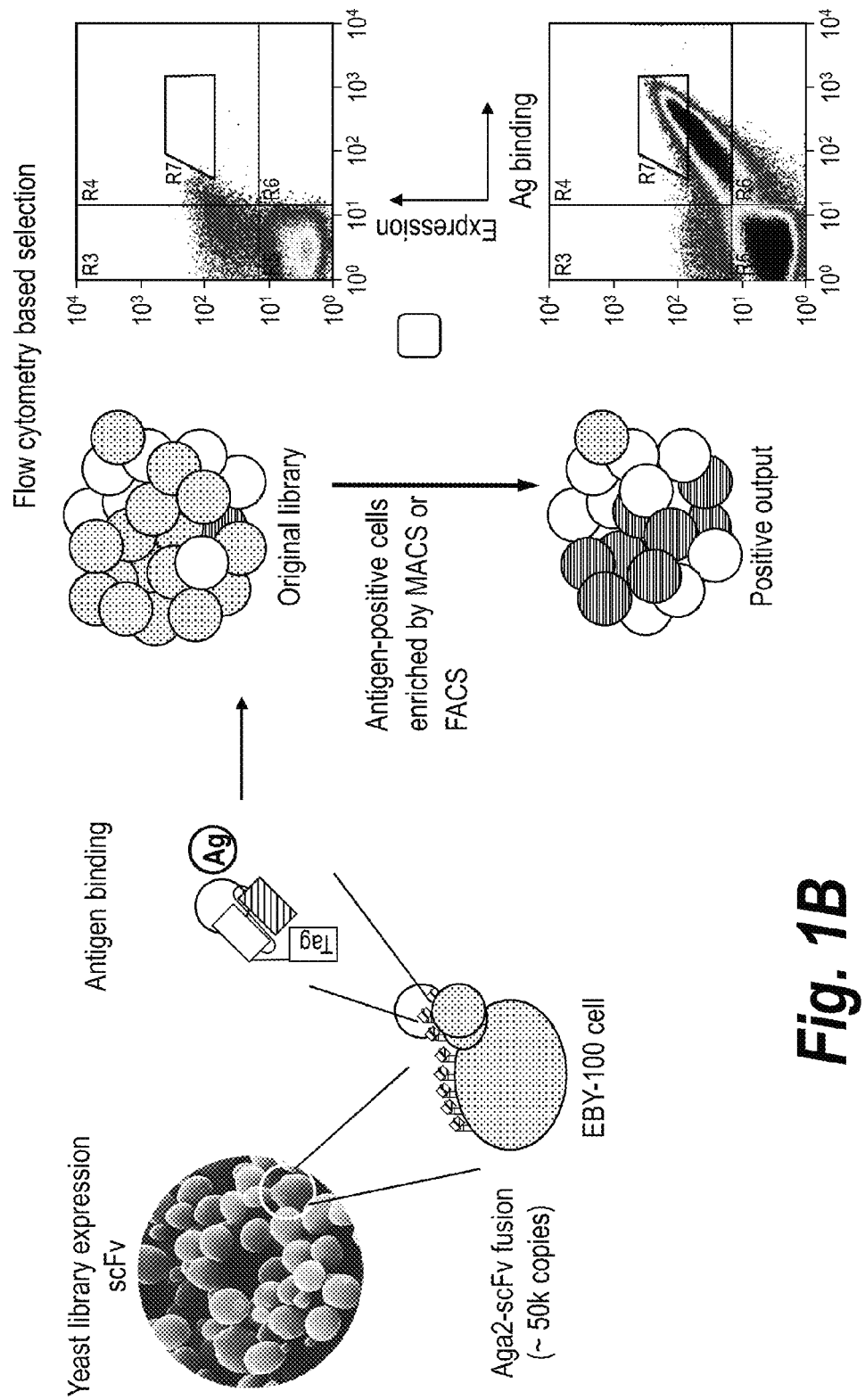
Figure 2A:
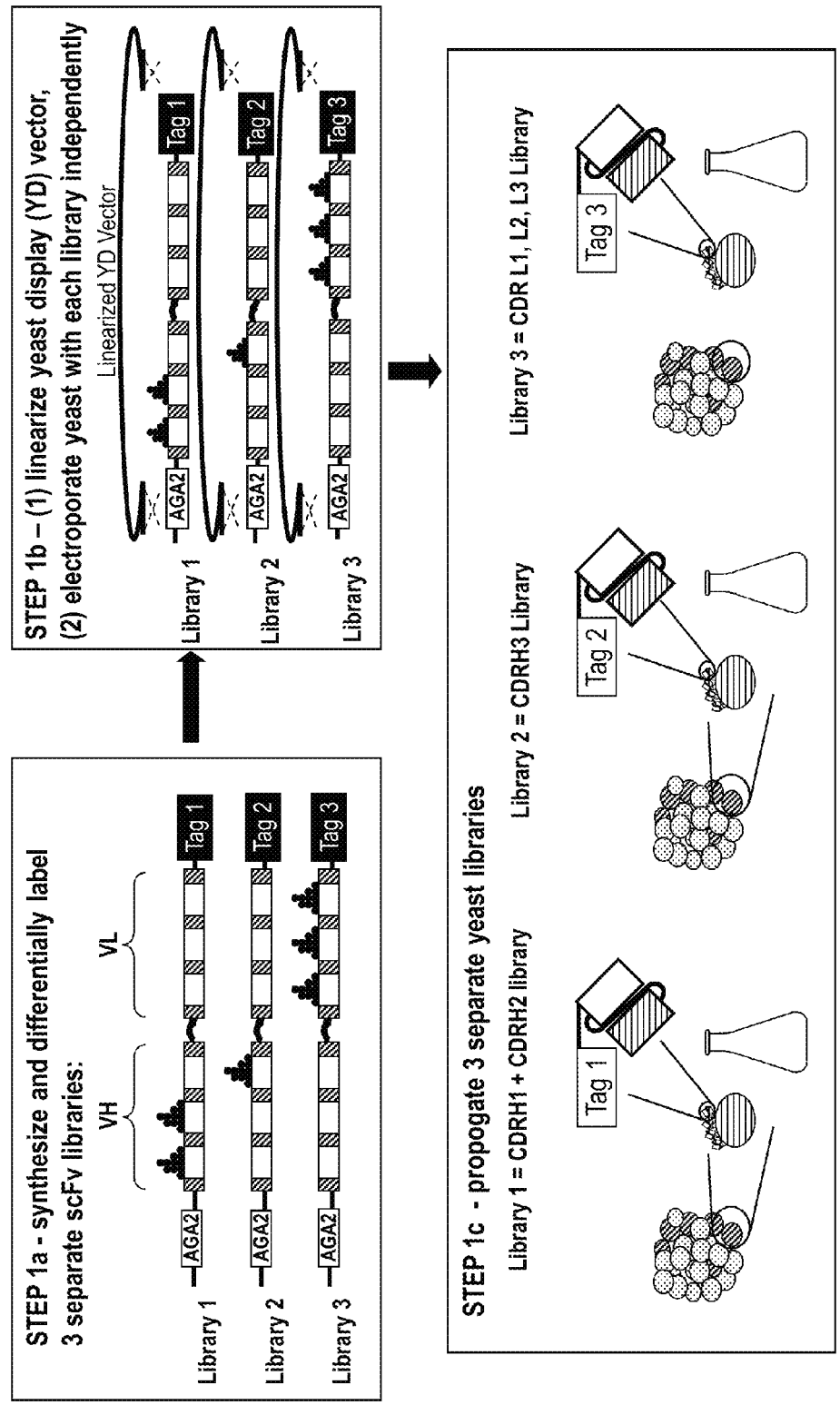
FIGS. 2A-D illustrate schematically an exemplary "multiplexing" process of the claimed invention.
Figure 2B:
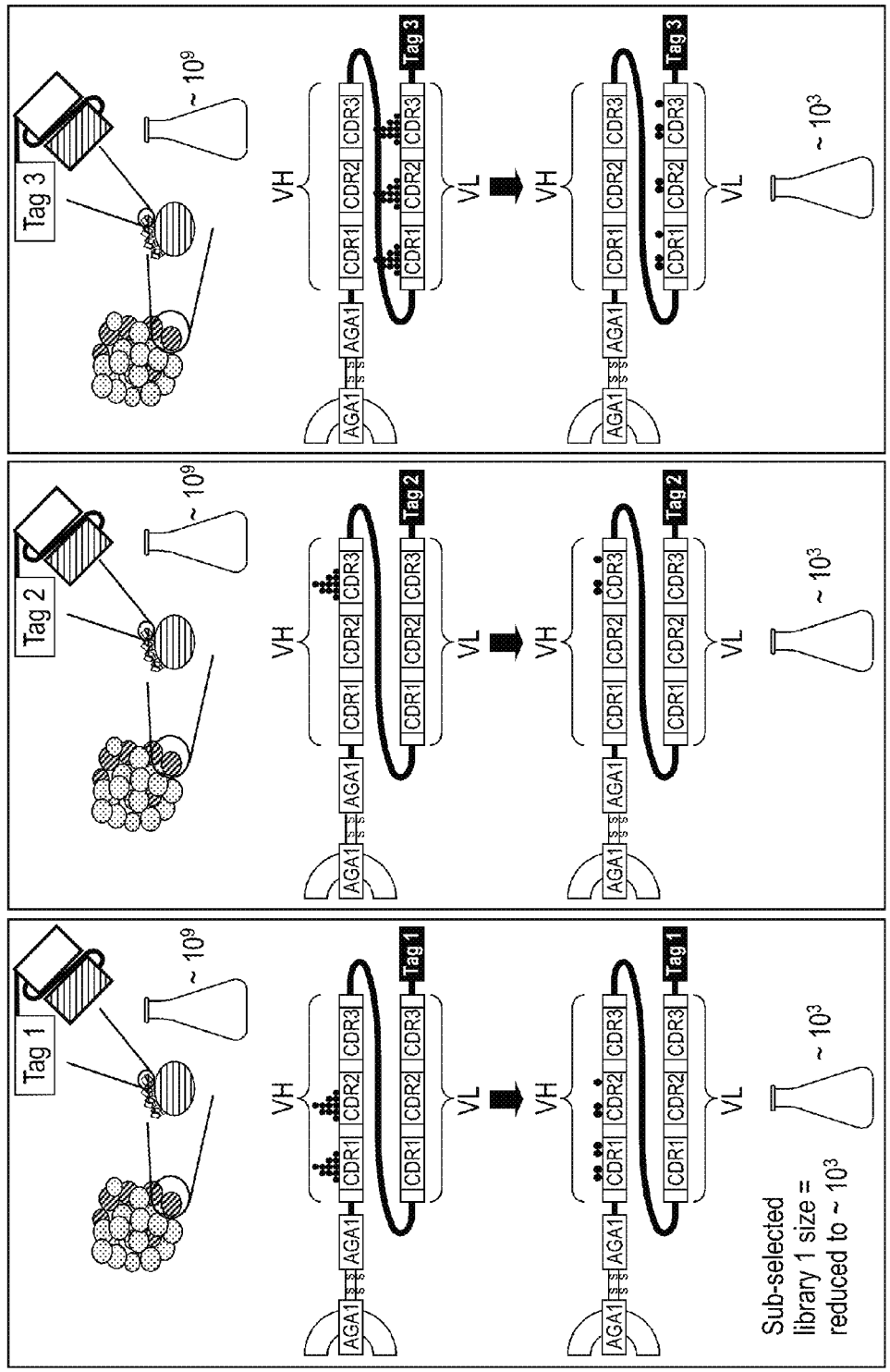
Figure 2C:
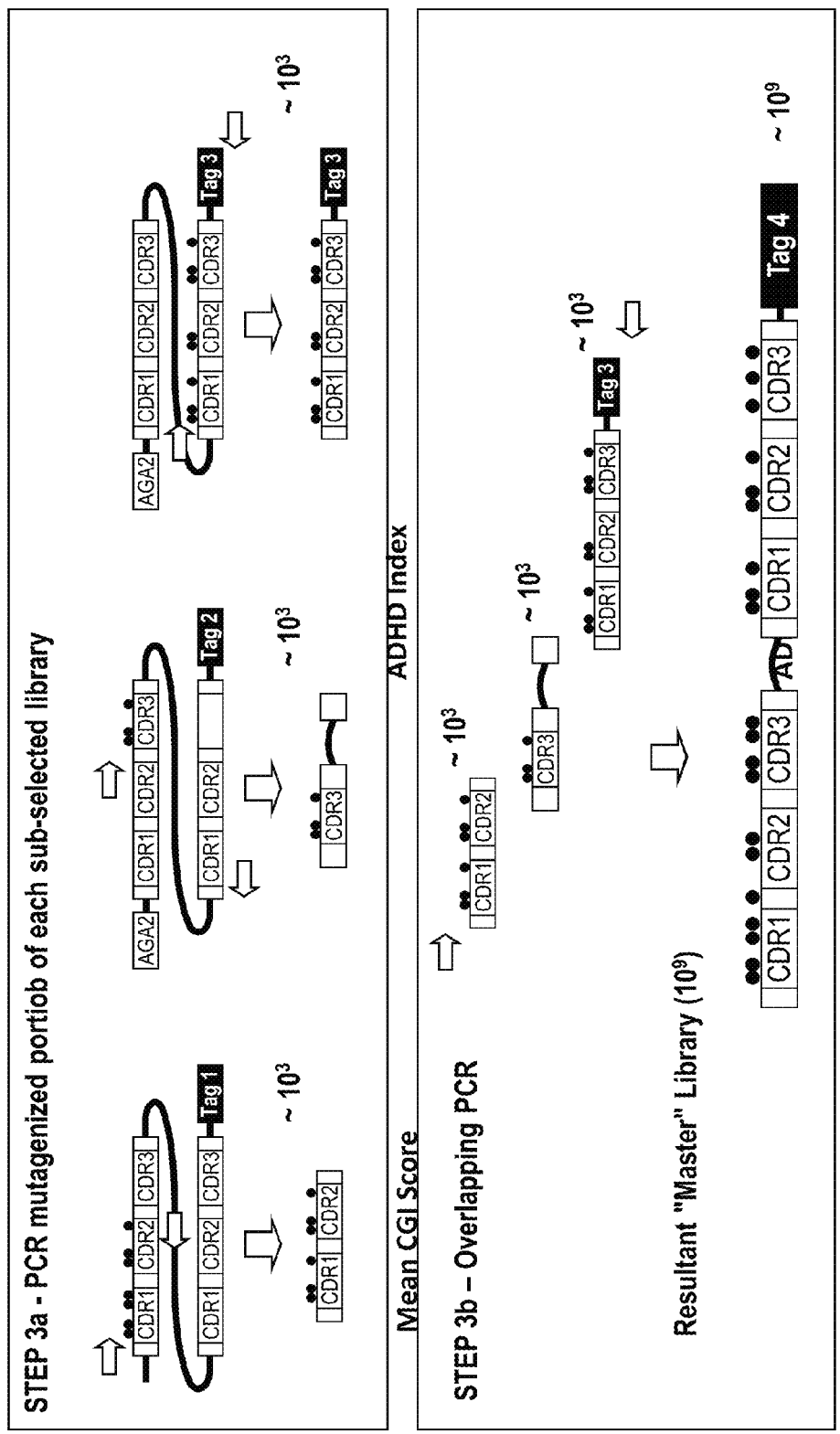
Figure 2D:
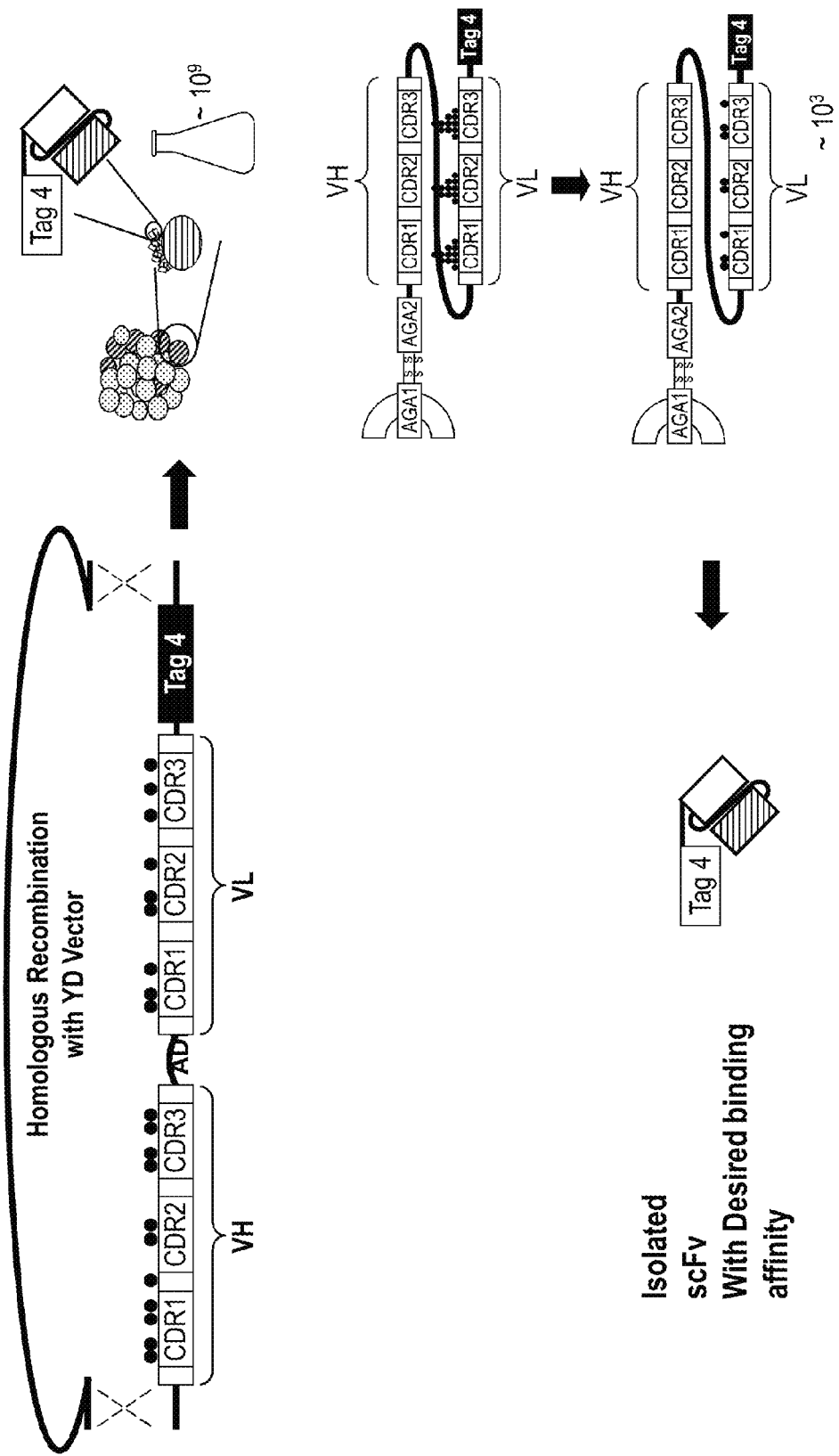

The present disclosure provides systems and methods for enhancing the throughput of antibody selection. Multiple DNA libraries encoding antibodies or their fragments are designed such that the encoded antibodies from different libraries are tagged differently. These libraries may be transformed into cells, including fungal cells. The variants of the antibodies may be displayed on the surface of the cells and flow cytometry may be used to sort the cells based on antigen binding affinity, binding kinetics, as well as different tags on the antibodies.

The present disclosure advances the art by providing systems and methods for enhancing the efficiency of in vitro antibody selection. Variants of one or more antibodies encoded by multiple libraries may be displayed on the extracellular surface of yeast cells. The libraries of antibodies may be incubated with a ligand (e.g., antigen) of interest. Antibodies bound to the antigen may be captured and differentially tagged antibodies from different libraries may be separated based on the different tags.

In one embodiment, the methods may include the step of introducing into a population of cells (or host cells) a library of polynucleotides that encode different variants (or mutants) of an antibody. The library of polynucleotides may be designed such that the encoded antibodies are displayed on the extracellular surface of the plasma membrane of the cells.

The host cells may be genetically engineered such that their glycosylation pathways are altered or modified to mimic those of the human immune cells. Examples of hosts may include but are not limited to phage, bacterial, yeast, or mammalian cells. In one aspect, the host cells are fungal cells. In another aspect, the fungal cells may be selected from the group consisting of *Saccharomyces cerevisiae*, *Saccharomyces carlsbergensis*, *Candida albicans*, *Candida kefyr*, *Candida tropicalis*, *Cryptococcus laurentii*, *Cryptococcus neoformans*, *Hansenula anomala*, *Hansenula polymorpha*, *Kluyveromyces fragilis*, *Kluyveromyces lactis*, *Kluyveromyces marxianus*, *Pichia pastoris*, *Rhodotorula rubra*, *Schizosaccharomyces pombe* and *Yarrowia lipolytica*. In another aspect, the host cells are of the genus *Saccharomyces*. In another aspect, the host cells are *Saccharomyces cerevisiae*.

The cells can also be bacterial or mammalian cells. Bacterial cells can include *E. coli*.

In another embodiment, at least two polynucleotide libraries are introduced into the population of cells by transformation. In one aspect, before the transformation, the cells may be a group (or population) of homogenous cells. After the transformation, the population of cells may become more heterogeneous with each transformed cells harboring at least one polynucleotide from the library.

In another embodiment, when two libraries of polynucleotides are used to transform the cells, the transformed cells may be categorized into two subpopulations of cells. The first subpopulation of cells may carry the first library of polynucleotides, while the second subpopulation of cells may carry the second library of polynucleotides. Selection methods may be used to select for cells that have been transformed and carry at least one polynucleotide from the libraries. In another aspect, selection methods may be used to select for cells that carry polynucleotide from one library but not polynucleotide from another library. It is to be understood that even under selection pressure, certain untransformed cells may survive even under selection pressure. In another aspect, other than the different exogenous polynucleotide(s) each subpopulation of cells carries, the first and the second subpopulation of cells may appear identical with respect to cell morphology.

In another embodiment, after transformation, the different subpopulations of cells may exist in the same culture and be allowed to grow under certain conditions such that the different antibodies encoded by the different polynucleotides are expressed and displayed on the outside surface of the cells. In one aspect, when the coding sequences of the antibodies are under control of a constitutive promoter, so that no specific induction is required to have the antibodies expressed. In another aspect, when the coding sequences of the antibodies are under control of an inducible promoter, certain conditions may be required to induce the expression of the antibodies. By way of example, the conditions that would allow the encoded antibodies to be expressed may include but are not limited to exposing the cells to a chemical, metabolic substrate, or temperature, among others.

In another embodiment, when at least two polynucleotide libraries are introduced into the cells, the first library of polynucleotides may encode variants of a first antibody or a fragment thereof, and a second library of polynucleotides may encode variants of a second antibody or a fragment thereof. Within each library, the variants may carry permutations of mutants clustered in the same complementarity determining region (CDR). Alternatively, the mutations in each library may span more than one CDR.

In one aspect, the first antibody and the second antibody may each have substantial affinity with a ligand of interest, for example, a protein antigen. For purpose of this disclosure, "substantial affinity" means interaction that is greater than non-specific interaction between two molecules. In another aspect, variants of the first antibody may carry mutations that are primarily located in a first CDR, and the variants of the second antibody may carry mutations that are primarily located in a second CDR, where the first CDR is different from said second CDR. In another aspect, the first CDR is the same as the second CDR and the one or more libraries encoded one or more antibody libraries that carry mutations all within the same CDR.

In one embodiment, the antibodies of the present disclosure may include a single chain variable fragment (ScFv). In another embodiment, the first antibody may contain a light chain variable fragment while the second antibody may contain a heavy chain variable fragment. In another embodiment, the variants of the first antibody may contain mutations in a light chain CDR, while the variants of the second antibody may contain mutations in a heavy chain CDR.

In another embodiment, the polynucleotide libraries may be designed such that the first antibodies are fused with a first detectable tag and the second antibodies are fused with a second detectable tag. In one aspect, the first detectable tag is different from the second detectable tag such that cells expressing the first antibodies and the second antibodies may be distinguished. Examples of such detectable tags include but are not limited to His, HA, c-myc, Flag, HSV, S, AcV5, E2, E, thioredoxin, GST, and StrepII tags.

Host cells displaying antibodies that possess a binding specificity for the antigen of interest may be identified by contacting the plurality of host cells with the antigen of interest and detecting the host cells that have the antigen of interest bound to the antibodies displayed thereupon. In one aspect, the antigen may be affixed to a fixed surface. In another aspect, the antigen may be attached to a substrate, such as, for example, a magnetic bead. In another aspect, the antigen may be fused with a detectable tag. In one aspect, the detectable tag fused to the antigen (or ligand) is different from the detectable tag fused to the antibodies.

In another embodiment, the plurality of host cells may be sorted based on the interaction between the antibodies and the ligand (e.g., antigen). In another aspect, when two or more libraries of polynucleotides are used for the selection process, the antibodies from the different libraries may be distinguished based on the different detectable tags each library of antibodies carries. For instance, when flow cytometry is used to sort the host cells, the gates may be set to distinguish the tags on the antigen, and the first and the second detectable tags on the different antibodies encoded by the different libraries of polynucleotides.

Thus, the host cells displaying an antibody or a fragment thereof with relatively high affinity with the antigen of interest may be identified and isolated using the methods disclosed here. In one embodiment, the processes of mixing the host cells with antigen and sorting may be repeated for one or more rounds until the cells displaying antibodies with the highest binding affinity and specificity are identified.

In one embodiment, a more effective yeast cell transformation process may be used to achieve larger antibody libraries. For instance, large antibody libraries with greater than $10^9$ independent clones may be constructed in yeast. This improved transformation process allows one to generate fewer antibody libraries for each antibody affinity maturation campaign. For example, 2-3 libraries may be sufficient for one antibody affinity maturation campaign as compared to more than 6 libraries as required previously. The improved transformation process may also enhance the ability to sample a greater diversity of antibody variants in each campaign. In various embodiments, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200, 300, 400, 500, 600, 700, 800, 900, 1000 or more libraries may be screened according to the methods disclosed herein.

In order to enhance the throughput of yeast display technology, a panel of expression vectors is constructed to enable multi-color FACS. Each individual antibody library may be barcoded (i.e., tagged). The barcoding or tagging can be achieved by any method known in the art. For example, a barcode or tag may be a unique peptide tag labeled by specific detecting reagents. Examples of peptide tags are provided above. The detecting reagents can be fluorochromes or fluorophores. After the multiple libraries of an antibody are expressed in the host cells, the cells may be pooled and simultaneously recognized as distinct populations by their colors on the cell sorter. The sorter may then parse up to a billion cells by their antigen binding affinity and barcoding peptide tags to separate tubes within a few hours. Thus, the disclosed system may help enhance library selection throughput by allowing multiplex library sort and analysis. Additionally, in conjunction with downstream molecular biology techniques, this multi-color cell sorting may provide a means to control the library cross-contamination and reduce loss in productivity due to cross-contamination.

Not only may libraries be distinctly tagged, but groups of libraries can also be simultaneously tagged. According to certain embodiments, a particular line of binding proteins may belong to more than one library. For example, multiple sub libraries may be part of one larger generic library. According to these embodiments, a binding protein includes a tag for every library of which it is a member. For example, a binding protein may be part of a main library and a sub-library. According to further embodiments, a binding protein could be a member of any number of sublibraries. A binding protein that is a member of a number of libraries can include a tag that represents its membership in each library. In certain embodiments, the binding proteins described herein include 1, 2, 3, 4, 5, 6, 7, 8, 9, 10, 11, 12, 13, 14, 15, 16, 17, 18, 19, 20 or more tags.

Fluorophores or fluorochromes that can be used according to the methods described herein include PerCP; R-PE; DyLight-488; Alexafluor 488; Alexafluor 633; APC; PE; DyLight-633; 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein; 5-Carboxytetramethylrhodamine (5 TAMRA); 5-Hydroxy Tryptamine (5-HAT); 5-ROX (carboxy-X-rhodamine); 6-Carboxyrhodamine 6G; 6-CR 6G; 6-JOE; 7-Amino-4-methylcoumarin; 7-Aminoactinomycin D (7-AAD); 7-Hydroxy-4-I methylcoumarin; 9-Amino-6-chloro-2-methoxyacridine (ACMA); ABQ; Acid Fuchsin; Acridine Orange; Acridine Red; Acridine Yellow; Acriflavin; Acriflavin Feulgen SITSA; Aequorin (Photoprotein); Alizarin Complexon; Alizarin Red; Allophycocyanin (APC); AMC, AMCA-S; Aminomethylcoumarin (AMCA); AMCA-X; Aminoactinomycin D; Aminocoumarin; Anilin Blue; Anthrocyl stearate; APC-Cy7; APTRA-BTC; APTS; Astrazon Brilliant Red 4G; Astrazon Orange R; Astrazon Red 6B; Astrazon Yellow 7 GLL; Atabrine; Auramine; Aurophosphine G; Aurophosphine; BAO 9 (Bisaminophenyloxadiazole); BCECF (high pH); BCECF (low pH); Berberine Sulphate; Beta Lactamase; BFP blue shifted GFP (Y66H); Blue Fluorescent Protein; BFP/GFP FRET; Bimane; Bisbenzemide; Bisbenzimide (Hoechst); bis-BTC; Blancophor FFG; Blancophor SV; Bodipy 492/515; Bodipy 493/503; Bodipy 500/510; Bodipy; 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/

676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; Brilliant Sulphoflavin FF; BTC; BTC-5N; Calcein; Calcein Blue; Calcium Crimson; Calcium Green; Calcium Green-1$Ca^{2+}$ Dye; Calcium Green-2 $Ca^{2+}$; Calcium Green-5N $Ca^{2+}$; Calcium Green-C18 $Ca^{2+}$; Calcium Orange; Calcofluor White; Carboxy-X-rhodamine (5-ROX); Cascade Blue™; Cascade Yellow; Catecholamine; CCF2 (GeneBlazer); CFDA; CFP (Cyan Fluorescent Protein); CFP/YFP FRET; Chlorophyll; Chromomycin A; Chromomycin A; CL-NERF; CMFDA; Coelenterazine; Coelenterazine cp; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM I Methylcoumarin; CTC; CTC Formazan; Cy2®; Cy3.1 8®; Cy3.5®; Cy3®; Cy5.1 8®; Cy5.5®; Cy5®; Cy7®; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3'DCFDA; DCFH (Dichlorodihydrofluorescein Diacetate); DDAO; DHR (Dihydrorhodamine 123); Di-4-ANEPPS; Di-8-ANEPPS (non-ratio); DiA (4-Di 16-ASP); Dichlorodihydrofluorescein Diacetate (DCFH); DiD-Lipophilic Tracer; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (111) chloride; EYFP; Fast Blue; FDA; Feulgen (Pararosaniline); FIF (Formaldehyd Induced Fluorescence); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; Fluor X; Fura Red® (high pH); Fura Red®/Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer; (CCF2); GFP (S65T); GFP red shifted (rsGFP); GFP wild type' non-UV excitation (wtGFP); GFP wild type, UV excitation (wtGFP); GFPuv; Gloxalic Acid; Granular blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1, high calcium; Indo-1 low calcium; Indodicarbocyanine (DiD); Indotricarbocyanine (DiR); Intrawhite Cf; JC-1; JO JO-1; JO-PRO-1; LaserPro; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; I Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxedidole; Noradrenaline; Nuclear Fast Red; i Nuclear Yellow; Nylosan Brilliant lavin EBG; Oregon Green™; Oregon Green® 488; Oregon Green® 500; Oregon Green® 514; Pacific Blue; Pararosaniline (Feulgen); PBFI; PE-Cy5; PE-Cy7; PerCP; PerCP-Cy5.5; PE-TexasRed (Red 613); Phloxin B (Magdala Red); Phorwite AR; Phorwite BKL; Phorwite Rev; Phorwite RPA; Phosphine 3R; PhotoResist; Phycoerythrin B [PE]; Phycoerythrin R [PE]; PKH26 (Sigma); PKH67; PMIA; Pontochrome Blue Black; POPO-1; POPO-3; PO-PRO-1; PO-I PRO-3; Primuline; Procion Yellow; Propidium lodid (P1); PyMPO; Pyrene; Pyronine; Pyronine B; Pyrozal Brilliant Flavin 7GF; QSY 7; Quinacrine Mustard; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine: Phalloidine; Rhodamine Red; Rhodamine WT; Rose Bengal; R-phycocyanine; R-phycoerythrin (PE); rsGFP; S65A; S65C; S65L; S65T; Sapphire GFP; SBFI; Serotonin; Sevron Brilliant Red 2B; Sevron Brilliant Red 4G; Sevron I Brilliant Red B; Sevron Orange; Sevron Yellow L; sgBFP® (super glow BFP); sgGFP™ (super glow GFP); SITS (Primuline; Stilbene Isothiosulphonic Acid); SNAFL calcein; SNAFL-1; SNAFL-2; SNARF calcein; SNARFI; Sodium Green; SpectrumAqua; SpectrumGreen; SpectrumOrange; Spectrum Red; SPQ (6-methoxy-N-(3 sulfopropyl) quinolinium); Stilbene; Sulphorhodamine B and C; Sulphorhodamine Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Reds; Texas Red-X™ conjugate; Thiadicarbocyanine (DiSC3); Thiazine Red™; Thiazole Orange; Thioflavin 5; Thioflavin S; Thioflavin TON; Thiolyte; Thiozole Orange; Tinopol CBS (Calcofluor White); TIER; TO-PRO-1; TO-PRO-3; TO-PRO-5; TOTO-1; TOTO-3; TriColor (PE-Cy5); TRITC TetramethylRodamineIsoThioCyanate; True Blue; Tru Red; Ultralite; Uranine B; Uvitex SFC; wt GFP; WW 781; X-Rhodamine; XRITC; Xylene Orange; Y66F; Y66H; Y66W; Yellow GFP; YFP; YO-PRO-1; YO-PRO3; YOYO-1; YOYO-3; Sybr Green; Thiazole orange (interchelating dyes); semiconductor nanoparticles such as quantum dots; or caged fluorophores (which can be activated with light or other electromagnetic energy source), or a combination thereof.

For purpose of the present disclosure, an antibody may contain a heavy chain or fragment thereof, a light chain or fragment thereof, or both heavy chain(s) and light chain(s). In another embodiment, the antibody to be displayed on the surface of a host cells may further include an amino acid sequence that targets the antibody or a fragment thereof to the extracellular surface of the plasma membrane.

In one embodiment, the antibody of this disclosure may contain a full length heavy chain fused to an amino acid sequence that targets the antibody to the extracellular surface of the plasma membrane. The antibody may further include a full length light chain. In another embodiment, the amino acid sequence that targets the antibody of this disclosure to the extracellular surface of the plasma membrane may be a transmembrane domain. By way of example, the transmembrane domain may be the GPI anchor domain. The antibody of this disclosure may also include the variable regions of the heavy and light chains forming a single-chain variable fragment (scFv).

The disclosure further relates to a vector containing polynucleotides that encode an antibody or a fragment thereof that may be displayed on the extracellular surface of the plasma membrane of a cell such as a yeast cell. In one embodiment, a vector of the disclosure is operable in a host cell to direct the expression and the display of an antibody or a fragment thereof on the extracellular surface of the plasma membrane.

It is to be noted that, as used in this specification and the claims, the singular forms "a," "an," and "the" include plural referents unless the context clearly dictates otherwise. Thus, for example, reference to "a molecule" includes reference to a mixture of two or more molecules. The terms "between" and "at least" as used herein are inclusive. For example, a range of "between 5 and 10" means any amount equal to or greater than 5 but equal to or smaller than 10.

Definitions

The term "antibody", as used herein, includes monoclonal antibodies (including full length monoclonal antibodies), polyclonal antibodies, multispecific antibodies (e.g., bispecific antibodies), chimeric antibodies, complementarity determining regions (CDR) grafted antibodies, humanized antibodies, human antibodies and antigen-binding fragments thereof, for example, an antibody light chain ($V_L$), an antibody heavy chain ($V_H$), a single chain antibody (scFv), a F(ab')$_2$ fragment, a Fab fragment, an Fd fragment, an Fv fragment, and a single domain antibody fragment (DAb). The term "immunoglobulin" may be used synonymously with antibody.

The term "chimeric antibody" is used to describe a protein comprising at least an antigen-binding portion of an immunoglobulin molecule that is attached by, for example, a peptide bond or peptide linker, to a heterologous protein or a peptide thereof. The "heterologous" protein can be a non-immunoglobulin or a portion of an immunoglobulin of a different species, class or subclass.

The term "complementarity determining region (CDR)" is used to describe hypervariable regions located in the $V_L$ and $V_H$ domains of antibodies. These regions often form the antigen binding site of the antibody.

The term "isolated antibody", as used herein, includes an antibody that has been identified and separated and/or recovered from a component of its natural environment. Contaminant components of its natural environment are materials which would interfere with diagnostic or therapeutic uses for the antibody, and may include enzymes, hormones, and other proteinaceous or non-proteinaceous solutes.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies.

The terms "dual variable domain immunoglobulin" or "DVD-Ig" refer to the multivalent binding proteins disclosed in, e.g., U.S. Pat. No. 8,258,268, which is herein incorporated by reference in its entirety. The terms "dual variable domain (DVD) binding protein" and "dual variable domain immunoglobin" refer to a binding protein that has at least two variable domains in each of its one or more binding arms (e.g., a pair of HC/LC)(see PCT Publication No. WO 02/02773). Each variable domain is able to bind to an antigen/ligand. In an embodiment, each variable domain binds different antigens/ligands or epitopes. In another embodiment, each variable domain binds the same antigen/ligand or epitope. In another embodiment, a dual variable domain binding protein has two identical antigen/ligand binding arms, with identical specifity and identical VD sequences, and is bivalent for each antigen to which it binds. In an embodiment, the DVD binding proteins may be monospecific, i.e., capable of binding one antigen/ligand or multispecific, i.e., capable of binding two or more antigens/ligands. DVD binding proteins comprising two heavy chain DVD polypeptides and two light chain DVD polypeptides are referred to as a DVD-Ig™. In an embodiment, each half of a four chain DVD binding protein comprises a heavy chain DVD polypeptide, and a light chain DVD polypeptide, and two variable domain binding sites. In an embodiment, each binding site comprises a heavy chain variable domain and a light chain variable domain with a total of 6 CDRs involved in antigen binding per antigen binding site. In a specific embodiment of the present invention, at least one binding site comprises a receptor binding site, capable of binding one or more receptor ligands.

The term "monovalent binding protein" refers to a binding protein comprising one antigen (ligand) binding site for each antigen. The term "multivalent binding protein" means a binding protein comprising two or more antigen (ligand) binding sites for the same antigen. In an embodiment, the multivalent binding protein is engineered to have three or more antigen binding sites, and is not a naturally occurring antibody. The term "multispecific binding protein" refers to a binding protein capable of binding two or more related or unrelated targets. In an embodiment, a monovalent binding proteins may be multispecific in that it possess one binding domain for each of the different target antigens.

The terms "single chain dual variable domain immunoglobulin" or "scDVD-Ig™" or scFvDVDIg™" refer to the antigen binding fragment of a DVD molecule that is analogous to an antibody single chain Fv fragment. scDVD-Ig™ are described in U.S. Ser. No. 61/746,659, incorporated herein by reference in its entirety. scDVD-Ig™ are generally of the formula VH1-(X1)n-VH2-X2-VL1-(X3)n-VL2 or VL1-(X1)n-VL2-X2-VH1-(X3)n-VH2, where VH1 is a first antibody heavy chain variable domain, X1 is a linker with the proviso that it is not a constant domain, VH2 is a second antibody heavy chain variable domain, X2 is a linker, VL1 is a first antibody light chain variable domain, X3 is a linker with the proviso that it is not a constant domain, VL2 is a second antibody light chain variable domain, and n is 0 or 1, where the VH1 and VL1, and the VH2 and VL2 respectively combine to form two functional antigen binding sites.

The terms "single chain dual variable domain Fab immunoglobulin" or "scDVDFab-Ig™" or scFvDVDFabIg™" refer to the antigen binding fragment of a DVD molecule that is analogous to an antibody Fab fragment. scDVD-IgFab™ are described in U.S. Ser. No. 61/746,659, incorporated herein by reference in its entirety. scDVD-IgFab™ are generally of the formula CH1-X0-VH1-(X1)n-VH2-X2-CL1-X4-VL1-(X3)n-VL2 or CL1-X0-VL1-(X1)n-VL2-X2-CH1-X4-VH1-(X3)n-VH2, wherein CH1 is a heavy chain constant domain, X0 is a linker with the proviso that it is not a constant domain, VH1 is a first antibody heavy chain variable domain, X1 is a linker with the proviso that it is not a constant domain, VH2 is a second antibody heavy chain variable domain, X2 is a linker, CL1 is a light chain heavy domain, X4 is a linker with the proviso that it is not a constant domain, VL1 is a first antibody light chain variable domain, X3 is a linker with the proviso that it is not a constant domain, VL2 is a second antibody light chain variable domain, and n is 0 or 1, and wherein the VH1 and VL1, and the VH2 and VL2 respectively combine to form two functional antigen binding sites. Optionally, the CL1 domain can be a kappa (hcκcor cκ) or a lambda (haλcor cλ) constant domain. In certain embodiments, CL1 is cκ.

The terms "DVD-Fab" or fDVD-Ig™" refer to the antigen binding fragment of a DVD-Ig™ molecule that is analogous to an antibody Fab fragment. fDVD-Ig™ are described in U.S. Ser. No. 61/746,663, incorporated herein by reference in its entirety. In certain embodiments, fDVD-Ig™ include a first polypeptide chain having the general formula VH1-(X1)n-VH2-C-(X2)n, wherein VH1 is a first heavy chain variable domain, X1 is a linker with the proviso that it is not a constant domain, VH2 is a second heavy chain variable domain, C is a heavy chain constant domain, X2 is a cell surface protein, and n is 0 or 1, and wherein the amino acid sequences of VH1, VH2 and/or X1 independently vary within the library. In certain embodiments, the fDVD-Ig™ also include a second polypeptide chain having the general formula VL1-(Y1)n-VL2-C, wherein VL1 is a first light chain variable domain, Y1 is a linker with the proviso that it is not a constant domain, VL2 is a second light chain variable domain, C is a light chain constant domain, n is 0 or 1, wherein the VH1 and VH2 of the first polypeptide chain and VL1 and VL2 of second polypeptide chains of the binding protein combine form two functional antigen binding sites. In certain embodiments, the first and second polypeptide chains combine to form a fDVD-Ig™.

The terms multi-specific and multivalent IgG-like molecules or "pDVD-Ig™" are capable of binding two or more proteins (e.g., antigens). pDVD-Ig™ are described in U.S. Ser. No. 61/746,617, incorporated herein by reference in its entirety. In certain embodiments, pDVD-Ig™ are disclosed which are generated by specifically modifying and adapting several concepts. These concepts include but are not limited to: (1) forming Fc heterodimer using CH3 "knobs-into-holes" design, (2) reducing light chain missing pairing by using CH1/CL cross-over, and (3) pairing two separate half IgG molecules at protein production stage using "reduction then oxidation" approach.

In one embodiment, a pDVD-Ig™ construct may be created by combining two halves of different DVD-Ig™ molecules, or a half DVD-Ig™ and half IgG molecule. A pDVD-Ig™ construct may be expressed from four unique constructs to create a monovalent, multi-specific molecules through the use of heavy chain CH3 knobs-into-holes design. In another embodiment, a pDVD-Ig™ construct may contain two distinct light chains, and may utilize structural modifications on the Fc of one arm to ensure the proper pairing of the light chains with their respective heavy chains. In one aspect, the heavy chain constant region CH1 may be swapped with a light chain constant region hCk on one Fab. In another aspect, an entire light chain variable region, plus hCk, may be swapped with a heavy chain variable region, plus CH1. pDVD-Ig™ construct vectors that accommodate these unique structural requirements are also disclosed.

In some embodiments, pDVD-Ig™ contain four polypeptide chains, namely, first, second, third and fourth polypeptide chains. In one aspect, the first polypeptide chain may contain VD1-(X1)n-VD2-CH-(X2)n, wherein VD1 is a first heavy chain variable domain, VD2 is a second heavy chain variable domain, CH is a heavy chain constant domain, X1 is a linker with the proviso that it is not a constant domain, and X2 is an Fc region. In another aspect, the second polypeptide chain may contain VD1-(X1)n-VD2-CL-(X2)n, wherein VD1 is a first light chain variable domain, VD2 is a second light chain variable domain, CL is a light chain constant domain, X1 is a linker with the proviso that it is not a constant domain, and X2 does not comprise an Fc region. In another aspect, the third polypeptide chain may contain VD3-(X3)n-VD4-CL-(X4)n, wherein VD3 is a third heavy chain variable domain, VD4 is a fourth heavy chain variable domain, CL is a light chain constant domain, X3 is a linker with the proviso that it is not a constant domain, and X4 is an Fc region. In another aspect, the fourth polypeptide chain may contain VD3-(X3)n-VD4-CH-(X4)n, wherein VD3 is a third light chain variable domain, VD4 is a fourth light chain variable domain, CH is a heavy chain constant domain, X3 is a linker with the proviso that it is not a constant domain, and X4 does not comprise an Fc region. In another aspect, n is 0 or 1, and the VD1 domains on the first and second polypeptide chains form one functional binding site for antigen A, the VD2 domains on the first and second polypeptide chains form one functional binding site for antigen B, the VD3 domains on the third and fourth polypeptide chains form one functional binding site for antigen C, and the VD4 domains on the third and fourth polypeptide chains form one functional binding site for antigen D. In one embodiment, antigens A, B, C and D may be the same antigen, or they may each be a different antigen. In another embodiment, antigens A and B are the same antigen, and antigens C and D are the same antigen.

As used herein "monobody DVD-Ig™" or "mDVD-Ig™" refers to a class of binding molecules wherein one binding arm has been rendered non-functional. mDVD-Ig™ are described in U.S. Ser. No. 61/746,615, incorporated herein by reference in its entirety. In one aspect, mDVD-Ig™ possesses only one functional arm capable of binding a ligand. In another aspect, the one functional arm may have one or more binding domains for binding to different ligands. The ligand may be a peptide, a polypeptide, a protein, an aptamer, a polysaccharide, a sugar molecule, a carbohydrate, a lipid, an oligonucleotide, a polynucleotide, a synthetic molecule, an inorganic molecule, an organic molecule, and combinations thereof.

In one embodiment, mDVD-Ig™ contains four polypeptide chains, wherein two of the four polypeptide chains comprise VDH-(X1)n-C-(X2)n. In one aspect, VDH is a heavy chain variable domain, X1 is a linker with the proviso that it is not CH1, C is a heavy chain constant domain, X2 is an Fc region, and n is 0 or 1. The other two of the four polypeptide chains comprise VDL-(X3)n-C-(X4)n, wherein VDL is a light chain variable domain, X3 is a linker with the proviso that it is not CH1, C is a light chain constant domain, X4 does not comprise an Fc region, and n is 0 or 1. In another aspect, at least one of the four polypeptide chains comprises a mutation located in the variable domain, wherein the mutation inhibits the targeted binding between the specific antigen and the mutant binding domain.

The Fc regions of the two polypeptide chains that have a formula of VDH-(X1)n-C-(X2)n may each contain a mutation, wherein the mutations on the two Fc regions enhance heterodimerization of the two polypeptide chains. In one aspect, knobs-into-holes mutations may be introduced into these Fc regions to achieve heterodimerization of the Fc regions. See Atwell et al. J. Mol. Biol. 1997, 270: 26-35.

As used herein "cross-over DVD-Ig™" or "coDVD-Ig™" refers to a DVD-Ig™ wherein the cross-over of variable domains is used to resolve the issue of affinity loss in the inner antigen-binding domains of some DVD-Ig™ molecules. coDVD-Ig™ are described in U.S. Ser. No. 61/746,619, incorporated herein by reference in its entirety. In certain specific embodiments, cross-over dual-variable-domain (DVD) Igs are generated by crossing over light chain and the heavy chain variable domains of a dual-variabledomain (DVD) Ig or Ig like protein. In another aspect, the length and sequence of the linkers linking the variable domains may be optimized for each format and antibody sequence/structure (frameworks) to achieve desirable properties. The disclosed concept and methodology may also be extended to Ig or Ig like proteins having more than two antigen binding domains.

In certain embodiments, the binding protein of the invention is a "half-DVD-Ig"™ derived from a DVD-Ig™ or any of the formats described herein, including a fDVD-Ig, pDVD-Ig, mDVD-Ig and coDVD-Ig. The half-DVD-Ig™ preferably does not promote cross-linking observed with naturally occurring antibodies which can result in antigen clustering and undesirable activities. See U.S. patent publication number 20120201746 published Aug. 9, 2012, and international publication number WO/2012/088302 published Jun. 28, 2012, each of which is incorporated by reference herein in its entirety.

The term "antigen", as used herein, includes an entity (e.g., a proteinaceous entity or peptide) to which an antibody specifically binds, and includes, e.g., a predetermined antigen to which both a parent antibody and modified antibody as herein defined bind. The target antigen may be polypeptide, carbohydrate, nucleic acid, lipid, hapten, or other naturally occurring or synthetic compound. Preferably, the target antigen is a polypeptide. The term "ligand" is synonymous with antigen.

The term, "antigen-specific" as used herein refers to an interaction between the CDR regions of the immunoglobulin molecule with an epitope of the antigen wherein the CDR regions of the immunoglobulin molecule binds to the epitope.

The terms "cell", "cell line", "cell culture", or "host cell", as used herein, includes "transformants", "transformed cells", or "transfected cells" and progeny thereof. Host cells within the scope of the disclosure include prokaryotic cells such as E. coli, lower eukaryotic cells such as yeast cells, and higher eukaryotic cells such as vertebrate cells, for example, mammalian cells.

For purpose of this disclosure, the term "polynucleotide library" or "library of polynucleotides" refers to a heterogeneous population of polynucleotides encoding a heterogeneous population of antibodies or a fragment thereof. The term "antibody library" or "library of antibodies" refers to the heterogeneous population of antibodies encoded by the polynucleotide library. In one embodiment, the antibodies or fragment thereof may include heterogeneous population of heavy chain variable regions. In another embodiment, the antibodies or fragment thereof may include a heterogeneous population of light chain variable regions. In another embodiment, the antibodies or fragment thereof may include a heterogeneous population of Fc regions. In another embodiment, the antibodies or fragment thereof may include a single chain variable fragment (ScFv).

The term "Immunoglobulin G" or "IgG" as used herein, are antibody molecules each composed of four peptide chains, two heavy chains and two light chains. Each IgG has two antigen binding sites. Other immunoglobulins, e.g., IgM, may be described in terms of polymers with the IgG structure considered the monomer. IgG molecules are synthesized and secreted by plasma B cells. IgG antibodies are molecules of about 150 kDa composed of four peptide chains. They contain two identical heavy chains of about 50 kDa and two identical light chains of about 25 kDa, thus they have a tetrameric quaternary structure. The two heavy chains are linked to each other and to a light chain each by disulfide bonds. The resulting tetramer has two identical halves, which together form the Y-like shape. Each end of the fork contains an identical antigen binding site. There are four IgG subclasses (IgG1, 2, 3, and 4).

The term "specifically binds," means that an antibody or antigen-binding fragment thereof forms a complex with an antigen that is relatively stable under physiologic conditions. Specific binding can be characterized by a dissociation constant of at least about $1\times10^{-6}$ M or smaller. In other embodiments, the dissociation constant is at least about $1\times10^{-7}$ M, $1\times10^{-8}$ M, or $1\times10^{-9}$ M. Methods for determining whether two molecules specifically bind are well known in the art and include, for example, equilibrium dialysis, surface plasmon resonance, and the like.

ABBREVIATIONS

Ab—Antibody
Ag—Antigen
APC—Allophycocyanin
DNA—deoxyribonucleic acid
ELISA—Enzyme Linked Immunosorbent Assay
FACS—flourescence-activated cell sorting
IgG—Immunoglobulin Gamma
IgM—Immunoglobulin Mu
MAb—Monoclonal Antibody
PCR—polymerase chain reaction
PE-R—Phycoerythrin
SA—Streptavidin In certain embodiments, the diverse library of binding proteins comprises a polypeptide chain having the general formula (VL1-(X1)n-VL2-X2-VH1-(X3)n-VH2, wherein VL1 is a first antibody light chain variable domain, X1 is a linker with the proviso that it is not a constant domain, VL2 is a second antibody light chain variable domain, X2 is a linker, VH1 is a first antibody heavy chain variable domain, X3 is a linker with the proviso that it is not a constant domain, VH2 is a second antibody heavy chain variable domain, and n is 0 or 1, wherein the VH1 and VL1, and the VH2 and VL2 respectively combine to form two functional antigen binding sites, and wherein the amino acid sequences of VL1, X1, VL2, X2, VH1, X3, and/or VH2 independently vary within the library.

In certain embodiments, the diverse library of binding proteins comprises a polypeptide chain having the general formula CL1-X0-VL1-(X1)n-VL2-X2-CH1-X4-VH1-(X3)n-VH2, wherein CL1 is a light chain constant domain, X0 is a linker with the proviso that it is not a constant domain, VL1 is a first antibody light chain variable domain, X1 is a linker with the proviso that it is not a constant domain, VL2 is a second antibody light chain variable domain, X2 is a linker, CH1 is a heavy chain constant domain, X4 is a linker with the proviso that it is not a constant domain, VH1 is a first antibody heavy chain variable domain, X3 is a linker with the proviso that it is not a constant domain, VH2 is a second antibody heavy chain variable domain, and n is 0 or 1, and wherein the VH1 and VL1, the VH2 and VL2 respectively combine to form two functional antigen binding site, and wherein the amino acid sequences of VH1, X1, VH2, X2, VL1, X3, and/or VL2 independently vary within the library. In certain embodiments, the CL1 light chain. Optionally, the CL1 domain can be a kappa (hcκcor cκ) or a lambda (haλor cλ) constant domain. In certain embodiments, CL1 is cκ.

In certain embodiments, X2 is a GS-rigid linker sequence. The GS rigid linker sequence can comprise an amino acid sequence selected from the sequences shown in FIG. 23B.

In certain embodiments, each binding proteins further comprises a cell surface anchoring moiety linked to the N or C terminus. In certain embodiments, the anchoring moiety is a cell surface protein. In one embodiment, the anchoring moiety is Aga2p.

In certain embodiments, the polypeptide chain is a scDVD or scDVDFab.

In certain embodiments, the amino acid sequence of at least one CDR of VH1, VH2, VL1or VL2 independently varies within the library. In one embodiment, the amino acid sequence of HCDR3 of VH1, VH2 independently vary within the library. In one embodiment, the amino acid sequence of HCDR1 and HCDR2 of VH1 or VH2 independently vary within the library. In one embodiment, the amino acid sequence of HCDR1, HCDR2 and HCDR3 of VH1 orVH2 independently vary within the library. In one embodiment, the amino acid sequence of HCDR3 of VL1 or VL2 independently vary within the library. In one embodiment, the amino acid sequence of HCDR1 and HCDR2 of VL1 or VL2 independently vary within the library. In one embodiment, the amino acid sequence of HCDR1, HCDR2 and HCDR3 of VL1 or VL2 independently vary within the library. In certain embodiments, X1 independently varies within the library. In certain embodiments, X2 independently varies within the library and wherein X2 is $(G_4S)n$, where n=1-10 (SEQ ID NO: 1). In certain embodiments, the library of binding proteins share at least 70, 75, 80, 85, 90, 95, 96, 97, 98, or 99 amino acid sequence identity with a reference binding protein. In certain embodiments, VH1 and VH2 of the reference binding protein specifically bind to different antigens.

Libraries of Binding Proteins
scDVD

In one aspect, the disclosure provides libraries of single-chain multivalent binding proteins (e.g., scDVD molecules). Such libraries are particularly useful for selecting multivalent binding proteins with improved properties relative to a reference binding molecule (e.g., improved binding kinetics or thermostability).

In certain embodiments, the library of binding proteins comprises a polypeptide chain having the general formula VH1-(X1)n-VH2-X2-VL1-(X3)n-VL2, wherein VH1 is a first heavy chain variable domain, X1 is a linker with the proviso that it is not a constant domain, VH2 is a second heavy chain variable domain, X2 is a linker, VL1 is a first light chain variable domain, X3 is a linker with the proviso that it is not a constant domain, VL2 is a second light chain variable domain, and n is 0 or 1, wherein the VH1 and VL1, and the VH2 and VL2 respectively combine to form two functional antigen binding sites, and wherein the amino acid sequences of VH1, X1, VH2, X2, VL1, X3, and/or VL2 independently vary within the library. In one embodiment, the polypeptide chain is a scDVD.

In certain embodiments, the diverse library of binding proteins comprises a polypeptide chain having the general formula CH1-X0-VH1-(X1)n-VH2-X2-CL1-X4-VL1-(X3)n-VL2, wherein CH1 is a heavy chain constant domain, X0 is a linker with the proviso that it is not a constant domain, VH1 is a first antibody heavy chain variable domain, X1 is a linker with the proviso that it is not a constant domain, VH2 is a second antibody heavy chain variable domain, X2 is a linker, CL1 is a light chain constant domain, X4 is a linker with the proviso that it is not a constant domain, VL1 is a first antibody light chain variable domain, X3 is a linker with the proviso that it is not a constant domain, VL2 is a second antibody light chain variable domain, and n is 0 or 1, and wherein the VH1 and VL1, the VH2 and VL2 respectively combine to form two functional antigen binding sites, and wherein the amino acid sequences of VH1, X1, VH2, X2, VL1, X3, and/or VL2 independently vary within the library. Optionally, the CL1 domain can be a kappa (hcκcor cκ) or a lambda (haλor cλ) constant domain. In certain embodiments, CL1 is cκ. In one embodiment, the polypeptide chain is a scDVDFab.

In certain embodiments, X2 is a GS-rigid linker sequence. The GS rigid linker sequence can comprise an amino acid sequence selected from the sequences shown in FIG. 23B.

In certain embodiments, the binding proteins further comprise a polypeptide chain having the general formula (VL1-(X1)n-VL2-X2-VH1-(X3)n-VH2, wherein VL1 is a first heavy chain variable domain, X1 is a linker with the proviso that it is not a constant domain, VL2 is a second heavy chain variable domain, X2 is a linker, VH1 is a first light chain variable domain, X3 is a linker with the proviso that it is not a constant domain, VH2 is a second light chain variable domain, and n is 0 or 1, wherein the VH1 and VL1, and the VH2 and VL2 respectively combine to form two functional antigen binding sites, and wherein the amino acid sequences of VL1, X1, VL2, X2, VH1, X3, and/or VH2 independently vary within the library. In one embodiment, the polypeptide chain is a scDVD.

In certain embodiments, the diverse library of binding proteins comprises a polypeptide chain having the general formula CL1-X0-VL1-(X1)n-VL2-X2-CH1-X4-VH1-(X3)n-VH2, wherein CL1 is a light chain constant domain, X0 is a linker with the proviso that it is not a constant domain, VL1 is a first antibody light chain variable domain, X1 is a linker with the proviso that it is not a constant domain, VL2 is a second antibody light chain variable domain, X2 is a linker, CH1 is a heavy chain constant domain, X4 is a linker with the proviso that it is not a constant domain, VH1 is a first antibody heavy chain variable domain, X3 is a linker with the proviso that it is not a constant domain, VH2 is a second antibody heavy chain variable domain, and n is 0 or 1, and wherein the VH1 and VL1, the VH2 and VL2 respectively combine to form two functional antigen binding site, and wherein the amino acid sequences of VH1, X1, VH2, X2, VL1, X3, and/or VL2 independently vary within the library. In certain embodiments, the CL1 light chain. Optionally, the CL1 domain can be a kappa (hcκcor cκ) or a lambda (haλor cλ) constant domain. In certain embodiments, CL1 is cκ. In one embodiment, the polypeptide chain is a scDVDFab.

In certain embodiments, X2 is a GS-rigid linker sequence. The GS rigid linker sequence can comprise an amino acid sequence selected from the sequences shown in FIG. 23B.

Any region of the polypeptide chains can be varied independently in the libraries disclosed herein. In certain embodiments, the amino acid sequences of at least one CDR of VH1, VH2, VL1 or VL2 independently varies within the library. In one embodiment, the amino acid sequences of HCDR3 of VH1, VH2 independently vary within the library. In one embodiment, the amino acid sequences of HCDR1 and HCDR2 of VH1 or VH2 independently vary within the library. In one embodiment, the amino acid sequences of HCDR1, HCDR2 and HCDR3 of VH1 or VH2 independently vary within the library. In one embodiment, the amino acid sequences of HCDR3 of VL1 or VL2 independently vary within the library. In one embodiment, the amino acid sequences of HCDR1 and HCDR2 of VL1 or VL2 independently vary within the library. In one embodiment, the amino acid sequences of HCDR1, HCDR2 and HCDR3 of VL1 or VL2 independently vary within the library.

The linker regions X1, X2 and/or X3 can be also be varied independently in the libraries disclosed herein. Any length and sequence of linkers can be employed. Suitable amino acid sequences for use in linker X1, X2 and/or X3 are set forth in FIG. 16 herein. In other embodiments, X2 is selected from the amino acid sequences set forth in FIG. 11B. In specific embodiments, X2 is selected from the amino acid sequences set forth in FIG. 11B when the polypeptide chain includes CH and CL domain.

In certain embodiments, the libraries disclosed herein are used in cell surface display techniques (e.g., yeast display as described in Wittrup, et al. U.S. Pat. No. 6,699,658, incorporated herein by reference). Accordingly, in certain embodiments, each binding protein in the library further comprises a cell surface anchoring moiety linked to the N and/or C terminus. Any molecule that can display the binding proteins on the surface of a cell can be employed including, without limitation, cell surface protein and lipids. In certain embodiments, the anchoring moiety comprise the Aga2p polypeptide.

In certain embodiments, each binding protein in the library further comprises an epitope tag that that can be recognized by binding protein (e.g., an antibody). Suitable tags include without limitation, include His, HA, c-myc, Flag, HSV, S, AcV5, E2, E, and StrepII tags.

In certain embodiments, the library of binding proteins are employed to affinity mature a reference binding protein (e.g., scDVD or scDVDFab). Accordingly, in certain embodiments, the library of binding proteins share at least 70, 75, 80, 85, 90, 95, 96, 97, 98, or 99 amino acid sequence identity with a reference binding protein (e.g., scDVD or scDVDFab). In certain embodiments, the VH1 and VH2 of the reference binding protein specifically bind to different antigens.

fDVD/DVD-Fab

In one aspect, the invention provides libraries of multivalent binding proteins (e.g., DVD-Ig molecules, (e.g., DVD-Fab molecules)). Such libraries are particularly useful for selecting multivalent binding proteins with improved properties relative to a reference binding molecule (e.g., improved binding kinetics or thermostability).

In certain embodiments, the library of binding proteins comprises a first polypeptide chain having the general formula VH1-(X1)n-VH2-C-(X2)n, wherein VH1 is a first heavy chain variable domain, X1 is a linker with the proviso that it is not a constant domain, VH2 is a second heavy chain variable domain, C is a heavy chain constant domain, X2 is a cell surface protein, and n is 0 or 1, and wherein the amino acid sequences of VH1, VH2 and/or X1 independently vary within the library. In one embodiment, the first polypeptide chain is a DVD-Ig heavy chain or a fragment thereof (e.g., a DVD-Fab heavy chain).

In certain embodiments, the binding proteins further comprise a second polypeptide chain having the general formula VL1-(Y1)n-VL2-C, wherein VL1 is a first light chain variable domain, Y1 is a linker with the proviso that it is not a constant domain, VL2 is a second light chain variable domain, C is a light chain constant domain, n is 0 or 1, wherein the VH1 and VH2 of the first polypeptide chain and VL1 and VL2 of second polypeptide chains of the binding protein combine form two functional binding sites. In one embodiment, the amino acid sequences of VL1, VL2 and/or Y1 independently vary within the library. In one embodiment, the second polypeptide chain is a DVD-Ig light chain or a fragment thereof (e.g., a DVD-Fab light chain).

Any region of the first or second polypeptide chains can be varied independently in the libraries of the invention. In certain embodiments, the amino acid sequences of at least one CDR of VH1, VH2, VL1 or VL2 independently varies within the library. In one embodiment, the amino acid sequences of HCDR3 of VH1, VH2 independently vary within the library. In one embodiment, the amino acid sequences of HCDR1 and HCDR2 of VH1 or VH2 independently vary within the library. In one embodiment, the amino acid sequences of HCDR1, HCDR2 and HCDR3 of VH1 or VH2 independently vary within the library. In one embodiment, the amino acid sequences of HCDR3 of VL1 or VL2 independently vary within the library. In one embodiment, the amino acid sequences of HCDR1 and HCDR2 of VL1 or VL2 independently vary within the library. In one embodiment, the amino acid sequences of HCDR1, HCDR2 and HCDR3 of VL1 or VL2 independently vary within the library.

The linker regions X1 and/or Y1 can be also be varied independently in the libraries of the invention. Any length and sequence of linkers can be employed. Suitable amino acid sequences for use in linker X1 and/or Y1 are set forth in Table 7 and/or 11 herein.

In certain embodiments, the libraries of the invention are used in cell surface display techniques (e.g., yeast display as described in Wittrup, et al. U.S. Pat. No. 6,699,658, incorporated herein by reference). Accordingly, in certain embodiments X2 comprises a cell surface anchor. Any molecule that can display the binding proteins on the surface of a cell can be employed in the invention including, without limitation, cell surface protein and lipids. In one embodiment, X2 comprises the Aga2p polypeptide and allows display of the binding protein on the surface of yeast that express the Aga1p polypeptide.

In certain embodiments, the library of binding proteins are employed to affinity mature a reference binding protein (e.g., DVD-Fab). Accordingly, in certain embodiments, the library of binding proteins share at least 70, 75, 80, 85, 90, 95, 96, 97, 98, or 99 amino acid sequence identity with a reference binding protein (e.g., DVD-Fab). In certain embodiments, the VH1 and VH2 of the reference binding protein specifically bind to different antigens.

In another aspect, the disclosure provides libraries of polynucleotides encoding the diverse library of binding proteins. The libraries can be produced by any art recognized means. In certain embodiments, the libraries are produced by combining portions of other libraries by overlap PCR In certain embodiments, libraries are produced by combining portions of other libraries by gap repair transformation in yeast cells. In certain embodiments, the nucleic acids encoding the binding proteins are operably linked to one or more expression control elements (e.g., promoters or enhancer elements).

In another aspect, the disclosure provides libraries of expression vectors comprising the diverse library of polynucleotides disclosed herein. Any vectors suitable of expressing the binding proteins can be employed.

In another aspect, the disclosure provides a library of transformed host cells, expressing the diverse library of binding proteins disclosed herein. In certain embodiments, the individual transformed cells in the library of transformed host cells express only one species from the diverse library binding proteins.

Any cells, prokaryotic or eukaryotic, are suitable for use as host cells. In certain embodiments, the host cells are yeast including, without limitation, *Saccharomyces cerevisiae, Saccharomyces carlsbergensis, Candida albicans, Candida*

*kefyr, Candida tropicalis, Cryptococcus laurentii, Cryptococcus neoformans, Hansenula anomala, Hansenula polymorpha, Kluyveromyces fragilis, Kluyveromyces lactis, Kluyveromyces marxianus, Pichia pastoris, Rhodotorula rubra, Schizosaccharomyces pombe* and *Yarrowia lipolytica.*

In certain embodiments, the expressed binding proteins are anchored on the surface of the host cell. Any means for anchoring can be employed. In certain embodiments, the binding proteins are anchored on the cell surface through Aga1p. This is usually achieved by the fusion of the Aga2p protein the N and/or C terminus of the binding protein.

Binding Protein Screening Methods

In another aspect, the disclosure provides a method of selecting a binding protein (e.g., an scDVD-Ig, an scDVD-Fab-Ig an fDVD-Ig, a pDVD-Ig, an mDVD-Ig and a coDVD-Ig or a half-DVD-Ig of any of these formats) that specifically binds to a target antigen. The method generally comprises: a) providing a diverse library of transformed host cells expressing a diverse library of binding proteins disclosed herein; b) contacting the host cells with the target antigen; and c) selecting a host cell that bind to the target antigen, thereby identifying a binding protein that specifically binds to a target antigen.

In another aspect, the disclosure provides a method of selecting a binding protein that specifically binds to a first and a second target antigen simultaneously. The method generally comprises: a) providing a diverse library of transformed host cells expressing a diverse library of binding proteins disclosed herein; b) contacting the host cells with the first and second target antigen; and c) selecting a host cell that bind to the first and second target antigen, thereby identifying a binding protein that specifically binds to a first and a second target antigen simultaneously.

In certain embodiments of the foregoing methods, host cells that bind to the first and/or second antigen are selected by Magnetic Activated Cell Sorting using magnetically labeled antigen. In certain embodiments of the foregoing methods, host cells that bind to the first and/or second antigen are selected by Fluorescence Activated Cell Sorting using fluorescently labeled antigen.

Any host cells, prokaryotic or eukaryotic, are suitable for use in the foregoing methods. In certain embodiments, the host cells are yeast including, without limitation, *Saccharomyces cerevisiae, Saccharomyces carlsbergensis, Candida albicans, Candida kefyr, Candida tropicalis, Cryptococcus laurentii, Cryptococcus neoformans, Hansenula anomala, Hansenula polymorpha, Kluyveromyces fragilis, Kluyveromyces lactis, Kluyveromyces marxianus, Pichia pastoris, Rhodotorula* rubra, *Schizosaccharomyces pombe* and *Yarrowia lipolytica.*

In certain embodiments, the expressed binding proteins are anchored on the surface of the host cell. Any means for anchoring can be employed. In certain embodiments, the binding proteins are anchored on the cell surface through Aga1p. This is usually achieved by the fusion of the Aga2p protein to one or more chain of the binding protein.

After selection of antigen-binding host cells, the polynucleotides encoding the binding proteins expressed by those cells can be isolated using any standard molecular biological means. These polynucleotides can be isolated and re-expressed in another cellular or acellular system as desired. Alternatively, these polynucleotides can be further modified and screened using the methods disclosed herein. In certain embodiments, the isolated polynucleotides are recombined with other polynucleotides (including libraries disclosed herein) to produce new, hybrid polynucleotides encoding novel binding proteins.

In certain embodiments, multiplex methods of screening libraries are employed. In such methods, each individual library is barcoded by one or more epitope tags that allows for differentiating one library or a subgroup or libraries from another library or a subgroup of libraries. Unique tag or tags are peptide sequences attached at the N-, C-, or both termini, or in the linker between VH and VL domains. The libraries are differentiated by binders (e.g., antibodies) to the epitope tags using flow cytometry or fluorescence activated cell sorting. The method of differentiation of libraries can be additive (a library having one or more tags distinct from the others) or subtractive (a library missing one ore more tags from the others). The libraries can be kept separately or combined (i.e. multiplexed) for analysis or cell sorting.

In the multiplex methods, the libraries are generally introduced to organisms that are amenable to magnetic and fluorescent activated cell sorting including, but not limited to, bacteria, yeast, and mammalian cells.

The libraries separated and distinguished by one or more tags can differ according to one or more of the following attributes: 1) antibody germline subgroups or sequences, light chain isotypes (kappa vs. lambda), or combinations thereof (e.g. specific VH/VL pairs); 2) natural or synthetic (or a combination thereof) antibody or TCR sequences; 3) cell type (B, T, plasma cells, etc); 4) tissues (peripheral blood, spleen, lymph node, bone marrow, tonsil, cord blood, etc); 5) species (human, mouse, rat, llama, rabbit, chicken, hamster, shark, etc); 6) protein scaffolds (antibodies, T cell receptors, etc); ormats (antibody and its fragments scFv, Fab, dAb, DVD-Ig, DVD-Fab, scDVD, scDVDFab, etc); 7) diversity and locations (framework vs. CDR diversity, HCDR3 size and diversity, HC vs. LC diversity, DVD-Ig linkers, domain orientation, etc; and/or 8) operation logistics (operators, lab locations, cell sorters, etc)

In certain embodiments, multiple diverse libraries are created, where each library contains clones that vary at a different discreet region of a reference binding protein. Each library is then screened separately for binding to the desired antigen(s) and the selected clones from each library are recombined to from a new library for screening. For example, to facilitate the affinity maturation of a reference binding protein, two distinct, diverse libraries can be created: a first diverse library in which only the HCDR1 and HCDR2 regions of a reference antibody are varied; and a second diverse library in which only the HCDR3 region of a reference antibody are varied. The first and the second library can be screened using the methods disclosed herein (e.g., using yeast display) to identify binding molecules with improved antigen binding characteristics. The polynucleotides encoding the selected binding proteins can then be recombined (e.g., by overlap PCR or yeast GAP repair) to form a third library comprising the HCDR1 and HCDR2 regions from the first library and the HCDR3 regions form second library. This third library can then be screened using the methods disclosed herein to identify binding proteins with further improved antigen binding characteristics.

Binding proteins selected using the methods disclosed herein can be isolated and re-expressed in another cellular or acellular system as desired.

The following examples are provided to illustrate the present disclosure, but are not intended to be limiting. The materials and methods used are presented as typical components and methods, and various substitutions or modifications may be made in view of the foregoing disclosure by one of skills in the art without departing from the principle and spirit of the present disclosure.

Certain experiments described in the Examples contain ingredients or materials that are in a size suitable for a small scale setting. It is important to note that these small scale tests may be scaled up and the principle of operation and the proportion of each ingredient in the system may equally apply to a larger scale system.

EXAMPLE 1

Construction of Antibody Libraries Having Different Tags and Use of the Same for Multiplexing Binding Analysis and Sorting In order to determine whether the use of different tags may enhance the yeast display technology, affinity maturation of h1A11, a DLL4 specific antibody, was performed using three detectable tags. Three antibody libraries containing limited mutations in different CDRs of h1A11 were constructed as described below.

Cloning of the barcoding peptide tags into pYDsTEV vector was performed by removing the original V5 peptide tag sequence from the vector and substitute it by other peptide tag sequences. Briefly, the fragment containing the V5 tag was excised by NotI and PmeI digestion (FIG. 3B). Different peptide tag sequences were synthesized and subcloned into the same position by homologous recombination in DH5α cells. Clones from the transformation were screened by bacteria colony PCR for the presence of the right tag. Two positive clones from the transformation were cultured and DNA was isolated for sequencing. A sequence confirmed clone was submitted to the Antibody Engine Plasmid Repository. The tags and the resulting pYDsTEV vectors are listed in Table 1.

TABLE 1

Peptide tags used on a panel of yeast expression vectors

| Peptide Tag | DNA sequence | SEQ ID NO: | Protein sequence | SEQ ID NO: | pYDsTEV vectors |
|---|---|---|---|---|---|
| HIS* | CATCATCACCATCACCAT | 2 | HHHHHH | 21 | |
| V5 | GGTAAGCCTATCCCTAACCCTC TCCTCGGTCTCGATTCTACG | 3 | GKPIPNPLLGLDST | 22 | 13767_pYDs_TEV_total |
| c-MYC | GAACAAAAACTTATTTCTGAAG AAGATCTG | 4 | EQKLISEEDL | 23 | pYDsTEV_c-MYC |
| HA | TACCCATACGATGTTCCGGATT ACGCT | 5 | YPYDVPDYA | 24 | pYDsTEV_HA |
| HSV | AGCCAGCCAGAACTCGCTCCT GAAGACCCAGAGGAC | 6 | SQPELAPEDPED | 25 | pYDsTEV_HSV |
| FLAG | GACTACAAGGACGACGACGAC AAG | 7 | DYKDDDDK | 26 | pYDsTEV_FLAG |
| StrepII | TGGAGCCATCCGCAGTTTGAG AAG | 8 | WSHPQFEK | 27 | pYDsTEV_StrepII |
| E2 | TCCAGCACCTCGAGTGATTTTC GAGATCGC | 9 | SSTSSDFRDR | 28 | pYDsTEV_E2 |
| S | AAGGAAACCGCGGCTGCCAAG TTTGAACGCCAGCATATGGATA GC | 10 | KETAAAKFERQHMDS | 29 | pYDsTEV_S |
| E | GGAGCGCCTGTACCATATCCG GATCCGCTGGAACCGCGC | 11 | GAPVPYPDPLEPR | 30 | pYDsTEV_E |
| AcV5 | AGCTGGAAGGATGCGAGCGGC TGGAGC | 12 | SWKDASGWS | 31 | pYDsTEV_AcV5 |
| T7 | ATGGCGAGCATGACCGGCGGC CAGCAGATGGGC | 13 | MASMTGGQQMG | 32 | pYDsTEV_AcV5 |
| KT3 | AAGCCTCCAACTCCACCTCCG GAACCGGAAACC | 14 | KPPTPPPEPET | 33 | pYDsTEV_AcV5 |
| MAT | CATAACCATCGCCACAAACATG GTGGAGGCTGC | 15 | HNHRHKHGGGC | 34 | pYDsTEV_AcV5 |
| AAV5 | AACTCCCAGCCTGCCAATCCA GGTACGACTGCAACT | 16 | NSQPANPGTTAT | 35 | pYDsTEV_AcV5 |
| ABCA5 | GATTATTCTTCGGAGACTTCCG AGGATGACGATAGTTTGAAG | 17 | DYSSETSEDDDSLK | 36 | pYDsTEV_AcV5 |
| ABCE1 | AAATTGAATTCCATCAAGGACG TTGAACAGAAGAAA | 18 | KLNSIKDVEQKK | 37 | pYDsTEV_AcV5 |
| Glu-Glu | GAAGAAGAATATATGCCAATGG AG | 19 | EEEYMPME | 38 | pYDsTEV_AcV5 |

TABLE 1-continued

Peptide tags used on a panel of yeast expression vectors

| Peptide Tag | DNA sequence | SEQ ID NO: | Protein sequence | SEQ ID NO: | pYDsTEV vectors |
|---|---|---|---|---|---|
| 2AU1 | GATACTTACAGATACATCGACACTTATCGCTACATT | 20 | DTYRYIDTYRYI | 39 | pYDsTEV_AcV5 |

*HIS tag is present in all pYDsTEV vectors downstream of all others tags.

These libraries were introduced into yeast cells by transformation. Variants of the h1A11 antibody were displayed on yeast cells and were selected against low concentration of biotinylated DLL4 by magnetic sorting followed by fluorescence activated cell sorting. Each library was differently tagged by FLAG, c-Myc or HA peptide tags, respectively. ScFv expression and antigen binding were monitored by flow cytometry as described below using the antibodies described on Table 2 and Table 3.

More specifically, the h1A11 antibody was expressed as ScFv on the surface of yeast cells using pYDsTEV vectors containing three different tags (AcV5, E or StrepII peptide tags). The differentially tagged antibodies were displayed on the surface of the yeast cells and were exposed to the same biotinylated antigen DLL4 under the same conditions and concentrations. ScFv expression was monitored by tags-specific antibodies generated in mouse (anti-AcV5; Abcam), goat (anti-E; Abcam) and rabbit (anti-StrepII; GeneScript), respectively. Fluorochrome labeled donkey anti-mouse (PerCP), anti-goat (PE) or anti-rabbit (DyLight488) antibodies (obtained from Jackson Immunoresearch) were used as secondary detection reagents (Table 3). Antigen binding was monitored by APC conjugated streptavidin or Dylight633 conjugated neutravidin. All samples were analyzed by flow cytometry using a FACS Cantoll cytometer and FACS Diva software version 4.3. Additional tag specific antibodies are described on Table 2.

TABLE 2

Commercially available anti-peptide tags antibodies used to monitor ScFv antibody expression on yeast

| Tag | Ab Source | Clone | Company | Cat # |
|---|---|---|---|---|
| S | Mouse | SBSTAGa | Abcam | ab24838 |
| S | Rabbit | Polyclonal | S tag antibody [SBSTAGa] | ab18588 |
| AcV5 | Mouse | AcV5 | Abcam. Rabbit S tag antibody | ab49581 |
| E2 | Mouse | 5E11 | Abcam. AcV5 tag antibody [AcV5] | ab977 |
| E | Rabbit | Polyclonal | T7 tag ® antibody [T7 Tag] | ab3397 |
| E | Goat | Polyclonal | Abcam | ab95868 |
| E | Chicken | Polyclonal | KT3 tag antibody [KT3] | ab18695 |
| StrepII | Mouse | Strep-tag | Abcam. E tag antibody | MCA2489 |
| StrepII | Rabbit | Polyclonal | Abcam. E tag antibody | A00626 |
| HA | Mouse | HA-7 | Sigma | H9658 |
| HA | Goat | Polyclonal | Abcam | ab9134 |
| HA | Rat (IgG1) | 3F10 | Roche | 11 867 423 |
| c-myc | Mouse | 9E10 | Sigma | M4439 |
| c-myc | Rabbit | Polyclonal | Sigma | C3956 |
| Flag | Mouse | M2 | Sigma | F3165 |
| Flag | Rabbit | Polyclonal | Sigma | F7425 |
| HSV | Rabbit | Polyclonal | Sigma | H6030 |

TABLE 3

Commercially available secondary reagents used to monitor ScFv antibody expression and binding on the surface of yeast

| Secondary reagent | Fluorocrome | Company | Cat # |
|---|---|---|---|
| F(ab')2 Frag. Donkey Anti-Rat IgG (H + L) | PerCp | Jackson ImmunoResearch | 712-126-150 |
| F(ab')2 Frag. Donkey Anti-Goat IgG (H + L) | R-PE | Jackson ImmunoResearch | 705-116-147 |
| F(ab')2 Frag. Donkey Anti-Rabbit IgG (H + L) | DyLight-488 | Jackson ImmunoResearch | 705-116-147 |
| F(ab')2 Frag. Goat Anti-Rabbit IgG (H + L) | R-PE | Jackson ImmunoResearch | 111-116-144 |
| F(ab')2 Frag. Goat Anti-Rabbit IgG (H + L) | Alexafluor 488 | Invitrogen | 711-486-152 |
| Chicken anti mouse IgG (H + L) | PerCP | Jackson ImmunoResearch | 111-116-144 |
| F(ab')2 Frag Donkey Anti-Mouse IgG (H + L) | Alexafluor 633 | ThermoScientific | 715-126-151 |

Optimal Ab-Ag binding conditions for library selections were identified by scouting experiments. The ideal conditions for the selection would be ones that best discriminate library populations with different binding affinities towards the antigen, DLL4. These conditions allowed detection of both bound Ag and library-specific tags so that the antigen-binding signal may be normalized against expression levels of the antibodies on the yeast cells.

The expression tags were used to normalize the antigen-binding signal for expression, thus eliminating artifacts due to host expression bias and allowing for fine discrimination between mutants. In order to show that the peptide tags in Table 1 are suitable for monitoring the scFv expression on the surface of the yeast cells, flow cytometry analysis of h1A11 scFv expression on the surface of yeast was monitored by using FLAG, HA, HSV or c-Myc tags, respectively. Although every tag had a unique mean fluorescence pattern (FIG. 4A), each tag was capable of differentiating between the relative levels of scFv expression.

Next, the libraries were sorted and collected for further analysis. The yeast cells were run in a FACSAria II cell sorter and the clones to select were gated according to their Ag binding and expression. In each round of selection, clones with the best affinity and expression were collected. The tag staining and the detection of scFv expression during selection helped eliminate artifacts due to host expression bias. This methodology allowed for fine discrimination between the mutants.

EXAMPLE 2

ScFv Antibody Binding is not Affected by the Use of Different Peptide Tags

Figure 4:
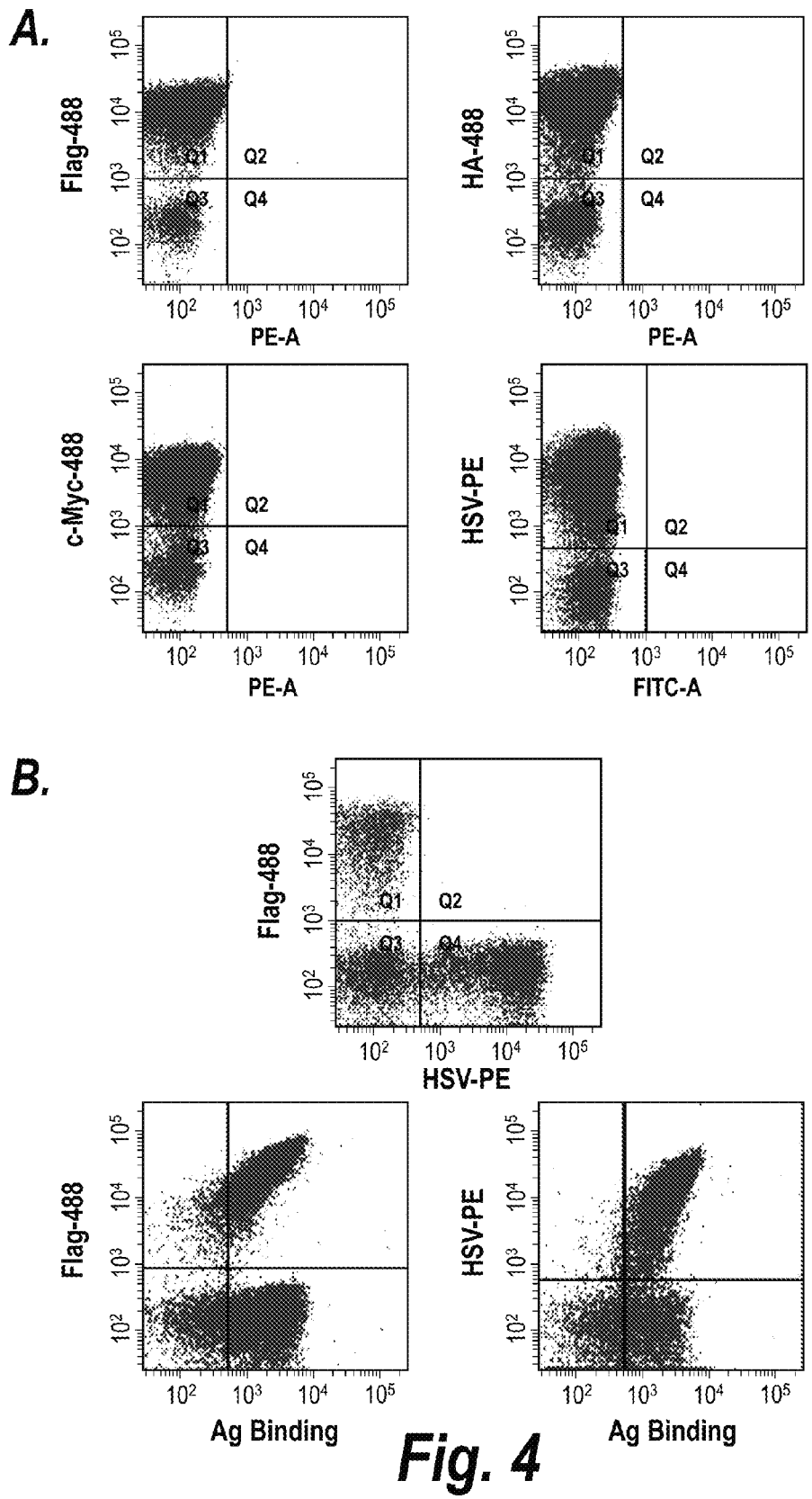
FIG. 4 shows ScFv expression monitored by flow cytometry analysis with four different epitope tags (cMyc, HA, HSV and FLAG) (FIG. 4A) or two different tags and biotinylated antigen (FIG. 4B).

Experiments were performed to determine if the use of multiple tags is compatible with multiplexed flow cytometry analysis of different tagged clones. Using different tagged scFv clones and/or libraries allows for multiplexing the expression and binding analysis, which may help simplifying the overall process and enhancing the throughput of the process. The right combination of detection reagents allowed for monitoring of the FLAG tagged h1A11 scFv expression in a mix with a HSV tagged clone (FIG. 4B). Based on the co-staining of the two different clones to monitor their expression using either anti-FLAG or anti-HSV antibodies, and the results obtained from the binding of the tagged scFv to the Ag, no background staining or cross-reactivity between the reagents were observed in the multiplexing assay. Both clones may be analyzed independently from each other by one single experiment. This approach may enhance library binding analysis and may also increase throughput of the antibody selection process.

Figure 5:
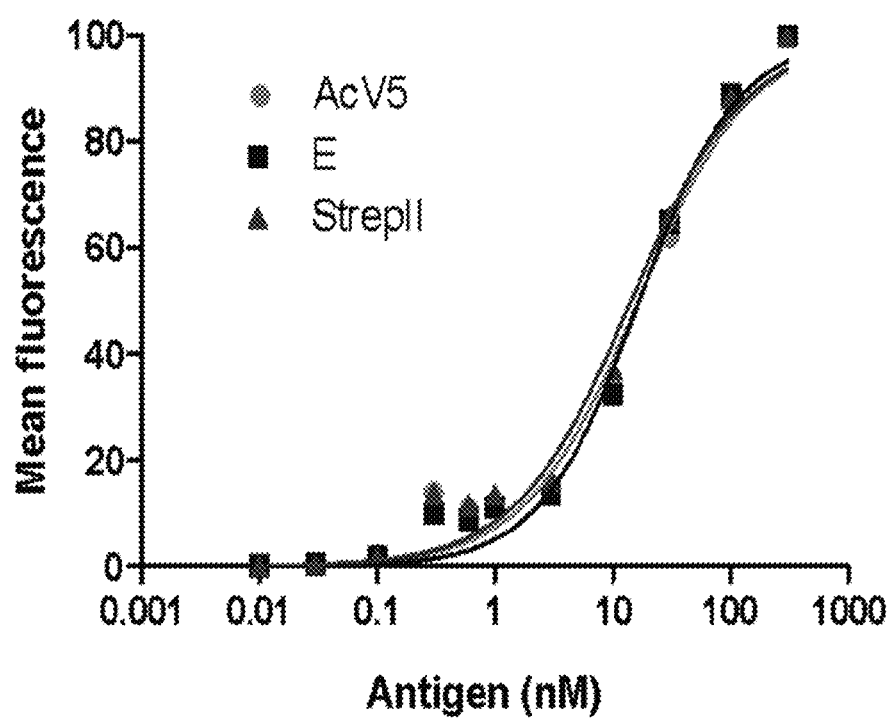
FIG. 5 shows the results of a binding analysis of the same ScFv antibody expressed on the surface of yeast using three different tags.

Tests were also performed to determine if any given antibody expressed as scFv maintained its binding affinity regardless of the detectable tag used to monitor its expression on the surface of yeast. The h1A11 antibody was expressed as scFv on the surface of yeast using pYDsTEV vectors with three different tags (AcV5, E or StrepII peptide tags; see Table 1). Each tagged version of this scFv was incubated with the same biotinylated antigen DLL4 under the same conditions and concentrations. ScFv expression was monitored by purified detection antibodies specific to each of the three different tags raised in mouse, goat and rabbit, respectively. Fluorochrome labeled donkey anti-mouse, goat or rabbit antibodies were used as detection reagents. Mean fluorescences were transformed (X=Log [X]) and a non-linear regression analysis was applied. There is no significant difference between the calculated $EC_{50}$ obtained when using different tags (16.4 nM, 16.7 nM and 14.8 nM, respectively). The scFv expression and binding remained unaltered regardless of the peptide tag being carried (FIG. 5). These results showed that scFv maintained its binding affinity regardless of the tag used to monitor its expression on the surface of yeast.

EXAMPLE 3

Figure 6:
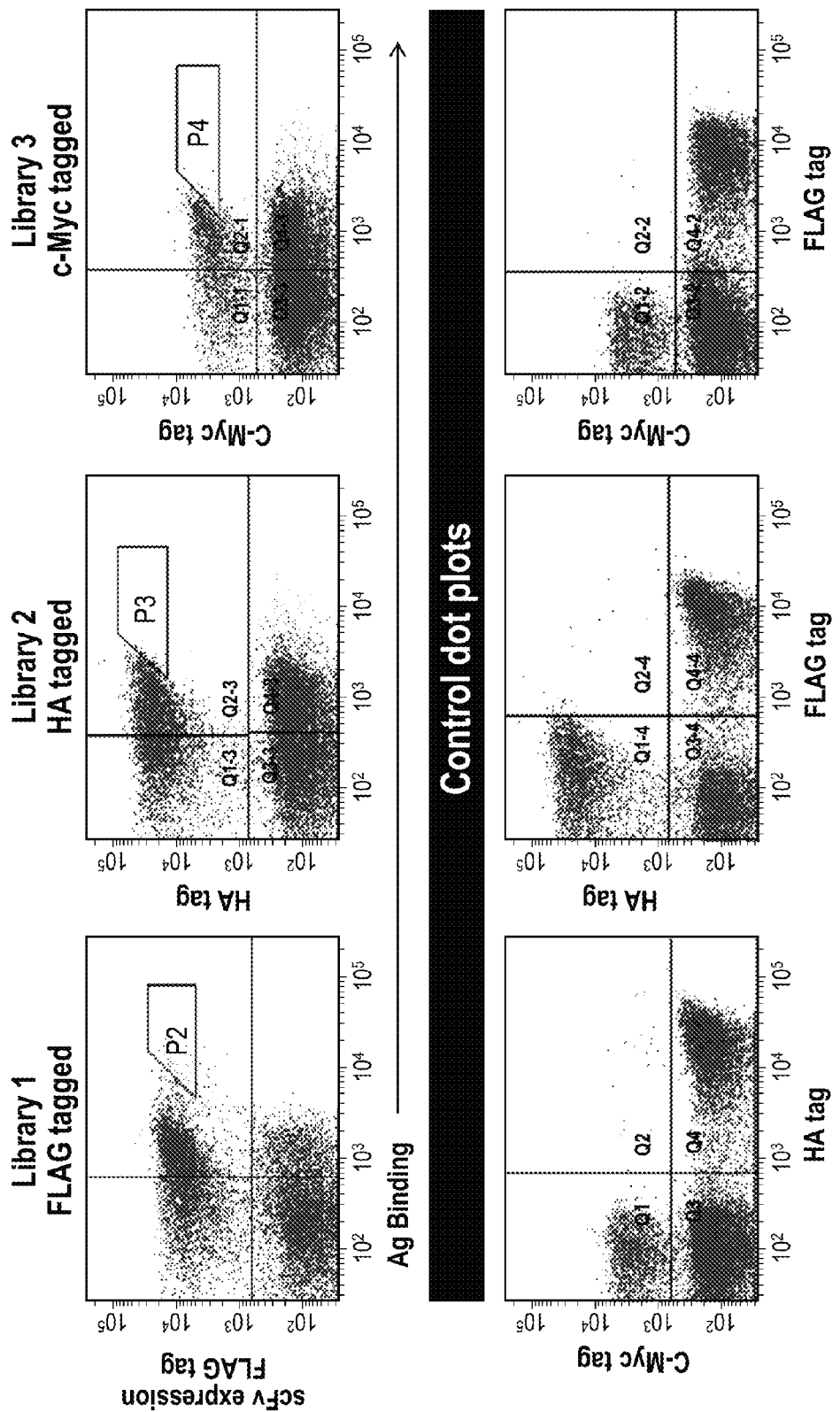
FIG. 6 shows the results of antigen binding analysis of three pooled libraries having different tags.

Multiplexing Binding Analysis of Differentially Tagged Antibody Libraries During Affinity Maturation of h1A11 Antibody The combined use of multiple tags to monitor scFv expression of different libraries significantly enhanced library selection throughput by allowing multiplex library sort and analysis. It is shown here that the analysis of three different h1A11 scFv libraries can be combined into one analysis of the pooled libraries when they are barcoded differently. Three antibody libraries were constructed with three different tags (FLAG, HA and c-Myc) during the affinity maturation of a humanized antibody to DLL4 (h1A11), as described in Example 1. Because each library contained different mutations in different CDRs, each library had a unique binding pattern to DLL4. The three libraries were pooled and the pooled libraries were incubated with the Ag DLL4. As shown in FIG. 6, each library, barcoded with a different tag, was bound to the antigen without interfering with the binding of the other libraries.

Based on these results, it is possible that the yeast cells may be gated and sorted from each of individual library into separate tubes (FIG. 6). The dot plot analysis demonstrates that there is a minimum to no unspecific labeling of the three tags (FIG. 6; control dot plots). P2, P3 and P4 represent the collecting gates. Cells in these gates would be collected into separated tubes, and will correspond to the "selection outputs." One of the advantages of the disclosed system is that the libraries could be combined or separated at any time depending on the needs of the selection strategy. There is no libraries cross contamination because each library is labeled by specific tags. Also, the end user has the tools to control whether and when to combine or separate the individual libraries.

EXAMPLE 4

Multi-Color Cell Sorting of Differentially Tagged Antibody Libraries During h1A11 Affinity Maturation As shown above, the use of multiple tags allows the use of a multiplexing approach for binding analysis. It is normal for an affinity maturation process to use highly diverse libraries of antibodies. Cell sorting of 1 to $3 \times 10^8$ are frequent in each affinity maturation campaign. Sorting that many cells using a FACSAria II with standard settings would take about two hours. Taking into consideration the time to prepare the libraries (antigen binding, ScFv expression, etc.) it is common to finish one round of selection per library in about three to five hours.

Figure 7:
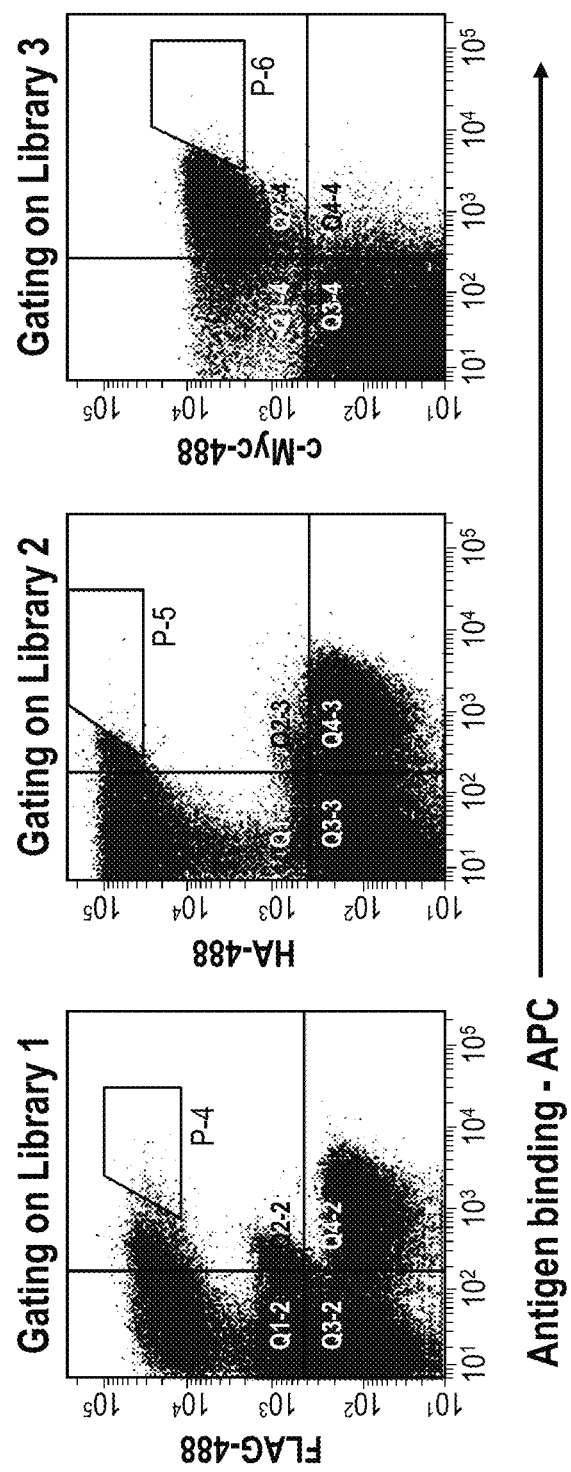
FIG. 7 shows the results of multi-color cell sorting of three pooled libraries into three separate outputs.

The use of different tags, in conjunction with multi-color cell sorting, may enhance the library selection throughput by combining libraries and multiplexing the sorting process. FIG. 7 shows the actual dot plot analysis and gating strategy during a multiplexed sort of three different libraries described above. FLAG-, HA- and c-Myc-tagged scFv libraries were pooled and incubated with DLL4. Simultaneous staining of the tags was performed as described above. The dot plot analysis showed that cells carrying different libraries may be separated based on tagging and antigen binding capabilities. By setting specific gates, individual libraries were sorted and collected back into separate tubes. P4, P5 and P6 gates were the collection gates used for collection. Cells collected into those gates would be cultured for further analysis. These cells were also called the selection outputs.

EXAMPLE 5

Multi-color Cell Sorting of Different Tagged Antibody Libraries During Affinity Maturation A similar multi-color sorting to the one shown in Example 4 was performed using different antibody libraries and different tags as described below.

h284 mAb

Figure 8:
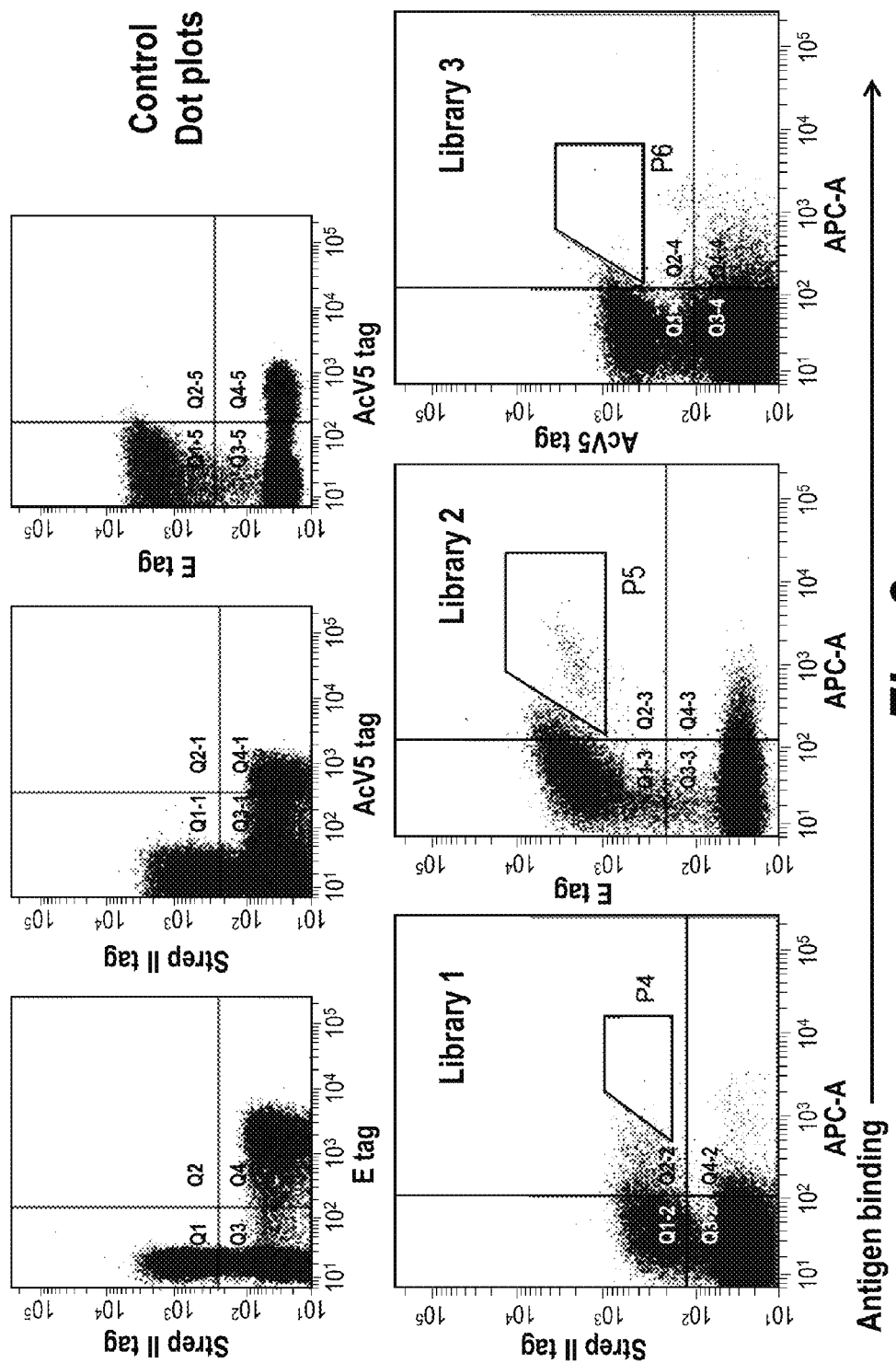
FIG. 8 shows the results of antigen binding analysis of three pooled libraries having different tags.

FIG. 8 shows dot plot analysis and gating strategy during a multiplexed sort of three different libraries. Strep II-, E- and AcV5-tagged scFv libraries were pooled and incubated with human ErbB3. Simultaneous staining of the tags was done as described above. The dot plot analysis shows a clear separation between the libraries by their tag and binding. The separation allowed drawing the sorting gate to collect the individual libraries back into separate tubes. P4, P5 and P6 gates are the actual collection gates.

AE20-8 mAb

Figure 9:
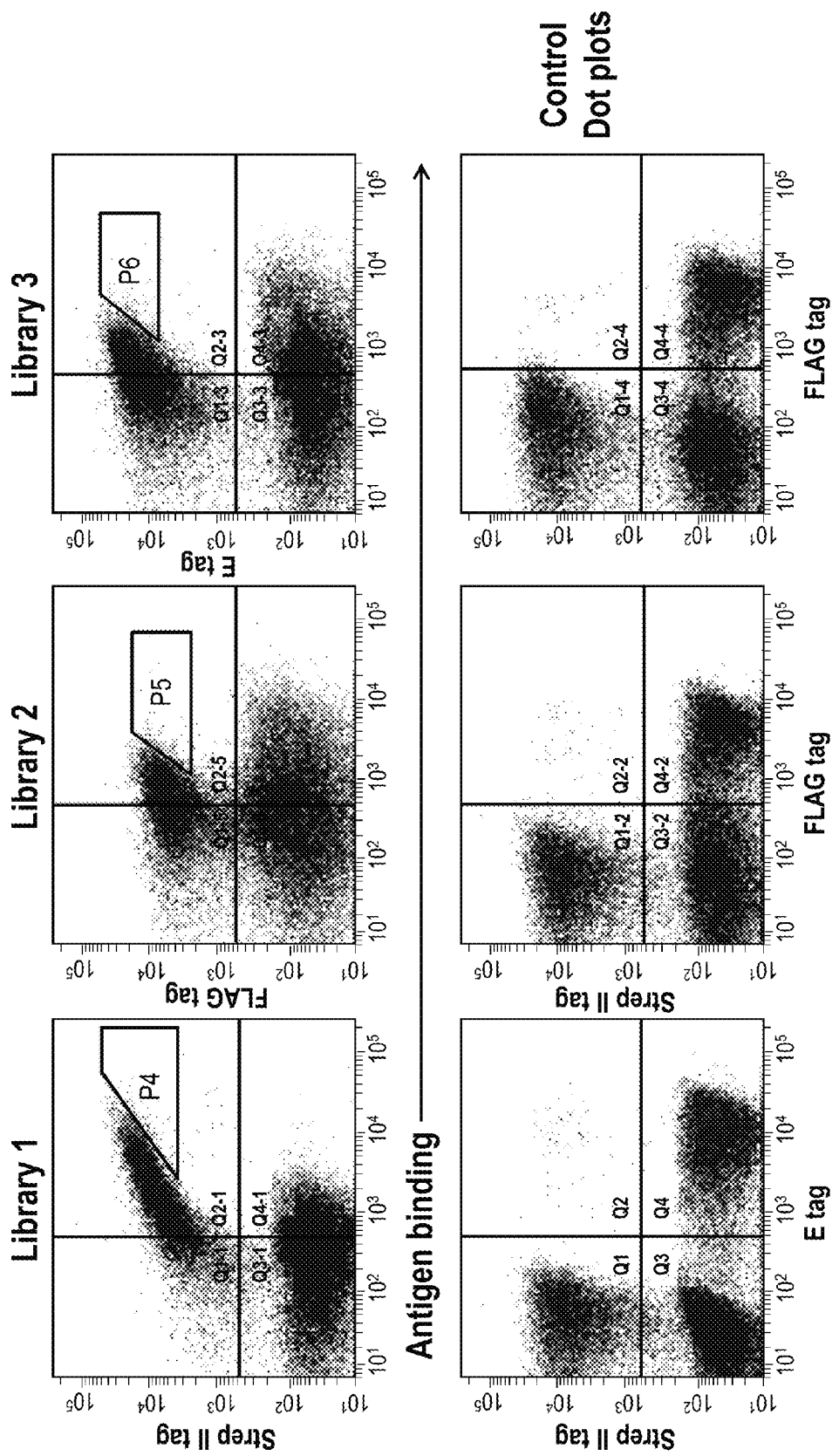
FIG. 9 shows the results of antigen binding analysis of three pooled libraries having different tags.

FIG. 9 shows dot plot analysis and gating strategy during a multiplexed sort of three different libraries. Strep II-, FLAG- and E-tagged scFv libraries were pooled and incubated with human Mesothelin. Simultaneous staining of the tags was done as described above. The dot plot analysis shows a clear separation between the libraries by their tag and binding. The separation allowed drawing the sorting gate to collect the individual libraries back into separate tubes. P4, P5 and P6 gates are the actual collection gates. Cells collected into those gates will be culture. These are the selection outputs.

h12H7 mAb

Figure 10:
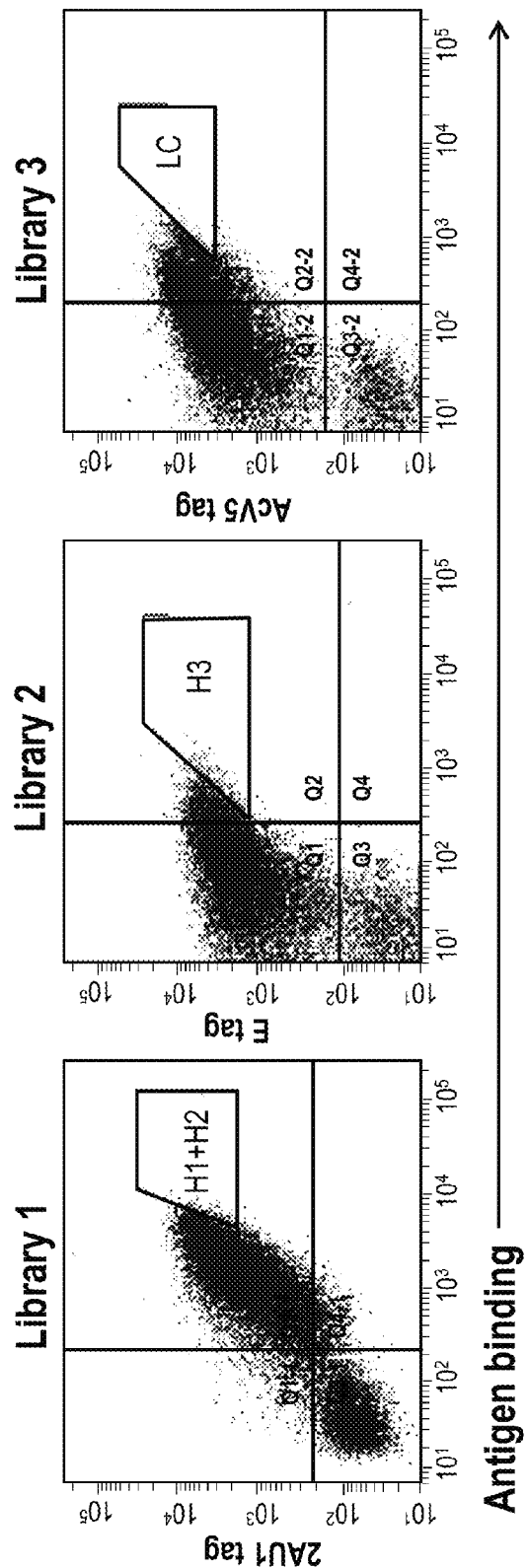
FIG. 10 shows the results of multi-color cell sorting of three pooled libraries into three separate outputs.

FIG. 10 shows the actual dot plot analysis and gating strategy during a multiplexed sort of three different libraries. 2AU1-, AcV5- and E-tagged scFv libraries were pooled and incubated with human ROR1. Simultaneous staining of the tags was done as described above. The dot plot analysis shows a clear separation between the libraries by their tag and binding. The separation allowed drawing the sorting gate to collect the individual libraries back into separate tubes.

AE21-5 mAb

Figure 11:
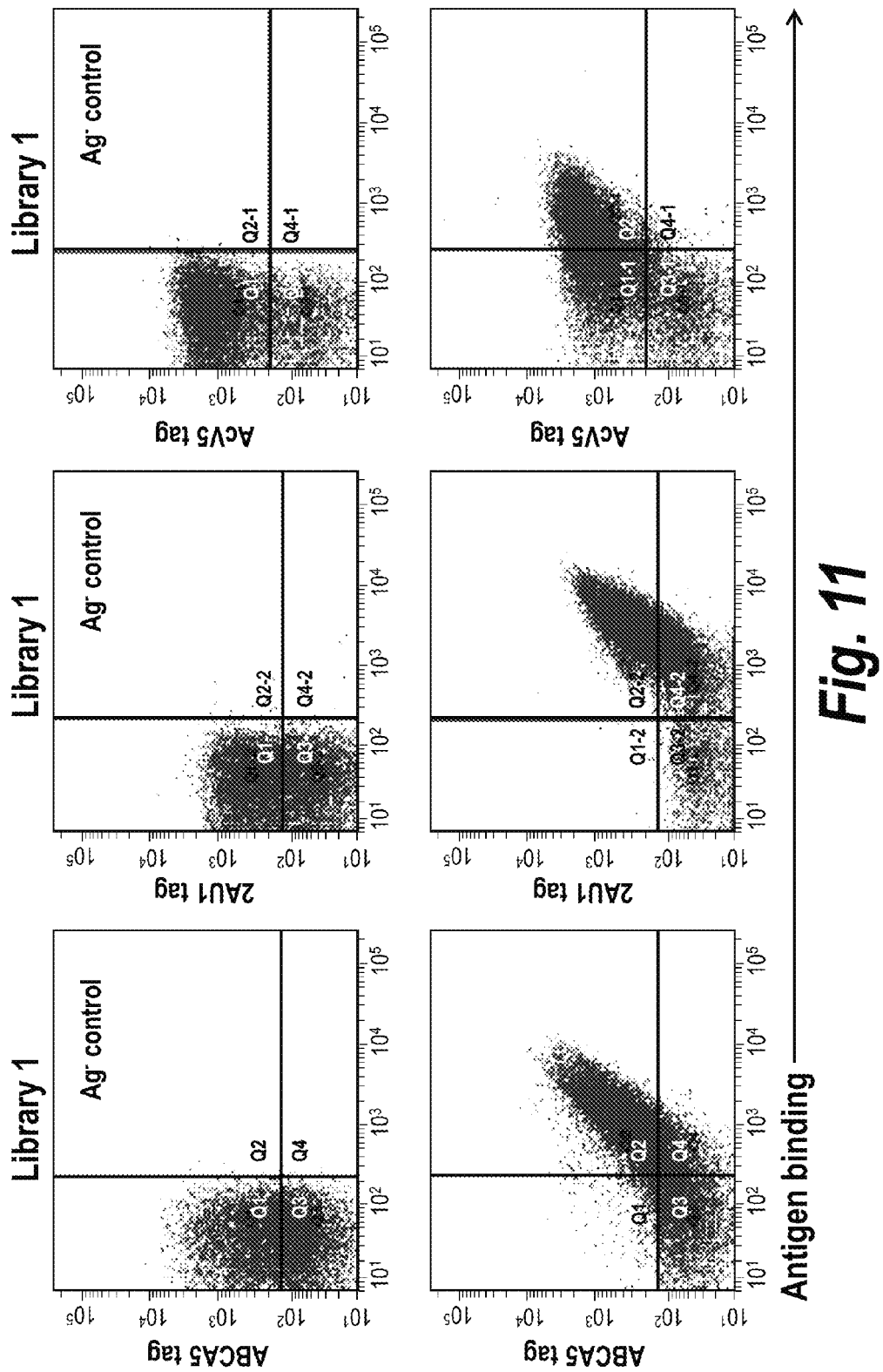
FIG. 11 shows the results of antigen binding analysis of three pooled libraries having different tags.

FIG. 11 shows the actual dot plot analysis and gating strategy during a multiplexed sort of three different libraries. ABCA5-, AcV5- and 2AU1-tagged scFv libraries were pooled and incubated with human CGRP. Simultaneous staining of the tags was done as described above. The dot plot analysis shows a clear separation between the libraries by their tag and binding. The separation allowed drawing the sorting gate to collect the individual libraries back into separate tubes.

EXAMPLE 6

Figure 12:
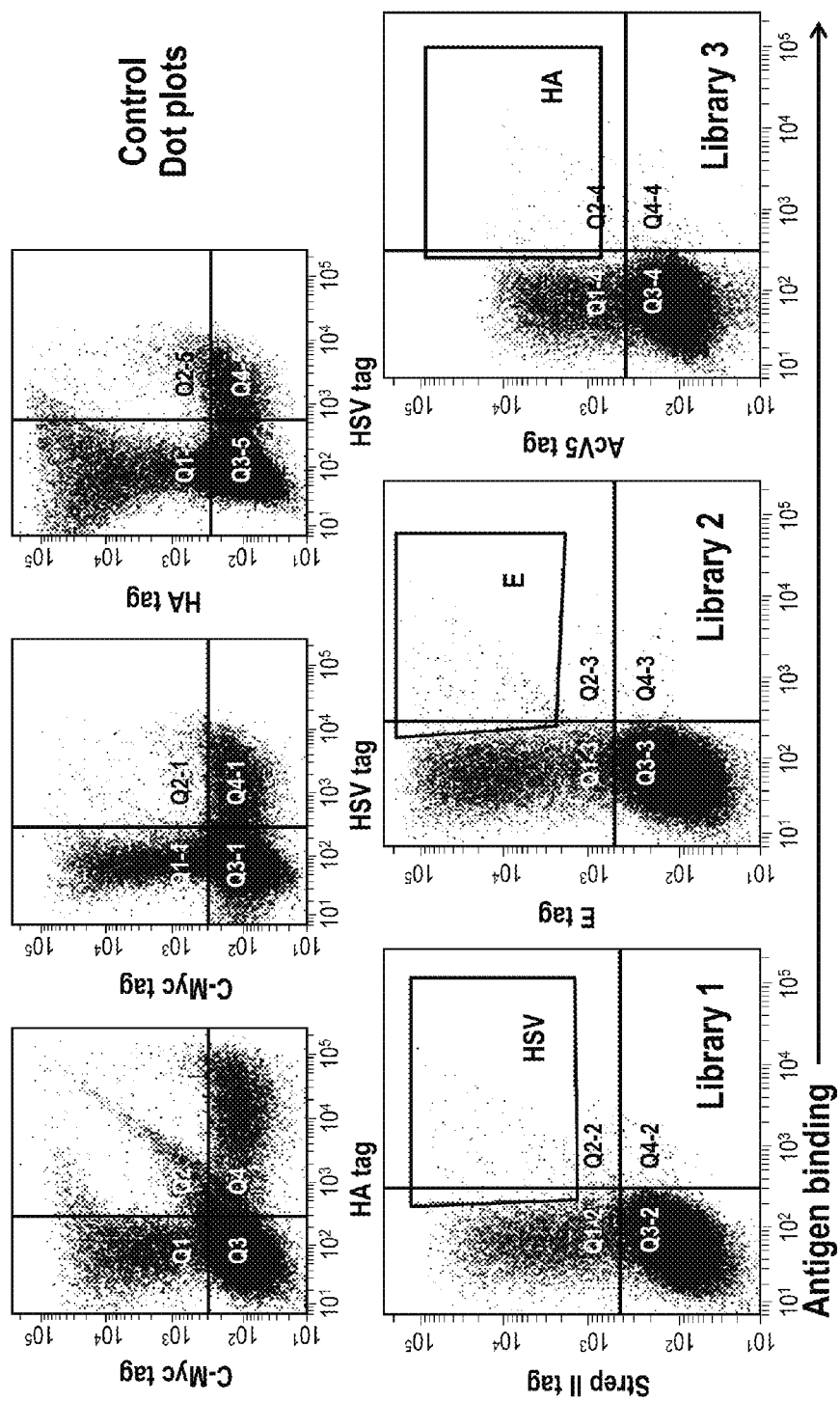
FIG. 12 shows the results of antigen binding analysis of three pooled libraries having different tags.

Multi-color Cell Sorting of Different Tagged Synthetic Antibody Libraries During Target Selection A similar multi-color sorting to the one shown in Example 4 was performed using synthetic antibody libraries and different tags as described below. FIG. 12 shows the actual dot plot analysis and gating strategy during a multiplexed sort of three different synthetic libraries. HA-, HSV- and AcV5-tagged scFv libraries were pooled and incubated with human target. Simultaneous staining of the tags was done as described above. The dot plot analysis shows a clear separation between the libraries by their tag and binding. The separation allowed drawing the sorting gate to collect the individual libraries back into separate tubes.

EXAMPLE 7

Figure 14:
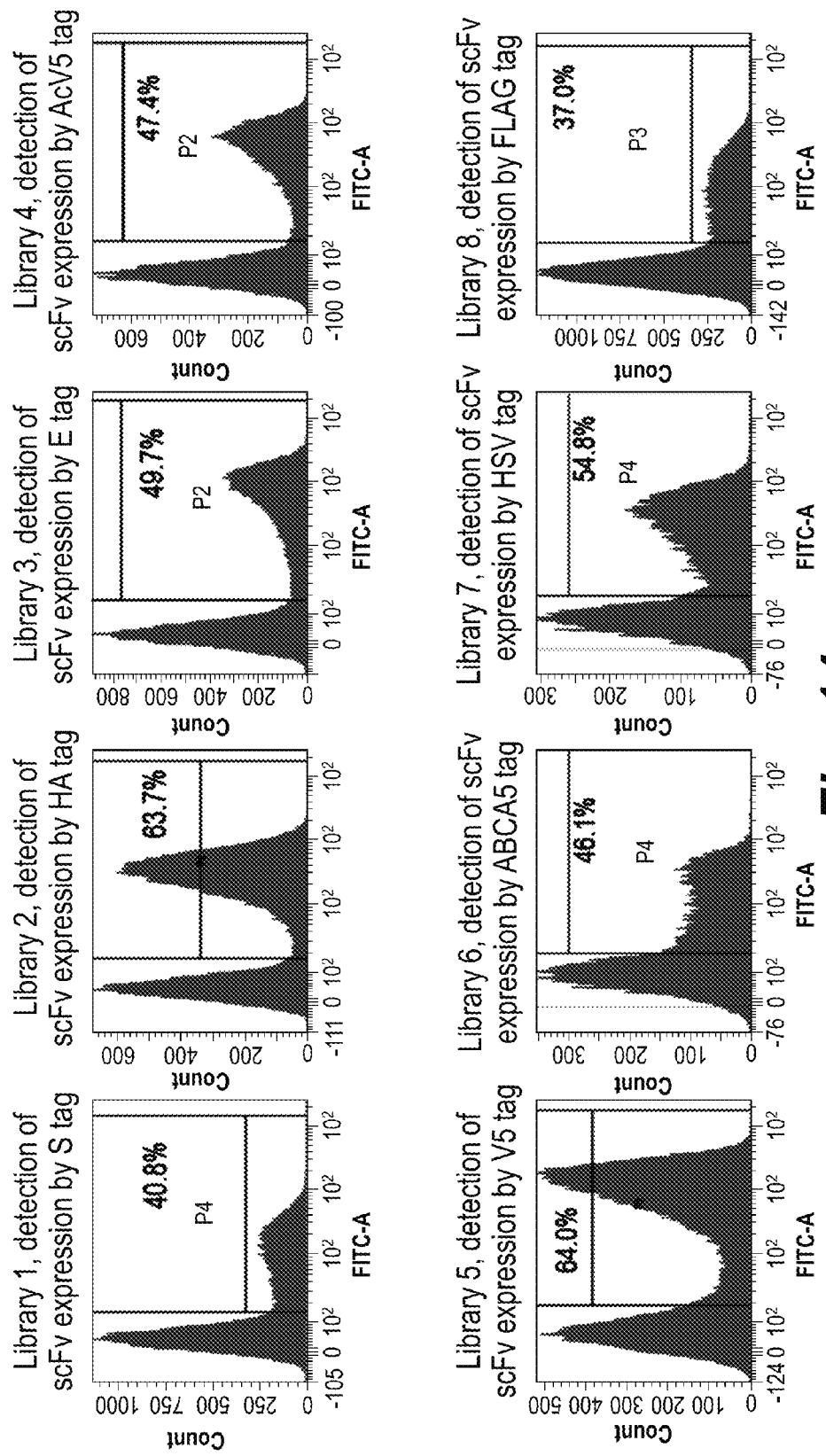
FIG. 14 is FACS analysis of libraries shown in FIG. 13.

Human Synthetic Libraries Suitable for Yeast Display Selection with Different Antigens Eight human synthetic antibody libraries were generated. Each library was composed of single preferred VH germline, highly diverse HCDR3 fragment ranging in size from 7 to 18 amino-acids, and mix of eight VK germlines (FIG. 13). Several amino-acid positions in HCDR1, HDR2, LCDR1, LCDR2, and LCDR3 were targeted for limited mutagenesis. Each library was tagged at the C-terminus with a library-specific epitope tag that allowed for individual detection, minimization of library cross-contaminations and for multiplexing library selections for best efficiency. Unselected libraries were tested for antibody expression on the surface of yeast by using their unique tag. FIG. 14 demonstrated the detection of each unique tag in each library by flow cytometry. All libraries expressed close to 50% with the exception of the library 8 where additional optimization of the detection reagents was required.

EXAMPLE 8

Generation of Single Chain Dual Variable Domain Molecules

Figure 15:
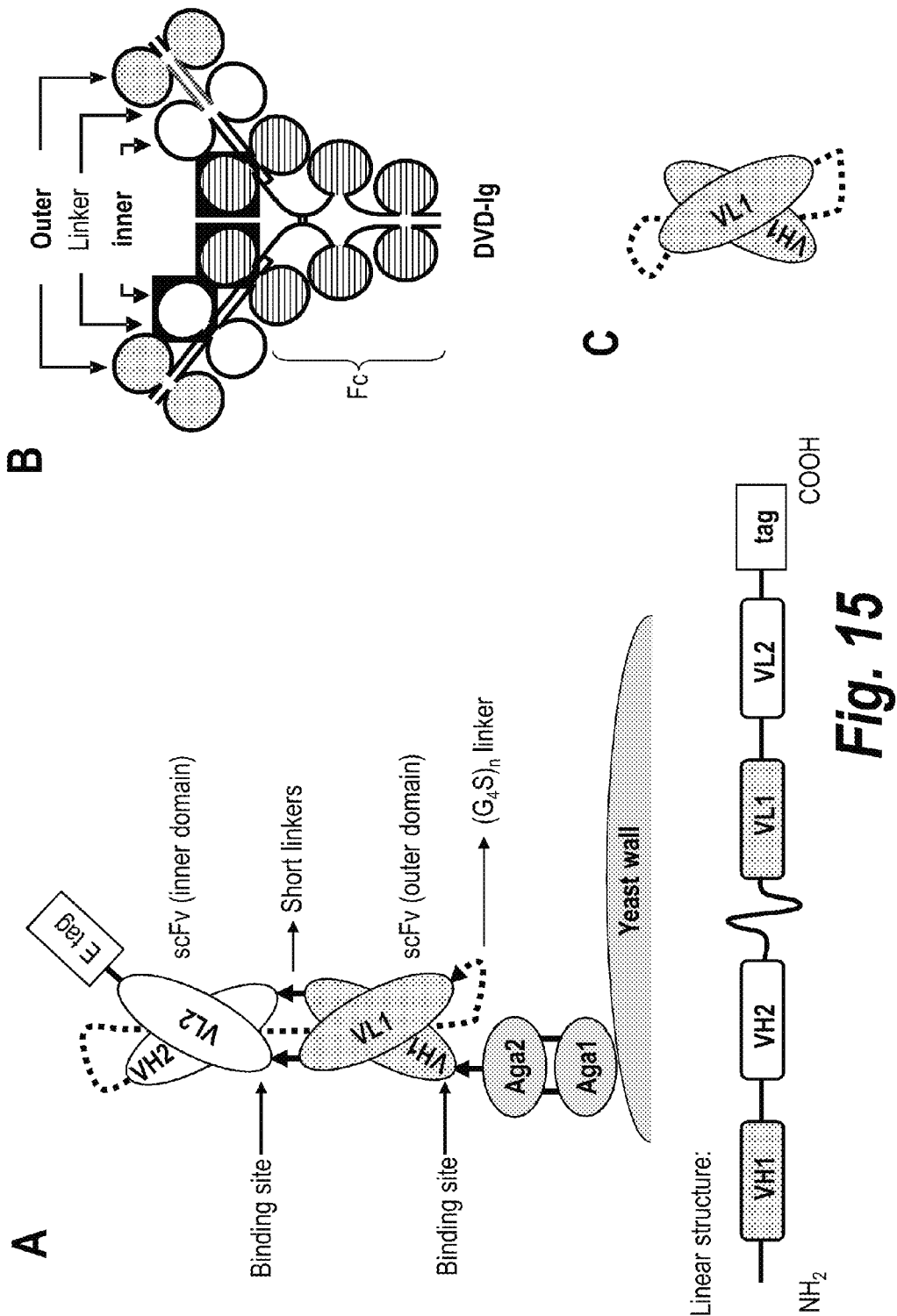
FIG. 15 depicts (A) an exemplary single chain dual variable domain (scDVD) molecules, (B) an exemplary full-length DVD-Ig molecule, and (C) an exemplary a single chain Fv molecule.

The design of a scDVD molecule derived from a DVD-Ig is shown schematically in FIG. 15. For comparison, the schematic diagrams of a DVD-Ig (FIG. 15B) and a scFv (FIG. 15C) have also been presented. The scDVD protein includes both the variable heavy and light chains of a DVD-Ig in their entirety with the carboxyl terminus of the VH domains tethered to the amino terminus of the VL domains through a Gly$_4$Ser peptide linker (SEQ ID NO: 40) of 30, 35, 40 or 45 amino acids. VH1 and VH2 are paired connected with a specific linker sequence of 6 to 14 amino acids. VL1 and VL2 are paired connected with a specific linker sequence (SL) of 6 amino acids. Sequences encoding the variable regions were PCR amplified from DVD-Ig expression vectors. Primers were designed in such a way that amplified DNAs have the necessary overlap sequence to perform additional overlapping PCRs. The final fragment contains the VH domains, the long Gly$_4$Ser linker (SEQ ID NO: 40), the VL domains and a peptide tag used to monitor expression of the scDVD on the surface of yeast. The construct is cloned by homologous recombination into a pYD yeast expression vector using DH5α chemically competent bacteria. Clones from the transformation were screened by bacteria colony PCR for the presence of the correct construct.

Figure 16:
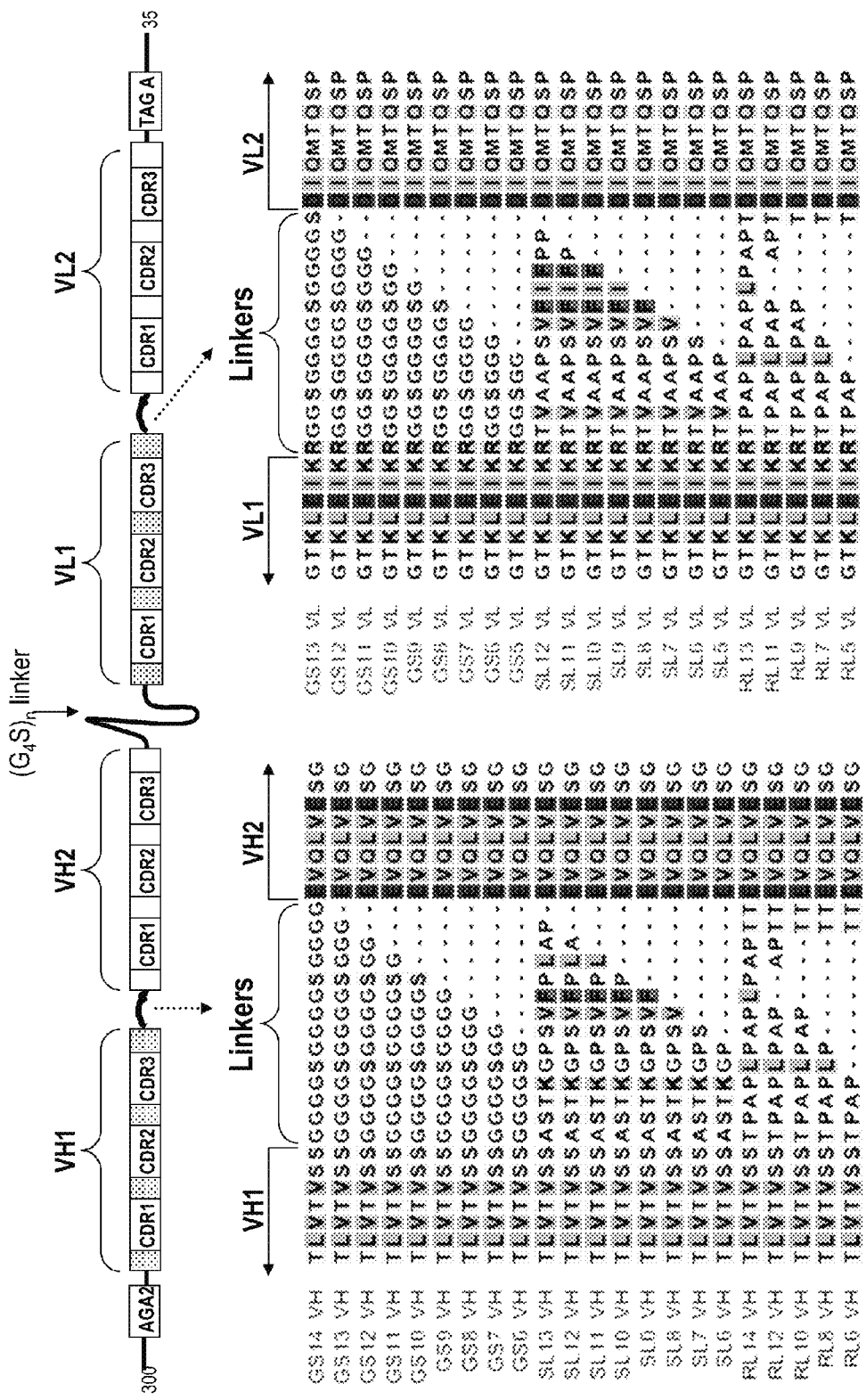
FIG. 16 is a schematic representation of an scDVD molecule and exemplary inter-variable domain linker amino acid sequences (SEQ ID NOS 197-240, top to bottom, left to right, respectively, in order of appearance).

Several different linker sequences were evaluated for linking the VH domains or VL domains (see FIG. 16). The SL linkers correspond to the first 6 to 14 amino acids amino acids of the IgG1 constant region (ASTKGPSVFPLAPS) (SEQ ID NO: 41), or corresponding to the first 6 to 14 amino acids of the IgK constant region (RTVAAPSVFIFPPS) (SEQ ID NO: 42). The GS linkers correspond to 6 to 14 amino acids with repeats of Gly$_4$Ser (SEQ ID NO: 40). The RL linkers correspond to sequences of 6 to 14 amino acids rich in Proline.

EXAMPLE 9 scDVD Expression on the Surface of Yeast

Figure 17:
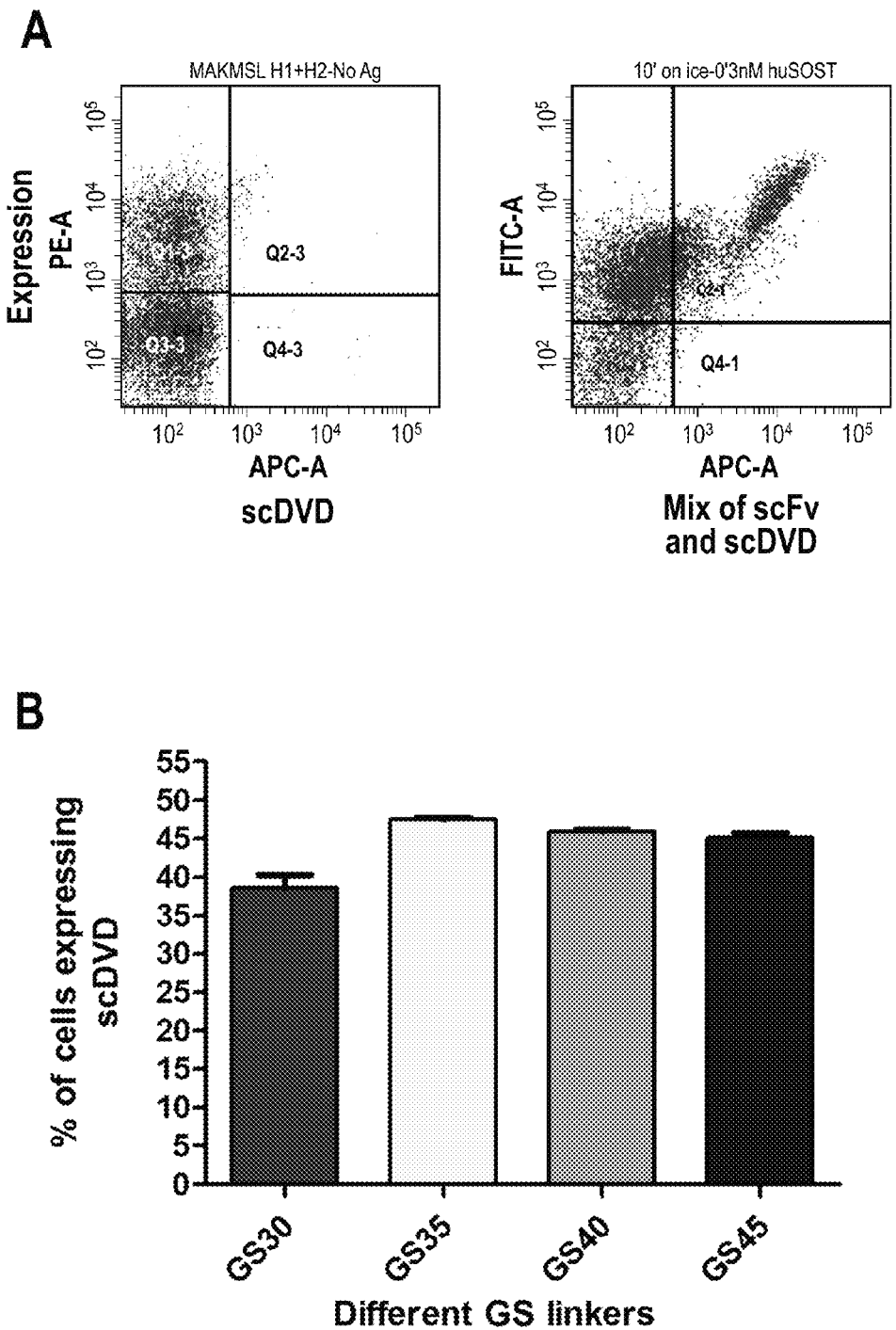
FIG. 17 depicts the results of flow cytometry assays measuring the cell surface expression of scDVD or scFv on yeast cells.

The expression of scDVD on the surface of yeast and the suitability of the selected epitope tags for monitoring expression were evaluated. scDVD expression on the surface of yeast was monitored by flow cytometry analysis using antibodies against scDVD epitope tags. The expression of scDVD on the surface of yeast was found to be comparable to that observed for scFv molecules, with about 50% of the yeast cells expressing the scDVD construct (FIG. 17A). However, scDVD expression shows a lower mean fluorescence intensity compared to scFv, suggesting a lower number of scDVD molecules were expressed by single cell. FIG. 17A (right dot-plot) shows this difference when two different yeast cultures (one expressing scDVD and another expressing scFv) are labeled together in the same tube. Both constructs are expressed in about 50% of the cells (data not shown) but scFv clones have a higher mean fluorescence.

The length of the long Gly₄Ser linker (SEQ ID NO: 40) did not greatly impact the ability of the cells to express the scDVD. A Gly₄Ser linker (SEQ ID NO: 40) of 30 amino acids seemed to have a negative impact on the expression while there was no difference in expression when using Gly₄Ser (SEQ ID NO: 40) of 35, 40 or 45 amino acids (FIG. 17B).

EXAMPLE 10 scDVD Retains the Ability of DVD-Ig to Bind Both Targets

Figure 18A:
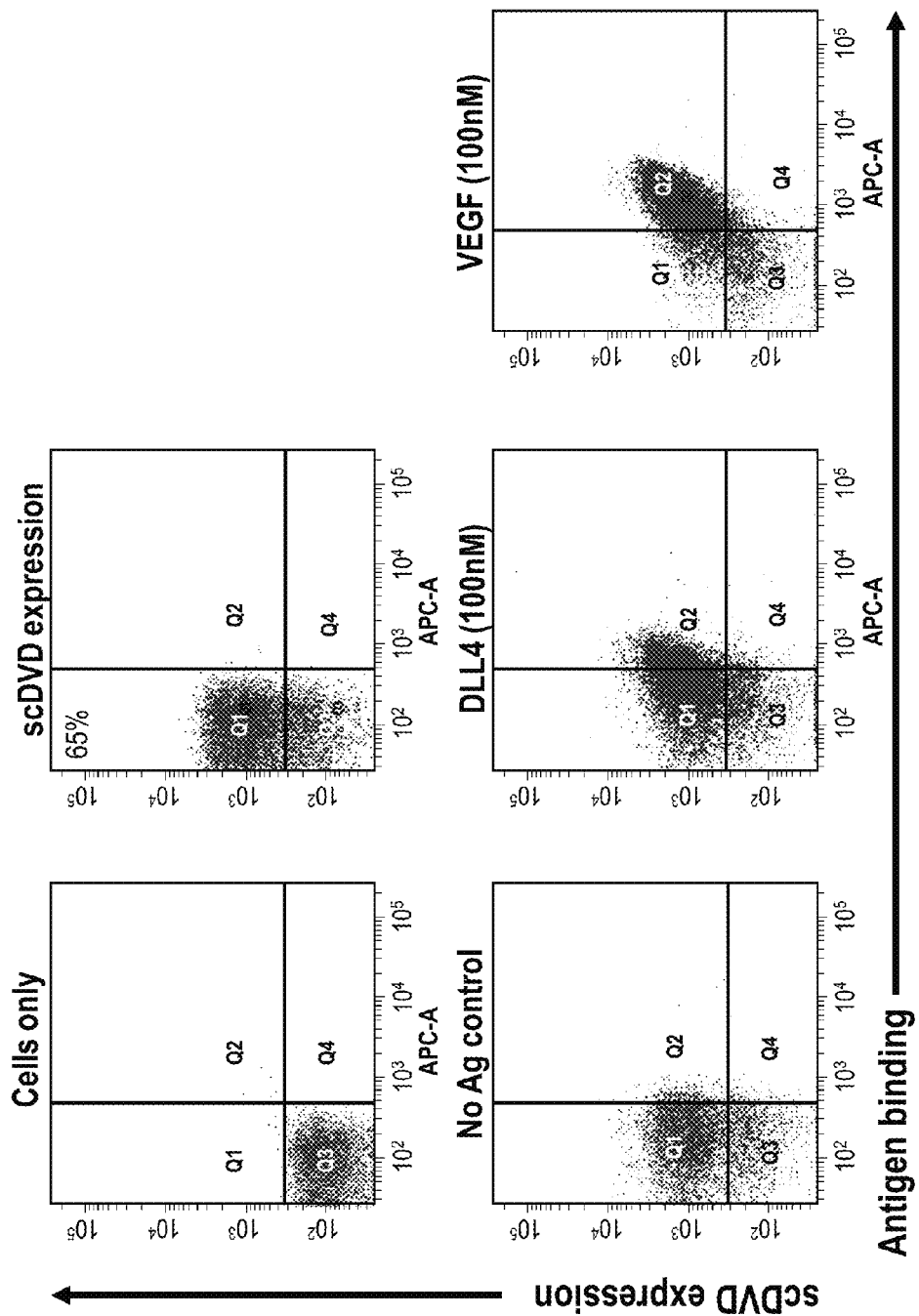
FIG. 18 depicts the results of flow cytometry assays measuring the binding of (A) DLL4 and/or VEGF to yeast cells expressing cell surface DLL4/VEGF-binding scDVD, and (B) SOST and/or TNFa to yeast cells expressing cell surface SOST/TNFa-binding scDVD.
Figure 18B:
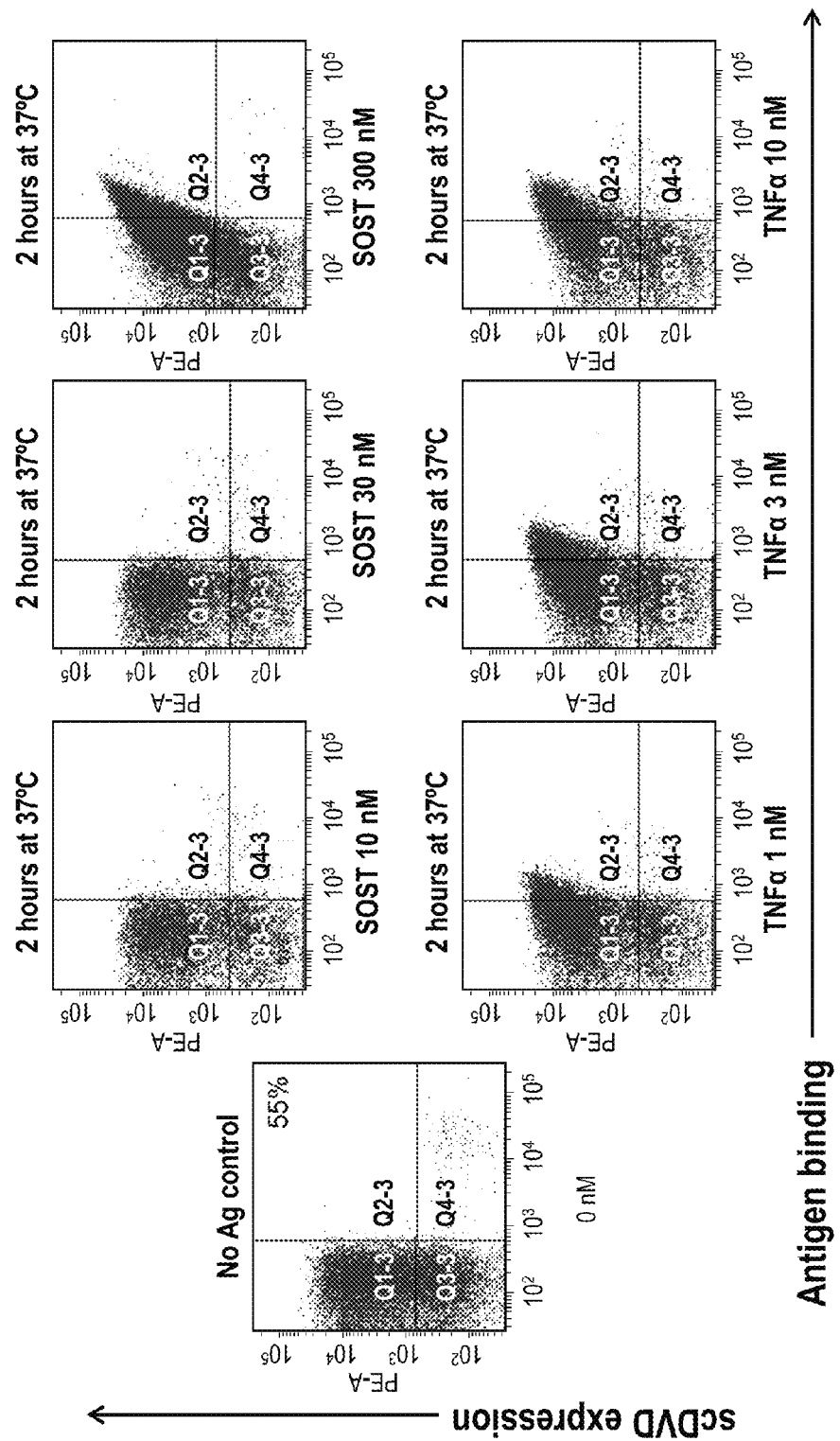

Two different DVD-Igs were expressed as scDVD on the surface of yeast using pYD vectors with three different tags (AcV5, E or StrepII peptide tags). Each construct was incubated with biotinylated antigens under the same conditions and concentrations. scDVD expression was monitored using epitope tags specific antibodies made in mouse, goat and rabbit, respectively. Fluorochrome labeled donkey anti-mouse, goat or rabbit antibodies were used as detection reagents. Mean fluorescence is shown in each individual dot-plot. DLL4/VEGF scDVD retains its ability to bind both DLL4 and/or VEGF (FIG. 18A). There is no difference in binding (mean fluorescence intensity) when the scDVD is incubated with DLL4, VEGF, or a mixture of the two antigens. The same findings were observed for TNF/SOST scDVD. This scDVD retains its ability to bind both TNF and/or Sclerostin (FIG. 18B). There is no difference in binding (mean fluorescence intensity) when the scDVD is incubated with TNF, SOST, or a mixture of the two antigens. Yeast cells express many copies of scDVD on the cell surface, accordingly, the simultaneous binding to both antigens could theoretically be due to some scDVD molecules on a cell binding to one antigen and other scDVD molecules on the same cell binding independently to the second antigen. However, the mean fluorescence do not change when the scDVD is incubated with one antigen, the other antigen or a mix of both antigens, suggesting that the scDVD molecules are binding both antigens simultaneously.

Figure 19:
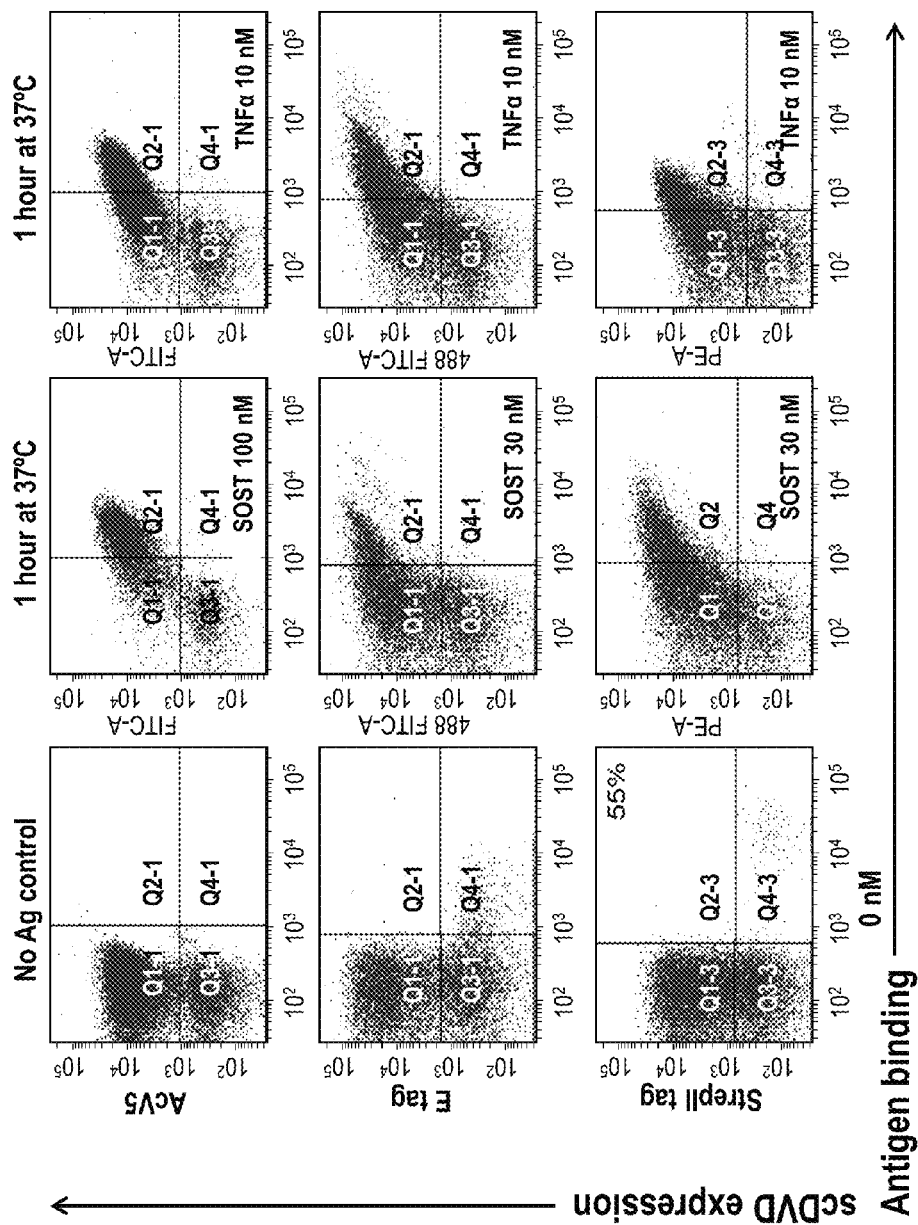
FIG. 19 depicts the results of flow cytometry assays measuring the binding of SOST and/or TNFa to yeast cells expressing cell surface SOST/TNFa-binding scDVD tagged with various epitope tags.

EXAMPLE 11 scDVD Binds Both Antigens Regardless the Tag Used to Monitor its Expression on the Surface of Yeast In yeast display, expression tags are used to monitor the antibody expression and to normalize the antigen-binding signal for expression, thus eliminating artifacts due to host expression bias. This allows for fine discrimination between mutants with different affinities towards their target. Experiments were performed to determine if any given functional DVD-Ig, when expressed as a scDVD, maintains its binding capabilities towards its two cognate targets regardless of the tag used to monitor its expression on the surface of yeast. Specifically, TNF/SOST DVD-Ig was expressed as scDVD on the surface of yeast using three different tags (AcV5, E or StrepII peptide tags). The three constructs were exposed to the same biotinylated antigens (TNF and Sclerostin) under the same conditions and concentrations. scDVD expression was monitored using tag-specific antibodies made in mouse (anti-AcV5; Abcam), goat (anti-E; Abcam) and rabbit (anti-StrepII; GeneScript). Fluorochrome labeled donkey anti-mouse (PerCP), goat (PE) or rabbit (DyLight488) antibodies were used as detection reagents (see Tables 4-6 herein). Antigen binding was monitored by APC conjugated streptavidin or Dylight633 conjugated neutravidin. All samples were analyzed by flow cytometry. FIG. 19 shows that it is feasible to use different peptide tags to monitor scDVD expression and binding on the surface of yeast.

EXAMPLE 12

Figure 20A:
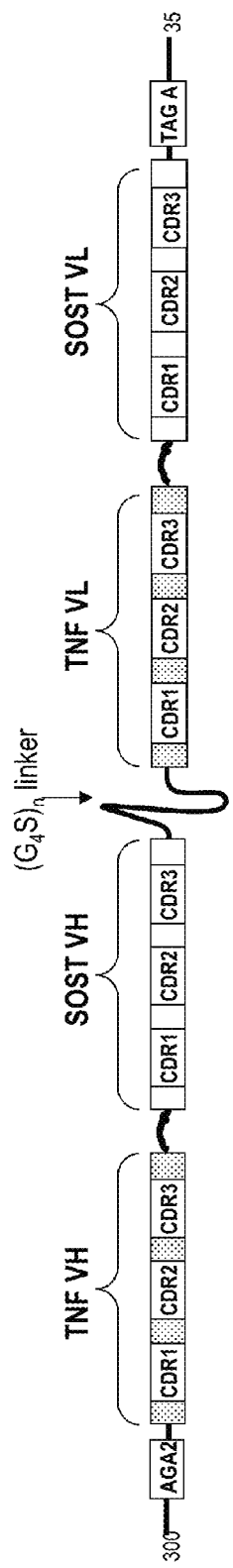
FIG. 20A and 20B disclose "G$_4$S" as SEQ ID NO: 40.
Figure 20B:
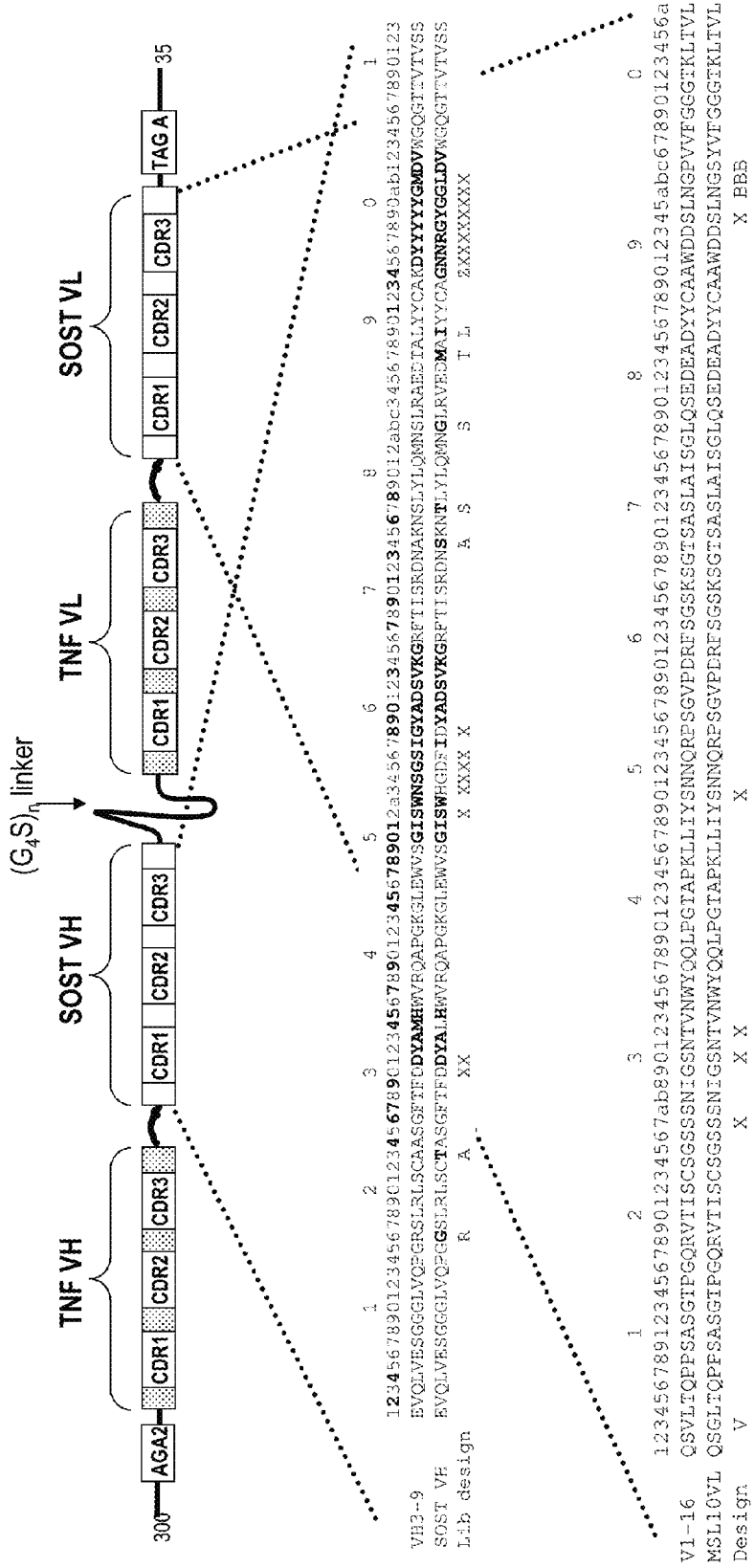

Binding Selection of a TNF/SOST scDVD Derived Library Demonstrate Expression and Binding Improvement Compare with the Parental scDVD In order to test the ability of scDVD format expressed on the surface of yeast to enhance and affinity mature DVD-Ig, an affinity maturation of a TNF/SOST DVD-Ig was performed using different libraries. These libraries were constructed to contain limited mutations in different CDRs of SOST variable domains. The TNF/SOST scDVD protein sequence is set forth in FIG. 20A. To design these libraries hypermutated CDR residues were identified from other human antibody sequences. The corresponding SOST CDR residues were then subjected to limited mutagenesis by PCR with primers having low degeneracy (79% parental nucleotide and 21% all other three nucleotides) at these positions to create three antibody libraries in the scDVD format suitable for yeast surface display. The first library (H1+H2) contained mutations in HCDR1 and HCDR2 of SOST VH domain. The second library (H3) contained mutations in HCDR3 of SOST VH domain and the third library (LC) contained mutations in all CDRs of SOST VL domain. To further increase the identity of SOST variable domains to the human germline framework sequence, a binary degeneracy (50% parental 50% germline) at certain positions were introduced into the libraries and certain residues were germline (see FIG. 20B). The introduced changes were as follows:

H1+H2 Library:
    Limited mutagenesis of residues: D30, D31, S52, H53, G54, D55, F56 and D58
    Germlining 7 residues: G16R, T23A, S74A, T77S, G82bS, M87T, I89L
H3 Library:
    Limited mutagenesis of residues: N95, N96, R97, G98, Y99, G100, G100a, L100b
    Germlining 7 residues: G16R, T23A, S74A, T77S, G82bS, M87T, I89L
    Binary degeneracy between SOST VH and germline at G94K
LC Library:
    Limited mutagenesis of residues: S27, S30, T32, S40, S94
    NNK randomization at residues N95a, G95b and S95c
    Binary degeneracy between SOST VL and germline at G3V These libraries (see FIG. 20B) were separately transformed and displayed on yeast cells and selected against low concentration of biotinylated Sclerostin and TNF by magnetic then fluorescence activated cell sorting. Each library was differently tagged by one of StrepII, FLAG or E peptide tags. scDVD expression and antigen binding were monitored by flow cytometry as described above using the antibodies described on Tables 5 and 6 herein.

Figure 20C:
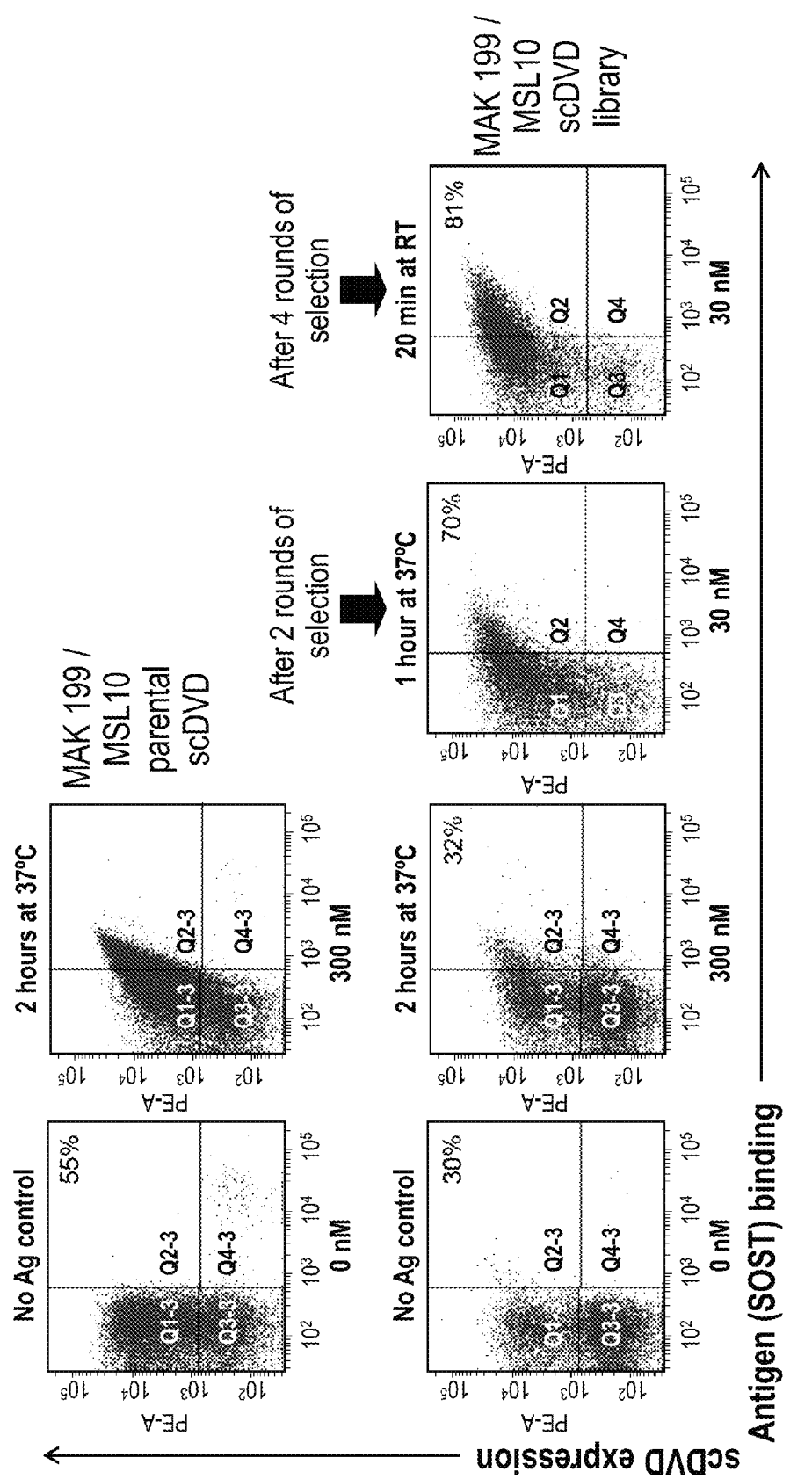
FIG. 20 depicts (A) the amino acid sequence of an exemplary SOST/TNFa-binding scDVD molecule (SEQ ID NO: 192), (B) an exemplary SOST/TNFa-binding scDVD library design, with the VH3-9 (SEQ ID NO: 193), SOST VH (SEQ ID NO: 194), V1-16 (SEQ ID NO: 195) and MSL10VL (SEQ ID NO: 196) sequences; (C) the results of flow cytometry assays measuring the binding of SOST to yeast cells expressing parental or affinity matured cell surface SOST/TNFa-binding scDVD, and (D) the results of flow cytometry assays measuring the binding of SOST to yeast cells expressing parental or affinity matured cell surface SOST/TNFa-binding scDVD.

After 2 and 4 rounds of selection, the binding towards Sclerostin was notably improved compared to the binding of the parental molecule. Parental TNF/SOST scDVD binds to 300 nM of Sclerostin after an incubation for 1 hour at 37° C. No binding was observed when the parental molecule was incubated with 30nM of Sclerostin. In contrast, after 2 rounds of selection the H3 library shows binding to 30 nM of Sclerostin, and after 4 round of selection the binding to 30 nM of Sclerostin is observed when the library output was incubated only for 20 minutes at room temperature (see FIG. 20C). Similar improvements were observed for the H1+H2 and LC libraries.

Figure 20D:
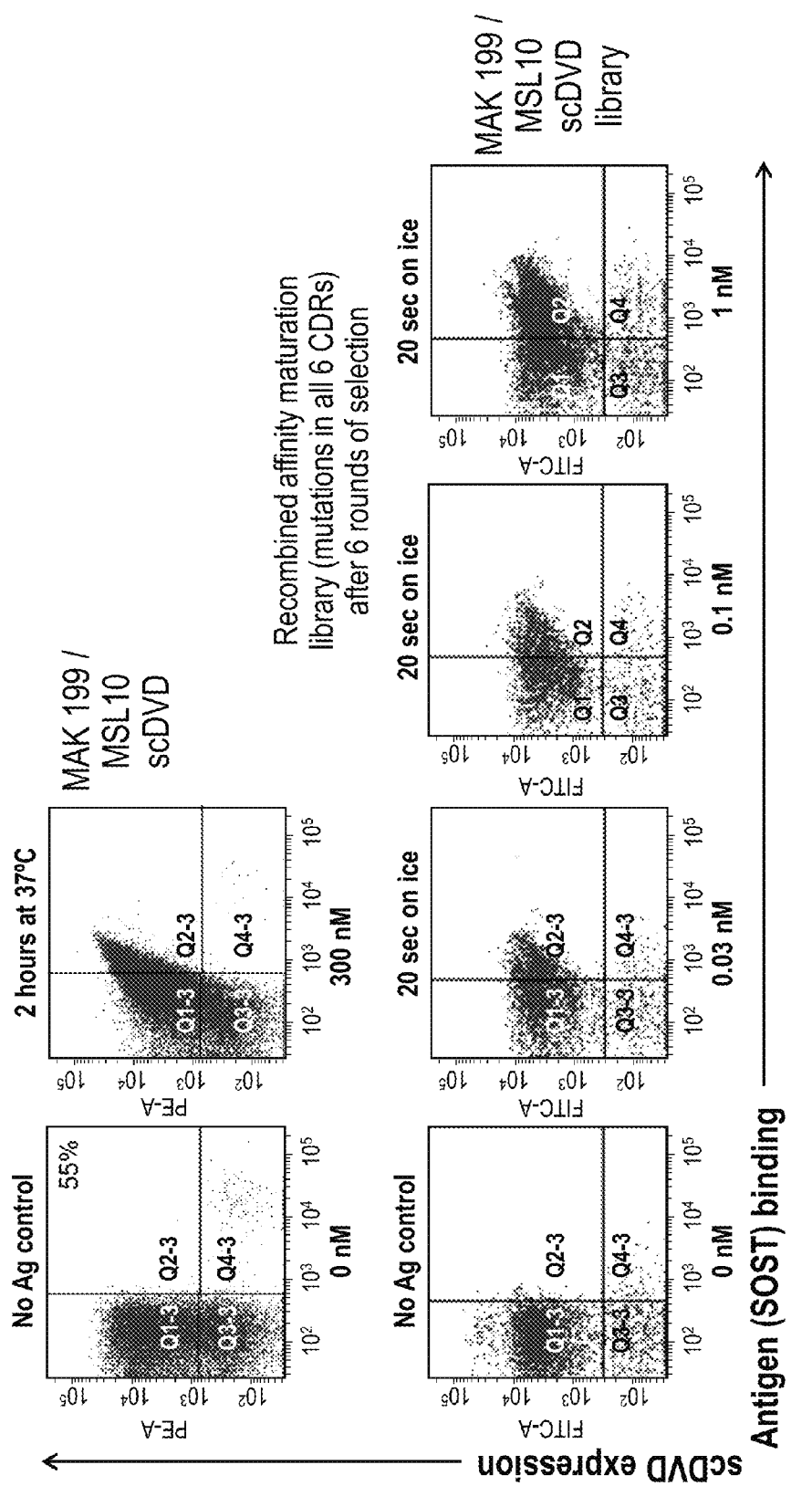

Once the diversity of each library is reduced to about $10^3$ the plasmid DNA from each output was isolated and the libraries are recombined by PCR into a new library (rHC+LC). This library was transformed into yeast cells and displayed on cell surfaces to be selected against biotinylated Sclerostin. After selection the improvement in affinity is very notorious. As pointed out the parental construct is able to bind Sclerostin at 300 nM when incubated for 1 hour at 37° C. rHC+LC library output after 6 round of selection is able to bind 0.1 nM of Sclerostin when incubated only for 20 seconds at 4° C. (FIG. 20D). Although, no formal quantification of the affinity is done, an improvement of more than 100 folds is expected based on this results. It is clear that scDVD based libraries could be selected and enriched for better binders.

EXAMPLE 13

Figure 21A:
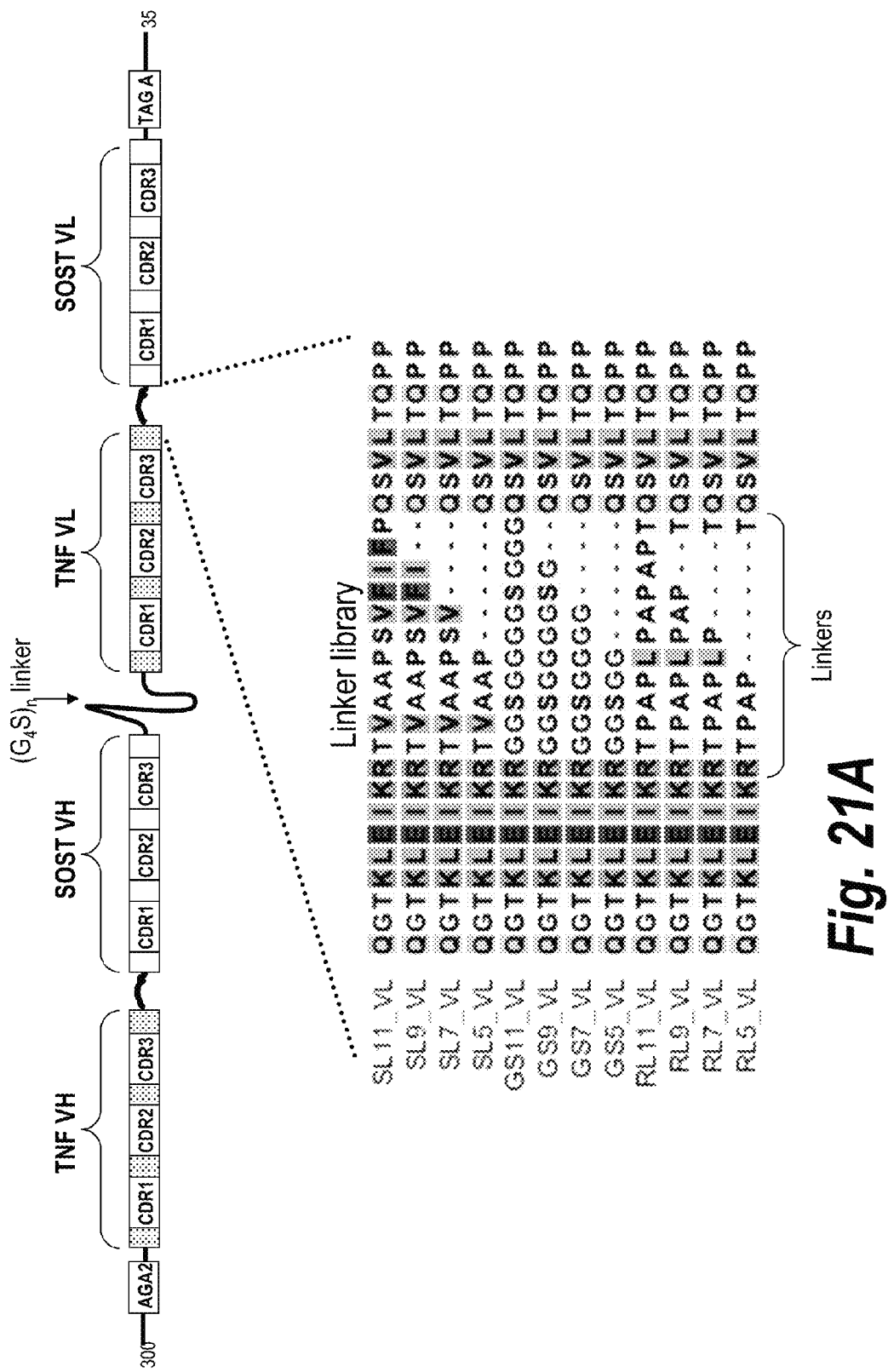
FIG. 21A discloses "G₄S" as SEQ ID NO: 40.

Binding Selection of TNF/SOST scDVD Libraries Shows Enrichment of SL Linkers between VL Domains As discussed above, there is a clear need for linker engineering during the construction and optimization of DVD-Ig antibodies. Steric hindrance due to the proximity of the outer variable domain to the ligand binding site of the inner VD could, at least partially, be responsible for a reduced affinity of a domain when engineered as the inner variable domain. Accordingly, experiments were performed to determine if the scDVD approach could be used to engineer linkers to pair VHs or VLs in a DVD-Ig. To this end, a TNF/SOST scDVD library was made by introducing 12 different linkers: four SL linkers corresponding to the first 6, 8, 10 and 12 amino acids amino acids of the IgK constant region; four GS linkers with repeats of $Gly_4Ser$ (SEQ ID NO: 40) of 6, 8, 10 and 12 amino acids; and four proline-rich RL linkers corresponding to 6, 8, 10 and 12 amino acids (see FIG. 21A). Additionally, residues S94, N95a, G95b and S95c of the LCDR3 of SOST VL were mutated by NNK randomization. After four rounds of selection using different concentrations of Sclerostin under different conditions, the library output showed enrichment in RL linkers especially of the longest size (12 and 10 amino acids; between 3 to 7 folds). Also, the GS linkers were significantly reduced (between 6 to 8 fold) (see FIG. 21B). This data clearly demonstrates that scDVD-based yeast surface display allows for the optimization and engineering of linkers to pair VHs or VLs.

TABLE 4

| Peptide tags used on a panel of yeast expression vectors | | | | | |
|---|---|---|---|---|---|
| Peptide Tag | DNA sequence | SEQ ID NO: | Protein sequence | SEQ ID NO: | pYDsTEV vectors |
| HIS* | CATCATCACCATCACCAT | 2 | HHHHHH | 21 | |
| V5 | GGTAAGCCTATCCCTAACCCT CTCCTCGGTCTCGATTCTACG | 3 | GKPIPNPLLGLDST | 22 | 13767_pYDs_TEV_total |
| c-MYC | GAACAAAAACTTATTTCTGA AGAAGATCTG | 4 | EQKLISEEDL | 23 | pYDsTEV_c-MYC |
| HA | TACCCATACGATGTTCCGGAT TACGCT | 5 | YPYDVPDYA | 24 | pYDsTEV_HA |
| HSV | AGCCAGCCAGAACTCGCTCC TGAAGACCCAGAGGAC | 6 | SQPELAPEDPED | 25 | pYDsTEV_HSV |
| FLAG | GACTACAAGGACGACGACGA GAAG | 7 | DYKDDDDK | 26 | pYDsTEV_FLAG |
| StrepII | TGGAGCCATCCGCAGTTTGA GAAG | 8 | WSHPQFEK | 27 | pYDsTEV_StrepII |
| E2 | TCCAGCACCTCGAGTGATTTT CGAGATCGC | 9 | SSTSSDFRDR | 28 | pYDsTEV_E2 |
| S | AAGGAAACCGCGGCTGCCAA GTTTGAACGCCAGCATATGG ATAGC | 10 | KETAAAKFERQHMDS | 29 | pYDsTEV_S |
| E | GGAGCGCCTGTACCATATCC GGATCCGCTGGAACCGCGC | 11 | GAPVPYPDPLEPR | 30 | pYDsTEV_E |
| AcV5 | AGCTGGAAGGATGCGAGCGG CTGGAGC | 12 | SWKDASGWS | 31 | pYDsTEV_AcV5 |

*HIS tag is present in all pYDsTEV vectors downstream of all others tags.

TABLE 5

Commercially available anti-peptide tags antibodies used to monitor ScDVD antibody expression on yeast.

| Tag | Ab Source | Clone | Source | Catalog # |
|---|---|---|---|---|
| S | Mouse | SBSTAGa | Abcam | ab24838 |
| S | Rabbit | Polyclonal | | ab18588 |
| AcV5 | Mouse | AcV5 | Abcam. Rabbit S tag antibody | ab49581 |
| E2 | Mouse | 5E11 | Abcam. AcV5 tag antibody | ab977 |
| E | Rabbit | Polyclonal | Abcam T7 tag ® | ab3397 |
| E | Goat | Polyclonal | Abcam | ab95868 |
| E | Chicken | Polyclonal | | ab18695 |
| StrepII | Mouse | Strep-tag | Abcam. E tag antibody | MCA2489 |
| StrepII | Rabbit | Polyclonal | Abcam. E tag antibody | A00626 |
| HA | Mouse | HA-7 | Sigma | H9658 |
| HA | Goat | Polyclonal | Abcam | ab9134 |
| HA | Rat (IgG1) | 3F10 | Roche | 11-867-423 |
| c-myc | Mouse | 9E10 | Sigma | M4439 |
| c-myc | Rabbit | Polyclonal | Sigma | C3956 |
| Flag | Mouse | M2 | Sigma | F3165 |
| Flag | Rabbit | Polyclonal | Sigma | F7425 |
| HSV | Rabbit | Polyclonal | Sigma | H6030 |

TABLE 6

Commercially available secondary reagents used to monitor scFv antibody expression and binding on the surface of yeast

| Secondary reagent | Fluorocrome | Source | Catalog # |
|---|---|---|---|
| F(ab')2 Frag. Donkey Anti-Rat IgG | PerCp | Jackson ImmunoResearch | 712-126-150 |
| F(ab')2 Frag. Donkey Anti-Goat IgG | R-PE | Jackson ImmunoResearch | |
| F(ab')2 Frag. Donkey Anti-Rabbit IgG | DyLight-488 | Jackson ImmunoResearch | 705-116-147 |
| F(ab')2 Frag. Goat Anti-Rabbit IgG | R-PE | Jackson ImmunoResearch | |
| F(ab')2 Frag. Goat Anti-Rabbit IgG | Alexafluor 488 | Invitrogen | 711-486-152 |
| Chicken anti mouse IgG (H + L) | PerCP | Jackson ImmunoResearch | 111-116-144 |
| F(ab')2 Frag Donkey Anti-Mouse IgG | Alexafluor 633 | ThermoScientific | 715-126-151 |

EXAMPLE 14

Figure 22:
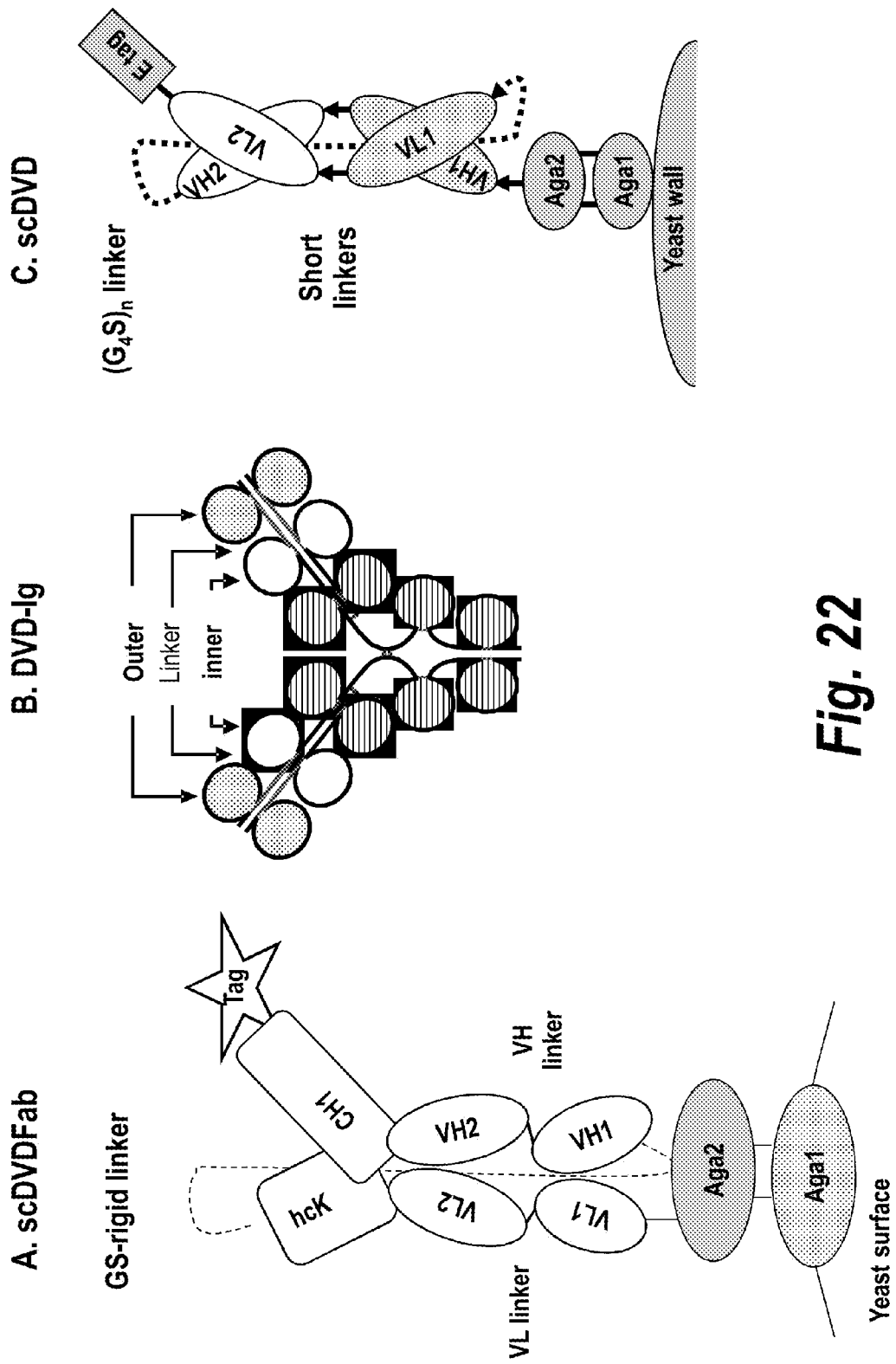
FIG. 22 is a schematic representation of exemplary scDVD libraries disclosed herein and multiplexing methods of using these libraries.

Generation of a Single Chain Dual Variable Domain Fab (scDVDFab) Including Constant Regions Another design of a scDVDFab antibody derived from a DVD-Ig is shown schematically in FIG. 22. For comparison, the schematic diagrams of a DVD-Ig (FIG. 22B) and a scDVD (FIG. 22C) have also been presented. In this example, the scDVDFab protein includes the variable heavy (VH) and light (VL) chains of a DVD-Ig in their entirety with the CH1 region of the heavy chain and the kappa constant region (Cκ) of the light chain. As shown in FIG. 22A, The VL domains fused to the Cκ(are tethered to the VH domains fused to the CH1 through a GS-rigid peptide linker of 41, 49, 57 or 65 amino acids from the carboxyl terminus of the Ck region to the amino terminus of the VH domains. These linkers are shown in greater detail below. VL1 and VL2 are paired connected with specific linkers already described and used in DVD-Igs and scDVD. The same is for VH1 and VH2 pair. FIG. 22A contains a schematic representation of a scDVDFab linear sequence.

Sequences encoding the variable regions were PCR amplified from the DVD-Ig expression vectors. Primers were designed in such a way that amplified DNAs had the necessary overlap sequence to perform additional overlapping PCRs. The final fragment contained the linear sequence represented in FIG. 23A plus a peptide tag used to monitor expression of the scDVDFab on the surface of yeast. The construct was cloned by homologous recombination into a pYD yeast expression vector using DH5α chemically competent bacteria. Clones from the transformation were screened by bacteria colony PCR for the presence of the right construct.

GS-rigid Linkers

The GS-rigid linkers were made by combinations of different Gly/Ser segments and proline rich rigid segments. The sequences of the linkers are below and a GS-rigid linker scheme could be found in FIG. 23B. More specifically the GS-rigid linkers are composed as follows:

N-terminus—$G_3SG_3$—left rigid segment—$G_2SG_2$—right rigid segment—$G_3SG_3$—C-terminus ("$G_3SG_3$" disclosed as SEQ ID NO: 43 and "$G_2SG_2$" disclosed as SEQ ID NO: 44)

where the rigid segments vary in length and amino acid composition. The following rigid segments have been tested:

Right rigid segment in the linkers:

```
        TPAPLPAPLPT    11  AA  (SEQ ID NO: 45)

TPAPTPAPLPAPLPT  15  AA  (SEQ ID NO: 46)

TPAPLPAPTPAPLPAPLPT  19  AA  (SEQ ID NO: 47)

TPAPLPAPLPAPTPAPLPAPLPT  23  AA  (SEQ ID NO: 48)
```

Left rigid segments in the linkers:

```
        TPLPAPLPAPT    11  AA  (SEQ ID NO: 49)

TPLPTPLPAPLPAPT  15  AA  (SEQ ID NO: 50)

TPLPAPLPTPLPAPLPAPT  19  AA  (SEQ ID NO: 51)

TPLPAPLPAPLPTPLPAPLPAPT  23  AA  (SEQ ID NO: 52)
```

41 aminoacids GS-rigid linker:

```
                                                 (SEQ ID NO: 53)
GGGSGGGTPLPAPLPAPTGGSGGTPAPLPAPLPTGGGSGGG
```

49 aminoacids GS-rigid linker:

```
                                                 (SEQ ID NO: 54)
GGGSGGGTPLPTPLPAPLPAPTGGSGGTPAPTPAPLPAPLPTGGGSGGG
```

57 aminoacids GS-rigid linker:

```
                                                 (SEQ ID NO: 55)
GGGSGGGTPLPAPLPTPLPAPLPAPTGGSGGTPAPTPAPTPAPLPAPL
PTGGGSGGG
```

65 aminoacids GS-rigid linker:

```
                                                 (SEQ ID NO: 56)
GGGSGGGTPLPAPLPAPLPTPLPAPLPAPTGGSGGTPAPTPAPTPAPT
PAPLPAPLPTGGGSGGG
```

Figure 24:
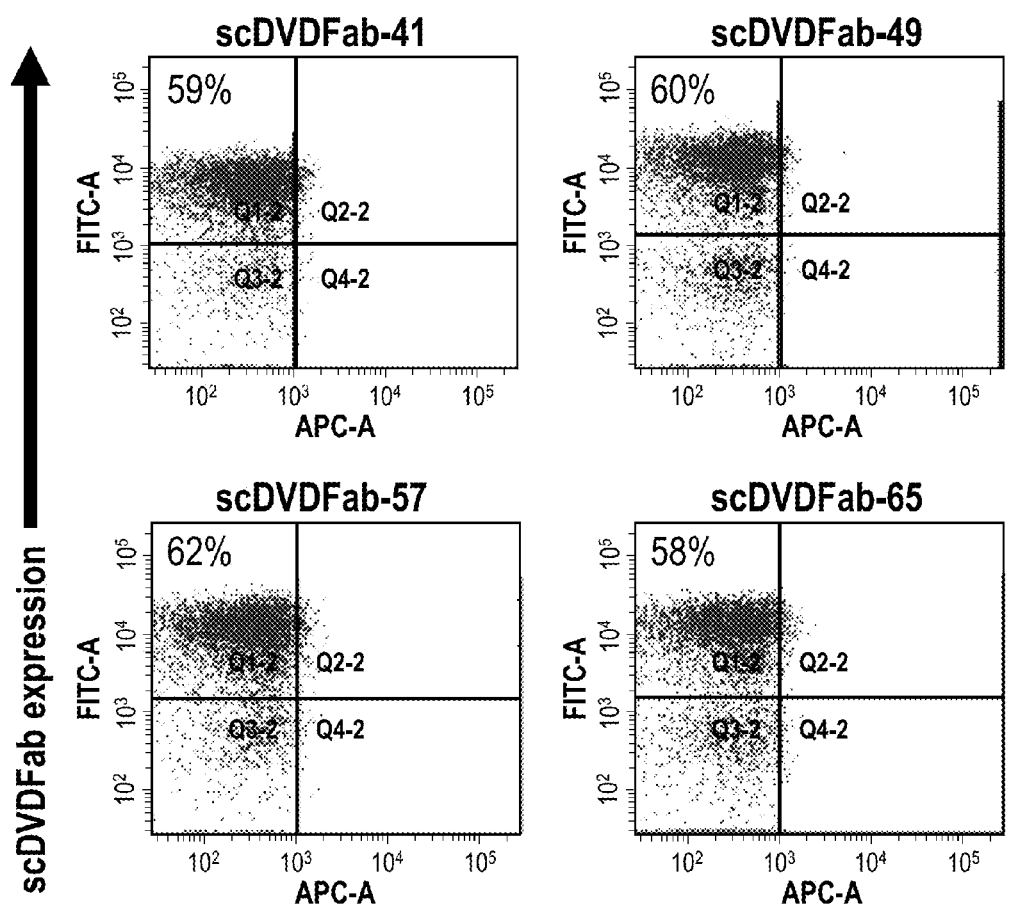
FIG. 24 depicts the results of flow cytometry assays measuring the expression of scDVDFab on the surface of yeast.

EXAMPLE 15 scDVDFab expression on the surface of yeast scDVDFab were expressed on the surface of yeast and the selected peptide tags were suitable for monitoring its expression. ScDVDFab expression on the surface of yeast was monitored by flow cytometry analysis and antibodies were used to detect peptide tags. A DVD-Ig was expressed as scDVDFab on the surface of yeast using pYD vectors and 4 different GS-rigid linkers. The expression of scDVDFab on the surface of yeast was comparable to that observed for scFv molecules reaching more than 50% of the yeast cells expressing the construct (FIG. 24). The length of the GS-rigid linker did not impact the ability of the cells to express the scDVDFab.

EXAMPLE 16

ScDVDFab Retained the Ability of DVD-Ig to Bind both Targets

Figure 25:
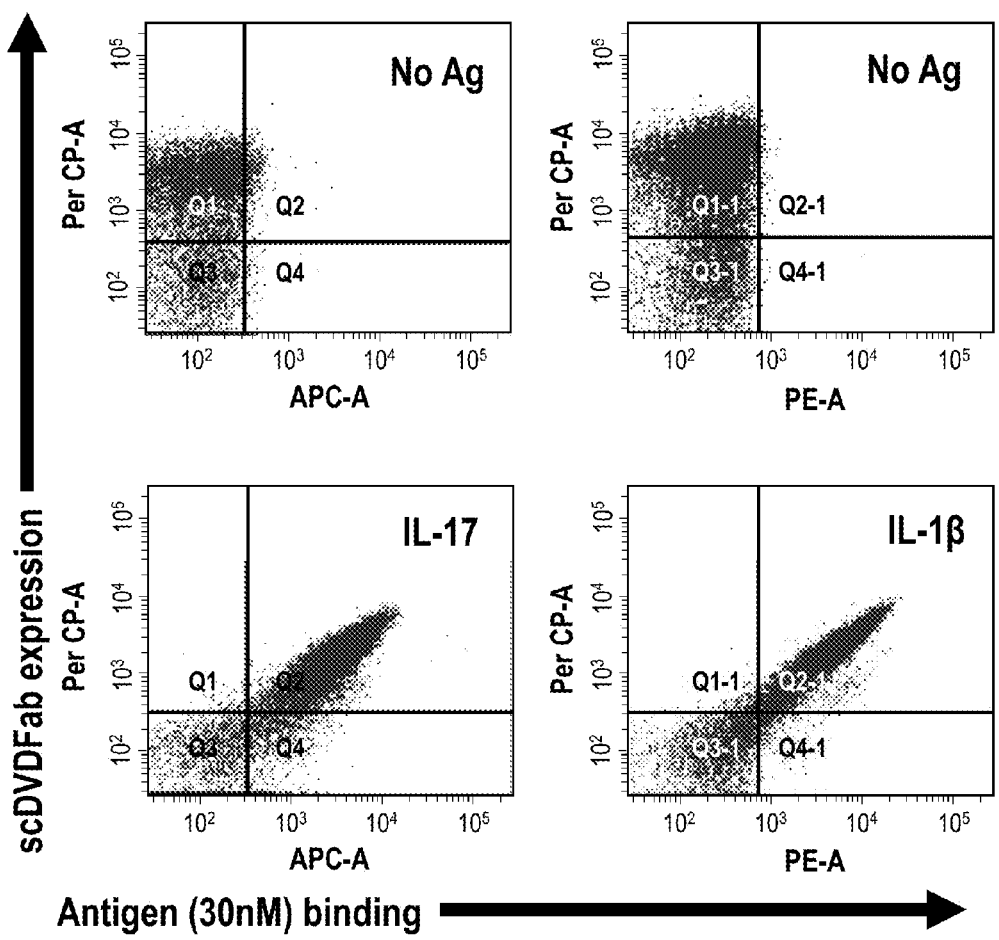
FIG. 25 depicts the results of flow cytometry assays showing that 1B/IL17 scDVDFab expressed on yeast retains its ability to bind both IL1B and/or IL17.

Functional DVD-Ig expressed as scDVDFab maintained its binding capabilities towards its two targets on the surface of yeast. A DVD-Igs was expressed as scDVDFab on the surface of yeast using pYD vectors. Aliquots of the yeast culture were incubated with biotinylated antigens. scDVD-Fab expression was monitored by purified tag-specific antibodies. Fluorochrome labeled secondary antibodies were used as detection reagents. IL-1B/IL17 scDVDFab retains its ability to bind both IL1B and/or IL17 (FIG. 25).

EXAMPLE 17

Figure 26:
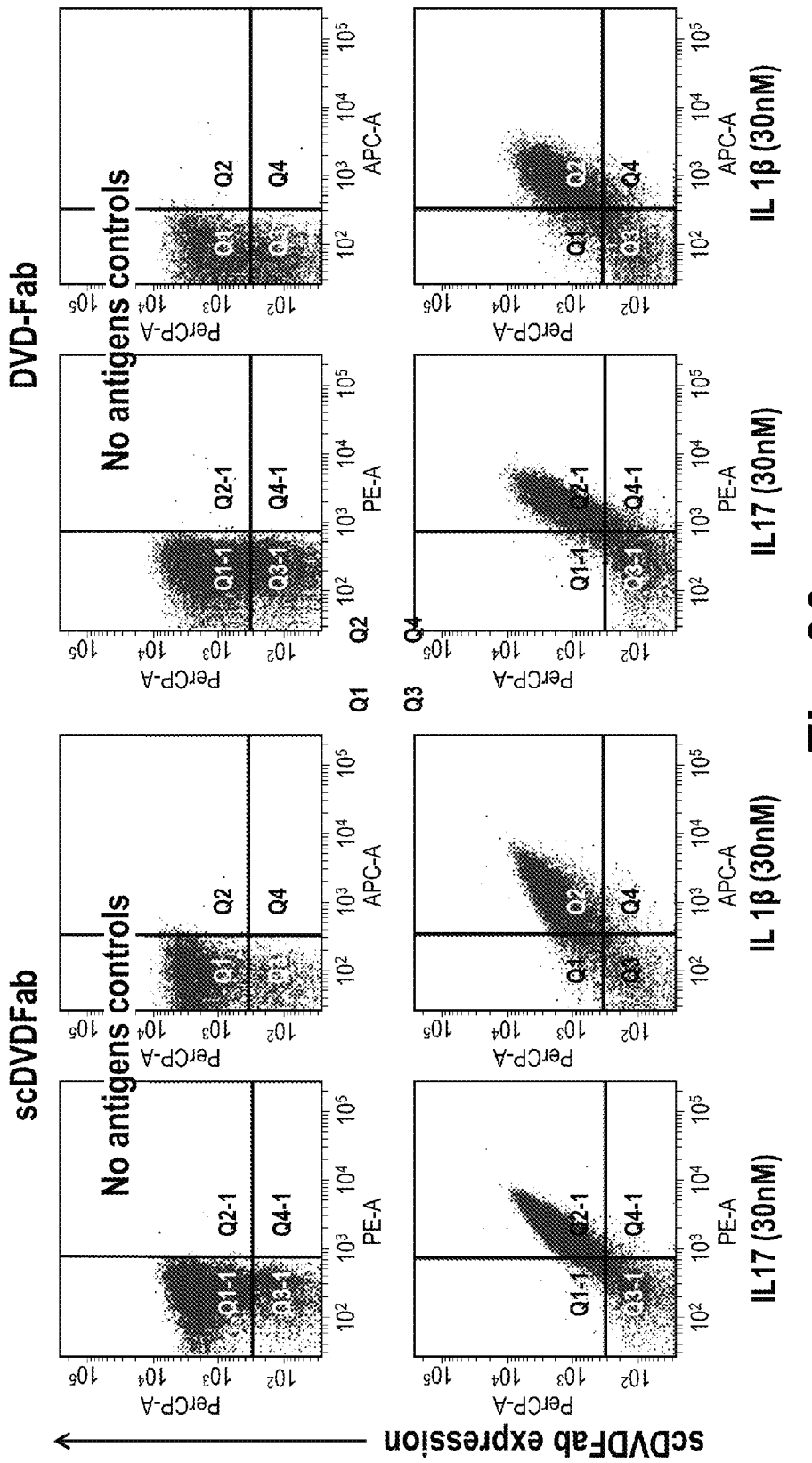
FIG. 26 depicts the results of flow cytometry assays showing that scDVDFab and DVD-Fab had similar binding profiles binding to both IL1B and 1L17 on the surface of yeast.
Figure 27:
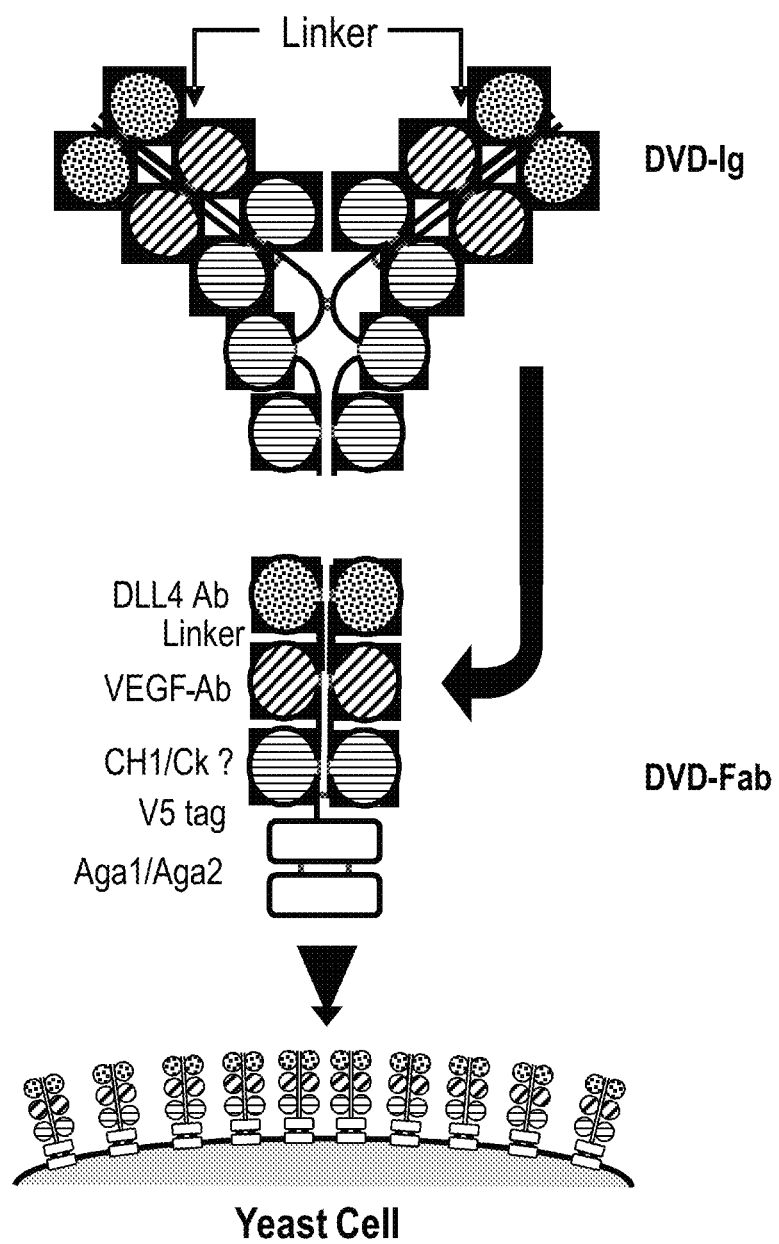
FIG. 27 depicts exemplary multivalent binding protein formats and cellular display methods.

Binding to both Targets is Comparable between scDVDFab and DVD-Fab Formats Expressed on the Surface of Yeast scDVDFab constructs bound both antigens in a similar way as the DVD-Fab bind them. A DVD-Ig was expressed as scDVDFab and DVD-Fab on the surface of yeast using pYD vectors. Aliquots of the yeast culture were incubated with biotinylated antigens. scDVDFab and DVD-Fab expression was monitored by purified tag-specific antibodies. Fluorochrome labeled secondary antibodies were used as detection reagents. The scDVDFab and DVD-Fab had similar binding profiles binding to both IL1B and 1L17 on the surface of yeast. There is a small increase in the mean fluorescence of scDVDFab compared to DVD-Fab (FIG. 26).

EXAMPLE 18

Construction of DVD-Fab Yeast Display Vector

A DLL4/VEGF DVD-Fab (comprising the VH and VL domains of anti-DLL4 clone h1A11.1 and an anti-VEGF antibody) was cloned into the yeast expression vector pFabB in a multiple step process. Briefly, the VH coding region of h1A11.1-short-Anti-VEGF was amplified from a different expression vector by PCR and inserted into pFabB vector (linearized with SpeI and SalI) by homologous recombination. The Vk coding region of h1A11.1-short-anti-VEGF was similarly amplified using 2-step overlapping PCR. The first PCR step amplified the h1A11.1-short-Anti-VEGF Vk region from a different expression vector, the second PCR step amplified the GAS leader sequence. The overlapping PCR product was then inserted into pFabB vector linearized with BamHI and BsiWI, containing the h1A11.1-short-Anti-VEGF VH correct sequence, by homologous recombination. After sequence confirmation, the pFabB-h1A11.1-SS-Anti-VEGF vector was transformed into chemically competent *S. cerevisiae* cells.

Upon induction of the cells, stainings were performed to confirm binding of the surface-expressed h1A11.1-SS-VEGF DVD-Fab to both DLL4 (human and murine) and VEGF. Expression of heavy and light chain on the surface of yeast was determined to be about 60%. After incubation of the cells with antigen for 1 h at 37C, binding to huDLL4 and muDLL4 at 100 nM was observed and of VEGF-Alexa647 at 300 nM.

EXAMPLE 19

Design and Construction of h1A11.1/VEGF DVD-Fab Library for Outer Domain Affinity Maturation Sequence alignment showed that the DLL4 antibody h1A11.1 shares the highest identity to human germlines VH3-7/JH4 and O2/JK2. Based on previous affinity maturation of mAb h1A11.1, only VH-CDR1 and VH-CDR2 were mutagenized. The h1A11.1 VH-CDR3 and VK sequences were left unchanged. To improve the affinity of h1A11.1 to DLL4, hypermutated CDR residues were identified from other human antibody sequences in the IgBLAST database that also shared high identity to germlines VH3-7. The corresponding h1A11.1 CDR residues were then subjected to limited mutagenesis by PCR with primers having low degeneracy at these positions to create one antibody library in the DVD-Ig Fab format suitable for use in affinity maturation procedure. The library contained mutations at residues 30, 31, 32, 35, 50, 52, 52a, 55, 56, 57 and 58 in the VH CDR1 and 2 (Kabat numbering). To further increase the identity of h1A11.1 to the human germline framework sequences, a binary degeneracy at VH position 76 (S/N) was introduced into the library. To construct the library for h1A11.1/VEGF VH multiple steps of overlapping PCR were performed using doped primers to introduce mutations in VH-CDR1 and VH-CDR2 of h1A11.1. The final library contained short linkers to separate the DLL4 and VEGF variable domains (short linker VH sequence=ASTKGP (SEQ ID NO: 57); short linker VL sequence=TVAAP (SEQ ID NO: 58)). The derived h1A11.1/VEGF VH PCR product was introduced into pFabB previously linearized with SpeI and SalI and containing h1A11.1/VEGF Vk coding sequence.

EXAMPLE 20

Sorting h1A11.1/VEGF DVD-Fab Yeast Display Library

Figure 28:
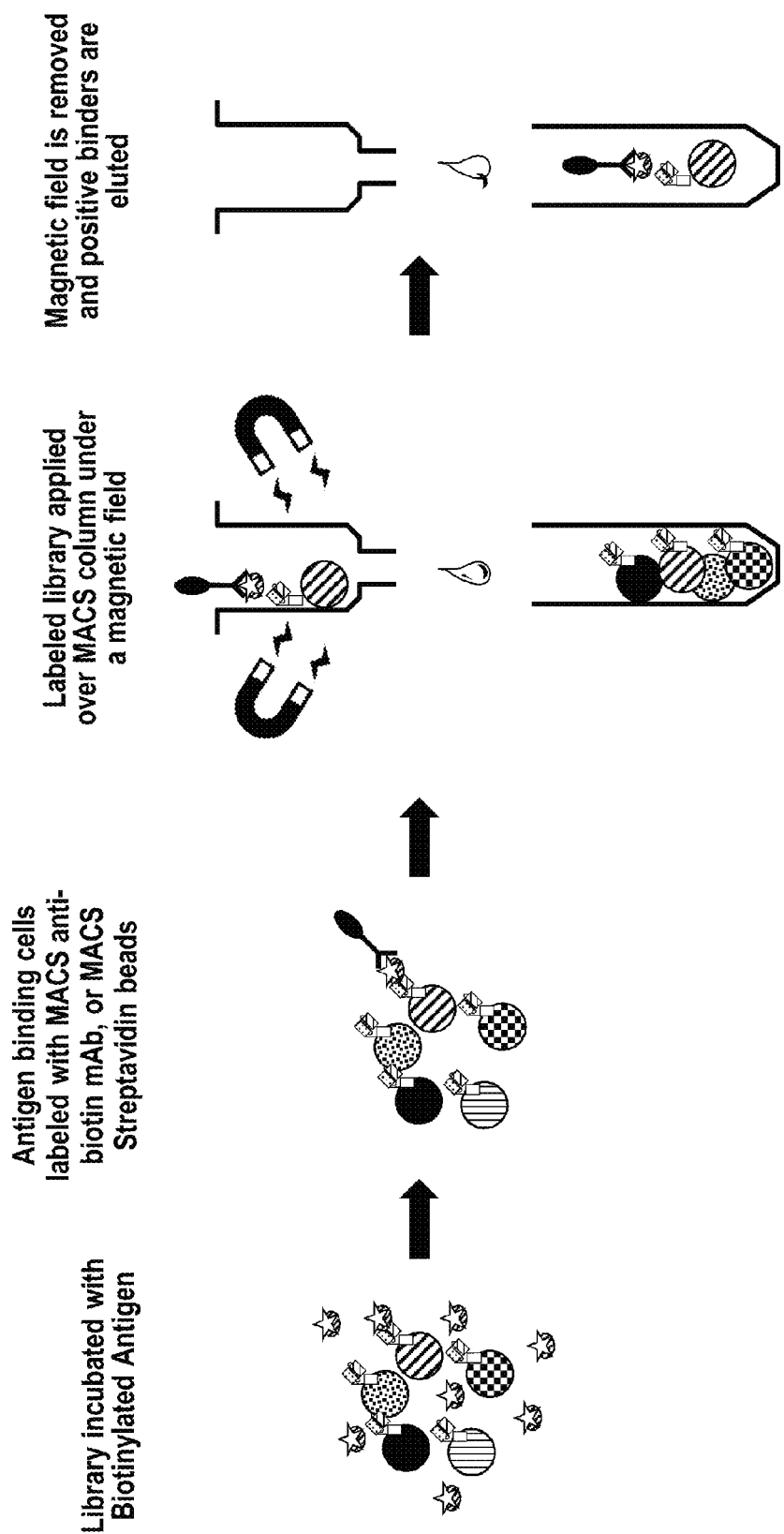
FIG. 28 is a schematic representation of an exemplary method of selecting for multivalent binding proteins using yeast cell surface display. Antigen-binding, binding protein-expressing yeast cells are selected by two rounds of MACS (Magnetic Activated Cell Sorting) and two rounds of FACS (Fluorescence Activated Cell Sorting).

The h1A11.1/VEGF DVD-Fab library described in Example 2 was transformed into EBY100 yeast cells and the library size determined to be $1.3 \times 10^9$. It was then displayed on the yeast cell surface and selected against DLL4 extracellular domain and VEGF by magnetic activated cell sorting (MACS) then fluorescence activated cell sorting (FACS). Two rounds of MACS were carried out by over-sampling the cells 10 folds and by using a 10-fold antigen excess. Similar conditions were used for the three rounds of sorting. Sorting was done by dual labeling of library cells, gating on the best DLL4 expressors and binders and by collecting the best simultaneous binders to DLL4 and VEGF. Conditions for MACS and FACS sorting are described in FIG. 28 where M=MACS and S=FACS sorting.

TABLE 7

Mutations in h1A11.1 VH Amino Acid Sequence for Outer Domain Affinity Maturation of DLL4/VEGF DVD-Fab

```
Mutated h1A11.1 VH Sequence (SEQ ID NO: 59)
EVQLVESGGGLVQPGGSLRLSCAASGFTFSNFPMAWVRQAPGKGLEWVATISSSDGTTYY
           RKL  T    S RW  ANSF
           NIY  P    K NS  VRIC
           KTV  K    I IL  RMPS
           IYI  G    P TY  DKNN
           GSR  D    A CR  WIML
           TRP  V    N FF  SAAR
           PPC  S    E WV  CYKQ
           MHS  E    R GT  YSRP
           LEN  Q    C DK  QFCI
           HDH  N      AG  MV H
           FCD  M       LP
           D  L        L
           C  F        G
           A

RDSVKGRFTISRDNAKNSLYLQMNSLRAEDTAVYYCARGYYNSPFAYWGQGTLVTVSS
      S
```

Selection for improved h1A11.1 affinity clones was carried out under the conditions set forth in Table 8 and amino acid sequences of affinity-modulated h1A11.1 clones were recovered for converting back to DVD-IgG format for further characterization (see Table 9). A total of 11 clones were identified through the second and third round of cell sorting, but only ten were converted to DVD-IgG format because clone h1A11.1-A02-53 had a cysteine in the CDR2.

TABLE 8

Conditions for MACS and FACS sorting of yeast expressing h1A11.1/VEGF DVD-Fab libraries

| Sort | Library | Ag [Ag] | Time | Temperature |
|---|---|---|---|---|
| M1 | h1A11.1 (H1 + H2) | 100 nM huDLL4-biotin | 1 h | 37° C. |
| M2 | h1A11.1 (H1 + H2) | 100 nM huDLL4-biotin | 1 h | 37° C. |
| M2S1 | h1A11.1 (H1 + H2) | 100 nM muDLL4-Alexa647 100 nM VEGF-biotin | 1 h | 37° C. |
| M2S2 | h1A11.1 (H1 + H2) | 25 nM muDLL4-Alexa647 100 nM VEGF-biotin | 15 min. | 37° C. |
| M2S3 | h1A11.1 (H1 + H2) | 3 nM muDLL4-Alexa647 300 nM VEGF-biotin | 5 min. | RT |

TABLE 9

Protein sequences of antibody clones identified from affinity maturation library for anti-DLL4 antibody h1A11.1 Affinity Matured Clones: Heavy Chain (VH) Regions

| | | | |
|---|---|---|---|
| h1A11.1-B9-S2 | EVQLVESGGGLVQPGGSLRLSCAASGFTFSHFPMAWVRQAPGKGLEWVASISSSDSTTNYRDSVKGRFTISRDNAKNSLYLQMNSLRAEDTAVYYCARGYYNSPFAYWGQGTLVTVSS (SEQ ID NO: 60) | | |
| | CDR1 | CDR2 | CDR3 |
| | SHFPMA (SEQ ID NO: 61) | SISSSDSTTNYRDSVKG (SEQ ID NO: 62) | GYYNSPFAY (SEQ ID NO: 63) |
| h1A11.1-G10-S2 | EVQLVESGGGLVQPGGSLRLSCAASGFTFKNFPMAWVRQAPGKGLEWVATISSSDLSTNYRDSVKGRFTISRDNAKNSLYLQMNSLRAEDTAVYYCARGYYNSPFAYWGQGTLVTVSS (SEQ ID NO: 64) | | |
| | CDR1 | CDR2 | CDR3 |
| | KNFPMA (SEQ ID NO: 65) | TISSSDLSTNYRDSVKG (SEQ ID NO: 66) | GYYNSPFAY (SEQ ID NO: 63) |
| h1A11.1-H3-S2 | EVQLVESGGGLVQPGGSLRLSCAASGFTFRNFPMAWVRQAPGKGLEWVASISSSDGTTNYRDSVKGRFTISRDNAKSSLYLQMNSLRAEDTAVYYCARGYYNSPFAYWGQGTLVTVSS (SEQ ID NO: 67) | | |
| | CDR1 | CDR2 | CDR3 |
| | RNFPMA (SEQ ID NO: 68) | SISSSDGTTNYRDSVKG (SEQ ID NO: 69) | GYYNSPFAY (SEQ ID NO: 63) |

TABLE 9-continued Protein sequences of antibody clones identified from
affinity maturation library for anti-DLL4 antibody h1A11.1
Affinity Matured Clones: Heavy Chain (VH) Regions

```
h1A11.1-   EVQLVESGGGLVQPGGSLRLSCAASGFTFRHFPMTWVRQAPGKGLEWVASI
F7-S2      SSSDGTINYRDSVKGRFTISRDNAKNSLYLQMNSLRAEDTAVYYCARGYYN
           SPFAYWGQGTLVTVSS (SEQ ID NO: 70)
           CDR1            CDR2                  CDR3
           RHFPMT          SISSSDGTINYRDSVKG     GYYNSPFAY
           (SEQ ID         (SEQ ID NO:72)        (SEQ ID NO:63)
           NO: 71)

h1A11.1-   EVQLVESGGGLVQPGGSLRLSCAASGFTFRNFPMAWVRQAPGKGLEWVATI
C1-S2      SSSDGTPAYRDSVKGRFTISRDNAKNSLYLQMNSLRAEDTAVYYCARGYYN
           SPFAYWGQGTLVTVSS (SEQ ID NO: 73)
           CDR1            CDR2                  CDR3
           RNFPMA          TISSSDGTPAYRDSVKG     GYYNSPFAY
           (SEQ ID         (SEQ ID NO: 74)       (SEQ ID NO: 63)
           NO: 68)

h1A11.1-   EVQLVESGGGLVQPGGSLRLSCAASGFTFRYFPMAWVRQAPGKGLEWVAAI
F12-S2     SGSDGTASYRDSVKGRFTISRDNAKNSLYLQMNSLRAEDTAVYYCARGYYN
           SPFAYWGQGTLVTVSS (SEQ ID NO: 75)
           CDR1            CDR2                  CDR3
           RYFPMA          AISGSDGTASYRDSVKG     GYYNSPFAY
           (SEQ ID         (SEQ ID NO: 77)       (SEQ ID NO: 63)
           NO: 76)

h1A11.1-   EVQLVESGGGLVQPGGSLRLSCAASGFTFNHFPMAWVRQAPGKGLEWVATI
G07-S2     SSSDWTPYYRDSVKGRFTISRDNAKNSLYLQMNSLRAEDTAVYYCARGYYN
           SPFAYWGQGTLVTVSS (SEQ ID NO: 78)
           CDR1            CDR2                  CDR3
           NHFPMA          TISSSDWTPYYRDSVKG     GYYNSPFAY
           (SEQ ID         (SEQ ID NO: 80)       (SEQ ID NO:63)
           NO: 79)

h1A11.1-   EVQLVESGGGLVQPGGSLRLSCAASGFTFQKYPMAWVRQAPGKGLEWVATI
A02-S3     SCSDGITHYRDSVKGRFTISRDNAKNSLYLQMNSLRAEDTAVYYCARGYYN
           SPFAYWGQGTLVTVSS (SEQ ID NO: 81)
           CDR1            CDR2                  CDR3
           QKYPMA          TISCSDGITHYRDSVKG     GYYNSPFAY
           (SEQ ID         (SEQ ID NO: 83)       (SEQ ID NO: 63)
           NO: 82)

h1A11.1-   EVQLVESGGGLVQPGGSLRLSCAASGFTFRHFPMAWVRQAPGKGLEWVATI
A04-S3     SSSDGATYYRDSVKGRFTISRDNAKSSLYLQMNSLRAEDTAVYYCARGYYN
           SPFAYWGQGTLVTVSS (SEQ ID NO: 84)
           CDR1            CDR2                  CDR3
           RHFPMA          TISSSDGATYYRDSVKG     GYYNSPFAY
           (SEQ ID         (SEQ ID NO: 86)       (SEQ ID NO: 63)
           NO: 85)

h1A11.1-   EVQLVESGGGLVQPGGSLRLSCAASGFTFRHFPMAWVRQAPGKGLEWVASI
A10-S3     SSSDGTSNYRDSVKGRFTISRDNAKSSLYLQMNSLRAEDTAVYYCARGYYN
           SPFAYWGQGTLVTVSS (SEQ ID NO: 87)
           CDR1            CDR2                  CDR3
           RHFPMA          SISSSDGTSNYRDSVKG     GYYNSPFAY
           (SEQ ID         (SEQ ID NO: 88)       (SEQ ID NO: 63)
           NO: 85)

h1A11.1-   EVQLVESGGGLVQPGGSLRLSCAASGFTFGHFPMAWVRQAPGKGLEWVATI
E06-S3     SSSDGATNYRDSVKGRFTISRDNAKNSLYLQMNSLRAEDTAVYYCARGYYN
           SPFAYWGQGTLVTVSS (SEQ ID NO: 89)
           CDR1            CDR2                  CDR3
           GHFPMA          TISSSDGATNYRDSVKG     GYYNSPFAY
           (SEQ ID         (SEQ ID NO: 91)       (SEQ ID NO: 63)
           NO: 90)
```

S2 and S3 clones refer to clones identified after either two rounds or three rounds of sorting respectively.

EXAMPLE 21

Characterization of DLL41VEGF DVD-Fab Affinity Maturation Outputs

The affinity matured DLL4/VEGF clones identified and described in Table 9 were converted into full DVD-Ig molecules. Primers complementary to the 5' and 3' ends of each clone were designed and clones were amplified by PCR and introduced into the mammalian expression vector pHybE by homologous recombination. After performing bacterial colony PCR one clone of each construct was confirmed correct, scaled up and transiently transfected into HEK-293 cells for expression. Protein supernatants were harvested and purified by protein A affinity chromatography. Clone h1A11.1-E06-S3 was not purified because it expressed very poorly in HEK-293 cells. Purified material was utilized for characterization of DVD-Ig molecules by SEC, MS, stability assay (see Table 10) and Biacore (see Table 11 and Table 12). Stability assays were carried out at 50 mg/ml DVD-Ig in 15 mM histidine buffer (pH6.0) at 5° C. Monomer percentage was monitored at days 0, 8 and 21.

TABLE 10

SEC, MS and stability assay data for affinity matured DLL4/VEGF clones

| DVD clone | % monomer | MS | Stability 5° C., 21 days* |
|---|---|---|---|
| h1A11.1-G10-S2-SS-Anti-VEGF | 83.3 | OK | no loss of monomer % |
| h1A11.1-F7-S2-SS-Anti-VEGF | 70.8 | OK | no loss of monomer % |
| h1A11.1-F12-S2-SS-Anti-VEGF | 63.6 | OK | no loss of monomer % |
| h1A11.1-C1-S2-SS-Anti-VEGF | 79.2 | OK | no loss of monomer % |
| h1A11.1-B9-S2-SS-Anti-VEGF | 70.5 | VL OK VH 5.54 Da diff. | no loss of monomer % |
| h1A11.1-H3-S2-SS-Anti-VEGF | 66.5 | OK | no loss of monomer % |
| h1A11.1-G7-S2-SS-Anti-VEGF | 73.2 | OK | no loss of monomer % |
| h1A11.1-A10-S3-SS-Anti-VEGF | 63.3 | OK | no loss of monomer % |
| h1A11.1-A04-S3-SS-Anti-VEGF | 61.3 | OK | no loss of monomer % |

*Samples h1A11.1-A10-S3-SS-Anti-VEGF and h1A11.1-A04-S3-SS-Anti-VEGF were tested at day 0, 7 and 47 days.

TABLE 11

Binding kinetics of DLL4/VEGF affinity maturation-derived DVD-Ig molecules to huDLL4

| DVD clone | Ka | Kd | $K_D$ | $K_D$ ratio (parental DVD/AM DVD) |
|---|---|---|---|---|
| h1A11.1-SS-Anti-VEGF | 1.33E+05 | 2.66E−03 | 2.00E−08 | 1.00 |
| h1A11.1-G10-S2-SS-Anti-VEGF | 1.35E+05 | 7.45E−05 | 5.54E−010 | 36.024 |
| h1A11.1-F7-S2-SS-Anti-VEGF | 5.7E+05 | 3.19E−04 | 5.56E−10 | 35.901 |
| h1A11.1-F12-S2-SS-Anti-VEGF | 1.60E+05 | 1.24E−04 | 7.76E−10 | 25.699 |
| h1A11.1-C1-S2-SS-Anti-VEGF | 1.21E+05 | 1.10E−04 | 9.11E−10 | 21.911 |
| h1A11.1-B9-S2-SS-Anti-VEGF | 1.15E+05 | 1.06E−04 | 9.23E−10 | 21.617 |
| h1A11.1-H3-S2-SS-Anti-VEGF | 1.30E+05 | 1.36E−03 | 1.04E−09 | 19.128 |
| h1A11.1-G7-S2-SS-Anti-VEGF | 1.17E+05 | 1.55E−04 | 1.32E−09 | 15.160 |
| h1A11.1-A10-S3-SL-Anti-VEGF | 1.34E+05 | 5.86E−05 | 4.39E−10 | 62.8 |
| h1A11.1-A04-S3-SL-Anti-VEGF | 1.25E+05 | 9.04E−05 | 7.23E−10 | 38.2 |

DVD = Dual Variable Domain Ig molecule;
E = multiply by 10 to indicated exponent;
Ka (M$^{-1}$s$^{-1}$);
Kd (s$^{-1}$);
$K_D$ (M);
SS (short linker in both VH and VL variable regions);
samples h1A11.1-A10-S3-SL-Anti-VEGF and h1A11.1-A04-S3-SL-Anti-VEGF were tested with short long linkers (for VH and VL respectively) as opposed to short short linkers

TABLE 12

Binding kinetics of DLL4/VEGF affinity maturation-derived DVD-Ig molecules to muDLL4

| DVD clone | Ka | Kd | $K_D$ | $K_D$ ratio (parental DVD/AM DVD) |
|---|---|---|---|---|
| h1A11.1-SS-Anti-VEGF | 4.79E+05 | 1.03E−02 | 2.14E−08 | 1.00 |
| h1A11.1-G10-S2-SS-Anti-VEGF | 2.07E+05 | 1.12E−04 | 5.39E−010 | 39.651 |
| h1A11.1-F7-S2-SS-Anti-VEGF | 1.34E+06 | 4.83E−04 | 3.61E−10 | 59.192 |
| h1A11.1-F12-S2-SS-Anti-VEGF | 2.24E+05 | 1.70E−04 | 7.04E−10 | 30.378 |
| h1A11.1-C1-S2-SS-Anti-VEGF | 1.86E+05 | 1.62E−04 | 8.70E−10 | 24.578 |
| h1A11.1-B9-S2-SS-Anti-VEGF | 1.67E+05 | 2.05E−04 | 1.23E−09 | 17.396 |
| h1A11.1-H3-S2-SS-Anti-VEGF | 1.97E+05 | 2.94E−04 | 1.49E−09 | 14.311 |
| h1A11.1-G7-S2-SS-Anti-VEGF | 1.69E+05 | 2.66E−04 | 1.57E−09 | 13.618 |
| h1A11.1-A10-S3-SS-Anti-VEGF | 1.71E+05 | 1.33E−04 | 7.74E−10 | 53.8 |
| h1A11.1-A04-S3-SS-Anti-VEGF | 1.80E+05 | 8.12E−05 | 4.51E−10 | 92.2 |

EXAMPLE 22

Design and Construction of DLL41VEGF DVD-Fab Linker Library

A DLL4/VEGF linker library was constructed using 3 different types of linkers: standard long/short linkers, GS linkers and rigid linkers (see Table 13 and/or 17 for amino acid sequences of linkers). Oligonucleotides containing each DNA linker sequence with 5' ends complementary to the DLL4 sequence of h1A11.1 and with 3' ends complementary to the VEGF sequence of Anti-VEGF were synthesized. Oligonucleotides were pooled in equimolar amounts in 6 different groups based on their type and on their length. PCR reactions were carried out separately with the 6 different oligonucleotide groups using DLL4/VEGF M2S-encoding DNA isolated from previous DLL4/VEGF affinity maturation (see Example 3) as template. Reactions for VH and VL linker libraries were carried out separately. Each PCR product was gel purified, concentrated and mixed in equimolar amounts to result in one final PCR product containing the linker library for VH and for VL separately. The VH and VL-containing PCR products were then combined into one product by overlapping PCR and recombined into pFabB expression vector linearized with SpeI, SalI, BsiWI and BamHI by yeast electroporation. Different ratios of vector and insert were used (ug vector/ug insert=4/12, 4/18 and 4/24) and derived populations of yeast cells were grown separately first then eventually were combined together in a manner that allowed each population to be oversampled 10-fold. Yeast colony PCR was performed on the pooled populations to determine the diversity of the final library. After sequence analysis the size of the final DLL4 M2S1 recombined linker library was determined to be $2.3 \times 10^7$ and the linker distribution of each linker subtype followed the predicted distribution (see Table 14). It was also observed that about 66% of the clones had a combination of different types of linkers for VH and VL, while about 34% had a combination of the same type of linker

TABLE 13

Amino acid sequences of linkers used for linker library construction

| Linker type | VH linker (name) | SEQ ID NO: | VL linker | SEQ ID NO: |
|---|---|---|---|---|
| Standard | ASTKGPSVFPLAP (VH13) | 92 | TVAAPSVFIFPP (VL12) | 93 |
| Standard | ASTKGPSVFPLA (VH12) | 94 | TVAAPSVFIFP (VL11) | 95 |
| Standard | ASTKGPSVFPL (VH11) | 96 | TVAAPSVFIF (VL10) | 97 |
| Standard | ASTKGPSVFP (VH10) | 98 | TVAAPSVFI (VL9) | 99 |
| Standard | ASTKGPSVF (VH9) | 100 | TVAAPSVF (VL8) | 101 |
| Standard | ASTKGPSV (VH8) | 102 | TVAAPSV (VL7) | 103 |
| Standard | ASTKGPS (VH7) | 104 | TVAAPS (VL6) | 105 |
| Standard | ASTKGP (VH6) | 106 | TVAAP (VL5) | 107 |
| GS | GGGGSGGGSGGGG (GS14VH) | 108 | GGSGGGSGGGGS (GS13VL) | 109 |
| GS | GGGGSGGGGSGGG (GS13VH) | 110 | GGSGGGGSGGGG (GS12VL) | 111 |
| GS | GGGGSGGGGSGG (GS12VH) | 112 | GGSGGGGSGGG (GS11VL) | 113 |
| GS | GGGGSGGGGSG (GS11VH) | 114 | GGSGGGGSGG (GS10VL) | 115 |
| GS | GGGGSGGGGS (GS10VH) | 116 | GGSGGGGSG (GS9VL) | 117 |
| GS | GGGGSGGGG (GS9VH) | 118 | GGSGGGGS (GS8VL) | 119 |
| GS | GGGGSGGG (GS8VH) | 120 | GGSGGGG (GS7VL) | 121 |
| GS | GGGGSGG (GS7VH) | 122 | GGSGGG (GS6VL) | 123 |
| GS | GGGGSG (GS6VH) | 124 | GGSGG (GS5VL) | 125 |
| Rigid linker | TPAPLPAPLPAPTT (RL14VH) | 126 | TPAPLPAPLPAPT (RL13VL) | 127 |
| Rigid linker | TPAPLPAPAPTT (RL12VH) | 128 | TPAPLPAPAPT (RL11VL) | 129 |
| Rigid linker | TPAPLPAPTT (RL10VH) | 130 | TPAPLPAPT (RL9VL) | 131 |
| Rigid linker | TPAPLPTT (RL8VH) | 132 | TPAPLPT (RL7VL) | 133 |
| Rigid linker | TPAPTT (RL6VH) | 134 | TPAPT (RL5VL) | 135 |

TABLE 14

Percentage linker distribution after linker library construction

| Linker type | VH linker Predicted % | VH linker Actual % | VL linker Predicted % | VL linker Actual % |
|---|---|---|---|---|
| Regular | 36.4 | 37 | 36.4 | 36.5 |
| GS | 40.9 | 42 | 40.9 | 47 |
| Rigid | 22.7 | 21 | 22.7 | 16.5 |

EXAMPLE 23

DLL4 M2S11VEGF Recombined Linker Library Sorting

Scouting experiments were performed to determine optimal condition for library sorting. Suitable selective conditions were found to be 3 nM muDLL4 and 300 nM VEGF. The DLL4 M2S1/VEGF linker library was oversampled by 10-fold and labeling was done with 10-fold antigen excess as described in Example 20. Different labeling and sorting was performed under a variety of conditions (see Table 15). Antigen binding was carried out at 37° C. for 15 minutes. A total of 5 different outputs were collected.

TABLE 15

Labeling and sorting conditions of DLL4M2S1/VEGF recombined linker library

| Library | Antigen [Ag] | Gate | Sort |
|---|---|---|---|
| DLL4 M2S1/ VEGF rec. linker library | 3 nM muDLL4 | Best muDLL4 binders | 1-Best muDLL4 binders |
| DLL4 M2S1/ VEGF rec. linker library | 3 nM muDLL4 300 nM VEGF | Best muDLL4 binders | 2-Best muDLL4 and VEGF simultaneous binders 3-Best muDLL4 binders regardless of VEGF binding |
| DLL4 M2S1/ VEGF rec. linker library | 3 nM muDLL4 300 nM VEGF | Best VEGF binders | 4-Best VEGF and muDLL4 simultaneous binders 5-Best VEGF binders regardless of muDLL4 binding |

Upon sequence analysis of the 5 different outputs it was concluded that the best way to sort the library is to perform double staining and collect the best simultaneous binders (by gating on either DLL4 or VEGF best binders first). After another scouting experiment to determine the best antigen binding conditions for the 5 libraries, a second round of sorting was performed. Simultaneous binding of 0.3 nM muDLL4 and 100 nM VEGF was carried out at room temperature for 5 minutes. Only sorted populations 2, 4 and 5 from the first round (see Table 15) were sorted in the second round. Labeling and sorting conditions are set forth in Table 16.

TABLE 16

Labeling and sorting conditions of DLL4M2S2/VEGF recombined linker library

| Library | Population | Antigen [Ag] | Gate | Sort |
|---|---|---|---|---|
| DLL4 M2S2/VEGF | 2 | 0.3 nM muDLL4 | Best muDLL4 | Best muDLL4 and VEGF |
| rec. linker library | | 100 nM VEGF | binders | simultaneous binders |
| DLL4 M2S2/VEGF | 4 | 0.3 nM muDLL4 | Best VEGF binders | Best muDLL4 and VEGF |
| rec. linker library | | 100 nM VEGF | | simultaneous binders |
| DLL4 M2S2/VEGF rec. linker library | 5 | 100 nM VEGF | Best VEGF binders | Best VEGF binders |

A third round of sorting is performed, based upon the library diversity after the second round of sorting. Specifically, a scouting experiment is first performed as described herein (see Example 6) to determine optimal antigen concentrations and, based on that result, a third round of sorting is performed. Population 5 is gated as in the second round of sorting (see Table 16) to identify linker pairs that are best suited for inner domain (anti-VEGF in this case) affinity improvement, independent of DLL4 affinity. Populations 2 and 4 are gated as in the second round of sorting (see Table 16) to identify DLL4/VEGF DVD-Ig molecules with improved DLL4 binding and possibly VEGF binding. Output yeast cells are plated on SDCAA plates and 96 colonies are picked from each plate. Sequence analysis of all outputs is performed to determine the diversity of each population and which linker pairs are preferred for inner domain (VEGF) affinity improvement, outer domain (DLL4) affinity improvement by maintaining and/or improving affinity of inner domain (Anti-VEGF).

EXAMPLE 24

Characterization of DLL4/VEGF DVD-Fab Recombinant Linker Library Output

The best performing DLL4/VEGF DVD-Fab recombinant linker library clones identified through several rounds of sorting are converted to DVD-Ig molecules and characterized as described in Example 21.

EXAMPLE 25

Design and Construction of VEGF/DLL4 DVD-Fab Linker Library for Inner Domain Affinity Maturation A VEGF/DLL4 linker library was constructed using 3 different types of linkers: standard long/short linkers, GS linkers and rigid linkers as in Example 22 (see Table 13 for amino acid sequences of linkers). Oligonucleotides containing each DNA linker sequence with 5' ends complementary to the VEGF sequence of Anti-VEGF and with 3' ends complementary to the DLL4 sequence of h1A11.1 were synthesized. Oligonucleotides were pooled in equimolar amounts in 6 different groups based on their type and on their length. PCR reactions were carried out separately with the 6 different oligonucleotide groups using pFabB-Anti-VEGF-G514-h1A11.1 parental vector DNA as template. Reactions for VH and VL linker libraries were carried out separately. Each PCR product was gel purified and concentrated and mixed in equimolar amounts so that to have a one final PCR product containing the linker library for VH and for VL separately. The VH and VL-containing PCR products were then combined into one product by overlapping PCR and recombined into pFabB expression vector linearized with SpeI, SalI, BsiWI and BamHI by yeast electroporation. A ratio of ug vector/ug insert=4/12 was used and derived population of yeast cells was grown. Yeast colony PCR was performed on the population to determine the diversity of the final library. After sequence analysis the size of the final VEGF/DLL4 linker library was determined to be $3.5 \times 10^7$ and all types of linkers were represented. After several rounds of sorting as described in Example 9, this library is recombined with h1A11.1 VH library for inner domain affinity maturation. This h1A11.1 VH library is designed as described in Example 2 and VEGF/DLL4 linker library-derived DNA are used as template for PCR. The derived VEGF/h1A11.1 VH PCR product are introduced into pFabB previously linearized with SpeI and SalI and containing VEGF/h1A11.1 Vk linker library coding sequence.

EXAMPLE 26

Sorting VEGF/h1A11.1 DVD-Fab Yeast Display Linker Library and Recombined Library for Inner Domain (H1A11.1) Affinity Maturation A VEGF/h1A11.1 DVD-Fab yeast display linker library is transformed into EBY100 yeast cells by electroporation and then displayed on cell surfaces and selected against DLL4 extracellular domain and VEGF by fluorescence activated cell sorting (FACS). Multiple rounds of sorting will be performed to reduce library diversity, in a similar manner to that set forth in Example 20. Specifically, sorting is performed by dual labeling of library cells, gating on the best DLL4 expressors and binders and by collecting the best simultaneous binders to DLL4 and VEGF. Selection for improved h1A11.1 affinity clones is then performed and amino acid sequences of affinity-modulated h1A11.1 clones are recovered for conversion to DVD-IgG format for further characterization.

EXAMPLE 27

Characterization of VEGF/DLL4 DVD-Fab Affinity Maturation Output

Affinity matured VEGF/DLL4 clones are converted into full DVD-Ig molecules and characterized as described in Example 21.

EXAMPLE 28

Apply Different Selection Conditions for DVD-Fab Yeast Library Sorting

A synthetic library of IL17/IL1α DVD-Fab is generated and recombined into pFabB yeast expression vectors by electroporation into yeast cells. Several IL17/IL1α DVD-Fab are selected based upon available data for multiple IL17/IL1α DVD-Ig molecules previously generated. These DVD-Ig molecules have been extensively characterized and have known binding affinities and potencies, solubility, stability and physicochemical properties. Several DVD-Ig molecules with good, acceptable and poor physicochemical properties are selected. These molecules are used as DNA template for PCR to construct the synthetic library. After being amplified they are mixed in equimolar amount before being transformed into yeast. The IL17/IL1α DVD-Fab library are selected using different conditions for sorting (salt concentration, buffer pH, different buffers, heating and possibly other methods). The selection pressure that allows selection of DVD-Ig molecules from the library with best physicochemical properties is determined. This method is optionally incorporated during affinity maturation of a DVD-Ig molecule to select not only for molecules with improved binding affinity but also with improved physicochemical properties.

EXAMPLE 29

Design and Construction of IL1β/IL17 Mix and Match DVD-Fab Library

A IL1β/IL17 mix and match library was constructed using 7 outer domain mAbs to IL1β, 3 inner domains mAbs to IL17, and 2 types of linkers of various lengths (see Table 17). The library was constructed using an overlapping PCR strategy. Oligonucleotides were designed and synthesized in two groups: (1) reverse primers that anneals to the outer domain mAb sequence and encodes the DNA sequence of shortest linker length of a linker type (i.e. VH6); and (2) forward primers that anneal to the inner domain sequence and encode the DNA sequence of the entirety of the linker Each mAb VH and VL was PCR amplified separately using the appropriate primers; for the inner domains all primer oligonucleotides were pooled by type (i.e. all Elbow VH). Each PCR product was cleaned up using Qiagen QiaQuick PCR purification kit and then pooled in equal amounts grouped by mAb lineage and linker type for a total of 16 PCR pools for the second round PCR. For example four pools were created for the VH1 domain: 1B12 lineage with Elbow linker; 1B12 lineage with GS linker; E26 lineage with Elbow linker; and E26 lineage with GS linker Heavy chain and light chains were each assembled in four separate PCR reactions, for example: (1) 1B12 lineage+Elbow linkers+B6 lineage, (2) 1B12 lineage+Elbow linkers+10F7M11, (3) 1B12 lineage+GS linkers+B6 lineage, (4) 1B12 lineage+GS linkers+10F7M11. The second round PCR reactions were gel purified and equal amounts of heavy chain PCR, light chain PCR, and promoter sequence PCR were used for the third round PCR. The third round PCR product was gel purified, concentrated, and then recombined with linearized pFabB expression vector by yeast electroporation. The pFabB expression vector was linearized by digestion with SalI, BsiWI, and BamHI followed by gel purification and concentration. Based on dilution plating, the library size was estimated at $3 \times 10^8$ members. After library yeast cells were grown, the library DNA was isolated from the yeast cells, transformed into *E. coli*, and colony PCR and sequencing performed to determine the distribution of the final library (see Table).

TABLE 17

Amino acid sequences of antibodies and linkers used for library construction

| Domain | Name | Amino Acid Sequence | SEQ ID NO: |
|---|---|---|---|
| VH Linker | Elbow VH6 | ASTKGP | 106 |
| VH Linker | Elbow VH7 | ASTKGPS | 104 |
| VH Linker | Elbow VH8 | ASTKGPSV | 102 |
| VH Linker | Elbow VH9 | ASTKGPSVF | 100 |
| VH Linker | Elbow VH10 | ASTKGPSVFP | 98 |
| VH Linker | Elbow VH11 | ASTKGPSVFPL | 96 |
| VH Linker | Elbow VH12 | ASTKGPSVFPLA | 94 |
| VH Linker | Elbow VH13 | ASTKGPSVFPLAP | 92 |
| VH Linker | GS VH 6 | GGGGSG | 124 |
| VH Linker | GS VH 7 | GGGGSGG | 122 |
| VH Linker | GS VH 8 | GGGGSGGG | 120 |
| VH Linker | GS VH 9 | GGGGSGGGG | 118 |
| VH Linker | GS VH 10 | GGGGSGGGGS | 116 |
| VH Linker | GS VH 11 | GGGGSGGGGSG | 114 |
| VH Linker | GS VH 12 | GGGGSGGGGSGG | 112 |
| VH Linker | GS VH 13 | GGGGSGGGGSGGG | 110 |
| VH Linker | GS VH 14 | GGGGSGGGGSGGGG | 108 |
| VL Linker | Elbow VL5 | TVAAP | 107 |
| VL Linker | Elbow VL6 | TVAAPS | 105 |
| VL Linker | Elbow VL7 | TVAAPSV | 103 |
| VL Linker | Elbow VL8 | TVAAPSVF | 101 |
| VL Linker | Elbow VL9 | TVAAPSVFI | 99 |
| VL Linker | Elbow VL10 | TVAAPSVFIF | 97 |
| VL Linker | Elbow VL11 | TVAAPSVFIFP | 95 |
| VL Linker | Elbow VL12 | TVAAPSVFIFPP | 93 |

TABLE 17-continued

Amino acid sequences of antibodies and linkers used for library construction

| Domain | Name | Amino Acid Sequence | SEQ ID NO: |
|---|---|---|---|
| VL Linker | GS VL 5 | GGSGG | 125 |
| VL Linker | GS VL 6 | GGSGGG | 123 |
| VL Linker | GS VL 7 | GGSGGGG | 121 |
| VL Linker | GS VL 8 | GGSGGGGS | 119 |
| VL Linker | GS VL 9 | GGSGGGGSG | 117 |
| VL Linker | GS VL 10 | GGSGGGGSGG | 115 |
| VL Linker | GS VL 11 | GGSGGGGSGGG | 113 |
| VL Linker | GS VL 12 | GGSGGGGSGGGG | 111 |
| VL Linker | GS VL 13 | GGSGGGGSGGGGS | 109 |
| VH1 | 1B12.13 | EVQLQESGPGLVKPSETLSLTCTVSGFSLS DYGVSWIRQPPGKGLEWIGLIWGSGDTY YNSPLKSRLTISKDNSKSQVSLKLSSVTAA DTAVYYCAKQTNIVVAYDLYSMDYWGQ GTLVTVSS | 136 |
| VH1 | 1B12.21 | EVQLQESGPGLVKPSETLSLTCTVSGFSLS EFGVSWIRQPPGKGLEWIGLIWGGGDTY YNSPLKSRLTISKDNSKSQVSLKLSSVTAA DTAVYYCAKQRNLWAYDLYGMDYWGQ GTLVTVSS | 137 |
| VH1 | 1B12.34 | EVQLQESGPGLVKPSETLSLTCTVSGFSLS DYGVSWIRQPPGKGLEWIGLIWGSGDTY YNSPLKSRLTISKDTSKSQVSLKLSSVTAA DTAVYYCAKQTNLWAYDLYSMDYWGQ GTLVTVSS | 138 |
| VH1 | 1B12.A1 | EVQLQESGPGLVKPSETLSLTCTVSGFSLR DYGVSWIRQPPGKGLEWLGLIWGSGDTY YNSPLKSRLTISKDTSKSQVSLKLSSVTAA DTAVYYCAKQTNIWGYDLYGMDYWGQ GTLVTVSS | 139 |
| VH1 | 1B12.A3 | EVQLQESGPGLVKPSETLSLTCTVSGFSLS DYGVSWIRQPPGKGLEWIGLIWGGGDTY YNSPLKSRLTISKDNSKSQVSLKLSSVTAA DTAVYYCARQTNLWAYDLYSMDYWGQ GTLVTVSS | 140 |
| VH1 | E26.13 | EVQLVESGGGVVQPGRSLRLSCSASGFIFS RYDMSWVRQAPGKGLEWVAYISHGGAG TYYPDSVKGRFTISRDNSKNTLFLQMDSL RPEDTGVYFCARGGVTKGYFDVWGQGT PVTVSS | 141 |
| VH1 | E26.35 | EVQLVESGGGVVQPGRSLRLSCSASGFIFS RYDMSWVRQAPGKGLEWVAYISHGGAG TYYPDSVKGRFTISRDNSKNTLFLQMDSL RAEDTAVYYCARGGVYKGYFDVWGQGT PVTVSS | 142 |
| VH2 | 10F7M11 | EVQLVQSGAEVKKPGSSVKVSCKASGYT FTDYEIHWVRQAPGQGLEWMGVNDPES GGTFYNQKFDGRVTLTADESTSTAYMEL SSLRSEDTAVYYCTRYSKWDSFDGMDY WGQGTTVTVSS | 143 |

TABLE 17-continued

Amino acid sequences of antibodies and linkers used for library construction

| Domain | Name | Amino Acid Sequence | SEQ ID NO: |
|---|---|---|---|
| VH2 | B6-17G | EVQLVQSGAEVKKPGSSVKVSCKASGGS FGGYGIGWVRQAPGQGLEWMGGITPFFG FADYAQKFQGRVTITADESTTTAYMELS GLTSDDTAVYYCARDPNEFWGGYYSTH DFDSWGQGTTVTSS | 144 |
| VH2 | B6-5G | EVQLVQSGAEVKKPGESVKISCKASGGSF RSYGISWVRQAPGQGLEWMGGITHFFGIT DYAQKFQGRVTITADESTTTAYMELSGLT SDDTAVYYCAREPNDFWGGYYDTHDFD SWGQGTTVTSS | 145 |
| VL1 | 1B12.13 | DIQMTQSPSSLSASVGDRVTITCQTSTDID DDLNWYQQKPGKAPKLLISLASTLRPGVP SRFSGSGSGTDFTFTISSLQPEDFATYYCL QSDRLPLTFGQGTKLEIKR | 146 |
| VL1 | 1B12.21 | DIQMTQSPSSLSASVGDRVTITCQTSQDID MDLNWYQQKPGKAPKLLISQGSTLWPGV PSRFSGSGSGTDFTFTISSLQPEDFATYYC LQTDSFPLTFGQGTKLEIKR | 147 |
| VL1 | 1B12.34 | DIQMTQSPSSLSASVGDRVTITCQASQDID DDLNWYQQKPGKAPKLLISLASILRPGVP SRFSGSGSGTDFTFTISSLQPEDFATYYCL QSDSFPLTFGQGTKLEIKR | 148 |
| VL1 | 1B12.A1 | DIQMTQSPSSLSASVGDRVTITCQASQDID MDLNWYQQKPGKAPKLLISQANTLPPGV PSRFSGSGSGTDFTFTISSLQPEDFATYYC LQSDWLPLTFGQGTKLEIKR | 149 |
| VL1 | 1B12.A3 | DIQMTQSPSSLSASVGDRVTITCQASTDID DDLNWYQQKPGKAPKLLISLGSTLRPGVP SRFSGSGSGTDFTFTISSLQPEDFATYYCL QSDRLPLTFGQGTKLEIKR | 150 |
| VL1 | E26 (13 & 35) | DIQMTQSPSSLSASVGDRVTITCRASGNIH NYLTWYQQTPGKAPKLLIYNAKTLADGV PSRFSGSGSGTDYTFTISSLQPEDIATYYC QHFWSIPYTFGQGTKLEIKR | 151 |
| VL2 | 10F7M11 | DIQMTQSPSSLSASVGDRVTITCRASSGIIS YIDWFQQKPGKAPKRLIYATFDLASGVPS RFSGSGSGTDYTLTISSLQPEDFATYYCRQ VGSYPETFGQGTKLEIKR | 152 |
| VL2 | B6-17G | EIVLTQSPDFQSVTPKEKVTITCRASQDIG SELHWYQQKPDQPPKLLIKYASHSTSGVP SRFSGSGSGTDFTLTINGLEAEDAGTYYC HQTDSLPYTFGPGTKVDIKR | 153 |
| VL2 | B6-5G | EIVLTQSPDFQSVTPKEKVTITCRASQNIG SELHWYQQKPDQSPKLLIKYASHSISGVP SRFSGSGSGTDFTLTINGLEAEDAATYYC HQSDTLPHTFGQGTKVDIKR | 154 |

TABLE 18

Domain distribution after library construction

| Domain | Type | Predicted % | Actual % |
|---|---|---|---|
| VH1 | 1B12 lineage | 50 | 45 |
|  | E26 lineage | 50 | 53 |
| VH linker | Elbow | 50 | 60 |
|  | GS | 50 | 38 |
| VH2 | B6 lineage | 50 | 32 |
|  | 10F7M11 | 50 | 64 |
| VL1 | 1B12 lineage | 50 | 47 |
|  | E26 lineage | 50 | 52 |
| VL linker | Elbow | 50 | 25 |
|  | GS | 50 | 73 |
| VL2 | B6 lineage | 50 | 33 |
|  | 10F7M11 | 50 | 67 |

EXAMPLE 30

Selection of IL1β/IL17 DVD-Fab Library by Flow Cytometry

Optimal selection conditions for library sorting were determined from scouting experiments to be 5 nM IL1β and 5 nM IL17. Multiple selection rounds were completed with increasing stringency (see Table 19). For all selections sort gates were chosen to take the best simultaneous binders to both IL1β and IL17. After each sort round library DNA was isolated from yeast cells, transformed into *E. coli*, and colony PCR sequencing performed to analyze the sort output. Listed in Table and Table are the output sequences from round 3. Library output clones are converted to full DVD-Ig format for characterization as described in Example 21.

TABLE 19

Labeling and sorting conditions for IL1β/IL17 DVD-Fab library

| Sort Round | Antigen Concentration | Incubation Temperature | Incubation Time | % cells sorted |
|---|---|---|---|---|
| R1 | 5 nM IL1β, 5 nM IL17 | RT | 5 minutes | 0.52% of total |
| R2 | 1 nM IL1β, 1 nM IL17 | RT | 1 minute | 0.35% of total |
| R3 | 1 nM IL1β, 1 nM IL17 | Ice | 1 minute | 0.17% of total |

TABLE 20

Round 3 output sequences for Heavy and Light chains

| Heavy chain | Count observed | Different LC pairs | Heavy chain sequence | SEQ ID NO: |
|---|---|---|---|---|
| E26.35 EL10 10F7M11 | 16 | 7 | EVQLVESGGGVVQPGRSLRLSCSASGFIFS RYDMSWVRQAPGKGLEWVAYISHGGAG TYYPDSVKGRFTISRDNSKNTLFLQMDSL RAEDTAVYYCARGGVYKGYFDVWGQGT PVTVSSASTKGPSVFPEVQLVQSGAEVKK PGSSVKVSCKASGYTFTDYEIHWVRQAP GQGLEWMGVNDPESGGTFYNQKFDGRV TLTADESTSTAYMELSSLRSEDTAVYYCT RYSKWDSFDGMDYWGQGTTVTVSS | 155 |
| E26.35 EL13 10F7M11 | 8 | 7 | EVQLVESGGGVVQPGRSLRLSCSASGFIFS RYDMSWVRQAPGKGLEWVAYISHGGAG TYYPDSVKGRFTISRDNSKNTLFLQMDSL RAEDTAVYYCARGGVYKGYFDVWGQGT PVTVSSASTKGPSVFPLAPEVQLVQSGAE VKKPGSSVKVSCKASGYTFTDYEIHWVR QAPGQGLEWMGVNDPESGGTFYNQKFD GRVTLTADESTSTAYMELSSLRSEDTAVY YCTRYSKWDSFDGMDYWGQGTTVTVSS | 156 |
| E26.35 EL12 10F7M11 | 7 | 4 | EVQLVESGGGVVQPGRSLRLSCSASGFIFS RYDMSWVRQAPGKGLEWVAYISHGGAG TYYPDSVKGRFTISRDNSKNTLFLQMDSL RAEDTAVYYCARGGVYKGYFDVWGQGT PVTVSSASTKGPSVFPLAEVQLVQSGAEV KKPGSSVKVSCKASGYTFTDYEIHWVRQ APGQGLEWMGVNDPESGGTFYNQKFDG RVTLTADESTSTAYMELSSLRSEDTAVYY CTRYSKWDSFDGMDYWGQGTTVTVSS | 157 |
| E26.35 EL6 10F7M11 | 5 | 2 | EVQLVESGGGVVQPGRSLRLSCSASGFIFS RYDMSWVRQAPGKGLEWVAYISHGGAG TYYPDSVKGRFTISRDNSKNTLFLQMDSL RAEDTAVYYCARGGVYKGYFDVWGQGT PVTVSSASTKGPEVQLVQSGAEVKKPGSS VKVSCKASGYTFTDYEIHWVRQAPGQGL EWMGVNDPESGGTFYNQKFDGRVTLTA DESTSTAYMELSSLRSEDTAVYYCTRYSK WDSFDGMDYWGQGTTVTVSS | 158 |
| E26.35 EL7 10F7M11 | 5 | 4 | EVQLVESGGGVVQPGRSLRLSCSASGFIFS RYDMSWVRQAPGKGLEWVAYISHGGAG TYYPDSVKGRFTISRDNSKNTLFLQMDSL RAEDTAVYYCARGGVYKGYFDVWGQGT PVTVSSASTKGPSVEVQLVQSGAEVKKPGS SVKVSCKASGYTFTDYEIHWVRQAPGQG LEWMGVNDPESGGTFYNQKFDGRVTLT ADESTSTAYMELSSLRSEDTAVYYCTRYS KWDSFDGMDYWGQGTTVTVSS | 159 |
| E26.35 EL8 10F7M11 | 5 | 3 | EVQLVESGGGVVQPGRSLRLSCSASGFIFS RYDMSWVRQAPGKGLEWVAYISHGGAG TYYPDSVKGRFTISRDNSKNTLFLQMDSL RAEDTAVYYCARGGVYKGYFDVWGQGT PVTVSSASTKGPSVEVQLVQSGAEVKKPG SSVKVSCKASGYTFTDYEIHWVRQAPGQ | 160 |

TABLE 20-continued

Round 3 output sequences for Heavy and Light chains

| | | | | |
|---|---|---|---|---|
| | | | GLEWMGVNDPESGGTFYNQKFDGRVTL TADESTSTAYMELSSLRSEDTAVYYCTRY SKWDSFDGMDYWGQGTTVTVSS | |
| E26.13 EL10 10F7M11 | 3 | 3 | EVQLVESGGGVVQPGRSLRLSCSASGFIFS RYDMSWVRQAPGKGLEWVAYISHGGAG TYYPDSVKGRFTISRDNSKNTLFLQMDSL RPEDTGVYFCARGGVTKGYFDVWGQGT PVTVSSASTKGPSVFPEVQLVQSGAEVKK PGSSVKVSCKASGYTFTDYEIHWVRQAP GQGLEWMGVNDPESGGTFYNQKFDGRV TLTADESTSTAYMELSSLRSEDTAVYYCT RYSKWDSFDGMDYWGQGTTVTVSS | 161 |
| E26.35 GS10 10F7M11 | 3 | 2 | EVQLVESGGGVVQPGRSLRLSCSASGFIFS RYDMSWVRQAPGKGLEWVAYISHGGAG TYYPDSVKGRFTISRDNSKNTLFLQMDSL RAEDTAVYYCARGGVYKGYFDVWGQGT PVTVSSGGGGSGGGGSEVQLVQSGAEVK KPGSSVKVSCKASGYTFTDYEIHWVRQA PGQGLEWMGVNDPESGGTFYNQKFDGR VTLTADESTSTAYMELSSLRSEDTAVYYC TRYSKWDSFDGMDYWGQGTTVTVSS | 162 |
| E26.13 EL13 10F7M11 | 2 | 2 | EVQLVESGGGVVQPGRSLRLSCSASGFIFS RYDMSWVRQAPGKGLEWVAYISHGGAG TYYPDSVKGRFTISRDNSKNTLFLQMDSL RPEDTGVYFCARGGVTKGYFDVWGQGT PVTVSSASTKGPSVFPLAPEVQLVQSGAE VKKPGSSVKVSCKASGYTFTDYEIHWVR QAPGQGLEWMGVNDPESGGTFYNQKFD GRVTLTADESTSTAYMELSSLRSEDTAVY YCTRYSKWDSFDGMDYWGQGTTVTVSS | 163 |
| E26.13 EL6 10F7M11 | 2 | 2 | EVQLVESGGGVVQPGRSLRLSCSASGFIFS RYDMSWVRQAPGKGLEWVAYISHGGAG TYYPDSVKGRFTISRDNSKNTLFLQMDSL RPEDTGVYFCARGGVTKGYFDVWGQGT PVTVSSASTKGPEVQLVQSGAEVKKPGSS VKVSCKASGYTFTDYEIHWVRQAPGQGL EWMGVNDPESGGTFYNQKFDGRVTLTA DESTSTAYMELSSLRSEDTAVYYCTRYSK WDSFDGMDYWGQGTTVTVSS | 164 |
| E26.13 EL8 10F7M11 | 2 | 2 | EVQLVESGGGVVQPGRSLRLSCSASGFIFS RYDMSWVRQAPGKGLEWVAYISHGGAG TYYPDSVKGRFTISRDNSKNTLFLQMDSL RPEDTGVYFCARGGVTKGYFDVWGQGT PVTVSSASTKGPSVEVQLVQSGAEVKKPG SSVKVSCKASGYTFTDYEIHWVRQAPGQ GLEWMGVNDPESGGTFYNQKFDGRVTL TADESTSTAYMELSSLRSEDTAVYYCTRY SKWDSFDGMDYWGQGTTVTVSS | 165 |
| E26.35 EL11 10F7M11 | 2 | 2 | EVQLVESGGGVVQPGRSLRLSCSASGFIFS RYDMSWVRQAPGKGLEWVAYISHGGAG TYYPDSVKGRFTISRDNSKNTLFLQMDSL RAEDTAVYYCARGGVYKGYFDVWGQGT PVTVSSASTKGPSVFPLEVQLVQSGAEVK KPGSSVKVSCKASGYTFTDYEIHWVRQA PGQGLEWMGVNDPESGGTFYNQKFDGR VTLTADESTSTAYMELSSLRSEDTAVYYC TRYSKWDSFDGMDYWGQGTTVTVSS | 166 |
| E26.35 EL9 10F7M11 | 2 | 2 | EVQLVESGGGVVQPGRSLRLSCSASGFIFS RYDMSWVRQAPGKGLEWVAYISHGGAG TYYPDSVKGRFTISRDNSKNTLFLQMDSL RAEDTAVYYCARGGVYKGYFDVWGQGT PVTVSSASTKGPSVFEVQLVQSGAEVKKP GSSVKVSCKASGYTFTDYEIHWVRQAPG QGLEWMGVNDPESGGTFYNQKFDGRVT LTADESTSTAYMELSSLRSEDTAVYYCTR YSKWDSFDGMDYWGQGTTVTVSS | 167 |
| 1B12mix EL13 10F7M11 | 1 | 1 | EVQLQESGPGLVKPSETLSLTCTVSGFSLS DYGVSWIRQPPGKGLEWLGLIWGSGDTY YNSPLKSRLTISKDTSKSQVSLKLSSVTAA DTAVYYCAKQTNIWGYDLYGMDYWGQ | 168 |

TABLE 20-continued

| | | | Round 3 output sequences for Heavy and Light chains | |
|---|---|---|---|---|
| | | | GTLVTVSSASTKGPSVFPLAPEVQLVQSG AEVKKPGSSVKVSCKASGYTFTDYEIHW VRQAPGQGLEWMGVNDPESGGTFYNQK FDGRVTLTADESTSTAYMELSSLRSEDTA VYYCTRYSKWDSFDGMDYWGQGTTVTV SS | |
| 1B12mix GS13 10F7M11 | 1 | 1 | EVQLQESGPGLVKPSETLSLTCTVSGFSLS DYGVSWIRQPPGKGLEWLGLIWGSDTY YNSPLKSRLTISKDTSKSQVSLKLSSVTAA DTAVYYCAKQTNIWGYDLYGMDYWGQ GTLVTVSSGGGGSGGGGSGGGEVQLVQS GAEVKKPGSSVKVSCKASGYTFTDYEIH WVRQAPGQGLEWMGVNDPESGGTFYNQ KFDGRVTLTADESTSTAYMELSSLRSEDT AVYYCTRYSKWDSFDGMDYWGQGTTVT VSS | 169 |
| 1B12.A1 EL12 10F7M11 | 1 | 1 | EVQLQESGPGLVKPSETLSLTCTVSGFSLR DYGVSWIRQPPGKGLEWLGLIWGSDTY YNSPLKSRLTISKDTSKSQVSLKLSSVTAA DTAVYYCAKQTNIWGYDLYGMDYWGQ GTLVTVSSASTKGPSVFPLAEVQLVQSGA EVKKPGSSVKVSCKASGYTFTDYEIHWV RQAPGQGLEWMGVNDPESGGTFYNQKF DGRVTLTADESTSTAYMELSSLRSEDTAV YYCTRYSKWDSFDGMDYWGQGTTVTVSS | 170 |
| 1B12.A1 EL13 10F7M11 | 1 | 1 | EVQLQESGPGLVKPSETLSLTCTVSGFSLR DYGVSWIRQPPGKGLEWLGLIWGSDTY YNSPLKSRLTISKDTSKSQVSLKLSSVTAA DTAVYYCAKQTNIWGYDLYGMDYWGQ GTLVTVSSASTKGPSVFPLAPEVQLVQSG AEVKKPGSSVKVSCKASGYTFTDYEIHW VRQAPGQGLEWMGVNDPESGGTFYNQK FDGRVTLTADESTSTAYMELSSLRSEDTA VYYCTRYSKWDSFDGMDYWGQGTTVTV SS | 171 |
| E26.35 GS11 10F7M11 | 1 | 1 | EVQLVESGGGVVQPGRSLRLSCSASGFIFS RYDMSWVRQAPGKGLEWVAYISHGGAG TYYPDSVKGRFTISRDNSKNTLFLQMDSL RAEDTAVYYCARGGVYKGYFDVWGQGT PVTVSSGGGGSGGGGSGEVQLVQSGAEV KKPGSSVKVSCKASGYTFTDYEIHWVRQ APGQGLEWMGVNDPESGGTFYNQKFDG RVTLTADESTSTAYMELSSLRSEDTAVYY CTRYSKWDSFDGMDYWGQGTTVTVSS | 172 |
| E26.35 GS14 10F7M11 | 1 | 1 | EVQLVESGGGVVQPGRSLRLSCSASGFIFS RYDMSWVRQAPGKGLEWVAYISHGGAG TYYPDSVKGRFTISRDNSKNTLFLQMDSL RAEDTAVYYCARGGVYKGYFDVWGQGT PVTVSSGGGGSGGGGSGGGGEVQLVQSG AEVKKPGSSVKVSCKASGYTFTDYEIHW VRQAPGQGLEWMGVNDPESGGTFYNQK FDGRVTLTADESTSTAYMELSSLRSEDTA VYYCTRYSKWDSFDGMDYWGQGTTVTV SS | 173 |
| E26.35 GS7 10F7M11 | 1 | 1 | EVQLVESGGGVVQPGRSLRLSCSASGFIFS RYDMSWVRQAPGKGLEWVAYISHGGAG TYYPDSVKGRFTISRDNSKNTLFLQMDSL RAEDTAVYYCARGGVYKGYFDVWGQGT PVTVSSGGGGSGGEVQLVQSGAEVKKPG SSVKVSCKASGYTFTDYEIHWVRQAPGQ GLEWMGVNDPESGGTFYNQKFDGRVTL TADESTSTAYMELSSLRSEDTAVYYCTRY SKWDSFDGMDYWGQGTTVTVSS | 174 |
| E26.35 GS8 10F7M11 | 1 | 1 | EVQLVESGGGVVQPGRSLRLSCSASGFIFS RYDMSWVRQAPGKGLEWVAYISHGGAG TYYPDSVKGRFTISRDNSKNTLFLQMDSL RAEDTAVYYCARGGVYKGYFDVWGQGT PVTVSSGGGGSGGGEVQLVQSGAEVKKP GSSVKVSCKASGYTFTDYEIHWVRQAPG | 175 |

TABLE 20-continued

Round 3 output sequences for Heavy and Light chains

| | | | QGLEWMGVNDPESGGTFYNQKFDGRVT LTADESTSTAYMELSSLRSEDTAVYYCTR YSKWDSFDGMDYWGQGTTVTVSS | |
|---|---|---|---|---|
| E26.35 GS9 10F7M11 | 1 | 1 | EVQLVESGGGVVQPGRSLRLSCSASGFIFS RYDMSWVRQAPGKGLEWVAYISHGGAG TYYPDSVKGRFTISRDNSKNTLFLQMDSL RAEDTAVYYCARGGVYKGYFDVWGQGT PVTVSSGGGGSGGGGEVQLVQSGAEVKK PGSSVKVSCKASGYTFTDYEIHWVRQAP GQGLEWMGVNDPESGGTFYNQKFDGRV TLTADESTSTAYMELSSLRSEDTAVYYCT RYSKWDSFDGMDYWGQGTTVTVSS | 176 |

| Light chain | Count ob- served | Dif- ferent HC pairs | Light chain sequence | |
|---|---|---|---|---|
| E26 GS12 10F7M11 | 22 | 12 | DIQMTQSPSSLSASVGDRVTITCRASGNIH NYLTWYQQTPGKAPKLLIYNAKTLADGV PSRFSGSGSGTDYTFTISSLQPEDIATYYC QHFWSIPYTFGQGTKLEIKRGGSGGGGSG GGGDIQMTQSPSSLSASVGDRVTITCRAS SGIISYIDWFQQKPGKAPKRLIYATFDLAS GVPSRFSGSGSGTDYTLTISSLQPEDFATY YCRQVGSYPETFGQGTKLEIKR | 177 |
| E26 GS13 10F7M11 | 16 | 8 | DIQMTQSPSSLSASVGDRVTITCRASGNIH NYLTWYQQTPGKAPKLLIYNAKTLADGV PSRFSGSGSGTDYTFTISSLQPEDIATYYC QHFWSIPYTFGQGTKLEIKRGGSGGGGSG GGGSDIQMTQSPSSLSASVGDRVTITCRA SSGIISYIDWFQQKPGKAPKRLIYATFDLA SGVPSRFSGSGSGTDYTLTISSLQPEDFAT YYCRQVGSYPETFGQGTKLEIKR | 178 |
| E26 GS9 10F7M11 | 9 | 8 | DIQMTQSPSSLSASVGDRVTITCRASGNIH NYLTWYQQTPGKAPKLLIYNAKTLADGV PSRFSGSGSGTDYTFTISSLQPEDIATYYC QHFWSIPYTFGQGTKLEIKRGGSGGGGSG DIQMTQSPSSLSASVGDRVTITCRASSGIIS YIDWFQQKPGKAPKRLIYATFDLASGVPS RFSGSGSGTDYTLTISSLQPEDFATYYCRQ VGSYPETFGQGTKLEIKR | 179 |
| E26 GS10 10F7M11 | 7 | 5 | DIQMTQSPSSLSASVGDRVTITCRASGNIH NYLTWYQQTPGKAPKLLIYNAKTLADGV PSRFSGSGSGTDYTFTISSLQPEDIATYYC QHFWSIPYTFGQGTKLEIKRGGSGGGGSG GDIQMTQSPSSLSASVGDRVTITCRASSGII SYIDWFQQKPGKAPKRLIYATFDLASGVP SRFSGSGSGTDYTLTISSLQPEDFATYYCR QVGSYPETFGQGTKLEIKR | 180 |
| E26 GS11 10F7M11 | 6 | 4 | DIQMTQSPSSLSASVGDRVTITCRASGNIH NYLTWYQQTPGKAPKLLIYNAKTLADGV PSRFSGSGSGTDYTFTISSLQPEDIATYYC QHFWSIPYTFGQGTKLEIKRGGSGGGGSG GGDIQMTQSPSSLSASVGDRVTITCRASS GIISYIDWFQQKPGKAPKRLIYATFDLASG VPSRFSGSGSGTDYTLTISSLQPEDFATYY CRQVGSYPETFGQGTKLEIKR | 181 |
| E26 EL7 10F7M11 | 5 | 2 | DIQMTQSPSSLSASVGDRVTITCRASGNIH NYLTWYQQTPGKAPKLLIYNAKTLADGV PSRFSGSGSGTDYTFTISSLQPEDIATYYC QHFWSIPYTFGQGTKLEIKRTVAAPSVDI QMTQSPSSLSASVGDRVTITCRASSGIISYI DWFQQKPGKAPKRLIYATFDLASGVPSRF SGSGSGTDYTLTISSLQPEDFATYYCRQV GSYPETFGQGTKLEIKR | 182 |
| E26 GS8 10F7M11 | 4 | 2 | DIQMTQSPSSLSASVGDRVTITCRASGNIH NYLTWYQQTPGKAPKLLIYNAKTLADGV PSRFSGSGSGTDYTFTISSLQPEDIATYYC QHFWSIPYTFGQGTKLEIKRGGSGGGGSD IQMTQSPSSLSASVGDRVTITCRASSGIISY IDWFQQKPGKAPKRLIYATFDLASGVPSR | 183 |

TABLE 20-continued

Round 3 output sequences for Heavy and Light chains

| | | | | |
|---|---|---|---|---|
| | | | FSGSGSGTDYTLTISSLQPEDFATYYCRQV GSYPETFGQGTKLEIKR | |
| E26 GS6 10F7M11 | 3 | 2 | DIQMTQSPSSLSASVGDRVTITCRASGNIH NYLTWYQQTPGKAPKLLIYNAKTLADGV PSRFSGSGSGTDYTFTISSLQPEDIATYYC QHFWSIPYTFGQGTKLEIKRGGSGGGDIQ MTQSPSSLSASVGDRVTITCRASSGIISYID WFQQKPGKAPKRLIYATFDLASGVPSRFS GSGSGTDYTLTISSLQPEDFATYYCRQVG SYPETFGQGTKLEIKR | 184 |
| 1B12.A1 EL8 10F7M11 | 2 | 2 | DIQMTQSPSSLSASVGDRVTITCQASQDID MDLNWYQQKPGKAPKLLISQANTLPPGV PSRFSGSGSGTDFTFTISSLQPEDFATYYC LQSDWLPLTFGQGTKLEIKRTVAAPSVFD IQMTQSPSSLSASVGDRVTITCRASSGIISY IDWFQQKPGKAPKRLIYATFDLASGVPSR FSGSGSGTDYTLTISSLQPEDFATYYCRQV GSYPETFGQGTKLEIKR | 185 |
| E26 GS5 10F7M11 | 2 | 1 | DIQMTQSPSSLSASVGDRVTITCRASGNIH NYLTWYQQTPGKAPKLLIYNAKTLADGV PSRFSGSGSGTDYTFTISSLQPEDIATYYC QHFWSIPYTFGQGTKLEIKRGGSGGDIQM TQSPSSLSASVGDRVTITCRASSGIISYIDW FQQKPGKAPKRLIYATFDLASGVPSRFSG SGSGTDYTLTISSLQPEDFATYYCRQVGS YPETFGQGTKLEIKR | 186 |
| 1B12.A1 GS7 10F7M11 | 1 | 1 | DIQMTQSPSSLSASVGDRVTITCQASQDID MDLNWYQQKPGKAPKLLISQANTLPPGV PSRFSGSGSGTDFTFTISSLQPEDFATYYC LQSDWLPLTFGQGTKLEIKRGGSGGGGDI QMTQSPSSLSASVGDRVTITCRASSGIISYI DWFQQKPGKAPKRLIYATFDLASGVPSRF SGSGSGTDYTLTISSLQPEDFATYYCRQV GSYPETFGQGTKLEIKR | 187 |
| 1B12 GS10 10F7M11 | 1 | 1 | DIQMTQSPSSLSASVGDRVTITCQASQDID MDMNWYQQKPGKAPKLLISQANTLPPG VHSRFSGSGSGTDFTFTISSLQPEDFATYY CLQSDWLPLTFGQGTKLEIKRGGSGGGGS GGDIQMTQSPSSLSASVGDRVTITCRASS GIISYIDWFQQKPGKAPKRLIYATFDLASG VPSRFSGSGSGTDYTLTISSLQPEDFATYY CRQVGSYPETFGQGTKLEIKR | 188 |
| E26 EL12 10F7M11 | 1 | 1 | DIQMTQSPSSLSASVGDRVTITCRASGNIH NYLTWYQQTPGKAPKLLIYNAKTLADGV PSRFSGSGSGTDYTFTISSLQPEDIATYYC QHFWSIPYTFGQGTKLEIKRTVAAPSVFIF PPDIQMTQSPSSLSASVGDRVTITCRASSG IISYIDWFQQKPGKAPKRLIYATFDLASGV PSRFSGSGSGTDYTLTISSLQPEDFATYYC RQVGSYPETFGQGTKLEIKR | 189 |
| E26 EL5 10F7M11 | 1 | 1 | DIQMTQSPSSLSASVGDRVTITCRASGNIH NYLTWYQQTPGKAPKLLIYNAKTLADGV PSRFSGSGSGTDYTFTISSLQPEDIATYYC QHFWSIPYTFGQGTKLEIKRTVAAPDIQM TQSPSSLSASVGDRVTITCRASSGIISYIDW FQQKPGKAPKRLIYATFDLASGVPSRFSG SGSGTDYTLTISSLQPEDFATYYCRQVGS YPETFGQGTKLEIKR | 190 |
| E26 EL6 10F7M11 | 1 | 1 | DIQMTQSPSSLSASVGDRVTITCRASGNIH NYLTWYQQTPGKAPKLLIYNAKTLADGV PSRFSGSGSGTDYTFTISSLQPEDIATYYC QHFWSIPYTFGQGTKLEIKRTVAAPSDIQ MTQSPSSLSASVGDRVTITCRASSGIISYID WFQQKPGKAPKRLIYATFDLASGVPSRFS GSGSGTDYTLTISSLQPEDFATYYCRQVG SYPETFGQGTKLEIKR | 191 |

TABLE 21

Round 3 output sequences for DVDs

| DVD | Count Observed |
|---|---|
| E26.35 + 10F7M11, EL10, GS12 | 6 |
| E26.35 + 10F7M11, EL10, EL7 | 3 |
| E26.35 + 10F7M11, EL10, GS11 | 3 |
| E26.35 + 10F7M11, EL6, GS13 | 3 |
| E26.35 + 10F7M11, EL8, GS12 | 3 |
| E26.35 + 10F7M11, EL12, GS12 | 2 |
| E26.35 + 10F7M11, EL12, GS13 | 2 |
| E26.35 + 10F7M11, EL12, GS6 | 2 |
| E26.35 + 10F7M11, EL13, GS10 | 2 |
| E26.35 + 10F7M11, GS10, GS13 | 2 |
| 1B12 mix + 10F7M11, EL13, GS10 | 1 |
| 1B12 mix + 10F7M11, GS13, EL8 | 1 |
| 1B12.A1 + 10F7M11, EL12, EL8 | 1 |
| 1B12.A1 + 10F7M11, EL13, GS7 | 1 |
| E26.13 + 10F7M11, EL10, GS10 | 1 |
| E26.13 + 10F7M11, EL10, GS12 | 1 |
| E26.13 + 10F7M11, EL10, GS9 | 1 |
| E26.13 + 10F7M11, EL13, GS11 | 1 |
| E26.13 + 10F7M11, EL13, GS5 | 1 |
| E26.13 + 10F7M11, EL6, GS10 | 1 |
| E26.13 + 10F7M11, EL6, GS12 | 1 |
| E26.13 + 10F7M11, EL8, GS12 | 1 |
| E26.13 + 10F7M11, EL8, GS9 | 1 |
| E26.35 + 10F7M11, EL10, GS10 | 1 |
| E26.35 + 10F7M11, EL10, GS13 | 1 |
| E26.35 + 10F7M11, EL10, GS6 | 1 |
| E26.35 + 10F7M11, EL10, GS9 | 1 |
| E26.35 + 10F7M11, EL11, GS12 | 1 |
| E26.35 + 10F7M11, EL11, GS9 | 1 |
| E26.35 + 10F7M11, EL12, EL5 | 1 |
| E26.35 + 10F7M11, EL13, EL12 | 1 |
| E26.35 + 10F7M11, EL13, EL6 | 1 |
| E26.35 + 10F7M11, EL13, GS12 | 1 |
| E26.35 + 10F7M11, EL13, GS13 | 1 |
| E26.35 + 10F7M11, EL13, GS8 | 1 |
| E26.35 + 10F7M11, EL13, GS9 | 1 |
| E26.35 + 10F7M11, EL6, GS12 | 1 |
| E26.35 + 10F7M11, EL7, GS11 | 1 |
| E26.35 + 10F7M11, EL7, GS12 | 1 |
| E26.35 + 10F7M11, EL7, GS13 | 1 |
| E26.35 + 10F7M11, EL7, GS9 | 1 |
| E26.35 + 10F7M11, EL8, EL7 | 1 |
| E26.35 + 10F7M11, EL8, GS13 | 1 |
| E26.35 + 10F7M11, EL9, GS11 | 1 |
| E26.35 + 10F7M11, EL9, GS9 | 1 |
| E26.35 + 10F7M11, GS10, GS12 | 1 |
| E26.35 + 10F7M11, GS11, GS8 | 1 |
| E26.35 + 10F7M11, GS14, GS10 | 1 |
| E26.35 + 10F7M11, GS7, GS12 | 1 |
| E26.35 + 10F7M11, GS8, GS9 | 1 |
| E26.35 + 10F7M11, GS9, GS13 | 1 |

EXAMPLE 31

Construction of Full-length DVD-Ig for Yeast Display

A DLL4/VEGF DVD (comprising the VH and VL domains of an anti-DLL4 antibody and an anti-VEGF antibody) was cloned into the pFabB yeast expression vector as both a DVD-Fab and full length DVD-Ig. Briefly, the VL coding region of the DVD was amplified and combined by overlapping PCR with a portion of the pFabB vector and the DVD heavy chain (either the VH region or the full VH+Fc), excluding stop codon. For the full length DVD another portion of the pFab vector was also included in the overlapping PCR for cloning purposes. For the DVD-Fab construct pFabB was linearized with BsiWI, BamHI, and SalI; for the DVD-Ig the pFabB was linearized with BsiWI, BamHI, and PacI and PCR products were inserted by homologous recombination. After sequence confirmation, the DVD-Fab and DVD-Ig yeast display vectors were transformed into chemically competent S. cerevisiae cells.

EXAMPLE 32

Flow Cytometric Analysis of Full-length DVD-Ig Yeast Cells

Yeast cells were induced for protein expression followed by flow cytometry staining experiments to verify display and antigen binding. Display of either DVD-Fab or DVD-Ig heavy chain was monitored by staining for a V5 tag, light chain was monitored by use of an anti-hCK reagent, and the presence of the full-length DVD-Ig was monitored by a polyclonal anti-hFc reagent. Table lists the percent of cells showing display of heavy chain and light chain using the various staining reagents. Note that only the full-length DVD-Ig shows reactivity with the anti-hFc reagent. Simultaneous antigen binding to both VEGF (visualized using biotinylated VEGF and streptavidin-PE) and DLL4 (Alexa647 conjugated DLL4) was observed for both DVD-Fab and DVD-Ig. Table shows the mean fluorescence intensity (MFI) for antigen binding of anti-V5 positive cells.

TABLE 22

Yeast cells binding to heavy chain and light chain reagents

| | % α-V5+ cells | % α-hFc+ cells | % α-hCK+ cells |
|---|---|---|---|
| DVD-Fab | 64 | 0 | 54 |
| DVD-Ig | 63 | 51 | 24 |

TABLE 23

Anti-V5 positive yeast cells simultaneously binding to VEGF and DLL4

| | No Ag MFI (PE) | VEGF MFI (PE) | No Ag MFI (Alexa 647) | DLL4 MFI (Alexa 647) |
|---|---|---|---|---|
| DVD-Fab | 168 | 493 | 30 | 333 |
| DVD-Ig | 194 | 333 | 35 | 105 |

All references, including but not limited to papers, patents and publication of patent applications cited throughout this disclosures, are hereby incorporated by reference as if the full contents are reproduced herein.

We claim:

1. A method of selecting binding proteins from a library that specifically bind to a target comprising:
   a) transfecting nucleic acids from a first nucleic acid library, a second nucleic acid library and a third nucleic acid library into host cells of an organism, wherein the nucleic acids encode binding proteins, wherein the nucleic acids in each nucleic acid library comprise a variable region in distinct regions of the nucleic acid molecules and wherein the nucleic acid molecules of each library encode a distinct tag, wherein for each library the distinct tag of substantially all of the nucleic acids of each library is substantially the same tag and wherein the distinct tag of substantially all of the nucleic acids of each library is distinct from the distinct tag of the nucleic acids of the other two libraries, and wherein the distinct tag specifically binds to an epitope distinct from the target;
   b) expressing the binding proteins encoded by the nucleic acid molecules on the surface of the host cells;
   c) exposing the host cells in each library to the target;
   d) selecting host cells expressing the binding proteins that specifically bind to the target; and
   e) detecting the distinct tag on each of the selected host cells expressing the binding proteins that specifically bind to the target thereby identifying which library each of the selected binding proteins belongs to.

2. The method of claim 1, wherein the nucleic acid molecules in each library are at least 99% homologous in the sequences outside of their respective variable regions.

3. The method of claim 1, wherein the variable regions of the nucleic acids of the first library do not overlap with the corresponding nucleic acids of variable regions of the nucleic acids of the second or third library.

4. The method of claim 1, wherein the variable regions of the nucleic acids of the second library do not overlap with the corresponding nucleic acids of variable regions of the nucleic acids of the first or third library.

5. The method of claim 1, wherein the variable regions of the nucleic acids of the third library do not overlap with the corresponding nucleic acids of variable regions of the nucleic acids of the first or second library.

6. The method of claim 1, further comprising
   f) amplifying the nucleic acid molecules that encode the selected binding proteins; and
   g) combining the amplified nucleic acid molecules, thereby forming a fourth library.

7. The method of claim 6, wherein the fourth library comprises nucleic acid molecules comprising variable regions from two or more nucleic acids expressing selected binding proteins from the first, second and/or third libraries.

8. The method of claim 6, further comprising
   h) expressing the binding proteins encoded by the fourth library on the cell surface of a population of host cells from an organism;

i) exposing the binding proteins on the surface of the host cells to the target; and j) selecting binding proteins that bind to the target.

9. The method of claim 1, wherein the binding protein is anchored on the surface of host cell with an anchoring molecule.

10. The method of claim 1, wherein the organism is a prokaryotic organism or an eukaryotic organism.

11. The method of claim 10, wherein the eukaryotic organism is selected from the group consisting of fungus, mammal, insect, fish, and bird.

12. The method of claim 11, wherein the fungus is yeast.

13. The method of claim 12, wherein the yeast is selected from the group consisting of *Saccharomyces cerevisiae*, *Saccharomyces carlsbergensis*, *Candida albicans*, *Candida kefyr*, *Candida tropicalis*, *Cryptococcus laurentii*, *Cryptococcus neoformans*, *Hansenula anomala*, *Hansenula polymorpha*, *Kluyveromyces fragilis*, *Kluyveromyces lactis*, *Kluyveromyces marxianus*, *Pichia pastoris*, *Rhodotorula rubra*, *Schizosaccharomyces pombe* and *Yarrowia lipolytica*.

14. The method of claim 13, wherein the yeast is *Saccharomyces cerevisiae*.

15. The method of claim 11, wherein the mammal is selected from human, ape, monkey, rat, mouse, dog, cat, hamster, goat and sheep.

16. The method of claim 10, wherein the prokaryotic organism is *E. coli*.

17. The method of claim 1, wherein the step of selecting is performed using fluorescence activated cell sorting (FACS).

18. The method of claim 1, wherein the tag is selected from the group consisting of histidine (His), hemagglutinin (HA), c-myc, Flag, HSV, S, AcV5, E2, E, T7, KT3, MAT, AAV5, ABCA5, ABCE1, Glu-Glu, 2AU1 and StrepII tags.

19. The method of claim 1, wherein each distinct tag further comprises a fluorophore or fluorochrome, wherein the fluorophore or fluorochrome associated with each distinct tag of each library is distinct from the fluorophore or fluorochrome associated with the distinct tag of the other two libraries.

20. The method of claim 1, wherein the binding protein is at least 70% homologous to a complementarity determining region (CDR) of a mammalian antibody.

21. The method of claim 20, wherein the mammal is selected from the group consisting of human, ape, monkey, rat, mouse, dog, cat, hamster, goat and sheep.

22. The method of claim 20, wherein the binding protein further comprises a sequence at least 70% homologous to the constant region of an antibody.

23. The method of claim 20, wherein the antibody is selected from the group consisting of an IgG, IgA, IgD and IgM antibody.

24. The method of claim 23, wherein the IgG antibody is selected from the group consisting of IgG1, IgG2, IgG3 and IgG4 antibodies.

25. The method of claim 1, wherein expression of the binding proteins is under control of an inducible promoter.

26. The method of claim 25, wherein the inducible promoter is induced by the presence of a chemical, a metabolic substrate or a temperature range.

27. The method of claim 1, wherein the binding proteins are at least 70% homologous to the same antibody.

28. The method of claim 27, wherein the antibody specifically binds the target.

29. The method of claim 1, wherein the variable region of the first library comprise a first CDR.

30. The method of claim 29, wherein the variable region of the second library comprises a second CDR.

31. The method of claim 30, wherein the variable region of the third library comprises a third CDR.

32. The method of claim 31, wherein the first, second and third CDRs are at least 70% homologous to the first, second and third CDRs of the same antibody.

33. The method of claim 1, wherein the binding proteins are single chain variable fragments (ScFv).

34. The method of claim 33, wherein the single chain variable fragment is a light chain variable fragment or a heavy chain variable fragment.

35. The method of claim 34, wherein the variable region of the first library comprises a light chain variable fragment.

36. The method of claim 33, wherein the variable region of the second library comprises a heavy chain variable fragment.

37. The method of claim 1, wherein the selecting step comprises attaching the target to a substrate, a fixed surface or a detectable tag.

38. The method of claim 1, further comprising 1, 2, 3, 4, 5, 6, 7, 8, 9, 10, 11, 12, 13, 14, 15, 16 or 17 additional nucleic acid libraries wherein the nucleic acids encode binding proteins, wherein the nucleic acids in each nucleic acid library comprise a variable region in distinct regions of the nucleic acid molecules and wherein the nucleic acid molecules of each library encode a distinct tag.

39. The method of claim 19, wherein the fluorochrome is selected from the group consisting of PerCP; R-PE; DyLight-488; Alexafluor 488; Alexafluor 633; APC; PE; DyLight-633; 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein; 5-Carboxytetramethylrhodamine (5-TAMRA); 5-Hydroxy Tryptamine (5-HAT); 5-ROX (carboxy-X-rhodamine); 6-Carboxyrhodamine 6G; 6-CR 6G; 6-JOE; 7-Amino-4-methylcoumarin; 7-Aminoactinomycin D (7-AAD); 7-Hydroxy-4-I methylcoumarin; 9-Amino-6-chloro-2-methoxyacridine (ACMA); ABQ; Acid Fuchsin; Acridine Orange; Acridine Red; Acridine Yellow; Acriflavin; Acriflavin Feulgen SITSA; Aequorin (Photoprotein); Alizarin Complexon; Alizarin Red; Allophycocyanin (APC); AMC, AMCA-S; Aminomethylcoumarin (AMCA); AMCA-X; Aminoactinomycin D; Aminocoumarin; Anilin Blue; Anthrocyl stearate; APC-Cy7; APTRA-BTC; APTS; Astrazon Brilliant Red 4G; Astrazon Orange R; Astrazon Red 6B; Astrazon Yellow 7 GLL; Atabrine; Auramine; Aurophosphine G; Aurophosphine; BAO 9 (Bisaminophenyloxadiazole); BCECF (high pH); BCECF (low pH); Berberine Sulphate; Beta Lactamase; BFP blue shifted GFP (Y66H); Blue Fluorescent Protein; BFP/GFP FRET; Bimane; Bisbenzemide; Bisbenzimide (Hoechst); bis-BTC; Blancophor FFG; Blancophor SV; Bodipy 492/515; Bodipy 493/503; Bodipy 500/510; Bodipy; 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; Brilliant Sulphoflavin FF; BTC; BTC-5N; Calcein; Calcein Blue; Calcium Crimson; Calcium Green; Calcium Green-1 $Ca^{2+}$Dye; Calcium Green-2 $Ca^{2+}$; Calcium Green-5N $Ca^{2+}$; Calcium Green-C18 $Ca^{2+}$; Calcium Orange; Calcofluor White; Carboxy-X-rhodamine (5-ROX); Cascade Yellow; Catecholamine; CCF2 (GeneBlazer); CFDA; CFP (Cyan Fluorescent Protein); CFP/YFP FRET; Chlorophyll; Chromomycin A; Chromomycin A; CL-NERF;

CMFDA; Coelenterazine; Coelenterazine cp; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM I Methylcoumarin; CTC; CTC Formazan; Cyanine2; Cyanine3.1 8; Cyanine3.5; Cyanine3; Cyanine5.1 8; Cyanine5.5; Cyanine5; Cyanine7; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3'DCFDA; DCFH (Dichlorodihydrofluorescein Diacetate); DDAO; DHR (Dihydrorhodamine 123); Di-4-ANEPPS; Di-8-ANEPPS (non-ratio); DiA (4-Di 16-ASP); Dichlorodihydrofluorescein Diacetate (DCFH); DiD-Lipophilic Tracer; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (111) chloride; EYFP; Fast Blue; FDA; Feulgen (Pararosaniline); FIF (Formaldehyd Induced Fluorescence); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; Fluor X; Glycine, N-[2-[(acetyloxy)methoxy]-2-oxoethyl]-N-[5-[2-[2-[bis[2-[(acetyloxy)methoxy]-2-oxoethyl]amino]-5-methylphenoxy]ethoxy]-2-[(5-oxo-2-thioxo-4-imidazolidinylidene)methyl]-6-benzofuranyl]-, (acetyloxy) methyl ester (high pH); Glycine, N-[2-[(acetyloxy) methoxy]-2-oxoethyl]-N-[5-[2-[2-[bis[2-[(acetyloxy) methoxy]-2-oxoethyl]amino]-5-methylphenoxy]ethoxy]-2-[(5-oxo-2-thioxo-4-imidazolidinylidene)methyl]-6-benzofuranyl]-, (acetyloxy)methyl ester Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer; (CCF2); GFP (S65T); GFP red shifted (rsGFP); GFP wild type' non-UV excitation (wtGFP); GFP wild type, UV excitation (wtGFP); GFPuv; Gloxalic Acid; Granular blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1, high calcium; Indo-1low calcium; Indodicarbocyanine (DiD); Indotricarbocyanine (DiR); Intrawhite Cf; JC-1; JO JO-1; JO-PRO-1; LaserPro; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; I Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxedidole; Noradrenaline; Nuclear Fast Red; i Nuclear Yellow; Nylosan Brilliant lavin E8G; 2,5-Pyrrolidinedione, 1-[[(2',7'-difluoro-3',6'-dihydroxy-3-oxospiro[isobenzofuran-1(3H),940-[9H]xanthen]-5-yl)carbonyl]oxy]; Pacific Blue; Pararosaniline (Feulgen); PBFI; PE-Cy5; PE-Cy7; PerCP; PerCP-Cy5.5; PE-TexasRed (Red 613); Phloxin B (Magdala Red); Phorwite AR; Phorwite BKL; Phorwite Rev; Phorwite RPA; Phosphine 3R; PhotoResist; Phycoerythrin B [PE]; Phycoerythrin R [PE]; PKH26 (Sigma); PKH67; PMIA; Pontochrome Blue Black; POPO-1; POPO-3; PO-PRO-1; PO-I PRO-3; Primuline; Procion Yellow; Propidium lodid (P1); PyMPO; Pyrene; Pyronine; Pyronine B; Pyrozal Brilliant Flavin 7GF; QSY 7; Quinacrine Mustard; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine: Phalloidine; Rhodamine Red; Rhodamine WT; Rose Bengal; R-phycocyanine; R-phycoerythrin (PE); rsGFP; S65A; S65C; S65L; S65T; Sapphire GFP; SBFI; Serotonin; Sevron Brilliant Red 2B; Sevron Brilliant Red 4G; Sevron I Brilliant Red B; Sevron Orange; super glow BFP; super glow GFP; SITS (Primuline; Stilbene Isothiosulphonic Acid); SNAFL calcein; SNAFL-1; SNAFL-2; SNARF calcein; SNARFI; Sodium Green; SpectrumAqua; SpectrumGreen; SpectrumOrange; Spectrum Red; SPQ (6-methoxy-N-(3 sulfopropyl) quinolinium); Stilbene; Sulphorhodamine B and C; Sulphorhodamine Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Reds; Thiadicarbocyanine (DiSC3); Thiazole Orange; Thioflavin 5; Thioflavin S; Thioflavin TON; Thiolyte; Thiozole Orange; Tinopol CBS (Calcofluor White); TIER; TO-PRO-1; TO-PRO-3; TO-PRO-5; TOTO-1; TOTO-3; TriColor (PE-Cy5); TRITC TetramethylRodamineIsoThioCyanate; True Blue; Tru Red; Ultralite; Uranine B; Uvitex SFC; wt GFP; WW 781; X-Rhodamine; XRITC; Xylene Orange; Y66F; Y66H; Y66W; Yellow GFP; YFP; YO-PRO-1; YO-PRO3; YOYO-1; YOYO-3; Sybr Green; Thiazole orange (interchelating dyes); semiconductor nanoparticles; quantum dots; caged fluorophores, and a combination thereof.

40. The method of claim 1, wherein substantially all of the nucleic acids in the nucleic acid libraries comprise one or more vectors.

41. The method of claim 40, wherein the vector is a yeast vector.

42. The method of claim 41, wherein the yeast vector is pYDsTEV.

43. The method of claim 20, wherein the antibody is h1A11.

44. The method of claim 1, wherein the variable region encodes one or more complementarity determining regions (CDRs).

* * * * *